(12) United States Patent
Rosse et al.

(10) Patent No.: US 8,399,455 B2
(45) Date of Patent: Mar. 19, 2013

(54) COMPOUNDS USEFUL AS CHEMOKINE RECEPTOR ANTAGONISTS

(75) Inventors: Gerard Rosse, Exton, PA (US); Linli Wei, Whtiehouse Station, NJ (US); Kenneth G. Carson, Princeton, NJ (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 143 days.

(21) Appl. No.: 12/577,853

(22) Filed: Oct. 13, 2009

(65) Prior Publication Data

US 2010/0234356 A1 Sep. 16, 2010

Related U.S. Application Data

(62) Division of application No. 11/320,298, filed on Dec. 28, 2005, now Pat. No. 7,635,698.

(60) Provisional application No. 60/639,913, filed on Dec. 29, 2004.

(51) Int. Cl.
*A61K 31/55* (2006.01)
*C07D 243/08* (2006.01)

(52) U.S. Cl. ........................... 514/218; 540/575

(58) Field of Classification Search .................. None
See application file for complete search history.

(56) References Cited

U.S. PATENT DOCUMENTS

| | | | |
|---|---|---|---|
| 3,265,698 A | 8/1966 | Allen, Jr. et al. | |
| 5,338,852 A | 8/1994 | Efange et al. | |
| 5,756,508 A | 5/1998 | Thompson et al. | |
| 5,773,442 A | 6/1998 | Akamatsu et al. | |
| 5,789,420 A | 8/1998 | Efange et al. | |
| 5,876,694 A | 3/1999 | Efange et al. | |
| 5,985,878 A | 11/1999 | Stokbroekx et al. | |
| 6,057,324 A | 5/2000 | Matsumoto et al. | |
| 6,166,037 A | 12/2000 | Budhu et al. | |
| 6,521,621 B1 | 2/2003 | Janssens et al. | |
| 6,642,226 B2 | 11/2003 | Kolczewski et al. | |
| 6,906,072 B1 | 6/2005 | Yamamoto et al. | |
| 6,930,104 B2 | 8/2005 | Kakihana et al. | |
| 6,977,265 B2 | 12/2005 | Du Bois et al. | |
| 7,291,618 B2 | 11/2007 | Hulin et al. | |
| 2002/0151547 A1 | 10/2002 | Kolczewski et al. | |
| 2003/0229121 A1 | 12/2003 | Du Bois et al. | |
| 2004/0157850 A1 | 8/2004 | Kakihana et al. | |
| 2004/0186135 A1 | 9/2004 | Dolle et al. | |
| 2004/0220193 A1 | 11/2004 | Yamamoto et al. | |
| 2005/0137211 A1 | 6/2005 | Blanco et al. | |
| 2005/0256310 A1 | 11/2005 | Hulin et al. | |
| 2006/0040950 A1 | 2/2006 | Janssens et al. | |
| 2006/0079498 A1 | 4/2006 | Hulin et al. | |
| 2006/0084658 A1 | 4/2006 | Yamamoto et al. | |
| 2006/0128721 A1 | 6/2006 | Janssens et al. | |
| 2006/0167008 A1 | 7/2006 | Janssens et al. | |
| 2006/0172994 A1 | 8/2006 | Carson et al. | |
| 2006/0217392 A1 | 9/2006 | Anilkumar et al. | |
| 2007/0021611 A1 | 1/2007 | McGuinness et al. | |
| 2007/0054919 A1 | 3/2007 | Rosenblum et al. | |
| 2007/0099897 A1 | 5/2007 | Hulin et al. | |
| 2007/0161664 A1 | 7/2007 | Hulin et al. | |

FOREIGN PATENT DOCUMENTS

| | | |
|---|---|---|
| EP | 0121972 A2 | 10/1984 |
| EP | 0542363 A2 | 5/1993 |
| EP | 0810215 A1 | 12/1997 |
| EP | 0905129 A1 | 3/1999 |
| EP | 1254895 A1 | 11/2002 |
| EP | 1382598 A1 | 1/2004 |
| GB | 1080680 | 8/1967 |
| JP | 43020190 | 8/1968 |
| WO | WO 93/10091 A2 | 5/1993 |
| WO | WO 93/24457 A1 | 12/1993 |
| WO | WO 97/16192 A1 | 5/1997 |
| WO | WO 97/26258 A1 | 7/1997 |
| WO | WO 99/09984 A1 | 3/1999 |
| WO | WO 00/66558 A1 | 11/2000 |
| WO | WO 02/062784 A1 | 8/2002 |
| WO | WO 02/079194 A1 | 10/2002 |
| WO | WO 03/004487 A1 | 1/2003 |
| WO | WO 03/020716 A1 | 3/2003 |
| WO | WO 03/033490 A1 | 4/2003 |
| WO | WO 03/045937 A1 | 6/2003 |
| WO | WO 2004/033428 A1 | 4/2004 |
| WO | WO 2004/056770 A2 | 7/2004 |
| WO | WO 2004/056772 A1 | 7/2004 |
| WO | WO 2004/056799 A2 | 7/2004 |
| WO | WO 2004/082623 A2 | 9/2004 |

(Continued)

OTHER PUBLICATIONS

International Search Report dated Jun. 1, 2006 issued in PCT Application No. PCT/US05/047327, which corresponds to U.S. Appl. No. 11/320,298.

(Continued)

*Primary Examiner* — Noble Jarrell
(74) *Attorney, Agent, or Firm* — Millennium Pharmaceuticals, Inc.

(57) ABSTRACT

The present invention relates to compounds useful as Chemokine Receptor antagonists. Compounds of general formula I are provided:

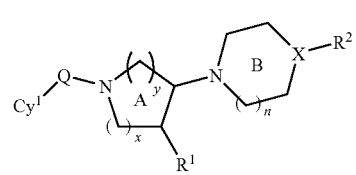

or pharmaceutically acceptable salts thereof. The invention also provides pharmaceutically acceptable compositions comprising said compounds and methods of using the compounds and compositions for the inhibition of Chemokine Receptors and also for the treatment of various diseases, conditions, or disorders, including acute or chronic inflammatory disease, cancer, and osteolytic bone disorders.

17 Claims, No Drawings

FOREIGN PATENT DOCUMENTS

| | | |
|---|---|---|
| WO | WO 2004/110415 A2 | 12/2004 |
| WO | WO 2005/030188 A2 | 4/2005 |
| WO | WO 2005/101838 A2 | 10/2005 |
| WO | WO 2005/116014 A1 | 12/2005 |
| WO | WO 2006/008644 A1 | 1/2006 |
| WO | WO 2006/088840 A1 | 8/2006 |
| WO | WO 2006/088919 A2 | 8/2006 |
| WO | WO 2006/088921 A2 | 8/2006 |

OTHER PUBLICATIONS

Assaad, Thaer, et al., "Synthesis and in vitro evaluation of N-substituted aza-trozamicol analogs as vesicular acetylcholine transporter ligands," *Bioorganic & Medicinal Chemistry Letters*, vol. 16, No. 10 (2006) pp. 2654-2657.

Coffeen, Paul R., et al., "Measurement of functional cholinergic innervation in rat heart with a novel vesamicol receptor ligand," *Nuclear Medicine & Biology*, vol. 23, No. 7 (1996) pp. 923-926.

Custers, Franciscus G. J., et al., "Vesamicol and some of its derivatives: Questionable ligands for selectively labelling acetylcholine transporters in rat brain," *European Journal of Pharmacology*, vol. 338, No. 2 (1997) pp. 177-183.

Efange, S.M.N., et al., "Nonsymmetrical bipiperidyls as inhibitors of vesicular acetylcholine storage," *Journal of Medicinal Chemistry*, vol. 36, No. 8 (1993) pp. 985-989.

Efange, S.M.N, et al., "Synthesis and tissue distribution of (m[$^{125}$I]iodobenzyl)trozamicol ([$^{125}$I]MIBT): potential radioligand for mapping central cholinergic innervation," *Journal of Medicinal Chemistry*, vol. 36, No. 12 (1993) pp. 1754-1760.

Efange, S.M.N., et al., "p-[$^{18}$F]fluorobenzyltrozamicol ([$^{18}$F]FBT): molecular decomposition-reconstitution approach to vesamicol receptor radioligands for positron emission tomography," *Applied Radiation and Isotopes*, vol. 45, No. 4 (1994) pp. 465-472.

Efange; Simon M. N., et al., "Vesamicol analogues as sigma ligands," *Biochemical Pharmacology*, vol. 49, No. 6 (1995) pp. 791-797.

Efange, Simon M. N., et al., "Age-related diminution of dopamine antagonist-stimulated vesamicol receptor binding," *The Journal of Nuclear Medicine*, vol. 37, No. 7 (Jul. 1996) pp. 1192-1196.

Efange, Simon M. N., et al., "N-hydroxyalkyl derivatives of 3β-phenyltropane and 1-methylspirol[1H-indoline-3,4'-piperidine]: vesamicol analogues with affinity for monoamine transporters," *Journal of Medicinal Chemistry*, vol. 40, No. 24 (1997) pp. 3905-3914.

Efange, Simon M. N., et al., "The vesamicol receptor ligand (+)-meta-[$^{125}$I]iodobenzyltrozamicol {(+)- [$^{125}$I]-MIBT} reveals blunting of the striatal cholinergic response to dopamine D2 receptor blockade in the 6-hydroxydopamine (6-OHDA)-lesioned rat: possible implications for Parkinson's disease," *Life Sciences*, vol. 58, No. 16 (1996) pp. 1367-1374.

Efange; S.M.N., et al., "Vesicular acetylcholine transporter density and Alzheimer's disease," *Neurobiology of Aging*, vol. 18, No. 4 (1997) pp. 407-413.

Efange, S.M.N., et al., "(+)-p-([$^{18}$F]fluorobenzyl)spirotrozamicol {(+)-[$^{18}$F]spiro-FBT}: synthesis and biological evaluation of a high-affinity ligand for the vesicular acetylcholine transporter (VAChT)," *Nuclear Medicine & Biology*, vol. 26, No. 2 (1999) pp. 189-192.

Gage, H. Donald, et al., "Reproducibility of repeated measures of cholingeric terminal density using [$^{18}$F](+)-4-fluorobenzyltrozamicol and PET in the Rhesus monkey brain," *Journal of Nuclear Medicine*, vol. 41, No. 12 (2000) pp. 2069-2076.

Gage, H. Donald, et al., "Morphine-induced spinal cholinergic activation: in vivo imaging with positron emission tomography," *Pain*, vol. 91, No. 1-2 (2001) pp. 139-145.

Gaina, C., et al., "Poiyimides containing 4,4'-bipyridinium units," *Journal of Applied Polymer Science*, vol. 94 (2004) pp. 2091-2100.

Hiessbock, Romana, et al., "Synthesis and in vitro multidrug resistance modulating activity of a series of dihydrobenzopyrans and tetrahydroquinolines," *Journal of Medicinal Chemistry*, vol. 42, No. 11 (1999) pp. 1921-1926.

Khare, A. B., et al., "N-(3-iodophenyl)trozamicol (IPHT) and related inhibitors of vesicular acetylcholine transport: synthesis and preliminary biological characterization," *Nuclear Medicine & Biology*, vol. 26, No. 6 (1999) pp. 609-617.

Mach, Robert H., et al., "Imaging of cholinergic terminals using the radiotracer [$^{18}$F](+)-4-fluorobenzyltrozamicol: in vitro binding studies and positron emission tomography studies in nonhuman primates," *Synapse*, vol. 25, No. 4 (1997) pp. 368-380.

Mach, Robert H., et al., "[$^{18}$F]4-fluorobenzyl iodide as a useful precursor in PET research: application in the development of dopaminergic and cholinergic radiotracers," *Synthesis and Applications of Isotopically Labelled Compounds*, vol. 8 Proceedings of the International Symposium, Boston, MA, USA, Jun. 1-5, 2003 (2004), meeting date 2003, pp. 183-186, editors: Dean, Dennis C., et al., publisher: John Wiley & Sons Ltd., Chichester, UK.

Staley, Julie K., et al., "Pharmacological characterization of the vesamicol analogue (+)-[$^{125}$I]MIBT in primate brain," *European Journal of Pharmacology*, vol. 338, No. 2 (1997) pp. 159-169.

Suero, Ruben, et al., "Synthesis of 3-aminopyrrolidines by cyclization of neutral C-centered α-aminoalkyl radicals," *Tetrahedron*, vol. 58, No. 31 (2002) pp. 6211-6221.

Sugiyama, Atsushi, et al., "Direct cardiac effects of a novel vesamicol receptor ligand, m-iodobenzyl-trozamicol, assessed in the canine isolated, blood-perfused heart preparations," *Journal of Cardiovascular Pharmacology*, vol. 34, No. 6 (1999) pp. 843-847.

Sugiyama, Atsushi, et al., "Effects of a novel vesamicol receptor ligand, m-(iodobenzyl)trozamicol, on the canine-isolated, blood-perfused atrioventricular node preparation," *Japanese Journal of Pharmacology*, vol. 82, No. 2 (2000) pp. 150-154.

"3-Piperidinepropanoic acid, 4-[4-(2-methoxypheny1)-1-piperazinyl]-1-(phenylmethyl)-, ethyl ester (CA Index Name)," CAS Registry No. 519018-38-3, entered May 22, 2003.

"3-Piperidinepropanoic acid, 4-[4-(2-fluorophenyl)-1-piperazinyl]-1-(phenylmethyl)-, ethyl ester (CA Index Name)," CAS Registry No. 519018-37-2, entered May 22, 2003.

"2,5-Pyrrolidinedione, 3-[(4-chlorophenyl)thiol]-4-[4-[3-chloro-5-(trifluoromethyl)-2-pyridinyl]-1-piperazinyl]-1-(phenylmethyl)-(CA Index Name)," CAS Registry No. 321433-54-9, entered Feb. 12, 2001.

International Search Report dated Jun. 1, 2006, issued in PCT Application No. PCT/US05/047096, which corresponds with U.S. Appl. No. 11/320,414 (U.S. Publication No. 2006/0172994 A1).

Chemical Abstract Services CAPLUS Database Abstract for JP 43020190 (B15), Aug. 30, 1968.

COMPOUNDS USEFUL AS CHEMOKINE RECEPTOR ANTAGONISTS

PRIORITY INFORMATION

The present application is a Divisional of U.S. patent application Ser. No. 11/320,298, filed Dec. 28, 2005, which claims priority under 35 U.S.C. §119(e) to U.S. Provisional Application No. 60/639,913, filed Dec. 29, 2004, entitled "Compounds Useful as Chemokine Receptor Antagonists", the entire contents of which are hereby incorporated by reference.

BACKGROUND OF THE INVENTION

Chemoattractant cytokines, Chemoattractant cytokines or chemokines are a family of proinflammatory mediators that are released by a wide variety of cells to promote recruitment and activation of cells such as T and B lymphocytes, eosinophils, basophils, and neutrophils (Luster et al. *New Eng. J. Med,* 1998, 338, 436). The chemokines are related in primary structure and contain four conserved cysteines, which form disulfide bonds. The chemokine family includes the C—X—C chemokines (α-chemokines), and the C—C chemokines (β-chemokines), in which the first two conserved cysteines are separated by an intervening residue, or are adjacent, respectively (Baggiolini, M. and Dahinden, C. A., *Immunology Today,* 1994, 15, 127).

Chemokines exert their biological activity by binding to specific cell-surface receptors belonging to the family of G-protein-coupled seven-transmembrane-domain proteins (Horuk, *Trends Pharm. Sci.* 1994, 15, 159) which are termed "chemokine receptors". On binding their cognate ligands, chemokine receptors then transduce signals important for the development and trafficking of specific leukocyte subsets (Baggiolini, et. al., *Nature* 1994, 15, 365). The chemokines and their cognate receptors have been implicated as being important mediators of inflammatory, and allergic diseases, disorders, and conditions, as well as autoimmune pathologies such as rheumatoid arthritis and atherosclerosis (see, Carter, *Current Opinion in Chemical Biology* 2002, 6, 510; Trivedi et al., *Ann. Reports Med. Chem.* 2000, 35, 191; Saunders et al., *Drug Disc. Today* 1999, 4, 80; and Premack et al., *Nature Medicine,* 1996, 2, 1174).

The first receptor for the C—C chemokines that was cloned and expressed binds the chemokines MIP-1α and RANTES. Accordingly, this MIP-1α/RANTES receptor was designated C—C chemokine receptor 1 (also referred to as CCR-1 or CKR-1; Neote, K., et al., *Cell,* 72:415-425 (1993); Horuk, R. et al., WO 94/11504, May 26, 1994; Gao, J.-I. et al., *J. Exp. Med.,* 177:1421-1427 (1993)). CCR1 also binds the chemokines CCL2 (MCP-1) CCL4 (MIP-1β), CCL7 (MCP-3), CCL8 (MCP-2), CCL13 (MCP-4), CCL14 (HCC-1), CCL15 (Lkn-1), CCL23 (MPIF-1). (Murphy P. M. et al., International Union of Pharmacology. XXII. Nomenclature for Chemokine Receptors, *Pharmacol. Reviews,* 52:145-176 (2000)).

Small molecule antagonists of the interaction between C—C chemokine receptors (e.g., CCR1) and their ligands, (e.g., CCL2 (MCP-1) CCL3 (MIP-1α), CCL4 (MIP-1β), CCL5 (RANTES), CCL7 (MCP-3), CCL8 (MCP-2), CCL13 (MCP-4), CCL14 (HCC-1), CCL15 (Lkn-1), or CCL23 (MPIF-1)), would inhibit those processes or cellular responses mediated by the binding of a chemokine to CCR1. Accordingly, these compounds would inhibit those pathogenic processes "triggered" by receptor ligand interactions (e.g., leukocyte migration, integrin activation, transient increases in the concentration of intracellular free calcium $[Ca^{++}]_i$, and/or granule release of proinflammatory mediators) and would be useful in the treatment of diseases, conditions, or disorders mediated by these pathogenic processes.

Indeed, there has been substantial interest in the discovery and development of antagonists of CCR1 for a treatment of a variety of disorders including, but not limited to rheumatoid arthritis, multiple sclerosis, transplant rejection, and allergic inflammation (see, Cascieri et al., *Curr. Opin. Chem. Biol.* 2000, 4, 420; Onuffer et al., *Trends Pharmacol. Sci,* 2002, 23, 459; and Pease et al., *Expert Opin. Investig. Drugs* 2005, 14, 785). Additionally, studies have suggested that CCR1 antagonists would be useful for the treatment of cancer, including multiple myeloma, and for the treatment of other bone disorders resulting from the chemotactic and other responses of osteoclasts to the CC chemokine macrophage inflammatory protein (MIP-1α) (see, *Exp. Hematol.* 2005, 33, 272; *J. Clin. Invest.* 2001, 108, 1833; *Cancer* 2003, 97, 813; and *Blood* 2003, 102, 311 and references cited therein).

There remains a need, however, for the discovery and development of antagonists of CCR1 for use in the treatment of diseases, conditions, and disorders mediated by the interaction of chemokine receptors and their ligands.

SUMMARY OF THE INVENTION

It has now been found that compounds of this invention, and pharmaceutically acceptable compositions thereof, are effective as inhibitors of the interaction between chemokine receptors and their ligands. In some embodiments, these compounds are effective as inhibitors of CCR1.

These compounds have general formula I:

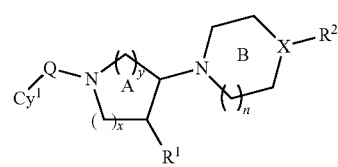

or pharmaceutically acceptable salts thereof, wherein $R^1$, $R^2$, X, n, x, y, Q, and $Cy^1$ are as defined generally and in subsets herein.

In general, these compounds, and pharmaceutical compositions thereof, are useful for treating or lessening the severity of a variety of acute or chronic inflammatory diseases, conditions, or disorders including, but not limited to, inflammatory arthritis, inflammatory demyelinating disease, chronic obstructive pulmonary disorder, atherosclerosis, arteriosclerosis, restenosis, ischemia/reperfusion injury, diabetes mellitus, psoriasis, inflammatory bowel diseases, rejection of a transplanted graft, graft versus host disease, allergy, or asthma. These compounds, and pharmaceutical compositions thereof, are also useful for treating cancer and osteolytic bone disorders.

In other embodiments, compounds of the invention are useful for treating diseases, conditions, or disorders characterized by pathogenic leukocyte recruitment, pathogenic leukocyte activation, or pathogenic leukocyte recruitment and activation.

DETAILED DESCRIPTION OF THE INVENTION

1. General Description of Compounds of the Invention:
The present invention relates to a compound of formula I:

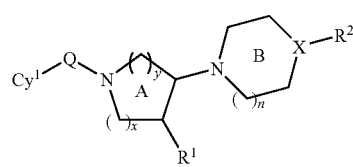

or a pharmaceutically acceptable salt thereof, wherein:

x and y are each independently 1 or 2, provided that x and y are not simultaneously 2;

$R^1$ is fluoro, —$R^3$, —$OR^4$, —$SR^4$, —$COOR^4$, —$COR^4$, —$CON(R^4)_2$, —$N(R^4)_2$, —$SO_2N(R^4)_2$, —$NR^4SO_2R^3$, —$NR^4COR^4$, $NR^4CON(R^4)_2$, —$CON(R^4)_2$, —$OCOR^4$, or —$OSO_2R^4$;

$R^3$ is an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur;

each occurrence of $R^4$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two $R^4$ on the same nitrogen atom, taken together with the nitrogen atom, form an optionally substituted 3-6-membered saturated, partially saturated, or aromatic ring having 0-2 additional heteroatoms independently selected from nitrogen, oxygen, or sulfur;

ring A is substituted with q occurrences of $R^A$, wherein q is 0-2 and each occurrence of $R^A$ is independently fluoro, —$SO_2N(R^C)_2$, —$OR^C$, —$SR^C$, —$SO_2R^C$, —$COR^C$, —$CO_2R^C$, —$N(R^C)_2$, —$CON(R^C)_2$, —$N(R^C)COR^C$, —$N(R^C)CO_2R^C$, —$N(R^C)CON(R^C)_2$, or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^A$, or $R^A$ and $R^1$, taken together with their intervening atom(s), form an optionally substituted spiro or fused 3-6-membered saturated or partially unsaturated ring having 0-3 heteroatoms independently selected from nitrogen, oxygen, or sulfur, wherein each occurrence of $R^C$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^C$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

ring B is substituted with r occurrences of —$R^B$ or -L-$R^B$, wherein r is 0-2, L is a $C_{1-4}$ alkylene and each occurrence of $R^B$ is independently fluoro, —$OR^D$, —$SR^D$, —$COR^D$, —$CO_2R^D$, —$N(R^D)_2$, —$CON(R^D)_2$, —$N(R^D)COR^D$, or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^B$, taken together with their intervening atom(s), form an optionally substituted spiro, fused or bridged 3-6-membered saturated, partially unsaturated, or aromatic ring having 0-3 heteroatoms independently selected from nitrogen, oxygen, or sulfur; wherein each occurrence of $R^D$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^D$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

n is 1 or 2;

$R^2$ is -T-$Cy^2$ or -$Cy^2$, wherein T, when present, is a $C_1$-$C_3$alkylene chain, wherein the alkylene chain is substituted with 0 or 1 occurrence of $R^{5a}$, and 0, 1, or 2 independent occurrences of $R^{5b}$, and wherein one or more methylene units in the $C_1$-$C_3$alkylene chain, as valency and stability permit, is optionally replaced by one or more independent occurrences of —$CR^{5c}$=$CR^{5c}$—, —CO—, —$SO_2$—, —O—, —S—, or —$NR^{5c}$—;

$R^{5a}$ is halogen, —CN, —$OR^{5c}$, —$N(R^{5c})_2$, —$SR^{5c}$, or an optionally substituted group selected from $C_1$-$C_6$aliphatic, or a 3-7-membered saturated, partially unsaturated, or aromatic monocyclic ring having 0-3 heteroatoms independently selected from nitrogen, oxygen, or sulfur;

$R^{5b}$ is an optionally substituted group selected from $C_1$-$C_6$aliphatic, or a 3-7-membered saturated, partially unsaturated, or aromatic monocyclic ring having 0-3 heteroatoms independently selected from nitrogen, oxygen, or sulfur;

$R^{5c}$ is hydrogen, or an optionally substituted group selected from $C_1$-$C_4$aliphatic, or a 3-7-membered saturated, partially unsaturated, or aromatic monocyclic ring having 0-3 heteroatoms independently selected from nitrogen, oxygen, or sulfur, or two occurrences of $R^{5c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

$Cy^2$ is an optionally substituted group selected from a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur;

wherein $Cy^2$ is substituted with m independent occurrences of —$R^{6a}$, -G-$R^{6a}$, or —V-G-$R^{6a}$, and k occurrences of =O, =S, =$NR^{7a}$, =$NR^{7b}$, —$R^{6b}$, -G-$R^{6b}$, or —V-G-$R^{6b}$, wherein:

m is 0-3;

k is 0-2;

V is —O—, —$N(R^{7a})$—, —S—, —SO—, —$SO_2$—, —$SO_2N(R^{7a})$—, —$N(R^{7a})SO_2$—, —CO—, —$CON(R^{7a})$—, —$N(R^{7a})CO$—, or —$CO_2$—;

G is an optionally substituted straight or branched $C_1$-$C_4$alkylene chain that is optionally replaced by —$CR^{7a}$=$CR^{7a}$—, —O—, —$N(R^{7a})$—, —S—, —SO—, —$SO_2$—, —$SO_2N(R^{7a})$—, —$N(R^{7a})SO_2$—, —CO—, —$CON(R^{7a})$—, —$N(R^{7a})CO$—, or —$CO_2$—, provided that the replacing group is not directly bonded to V, —$R^{6a}$, or —$R^{6b}$;

each occurrence of —$R^{6a}$ is independently optionally substituted $C_1$-$C_6$ aliphatic, halogen, —$OR^{7a}$, —CN, —$NO_2$, —$SR^{7a}$, —$SO_2N(R^{7a})_2$, —$NR^{7a}SO_2R^{7b}$, —$SO_2R^{7a}$, —$COR^{7a}$, —$CO_2R^{7a}$, —$N(R^{7a})_2$, —$CON(R^{7a})_2$, —$N(R^{7a})COR^{7a}$, —$N(R^{7a})CO_2R^{7a}$, or —$N(R^{7a})CON(R^{7a})_2$;

each occurrence of —$R^{6b}$ is independently —$OR^{7b}$, —$SR^{7b}$, —$SO_2N(R^{7b})(R^{7c})$, $NR^{7c}SO_2R^{7b}$, —$SO_2R^{7b}$, —$COR^{7b}$, —$CO_2R^{7b}$, —$N(R^{7b})(R^{7c})$, —$CON(R^{7b})(R^{7c})$, —$N(R^{7c})COR^{7b}$, —$N(R^{7c})CO_2R^{7b}$, —$N(R^{7c})CON(R^{7b})(R^{7c})$, or an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring system having 0-5 heteroatoms independently selected from nitrogen, oxygen, or sulfur; or two occurrences of $R^{6b}$, taken together with their intervening atom(s), form a spiro, fused, or bridged optionally substituted 5-7-membered saturated, partially unsaturated, or aromatic ring having 0-3 heteroatoms independently selected from nitrogen, oxygen, or sulfur;

each occurrence of $R^{7a}$ is hydrogen or an optionally substituted $C_1$-$C_6$aliphatic group;

each occurrence of $R^{7b}$ is an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and each occurrence of $R^{7c}$ is hydrogen or an optionally substituted group selected from a $C_1$-$C_6$aliphatic group, a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; or $R^{7b}$ and $R^{7c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

X is N or $CR^8$, wherein $R^8$ is fluoro, —$R^9$, —$OR^9$, —$N(R^9)_2$, —$SR^9$, —$OCOR^9$, —$COOR^9$, —CN, —CON$(R^9)_2$, —$COR^9$, —$SO_2R^9$, —$SOR^9$, —$NR^9SO_2R^9$, or —$SO_2N(R^9)_2$, wherein each occurrence of $R^9$ is independently hydrogen or an optionally substituted $C_1$-$C_6$aliphatic group; or when X is $CR^8$, $R^8$ and $R^2$, taken together with the carbon atom to which they are bound, form an optionally substituted 3-6-membered spiro ring having 0-3 heteroatoms independently selected from nitrogen, oxygen, or sulfur;

Q is a $C_1$-$C_3$alkylene chain, wherein the alkylene chain is substituted with 0 or 1 occurrence of $R^{5d}$, and 0, 1, or 2 independent occurrences of $R^{5e}$, wherein one or more methylene units in the $C_1$-$C_3$alkylene chain, as valency and stability permit, is optionally replaced by one or more independent occurrences of —$CR^{5f}$=$CR^{5f}$—, —CO—, —$SO_2$—, —O—, —S—, or —$NR^{5f}$—, wherein $R^{5d}$ is $R^{5a}$, $R^{5e}$ is $R^{5b}$, and $R^{5f}$ is $R^{5c}$;

$Cy^1$ is an optionally substituted group selected from a 5-8-membered partially unsaturated or aromatic unsaturated monocyclic ring having 0-3 heteroatoms independently selected from nitrogen, oxygen, or sulfur, or an 8-14-membered partially unsaturated or aromatic bicyclic or tricyclic ring system having 0-5 heteroatoms independently selected from nitrogen, oxygen, or sulfur;

wherein $Cy^1$ is substituted with p independent occurrences of —$R^{10a}$, -J-$R^{10a}$, or W-J-$R^{10a}$, and j occurrences of =O, =S, =$NR^{11a}$, =$NR^{11b}$, —$R^{10b}$, -J-$R^{10b}$, or —W-J-$R^{10b}$, wherein:

p is 0-3;
j is 0-2;
W is —O—, —$N(R^{11a})$—, —S—, —SO—, —$SO_2$—, —$SO_2N(R^{11a})$—, —$N(R^{11a})SO_2$—, —CO—, —CON$(R^{11a})$—, —$N(R^{11a})$CO—, or —$CO_2$—;

J is an optionally substituted straight or branched $C_1$-$C_4$alkylene chain that is optionally replaced by —$CR^{11a}$=$CR^{11a}$—, —O—, —$N(R^{11a})$—, —S—, —SO—, —$SO_2$—, —$SO_2N(R^{11a})$—, —$N(R^{11a})SO_2$—, —CO—, —CON$(R^{11a})$—, —$N(R^{11a})$CO—, or —$CO_2$—, provided that the replacing group is not directly bonded to W, —$R^{10a}$, or —$R^{10b}$;

each occurrence of —$R^{10a}$ is independently optionally substituted $C_1$-$C_6$ aliphatic, halogen, —$OR^{11a}$, —CN, —$NO_2$, —$SR^{11a}$, —$SO_2N(R^{11a})_2$, —$NR^{11a}SO_2R^{11a}$, —$SO_2R^{11a}$, —$COR^{11a}$, —$CO_2R^{11a}$, —$N(R^{11a})_2$, —CON$(R^{11a})_2$, —$N(R^{11a})COR^{11a}$, —$N(R^{11a})CO_2R^{11a}$, or —$N(R^{11a})CON(R^{11a})_2$;

each occurrence of —$R^{10b}$ is independently —$OR^{11b}$, —$SR^{11b}$, —$SO_2N(R^{11b})(R^{11c})$, —$NR^{11c}SO_2R^{11b}$, —$SO_2R^{11b}$, —$COR^{11b}$, —$CO_2R^{11b}$, —$N(R^{11b})(R^{11c})$, —CON$(R^{11b})(R^{11c})$, —$N(R^{11c})COR^{11b}$, —$N(R^{11c})CO_2R^{11b}$, —$N(R^{11c})CON(R^{11b})(R^{11c})$, or an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring system having 0-5 heteroatoms independently selected from nitrogen, oxygen, or sulfur; or two occurrences of $R^{10b}$, taken together with their intervening atom(s), form a spiro, fused, or bridged optionally substituted 5-7-membered saturated, partially unsaturated, or aromatic ring having 0-3 heteroatoms independently selected from nitrogen, oxygen, or sulfur;

each occurrence of $R^{11a}$ is hydrogen or an optionally substituted $C_1$-$C_6$aliphatic group;

each occurrence of $R^{11b}$ is an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and each occurrence of $R^{11c}$ is hydrogen or an optionally substituted group selected from a $C_1$-$C_6$aliphatic group, a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; or $R^{11b}$ and $R^{11c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur.

In some embodiments, for compounds of formula I one or more, or all of, the following conditions apply:

A) when ring A is

Q is —$SO_2$—, q is 0, r is 0, $Cy^1$ is (4-Me)-phenyl, $R^1$ is —$CH_2$COOEt, n is 1, X is N, and T is absent, then $Cy^2$ is other than unsubstituted phenyl;

B) when ring A is then:
i) when Q is $CH_2$, $R^1$ is —OH, q is 0, r is 0, n is 1, X is CH, and $R^2$ is unsubstituted phenyl, then $Cy^1$ is other than unsubstituted phenyl, or if $Cy^1$ is phenyl and p is 1, then $R^{10a}$ is other than —F, —I, —Br, or -Me; or ii) when Q is C=O, $R^1$ is —OH, q is 0, r is 0, n is 1, X is CH, and $R^2$ is unsubstituted phenyl, then $Cy^1$ is other than unsubstituted phenyl, or phenyl substituted with one occurrence of —I; and C) when A is

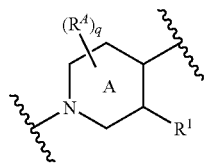

then:
i) when Q is CHMe, $R^1$ is Me, n is 1, q is 0, r is 0, $Cy^1$ is pyrimidin-5-yl, and X is CH, then $R^2$ is other than

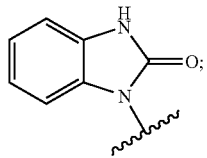 [SMILES: *n1c(=O)[nH]c2ccccc21]

ii) when Q is $CH_2$, $R^1$ is Me, q is 0, r is 0, n is 1, $Cy^1$ is unsubstituted phenyl, and X is N, then $R^2$ is other than p-CN-phenyl;

iii) when Q is $CH_2$, $R^1$ is OH, q is 0, r is 0, n is 1, X is CH, and $R^2$ is unsubstituted phenyl then $Cy^1$ is other than unsubstituted phenyl, or if $Cy^1$ is phenyl, and p is 1, then $R^{10a}$ is other than —Br or —I; and iv) $R^1$ is other than phenyl.

2. Compounds and Definitions:

Compounds of this invention include those described generally above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40°, in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound. By way of example, in a compound of formula (I), if Ring B is substituted with two substituents —$R^b$, each substituent is selected from the group of defined values for $R^b$, and the two values selected may be the same or different.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I, The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$(as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$aromatic hydrocarbon moiety comprising one to three aromatic rings. Preferably, the aryl group is a $C_{6-10}$aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^{30}$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein.

An alkylene chain also can be optionally replaced by a functional group. An alkylene chain is "replaced" by a functional group when an internal methylene unit is replaced with the functional group. Examples of suitable "replacing functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroaralkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^\circ$, —S(O)R$^\circ$, —SO$_2$R$^\circ$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^\circ$, —NR$^+$CO$_2$R$^+$, —NR$^+$SO$_2$R$^\circ$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^\circ$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^\circ$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^\circ$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^\circ$=N—NHSO$_2$R$^\circ$ or =N—R* where R$^\circ$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of OR$^+$

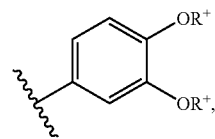

these two occurrences of R$^+$ are taken together with the oxygen atoms to which they are bound to form a fused 6-membered oxygen containing ring:

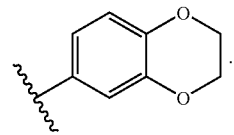 [SMILES: *c1ccc2c(c1)OCCO2]

It will be appreciated that a variety of other rings (e.g., spiro and bridged rings) can be formed when two independent occurrences of R$^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It is to be understood that, when a disclosed compound has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer free of other diastereomers, a pair of diastereomers free from other diasteromeric pairs, mixtures of diasteromers, mixtures of diasteromeric pairs, mixtures of diasteromers in which one diastereomer is enriched relative to the other diastereomer(s) and mixtures of diastereomeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95% 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds:

As described generally above for compounds of formula I, x and y are each independently 1 or 2, provided that x and y are not simultaneously 2. In certain embodiments, x and y are each 1 and ring A is:

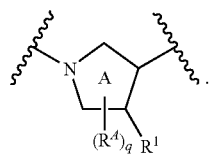

In other embodiments, x is 2, y is 1, and ring A is:

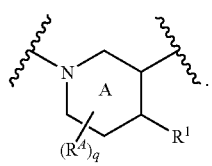

In still other embodiments, x is 1, y is 2, and ring A is:

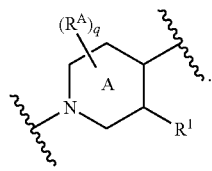

Accordingly, in some embodiments, compounds of any one of formulae II, III, or IV are provided:

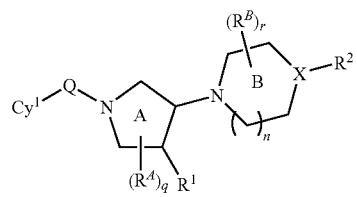

II

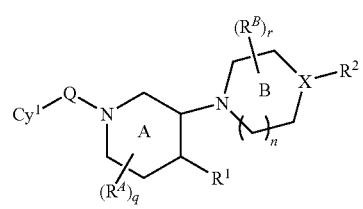

III

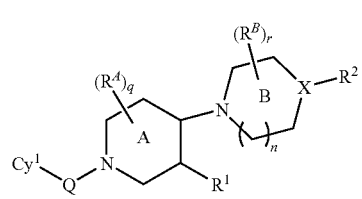

IV

In still other embodiments for compounds of formulae II, III, and IV, n is 1 and compounds of any one of formulae II-A, III-A, or IV-A are provided:

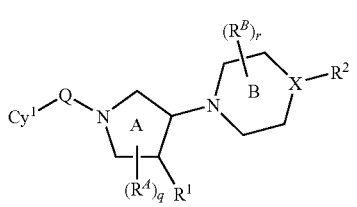

II-A

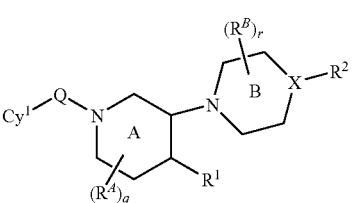

III-A

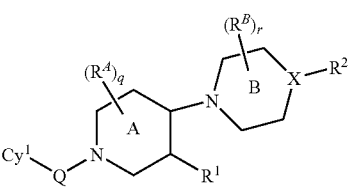

IV-A

In still other embodiments for compounds of formulae II, III, and IV, n is 2 and compounds of any one of formulae II-B, III-B, or IV-B are provided:

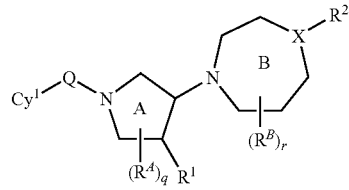

II-B

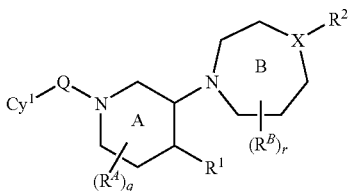

III-B

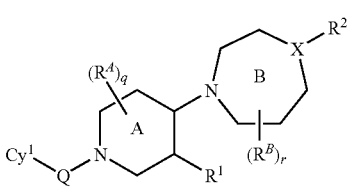

IV-B

It will be appreciated that, for each of the compounds described generally above (I, II, III, IV, II-A, II-B, III-A, III-B, IV-A, or IV-B), that each substituent can be defined independently of each of the other substituents and thus any combination of substituents subsets (as described in more detail below) may be utilized to describe the compounds of the invention.

In certain embodiments, for compounds described above and herein, $R^1$ is —$OR^4$, halogen, —$OCOR^4$, —$NR^4SO_2R^3$, or —$NR^4COR^4$. In other embodiments, $R^1$ is —$OR^4$, —OCO($C_1$-$C_6$alkyl), —$NHSO_2(C_1$-$C_6$alkyl), —$NHCO(C_1$-$C_6$alkyl), or —F. In yet other embodiments, $R^1$ is —OH, —O($C_1$-$C_6$alkyl), —OCO($C_1$-$C_6$alkyl), —$NHSO_2(C_1$-$C_6$alkyl), $NHCO(C_1$-$C_6$alkyl), or —F. In still other embodiments, $R^1$ is —$OR^4$. In yet other embodiments, $R^1$ is —O($C_1$-$C_6$alkyl) or is —OH.

In other embodiments, for compounds described above and herein, q is 0, 1, or 2, and —$R^4$ is fluoro, an optionally substituted linear or branched $C_1$-$C_6$alkyl, an optionally substituted $C_3$-$C_6$cycloalkyl ring, or two occurrences of $R^4$, taken together with the carbon atom(s) to which they are bound form an optionally substituted fused or spiro $C_3$-$C_6$cycloalkyl ring. In yet other embodiments, q is 0 or 1 and —$R^4$ is optionally substituted linear or branched $C_1$-$C_6$alkyl, or halogen. In still other embodiments, q is 0 or 1 and —$R^4$ is —$CH_3$, —$CH_2CH_3$, or F. In yet other embodiments, q is 0.

In still other embodiments for compounds described above and herein, $R^1$ and $R^4$, taken together with the carbon atom(s) to which they are bound form an optionally substituted fused or spiro $C_3$-$C_6$cycloalkyl ring.

In yet other embodiments, for compounds of general formula II and subsets thereof, q is 1 and ring A has the structure:

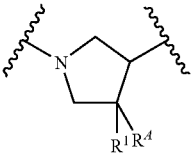

wherein $R^1$ is —OH, —O($C_1$-$C_6$alkyl), —OCO($C_1$-$C_6$alkyl), —$NHSO_2(C_1$-$C_6$alkyl), —$NHCO(C_1$-$C_6$alkyl), or F; and —$R^4$ is optionally substituted linear or branched $C_1$-$C_6$alkyl, or halogen. In still other embodiments, for compounds of general formula II and subsets thereof, q is 1 and ring A has the structure:

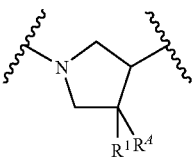

wherein $R^1$ is —$OR^4$, and —$R^4$ is —$CH_3$, $CH_2CH_3$, or F.

In some embodiments for compounds described generally above and herein, r is 0, 1, or 2, and —$R^B$ is fluoro, or an optionally substituted group selected from $C_1$-$C_6$alkyl, $C_3$-$C_6$cycloalkyl, or a fused or bridged 5- or 6-membered saturated ring having 0 heteroatoms. In other embodiments, r is 0, 1, or 2, and —$R^B$ is $C_1$-$C_3$alkyl, or two occurrences of $R^B$, taken together with their intervening atom(s), form an optionally substituted fused or bridged 5 or 6-membered saturated, partially unsaturated, or aromatic ring having 0 heteroatoms. In yet other embodiments, r is 0, 1 or 2, and —$R^B$ is $C_1$-$C_3$alkyl. In still other embodiments, r is 1 or 2 and —$R^B$ is methyl.

In certain embodiments for compounds described above and herein $R^2$ is -$Cy^2$, or -T-$Cy^2$, and when X is N, then T, when present, is a $C_1$-$C_3$alkylene chain substituted with 0 or 1 occurrence of $R^{5a}$, and 0, 1, or 2 independent occurrences of $R^{5b}$, and the $C_1$-$C_3$alkylene chain is optionally replaced by —CO— or —$SO_2$. In other embodiments, when X is $CR^8$, then T, when present, is a $C_1$-$C_3$alkylene chain substituted with 0 or 1 occurrence of $R^{5a}$, and 0, 1, or 2 independent occurrences of $R^{5b}$, and the $C_1$-$C_3$alkylene chain is optionally replaced by —$CR^{5c}$=$CR^{5c}$—, —CO—, —O—, —S—, or —$NR^{5c}$—, and $R^8$ is hydrogen, $C_1$-$C_3$alkyl, —OH, —O($C_1$-$C_3$alkyl), —$NH_2$, —N($C_1$-$C_3$alkyl)$_2$, —SH, —S($C_1$-$C_3$alkyl), —CO($C_1$-$C_3$alkyl), —COOH, or —COO($C_1$-$C_3$alkyl). In yet other embodiments, $R^2$ is -$Cy^2$, or -T-$Cy^2$, and X is N and T, when present, is —$CH_2$—, —CO—, —$CH_2CH$=$CH$—, or —$CH_2CH_2$—. In still other embodiments, X is $CR^8$, and T, when present, is —$NR^{5c}$—, or —O—, and $R^8$ is hydrogen, $C_1$-$C_3$alkyl, —OH, or —O($C_1$-$C_3$alkyl). In other embodiments, X is N, and T, when present, is —CO—, or —$CH_2$—. In still other embodiments, X is $CR^8$, and T, when present, is —O— or —$NR^{5c}$—, and $R^8$ is hydrogen, $C_1$-$C_3$alkyl, —OH, or —O($C_1$-$C_3$alkyl).

In yet other embodiments, for compounds described above and herein $Cy^2$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur.

In still other embodiments for compounds described above and herein $Cy^2$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, or indazolyl;

In yet other embodiments for compounds described above and herein $Cy^2$ is:

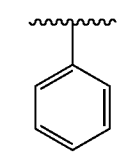

a

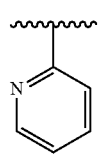

b-i

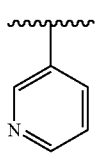

b-ii

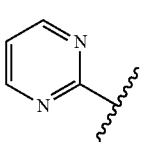

c-i

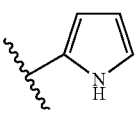

l-i

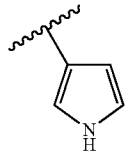

l-ii

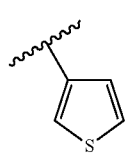

n-i

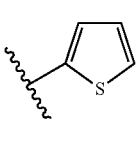

n-ii

-continued

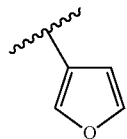

s-i

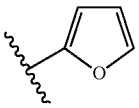

s-ii

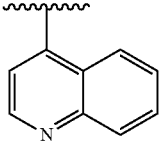

w-i

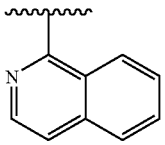

x-i

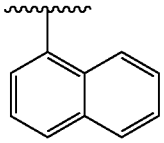

bb-i

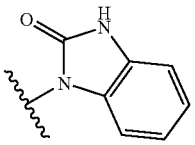

cc

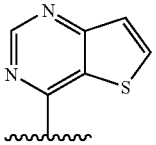

mm-i

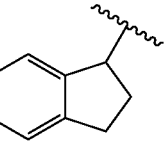

nn-i

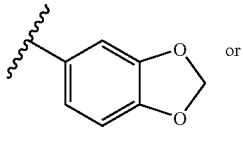

qq-i or

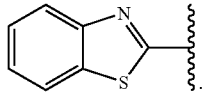

rr

In other embodiments for compounds described above and herein $Cy^2$ is:

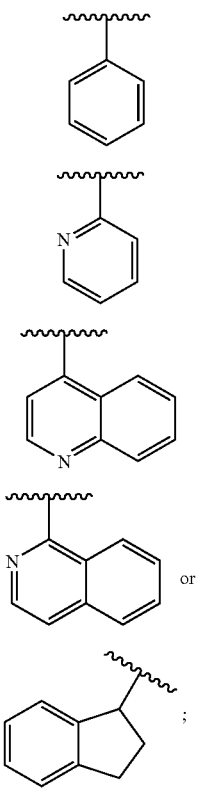

As described generally above, $Cy^2$ is substituted with 0, 1, or 2 independent occurrences of —$R^{6a}$, -G-$R^{6a}$, or —V-G-$R^{6a}$, and 0 or 1 occurrence of =O, =S, =$NR^{7a}$, =$NR^{7b}$, —$R^{6b}$, -G-$R^{6b}$, or —V-G-$R^{6b}$, wherein:

each occurrence of —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —$CON(R^{7a})_2$, —$(CH_2)_{1-4}CON(R^{7a})_2$, —$N(R^{7a})_2$, —$(CH_2)_{1-4}N(R^{7a})_2$, —$SO_2N(R^{7a})_2$, —$(CH_2)_{1-4}SO_2N(R^{7a})_2$, —$NR^{7a}SO_2R^{7b}$, or —$(CH_2)_{1-4}NR^{7a}SO_2R^{7a}$, or an optionally substituted $C_1$-$C_6$ aliphatic group; and each occurrence of —$R^{6b}$, -G-$R^{6b}$, or —V-G-$R^{6b}$ is —$OR^{7b}$, —$(CH_2)_{1-4}OR^{7b}$, —$SR^{7b}$, —$(CH_2)_{1-4}SR^{7b}$, —$COOR^{7b}$, —$(CH_2)_{1-4}COOR^{7b}$, —$COR^{7b}$, —$(CH_2)_{1-4}COR^{7b}$, —$CON(R^{7b})(R^{7c})$, —$(CH_2)_{1-4}CON(R^{7b})(R^{7c})$, —$N(R^{7b})(R^{7c})$, —$(CH_2)_{1-4}N(R^{7b})(R^{7c})$, —$SO_2N(R^{7b})(R^{7c})$, —$(CH_2)_{1-4}SO_2N(R^{7b})(R^{7c})$, —$NR^{7c}SO_2R^{7b}$, —$(CH_2)_{1-4}NR^{7c}SO_2R^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially saturated, or aromatic bicyclic ring having 0-5 heteroatoms independently selected from nitrogen, oxygen, or sulfur.

In other embodiments $Cy^2$ is substituted with:

0, 1, or 2 occurrences of —$R^{6a}$ and each occurrence of —$R^{6a}$, when present, is independently —Cl, —Br, —F, —CN, —$NO_2$, —$OR^{7a}$, —$SR^{7a}$, —$N(R^{7a})_2$, —$COOR^{7a}$, —$COR^{7a}$, —$SO_2N(R^{7a})_2$, —$NR^{7a}SO_2R^{7b}$, —$CON(R^{7a})_2$, —$NR^{7a}COR^{7a}$, or optionally substituted $C_1$-$C_6$ alkyl, wherein each occurrence of $R^{7a}$ is independently hydrogen, or optionally substituted $C_1$-$C_6$ alkyl; and 0 or 1 occurrence of —$R^{6b}$, wherein —$R^{6b}$, when present is —$OR^{7b}$, —$SR^{7b}$, —$N(R^{7b})(R^{7c})$, —$COOR^{7b}$, —$COR^{7b}$, —$SO_2N(R^{7b})(R^{7c})$, —$NR^{7c}SO_2R^{7b}$, —$CON(R^{7b})(R^{7c})$, —$NR^{7c}COR^{7b}$, or an optionally substituted 3-6-membered saturated, partially unsaturated, or aromatic ring having 0-3 heteroatoms independently selected from nitrogen, oxygen, or sulfur, wherein each occurrence of $R^{7b}$ is independently an optionally substituted 3-6-membered saturated, partially unsaturated, or aromatic ring having 0-3 heteroatoms independently selected from nitrogen, oxygen, or sulfur, and each occurrence of $R^{7c}$ is independently hydrogen or an optionally substituted group selected from $C_1$-$C_6$ alkyl or an optionally substituted 3-6-membered saturated, partially unsaturated, or aromatic ring having 0-3 heteroatoms independently selected from nitrogen, oxygen, or sulfur.

In still other embodiments $Cy^2$ is substituted with 0, 1, or 2 occurrences of —$R^{6a}$ and each occurrence of —$R^{6a}$, when present, is independently —Cl, —Br, —F, —CN, —$OCH_3$, —$OCH_2CH_3$, —$OCH_2CH_2CH_3$, —$CF_3$, —$CH_3$, —$CH_2CH_3$, —$CH_2CH_2CH_3$, —$CH(CH_3)_2$, —$C(CH_3)_3$, —COOH, —$COOCH_3$, —$COOCH_2CH_3$.

In yet other embodiments for compounds described above and herein $Cy^2$ is:

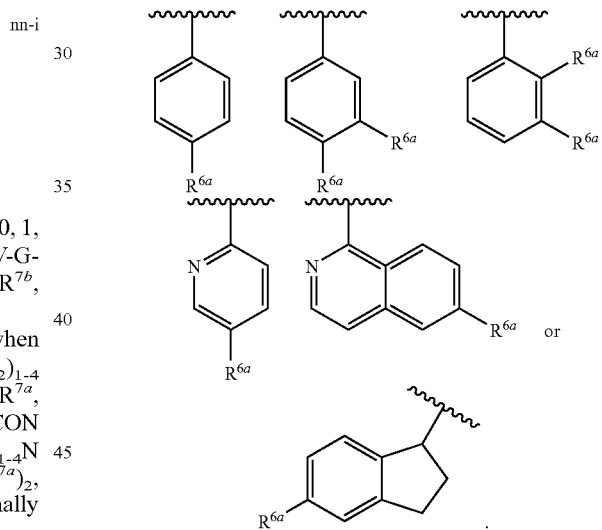

and each occurrence of $R^{6a}$ is independently —Cl, —Br, —$CH_3$, —$CF_3$, or —F.

In still other embodiments $Cy^2$ is phenyl substituted with 1 or 2 occurrences of —$R^{6a}$, and each occurrence of —$R^{6a}$ is independently —Cl, —F, —$CF_3$, —$CH_3$, or —Br. In other embodiments, $Cy^2$ is phenyl substituted with 1 occurrence of —$R^{6a}$, and —$R^{6a}$ is —Cl.

In some embodiments for compounds described above and herein Q is —CO—, —$C(R^{5d})(R^{5e})$—, —$COC(R^{5d})(R^{5e})$—, —$NR^{5f}CO$—, —$SO_2$—, —OCO—, —$C(R^{5d})(R^{5e})CO$—, —$C(R^{5d})(R^{5e})OCO$—, or —$CR^{5e}$=$CR^{5e}CO$—. In other embodiments, Q is —CO—, —$CH_2$, —$COCH_2$—, —$CH_2CO$—, —$CH_2OCO$—, —$SO_2$—, or —$C(R^{5d})(R^{5e})CO$—, wherein $R^{5d}$ is hydrogen, optionally substituted $C_1$-$C_3$ alkyl, optionally substituted phenyl, —OH, or —$NH_2$, and $R^{5e}$ is hydrogen, optionally substituted $C_1$-$C_3$ alkyl, or optionally substituted phenyl. In yet other embodiments, Q is —CO—.

In yet other embodiments, for compounds described above and herein Cy¹ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur.

In still other embodiments for compounds described above and herein Cy¹ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, anthracenyl, fluorenyl, dibenzopyranyl, or indazolyl;

In other embodiments for compounds described above and herein Cy¹ is:

-continued

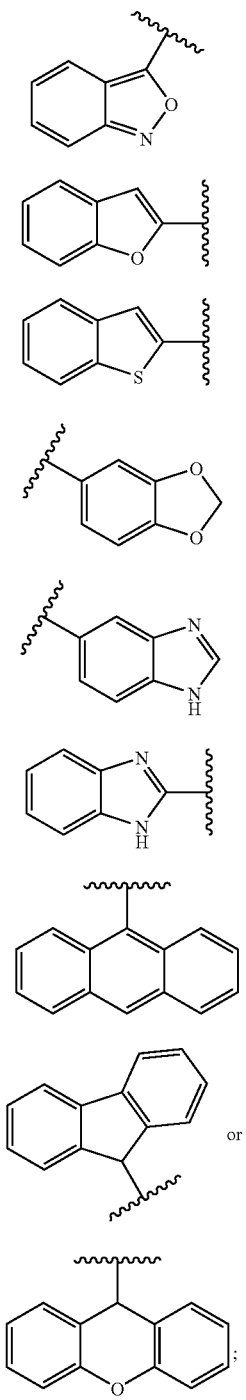

xLii-a xLiv-a xLiv-b xLvi xLvii xLviii

In still other embodiments for compounds described above and herein Cy$^1$ is:

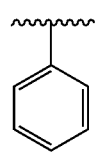

i

-continued

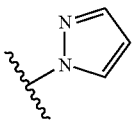

xxxii-a

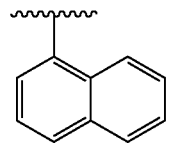

xxxiii-a

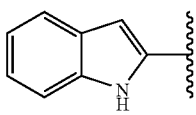

xxxiv-a

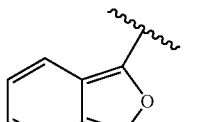

xxxii-a or

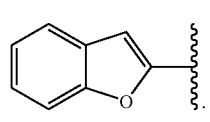

xxxiii-a xi-a xxix-a xxxi-a

In yet other embodiments for compounds described above and herein Cy$^1$ is phenyl.

As described generally above, Cy$^1$ is substituted with 0, 1, 2, or 3 independent occurrences of —R$^{10a}$, -J-R$^{10a}$, or —W-J-R$^{10a}$, and 0 or 1 occurrence of =O, =S, =NR$^{11a}$, =NR$^{11b}$, —R$^{10b}$, -J-R$^{10b}$, or —W-J-R$^{10b}$, wherein:

each occurrence of —R$^{10a}$, -J-R$^{10a}$, or —W-J-R$^{10a}$, when present, is independently —CN, —NO$_2$, —OR$^{11a}$, —(CH$_2$)$_{1-4}$OR$^{11a}$, —SR$^{11a}$, —(CH$_2$)$_{1-4}$SR$^{11a}$, halogen, —COOR$^{11a}$, —(CH$_2$)$_{1-4}$COOR$^{11a}$, —COR$^{11a}$, —(CH$_2$)$_{1-4}$COR$^{11a}$, —CON(R$^{11a}$)$_2$, —(CH$_2$)$_{1-4}$CON(R$^{11a}$)$_2$, —N(R$^{11a}$)$_2$, —(CH$_2$)$_{1-4}$N(R$^{11a}$)$_2$, —SO$_2$N(R$^{11a}$)$_2$, —(CH$_2$)$_{1-4}$SO$_2$N(R$^{11a}$)$_2$, —NR$^{11a}$SO$_2$R$^{11a}$, or —(CH$_2$)$_{1-4}$NR$^{11a}$SO$_2$R$^{11a}$, or an optionally substituted C$_1$-C$_6$aliphatic group; and each occurrence of —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_2$)$_{1-4}$SR$^{11b}$, —COOR$^{11b}$, —(CH$_2$)$_{1-4}$COOR$^{11b}$, —COR$^{11b}$, —(CH$_2$)$_{1-4}$COR$^{11b}$, —CON(R$^{11b}$)(R$^{11c}$), —(CH$_2$)$_{1-4}$CON(R$^{11b}$)(R$^{11c}$), —N(R$^{11b}$)(R$^{11c}$), —(CH$_2$)$_{1-4}$N(R$^{11b}$)(R$^{11c}$), —SO$_2$N(R$^{11b}$)(R$^{11c}$), —(CH$_2$)$_{1-4}$SO$_2$N(R$^{11b}$)(R$^{11c}$), —NR$^{11c}$SO$_2$R$^{11b}$, —(CH$_2$)$_{1-4}$NR$^{11c}$SO$_2$R$^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In certain embodiments Cy$^1$ is substituted with:
0, 1, or 2 occurrences of —R$^{10a}$ and each occurrence of —R$^{10a}$, when present, is independently —Cl, —Br, —F, —CN, —NO$_2$, —OR$^{11a}$, —SR$^{11a}$, —N(R$^{11a}$)$_2$, —NR$^{11a}$COR$^{11a}$, —CON(R$^{11a}$)$_2$, —SO$_2$N(R$^{11a}$)$_2$, —NR$^{11a}$SO$_2$R$^{11a}$, COOR$^{11a}$, COR$^{11a}$, or optionally substituted C$_1$-C$_6$alkyl, wherein each occurrence of R$^{11a}$ is independently hydrogen, or optionally substituted C$_1$-C$_6$alkyl; and 0 or 1 occurrence of —$R^{10b}$, J-$R^{10b}$, or W-J-$R^{10b}$, wherein W is —N($R^{11b}$) or —O—, J is a $C_1$-$C_2$alkyl chain, and —$R^{10b}$, when present is —$OR^{11b}$, —$SR^{11b}$, —N($R^{11b}$)($R^{11c}$), —$NR^{11c}COR^{11b}$, CON($R^{11b}$)($R^{11c}$), —$SO_2N(R^{11c})$($R^{11b}$), —$NR^{11c}SO_2R^{11b}$, —$COOR^{11b}$, $COR^{11b}$, or an optionally substituted 3-6-membered saturated, partially unsaturated, or aromatic ring having 0-3 heteroatoms independently selected from nitrogen, oxygen, or sulfur, wherein each occurrence of $R^{11b}$ is independently an optionally substituted 3-6-membered saturated, partially unsaturated, or aromatic ring having 0-3 heteroatoms independently selected from nitrogen, oxygen, or sulfur, and each occurrence of $R^{11c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur.

In other embodiments $Cy^1$ is substituted with:

0, 1, or 2 occurrences of $R^{10a}$, and each occurrence of —$R^{10a}$ is independently —Cl, —Br, —F, —$NO_2$, —CN, —$OCH_3$, —$OCH_2CH_3$, —$OCH_2CH_2CH_3$, —$CF_3$, —$OCF_3$, —$CH_3$, —$CH_2CH_3$, —$CH_2CH_2CH_3$, —$C(CH_3)_3$, —CH($CH_3$)$_2$, —$NHCOCH_3$, —$NHCONHCH_3$, —$SCH_3$, —$SCH_2CH_3$, —$SCH_2CH_2CH_3$, —$NHCH_3$, —$SO_2NH_2$, —COOH, —$COOCH_3$, —$NHCH_3$, —N($CH_3$)$_2$, —NH($CH_2CH_3$), —N($CH_2CH_3$)$_2$, —$OC(CH_3)_2CO_2H$, —$OCH_2CO_2H$, or —$C(CH_3)_2OH$ and 0 or 1 occurrence of —$R^{10b}$, J-$R^{10b}$, or W-J-$R^{10b}$, and —$R^{10b}$, or W-J-$R^{10b}$ is phenyl, benzyl, —NHCO(phenyl), —NHCO(benzyl), —NH(phenyl), —$NHCH_2$(phenyl), —NH(benzyl), —S(phenyl), —S(benzyl), —O(phenyl), or —O(benzyl), wherein the phenyl and benzyl groups are optionally substituted.

In yet other embodiments, $Cy^1$ is substituted with 1, 2, or 3 occurrences of $R^{10a}$, and each occurrence of $R^{10a}$ is independently —Cl, —Br, —F, —$CH_3$, or —$CF_3$.

It will be appreciated that in still other embodiments, certain combinations of substituents are preferred. In some embodiments, certain variables for compounds of general formula I (and subsets thereof as depicted by general formulae II, III, and IV, and subsets thereof) are selected from:

a) $R^1$ is —$OR^4$, halogen, —$OCOR^4$, —$NR^4SO_2R^3$, or —$NR^4COR^4$; q is 0, 1, or 2, and —$R^A$ is fluoro, an optionally substituted linear or branched $C_1$-$C_6$alkyl, an optionally substituted $C_3$-$C_6$cycloalkyl ring, or two occurrences of $R^A$, taken together with the carbon atom(s) to which they are bound form an optionally substituted fused or spiro $C_3$-$C_6$cycloalkyl ring; or $R^1$ and $R^4$, taken together with the carbon atom(s) to which they are bound form an optionally substituted fused or spiro $C_3$-$C_6$cycloalkyl ring;

b) r is 0, 1, or 2, and —$R^B$ is fluoro, or an optionally substituted group selected from $C_1$-$C_6$alkyl, $C_3$-$C_6$cycloalkyl, or a fused or bridged 5- or 6-membered saturated ring having 0 heteroatoms;

c) $R^2$ is -$Cy^2$ or -T-$Cy^2$, and when X is N, T, when present, is a $C_1$-$C_3$alkylene chain substituted with 0 or 1 occurrence of $R^{5a}$, and 0, 1, or 2 independent occurrences of $R^{5b}$, and wherein the $C_1$-$C_3$alkylene chain is optionally replaced by —CO— or —$SO_2$, or when X is $CR^8$, T, when present, is a $C_1$-$C_3$alkylene chain substituted with 0 or 1 occurrence of $R^{5a}$, and 0, 1, or 2 independent occurrences of $R^{5b}$, and wherein one or more methylene units in the $C_1$-$C_3$alkylene chain, as valency and stability permit, is optionally replaced by —$CR^{5c}$=$CR^{5c}$—, —CO—, —O—, —S—, or —$NR^{5c}$—, and $R^8$ is hydrogen, $C_1$-$C_3$alkyl, —OH, —O($C_1$-$C_3$alkyl), —$NH_2$, —N($C_1$-$C_3$alkyl)$_2$, —SH, —S($C_1$-$C_3$alkyl), —CO($C_1$-$C_3$alkyl), —COOH, or —COO($C_1$-$C_3$alkyl);

$Cy^2$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur, wherein $Cy^2$ is substituted with 0, 1, or 2 independent occurrences of —$R^{6a}$, -G-$R^{6a}$, or —V-G-$R^{6a}$, and 0 or 1 occurrence of =O, =S, =$NR^{7a}$, =$NR^{7b}$, —$R^{6b}$, -G-$R^{6b}$, or —V-G-$R^{6b}$, wherein:

each occurrence of —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —$CON(R^{7a})_2$, —$(CH_2)_{1-4}CON(R^{7a})_2$, —$N(R^{7a})_2$, —$(CH_2)_{1-4}N(R^{7a})_2$, —$SO_2N(R^{7a})_2$, —$(CH_2)_{1-4}SO_2N(R^{7a})_2$, —$NR^{7a}SO_2R^{7b}$, or —$(CH_2)_{1-4}NR^{7a}SO_2R^{7b}$, or an optionally substituted $C_1$-$C_6$aliphatic group; and each occurrence of —$R^{6b}$, -G-$R^{6b}$, or —V-G-$R^{6b}$ is —$OR^{7b}$, —$(CH_2)_{1-4}OR^{7b}$, —$SR^{7b}$, —$(CH_2)_{1-4}SR^{7b}$, —$COOR^{7b}$, —$(CH_2)_{1-4}COOR^{7b}$, —$COR^{7b}$, —$(CH_2)_{1-4}COR^{7b}$, —$CON(R^{7b})(R^{7c})$, —$(CH_2)_{1-4}CON(R^{7b})(R^{7c})$, —$N(R^{7b})(R^{7c})$, —$(CH_2)_{1-4}N(R^{7b})(R^{7c})$, —$SO_2N(R^{7b})(R^{7c})$, —$(CH_2)_{1-4}SO_2N(R^{7b})(R^{7c})$, —$NR^{7c}SO_2R^{7b}$, —$(CH_2)_{1-4}NR^{7c}SO_2R^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur;

d) Q is —CO—, —$C(R^{5d})(R^{5e})$—, —$COC(R^{5d})(R^{5e})$—, —$NR^{5f}CO$—, —$SO_2$—, —OCO—, —$C(R^{5d})(R^{5e})CO$—, —$C(R^{5d})(R^{5e})OCO$—, or —$CR^{5e}$=$CR^{5e}CO$—; and e) $Cy^1$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur, wherein $Cy^1$ is substituted with 0, 1, 2, or 3 independent occurrences of —$R^{10a}$, -J-$R^{10a}$, or —W-J-$R^{10a}$, and 0 or 1 occurrence of =O, =S, =$NR^{11a}$, =$NR^{11b}$, —$R^{10b}$, -J-$R^{10b}$, or —W-J-$R^{10b}$, wherein:

each occurrence of —$R^{10a}$, -J-$R^{10a}$, or —W-J-$R^{10a}$, when present, is independently —CN, —$NO_2$, —$OR^{11a}$, —$(CH_2)_{1-4}OR^{11a}$, —$SR^{11a}$, —$(CH_2)_{1-4}SR^{11a}$, halogen, —$COOR^{11a}$, —$(CH_2)_{1-4}COOR^{11a}$, —$COR^{11a}$, —$(CH_2)_{1-4}COR^{11a}$, —$CON(R^{11a})_2$, —$(CH_2)_{1-4}CON(R^{11a})_2$, —$N(R^{11a})_2$, —$(CH_2)_{1-4}N(R^{11a})_2$, —$SO_2N(R^{11a})_2$, —$(CH_2)_{1-4}SO_2N(R^{11a})_2$, —$NR^{11a}SO_2R^{11a}$, or —$(CH_2)_{1-4}NR^{11a}SO_2R^{11a}$, or an optionally substituted $C_1$-$C_6$aliphatic group; and each occurrence of —$R^{10b}$, -J-$R^{10b}$, or —W-J-$R^{10b}$ is —$OR^{11b}$, —$(CH_2)_{1-4}OR^{11b}$, —$SR^{11b}$, —$(CH_2)_{1-4}SR^{11b}$, —$COOR^{11b}$, —$(CH_2)_{1-4}COOR^{11b}$, —$COR^{11b}$, —$(CH_2)_{1-4}COR^{11b}$, —$CON(R^{11b})(R^{11c})$, —$(CH_2)_{1-4}CON(R^{11b})(R^{11c})$, —$N(R^{11b})(R^{11c})$, —$(CH_2)_{1-4}N(R^{11b})(R^{11c})$, —$SO_2N(R^{11b})(R^{11c})$, —$(CH_2)_{1-4}SO_2N(R^{11b})(R^{11c})$, —$NR^{11c}SO_2R^{11b}$, —$(CH_2)_{1-4}NR^{11c}SO_2R^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In other embodiments, certain variables for compounds of general formula I (and subsets thereof as depicted by general formulae II, III, and IV, and subsets thereof) are selected from:

a) $R^1$ is —$OR^4$, halogen, —$OCOR^4$, —$NR^4SO_2R^3$, or —$NR^4COR^4$; q is 0, 1, or 2, and —$R^A$ is fluoro, an optionally substituted linear or branched $C_1$-$C_6$alkyl, an optionally substituted $C_3$-$C_6$cycloalkyl ring, or two occurrences of $R^A$, taken together with the carbon atom(s) to which they are bound form an optionally substituted fused or spiro $C_3$-$C_6$cycloalkyl ring; or $R^1$ and $R^A$, taken together with the carbon atom(s) to which they are bound form an optionally substituted fused or spiro $C_3$-$C_6$cycloalkyl ring;

b) r is 0, 1, or 2, and —$R^B$ is fluoro, or an optionally substituted group selected from $C_1$-$C_6$alkyl, $C_3$-$C_6$cycloalkyl, or a fused or bridged 5- or 6-membered saturated ring having 0 heteroatoms;

c) $R^2$ is -$Cy^2$ or -T-$Cy^2$, and when X is N, then T, when present, is a $C_1$-$C_3$alkylene chain substituted with 0 or 1 occurrence of $R^{5a}$, and 0, 1, or 2 independent occurrences of $R^{5b}$, and wherein the $C_1$-$C_3$alkylene chain is optionally replaced by —CO— or —$SO_2$—, or when X is $CR^8$, then T, when present, is a $C_1$-$C_3$alkylene chain substituted with 0 or 1 occurrence of $R^{5a}$, and 0, 1, or 2 independent occurrences of $R^{5b}$, and wherein one or more methylene units in the $C_1$-$C_3$alkylene chain, as valency and stability permit, is optionally replaced by —$CR^{5c}$=$CR^{5c}$—, —CO—, —O—, —S—, or —$NR^{5c}$—, and $R^8$ is hydrogen, $C_1$-$C_3$alkyl, —OH, —O($C_1$-$C_3$alkyl), —$NH_2$, —N($C_1$-$C_3$alkyl)$_2$, —SH, —S($C_1$-$C_3$alkyl), —CO($C_1$-$C_3$alkyl), —COOH, or —COO($C_1$-$C_3$alkyl);

$Cy^2$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-one, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, indazolyl, anthracenyl, fluorenyl, indanyl or xanthenyl;

wherein $Cy^2$ is substituted with 0, 1, or 2 independent occurrences of —$R^{6a}$, -G-$R^{6a}$, or —V-G-$R^{6a}$, and 0 or 1 occurrence of =O, =S, =$NR^{7a}$, —$NR^{7b}$, —$R^{6b}$, -G-$R^{6b}$, or —V-G-$R^{6b}$, wherein:

each occurrence of —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —CON$(R^{7a})_2$, —$(CH_2)_{1-4}CON(R^{7a})_2$, —N$(R^{7a})_2$, —$(CH_2)_{1-4}N(R^{7a})_2$, —$SO_2N(R^{7a})_2$, —$(CH_2)_{1-4}SO_2N(R^{7a})_2$, —$NR^{7a}SO_2R^{7b}$, or —$(CH_2)_{1-4}NR^{7a}SO_2R^{7b}$, or an optionally substituted $C_1$-$C_6$aliphatic group; and each occurrence of —$R^{6b}$, -G-$R^{6b}$, or —V-G-$R^{6b}$ is —$OR^{7b}$, —$(CH_2)_{1-4}OR^{7b}$, —$SR^{7b}$, —$(CH_2)_{1-4}SR^{7b}$, —$COOR^{7b}$, —$(CH_2)_{1-4}COOR^{7b}$, —$COR^{7b}$, —$(CH_2)_{1-4}COR^{7b}$, —CON$(R^{7b})(R^{7c})$, —$(CH_2)_{1-4}CON(R^{7b})(R^{7c})$, —N$(R^{7b})(R^{7c})$, —$(CH_2)_{1-4}N(R^{7b})(R^{7c})$, —$SO_2N(R^{7b})(R^{7c})$, —$(CH_2)_{1-4}SO_2N(R^{7b})(R^{7c})$, —$NR^{7c}SO_2R^{7b}$, —$(CH_2)_{1-4}NR^{7c}SO_2R^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur;

d) Q is —CO—, —C$(R^{5d})(R^{5e})$—, —COC$(R^{5d})(R^{5e})$—, —$NR^{5f}$CO—, —$SO_2$—, —OCO—, —C$(R^{5d})(R^{5e})$CO—, —C$(R^{5d})(R^{5e})$OCO—, or —$CR^{5e}$=$CR^{5e}$CO—; and e) $Cy^1$ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-one, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, indazolyl, anthracenyl, fluorenyl, indanyl, or xanthenyl; wherein $Cy^1$ is substituted with 0, 1, 2, or 3 independent occurrences of —$R^{10a}$, -J-$R^{10a}$, or —W-J-$R^{10a}$, and 0 or 1 occurrence of =O, =S, =$NR^{11a}$, =$NR^{11b}$, —$R^{10b}$, -J-$R^{10b}$, or —W-J-$R^{10b}$, wherein:

each occurrence of —$R^{10a}$, -J-$R^{10a}$, or —W-J-$R^{10a}$, when present, is independently —CN, —$NO_2$, —$OR^{11a}$, —$(CH_2)_{1-4}OR^{11a}$, —$SR^{11a}$, —$(CH_2)_{1-4}SR^{11a}$, halogen, —$COOR^{11a}$, —$(CH_2)_{1-4}COOR^{11a}$, —$COR^{11a}$, —$(CH_2)_{1-4}COR^{11a}$, —CON$(R^{11a})_2$, —$(CH_2)_{1-4}CON(R^{11a})_2$, —N$(R^{11a})_2$, —$(CH_2)_{1-4}N(R^{11a})_2$, —$SO_2N(R^{11a})_2$, —$(CH_2)_{1-4}SO_2N(R^{11a})_2$, —$NR^{11a}SO_2R^{11a}$, or —$(CH_2)_{1-4}NR^{11a}SO_2R^{11a}$, or an optionally substituted $C_1$-$C_6$aliphatic group; and each occurrence of —$R^{10b}$, -J-$R^{10b}$, or —W-J-$R^{10b}$ is —$OR^{11b}$, —$(CH_2)_{1-4}OR^{11b}$, —$SR^{11b}$, —$(CH_2)_{1-4}SR^{11b}$, —$COOR^{11b}$, —$(CH_2)_{1-4}COOR^{11b}$, —$COR^{11b}$, —$(CH_2)_{1-4}COR^{11b}$, —CON$(R^{11b})(R^{11c})$, —$(CH_2)_{1-4}CON(R^{11b})(R^{11c})$, —N$(R^{11b})(R^{11c})$, —$(CH_2)_{1-4}N(R^{11b})(R^{11c})$, —$SO_2N(R^{11b})(R^{11c})$, —$(CH_2)_{1-4}SO_2N(R^{11b})(R^{11c})$, —$NR^{11c}SO_2R^{11b}$, —$(CH_2)_{1-4}NR^{11c}SO_2R^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In yet other embodiments, certain variables for compounds of general formula I (and subsets thereof as depicted by general formulae II, III, and IV, and subsets thereof) are further selected from:

a) $R^1$ —OH, —O($C_1$-$C_6$alkyl), —OCO($C_1$-$C_6$alkyl), —$NHSO_2$($C_1$-$C_6$alkyl), —NHCO($C_1$-$C_6$alkyl), or —F;

b) q is 0 or 1 and —$R^A$ is optionally substituted linear or branched $C_1$-$C_6$alkyl, or halogen;

c) r is 0, 1, or 2, and —$R^B$ is $C_1$-$C_3$alkyl, or two occurrences of $R^B$, taken together with their intervening atom(s), form an optionally substituted fused or bridged 5 or 6-membered saturated, partially unsaturated, or aromatic ring having 0 heteroatoms;

d) $R^2$ is -$Cy^2$ or -T-$Cy^2$, and

X is N and T, when present, is —$CH_2$—, —CO—, —$CH_2CH$=CH—, or —$CH_2CH_2$—, or X is $CR^8$, and T, when present, is —$NR^{5c}$—, or —O—, and $R^8$ is hydrogen, $C_1$-$C_3$alkyl, —OH, or —O($C_1$-$C_3$alkyl); and Cy² is:

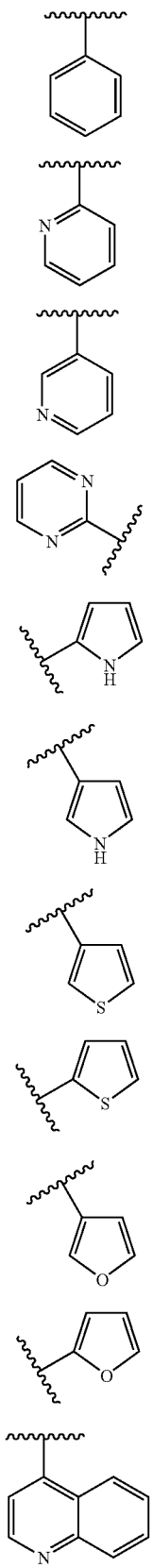

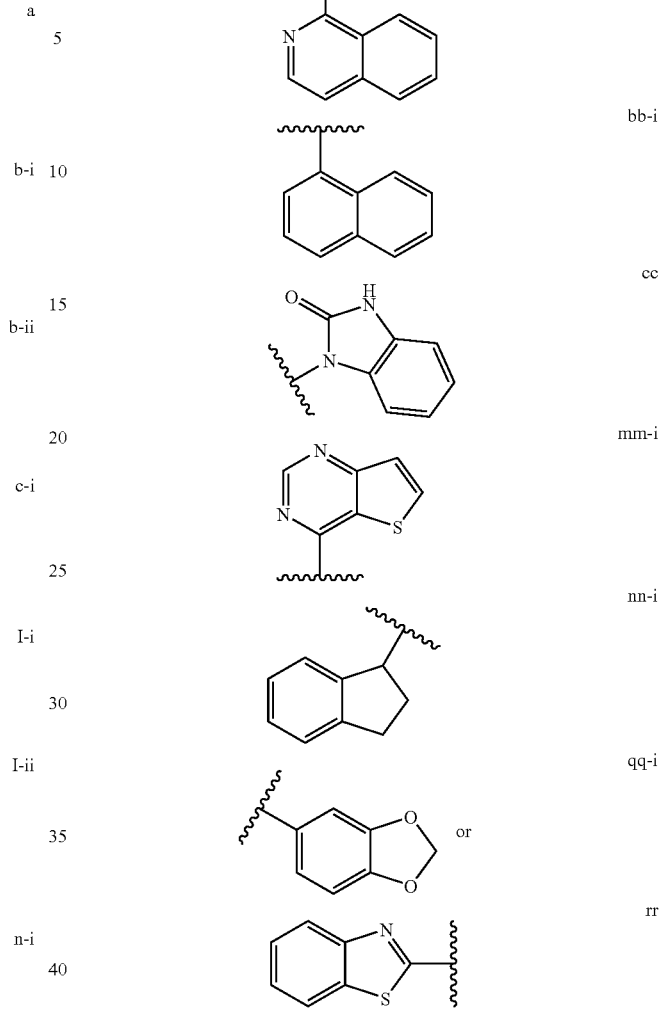

wherein Cy² is substituted with:
0, 1, or 2 occurrences of —R$^{6a}$ and each occurrence of —R$^{6a}$, when present, is independently —Cl, —Br, —F, —CN, —NO$_2$, —OR$^{7a}$, —SR$^{7a}$, —N(R$^{7a}$)$_2$, —COOR$^{7a}$, —COR$^{7a}$, —SO$_2$N(R$^{7a}$)$_2$, —NR$^{7a}$SO$_2$R$^{7b}$, —CON(R$^{7a}$)$_2$, —NR$^{7a}$COR$^{7a}$, or optionally substituted C$_1$-C$_6$alkyl, wherein each occurrence of R$^{7a}$ is independently hydrogen, or optionally substituted C$_1$-C$_6$alkyl; and 0 or 1 occurrence of —R$^{6b}$, wherein —R$^{6b}$, when present is —OR$^{7b}$, —SR$^{7b}$, —N(R$^{7b}$)(R$^{7c}$), —COOR$^{7b}$, —COR$^{7b}$, —SO$_2$N(R$^{7b}$)(R$^{7c}$), —NR$^{7c}$SO$_2$R$^{7b}$, —CON(R$^{7b}$)(R$^{7c}$), —NR$^{7c}$COR$^{7b}$, or an optionally substituted 3-6-membered saturated, partially unsaturated, or aromatic ring having 0-3 heteroatoms independently selected from nitrogen, oxygen, or sulfur, wherein each occurrence of R$^{7b}$ is independently an optionally substituted 3-6-membered saturated, partially unsaturated, or aromatic ring having 0-3 heteroatoms independently selected from nitrogen, oxygen, or sulfur, and each occurrence of R$^{7c}$ is independently hydrogen or an optionally substituted group selected from C$_1$-C$_6$alkyl or an optionally substituted 3-6-membered saturated, partially unsaturated, or aromatic ring having 0-3 heteroatoms independently selected from nitrogen, oxygen, or sulfur;

e) Q is —CO—, —CH$_2$, —COCH$_2$—, —CH$_2$CO—, —CH$_2$OCO—, —SO$_2$—, or —C(R$^{5d}$)(R$^{5e}$)CO—, wherein $R^{5d}$ is hydrogen, optionally substituted $C_1$-$C_3$alkyl, optionally substituted phenyl, —OH, or —NH$_2$, and $R^{5e}$ is hydrogen, optionally substituted $C_1$-$C_3$alkyl, or optionally substituted phenyl;

f) Cy$^1$ is

-continued

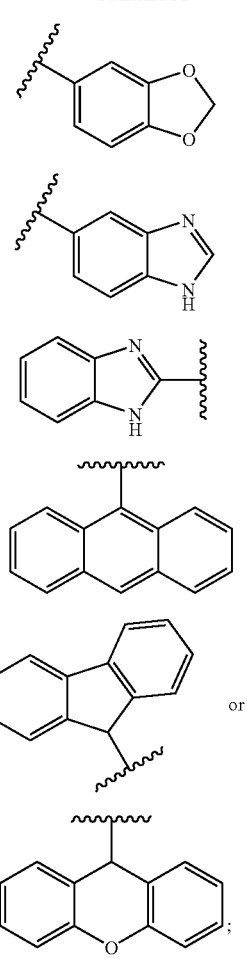

xLii-a xLiv-a xLiv-b xLvi xLvii xLviii wherein Cy¹ is substituted with:

0, 1, or 2 occurrences of —$R^{10a}$ and each occurrence of —$R^{10a}$, when present, is independently —Cl, —Br, —F, —CN, —$NO_2$, —$OR^{11a}$, —$SR^{11a}$, —$N(R^{11a})_2$, —$NR^{11a}COR^{11a}$, —$CON(R^{11a})_2$, —$SO_2N(R^{11a})_2$, —$NR^{11a}SO_2R^{11a}$, $COOR^{11a}$, $COR^{11a}$, or optionally substituted $C_1$-$C_6$alkyl, wherein each occurrence of $R^{11a}$ is independently hydrogen, or optionally substituted $C_1$-$C_6$alkyl; and 0 or 1 occurrence of —$R^{10b}$, J-$R^{10b}$, or W-J-$R^{10b}$, wherein W is —$N(R^{11b})$ or —O—, J is a $C_1$-$C_2$alkyl chain, and —$R^{10b}$, when present is —$OR^{11b}$, —$SR^{11b}$, —$N(R^{11b})(R^{11c})$, —$NR^{11c}COR^{11b}$, $CON(R^{11b})(R^{11c})$, —$SO_2N(R^{11c})(R^{11b})$, —$NR^{11c}SO_2R^{11b}$, —$COOR^{11b}$, $COR^{11b}$, or an optionally substituted 3-6-membered saturated, partially unsaturated, or aromatic ring having 0-3 heteroatoms independently selected from nitrogen, oxygen, or sulfur, wherein each occurrence of $R^{11b}$ is independently an optionally substituted 3-6-membered saturated, partially unsaturated, or aromatic ring having 0-3 heteroatoms independently selected from nitrogen, oxygen, or sulfur, and each occurrence of $R^{11c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur.

In yet other embodiments, certain variables for compounds of general formula I (and subsets thereof as depicted by general formulae II, III, and IV, and subsets thereof) are further selected from:

a) $R^1$ is —OH, or —O($C_1$-$C_6$alkyl);
b) q is 0 or 1 and —$R^A$ is —$CH_3$, —$CH_2CH_3$, or F;
c) r is 0, 1 or 2, and —$R^B$ is $C_1$-$C_3$alkyl;
d) X is N, $R^2$ is -T-Cy², T is —$CH_2$— or —CO—; and Cy² is:

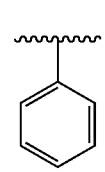

a

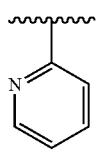

b-i

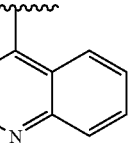

w-i

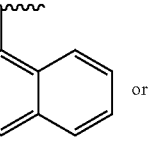

x-i or

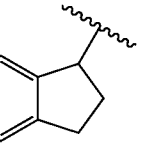

nn-i

;

wherein Cy² is substituted with 0, 1, or 2 occurrences of —$R^{6a}$ and each occurrence of —$R^{6a}$, when present, is independently —Cl, —Br, —F, —CN, —$OCH_3$, —$OCH_2CH_3$, —$OCH_2CH_2CH_3$, —$CF_3$, —$CH_2CH_3$, —$CH_2CH_2CH_3$, —$CH(CH_3)_2$, —$C(CH_3)_3$, —COOH, —$COOCH_3$, —$COOCH_2CH_3$;

e) Q is —CO—;
f) Cy¹ is:

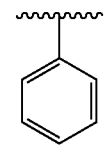

i

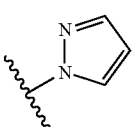

xi-a

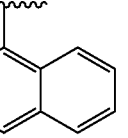

xxix-a

-continued

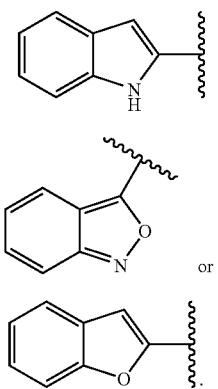

xxxi-a xxxii-a xxxiii-a wherein Cy¹ is substituted with:

0, 1, or 2 occurrences of $R^{10a}$, and each occurrence of $-R^{10a}$ is independently —Cl, —Br, —F, —NO$_2$, —CN, —OCH$_3$, —OCH$_2$CH$_3$, —OCH$_2$CH$_2$CH$_3$, —CF$_3$, —OCF$_3$, —CH$_3$, —CH$_2$CH$_3$, —CH$_2$CH$_2$CH$_3$, —C(CH$_3$)$_3$, —CH(CH$_3$)$_2$, —NHCOCH$_3$, —NHCONHCH$_3$, —SCH$_3$, —SCH$_2$CH$_3$, —SCH$_2$CH$_2$CH$_3$, —NH$_2$, —NHCH$_3$, —SO$_2$NH$_2$, —COOH, —COOCH$_3$, —NHCH$_3$, —N(CH$_3$)$_2$, —NH(CH$_2$CH$_3$), —N(CH$_2$CH$_3$)$_2$, —OC(CH$_3$)$_2$CO$_2$H, —OCH$_2$CO$_2$H, or —C(CH$_3$)$_2$OH and 0 or 1 occurrence of $-R^{10b}$, $J-R^{10b}$, or $W-J-R^{10b}$, and $-R^{10b}$, $J-R^{10b}$, or $W-J-R^{10b}$ is phenyl, benzyl, —NHCO(phenyl), —NHCO(benzyl), —NH(phenyl), —NHCH$_2$(phenyl), —NH(benzyl), —S(phenyl), —S(benzyl), —O(phenyl), or —O(benzyl), wherein the phenyl and benzyl groups are optionally substituted.

In still other embodiments, compounds of general formula II-A are provided

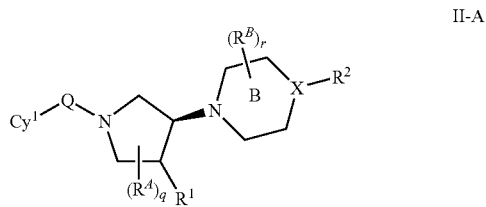

II-A wherein the substituents are selected from:

a) R¹ is —OH, —O(C$_1$-C$_6$alkyl), halogen, —OCOR⁴, —NR⁴SO$_2$R³, or —NR⁴COR⁴; q is 0, 1, or 2, and —R$^A$ is fluoro, an optionally substituted linear or branched C$_1$-C$_6$alkyl, or an optionally substituted C$_3$-C$_6$cycloalkyl ring;

b) r is 0, 1, or 2, and —R$^B$ is fluoro, or an optionally substituted group selected from C$_1$-C$_6$alkyl, C$_3$-C$_6$cycloalkyl, or a fused or bridged 5- or 6-membered saturated ring having 0 heteroatoms;

c) R² is -Cy² or -T-Cy², and when X is N, then T, when present, is —CO—, —CH$_2$—, —CH$_2$CH=CH—, or —CH$_2$CH$_2$—, or when X is CR⁸, then T, when present, is —O— or —NR$^{5c}$—, and R⁸ is hydrogen, C$_1$-C$_3$alkyl, —OH, —O(C$_1$-C$_3$alkyl), —NH$_2$, —N(C$_1$-C$_3$alkyl)$_2$, —SH, —S(C$_1$-C$_3$alkyl), —CO(C$_1$-C$_3$alkyl), —COOH, or —COO(C$_1$-C$_3$alkyl);

Cy² is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, or indazolyl;

wherein Cy² is substituted with 0, 1, or 2 independent occurrences of —R$^{6a}$, -G-R$^{6a}$, or —V-G-R$^{6a}$, and 0 or 1 occurrence of =O, =S, =NR$^{7a}$, =NR$^{7b}$, —R$^{6b}$, -G-R$^{6b}$, or —V-G-R$^{6b}$, wherein:

each occurrence of —R$^{6a}$, -G-R$^{6a}$, or —V-G-R$^{6a}$, when present, is independently —CN, —NO$_2$, —OR$^{7a}$, —(CH$_2$)$_{1-4}$OR$^{7a}$, —SR$^{7a}$, —(CH$_2$)$_{1-4}$SR$^{7a}$, halogen, —COOR$^{7a}$, —(CH$_2$)$_{1-4}$COOR$^{7a}$, —COR$^{7a}$, —(CH$_2$)$_{1-4}$COR$^{7a}$, —CON(R$^{7a}$)$_2$, —(CH$_2$)$_{1-4}$CON(R$^{7a}$)$_2$, —N(R$^{7a}$)$_2$, —(CH$_2$)$_{1-4}$N(R$^{7a}$)$_2$, —SO$_2$N(R$^{7a}$)$_2$, —(CH$_2$)$_{1-4}$SO$_2$N(R$^{7a}$)$_2$, —NR$^{7a}$SO$_2$R$^{7b}$, or —(CH$_2$)$_{1-4}$NR$^{7a}$SO$_2$R$^{7b}$, or an optionally substituted C$_1$-C$_6$aliphatic group; and each occurrence of —R$^{6b}$, -G-R$^{6b}$, or —V-G-R$^{6b}$ is —OR$^{7b}$, —(CH$_2$)$_{1-4}$OR$^{7b}$, —SR$^{7b}$, —(CH$_2$)$_{1-4}$SR$^{7b}$, —COOR$^{7b}$, —(CH$_2$)$_{1-4}$COOR$^{7b}$, —COR$^{7b}$, —(CH$_2$)$_{1-4}$COR$^{7b}$, —CON(R$^{7b}$)(R$^{7c}$), —(CH$_2$)$_{1-4}$CON(R$^{7b}$)(R$^{7c}$), —N(R$^{7b}$)(R$^{7c}$), —(CH$_2$)$_{1-4}$N(R$^{7b}$)(R$^{7c}$), —SO$_2$N(R$^{7b}$)(R$^{7c}$), —(CH$_2$)$_{1-4}$SO$_2$N(R$^{7b}$)(R$^{7c}$), —NR$^{7c}$SO$_2$R$^{7b}$, —(CH$_2$)$_{1-4}$NR$^{7c}$SO$_2$R$^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur;

d) Q is —CO—, —C(R$^{5d}$)(R$^{5e}$)—, —COC(R$^{5d}$)(R$^{5e}$)—, —NR$^{5f}$CO—, —SO$_2$—, —OCO—, —C(R$^{5d}$)(R$^{5e}$)CO—, —C(R$^{5d}$)(R$^{5e}$)OCO—, or —CR$^{5e}$=CR$^{5c}$CO—; and e) Cy¹ is selected from phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-onyl, quinolinyl, isoquinolinyl, quinazolinyl, quinoxalinyl, [1,8]naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, or indazolyl;

wherein Cy¹ is substituted with 0, 1, 2, or 3 independent occurrences of —R$^{10a}$, -J-R$^{10a}$, or —W-J-R$^{10a}$, and 0 or 1 occurrence of =O, =S, =NR$^{11a}$, =NR$^{11b}$, —R$^{10b}$, -J-R$^{10b}$, or —W-J-R$^{10b}$, wherein: each occurrence of —R$^{10a}$, -J-R$^{10a}$, or —W-J-R$^{10a}$, when present, is independently —CN, —NO$_2$, —OR$^{11a}$, —(CH$_2$)$_{1-4}$OR$^{11a}$, —SR$^{11a}$, —(CH$_2$)$_{1-4}$SR$^{11a}$, halogen, —COOR$^{11a}$, —(CH$_2$)$_{1-4}$COOR$^{11a}$, —COR$^{11a}$, —(CH$_2$)$_{1-4}$COR$^{11a}$, —CON(R$^{11a}$)$_2$, —(CH$_2$)$_{1-4}$CON(R$^{11a}$)$_2$, —N(R$^{11a}$)$_2$, —(CH$_2$)$_{1-4}$N(R$^{11a}$)$_2$, —SO$_2$N(R$^{11a}$)$_2$, —(CH$_2$)$_{1-4}$SO$_2$N(R$^{11a}$)$_2$, —NR$^{11a}$SO$_2$R$^{11a}$, or —(CH$_2$)$_{1-4}$NR$^{11a}$SO$_2$R$^{11a}$, or an optionally substituted C$_1$-C$_6$aliphatic group; and each occurrence of —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_2$)$_{1-4}$SR$^{11b}$, —COOR$^{11b}$, —(CH$_2$)$_{1-4}$COOR$^{11b}$, —COR$^{11b}$, —(CH$_2$)$_{1-4}$ $COR^{11b}$, —$CON(R^{11b})(R^{11c})$, —$(CH_2)_{1-4}CON(R^{11b})(R^{11c})$, —$N(R^{11b})(R^{11c})$, —$(CH_2)_{1-4}N(R^{11b})(R^{11c})$, —$SO_2N(R^{11b})(R^{11c})$, —$(CH_2)_{1-4}SO_2N(R^{11b})(R^{11c})$, —$NR^{11c}SO_2R^{11b}$, —$(CH_2)_{1-4}NR^{11c}SO_2R^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

In yet other embodiments, compounds of formula II-A-i are provided

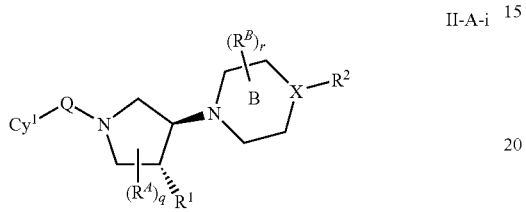

II-A-i and substituents are further selected from:

a) $R^1$ is —OH, —$O(C_1-C_6\text{alkyl})$, halogen, —$OCOR^4$, —$NR^4SO_2R^3$, or —$NR^4COR^4$; q is 0, 1, or 2, and —$R^A$ is fluoro, an optionally substituted linear or branched $C_1-C_6$alkyl, or an optionally substituted $C_3-C_6$cycloalkyl ring;

b) r is 0, 1, or 2, and —$R^B$ is —$R^B$ is $C_1-C_3$alkyl, or two occurrences of $R^B$, taken together with their intervening atom(s), form an optionally substituted fused or bridged 5 or 6-membered saturated, partially unsaturated, or aromatic ring having 0 heteroatoms;

c) $Cy^2$ is:

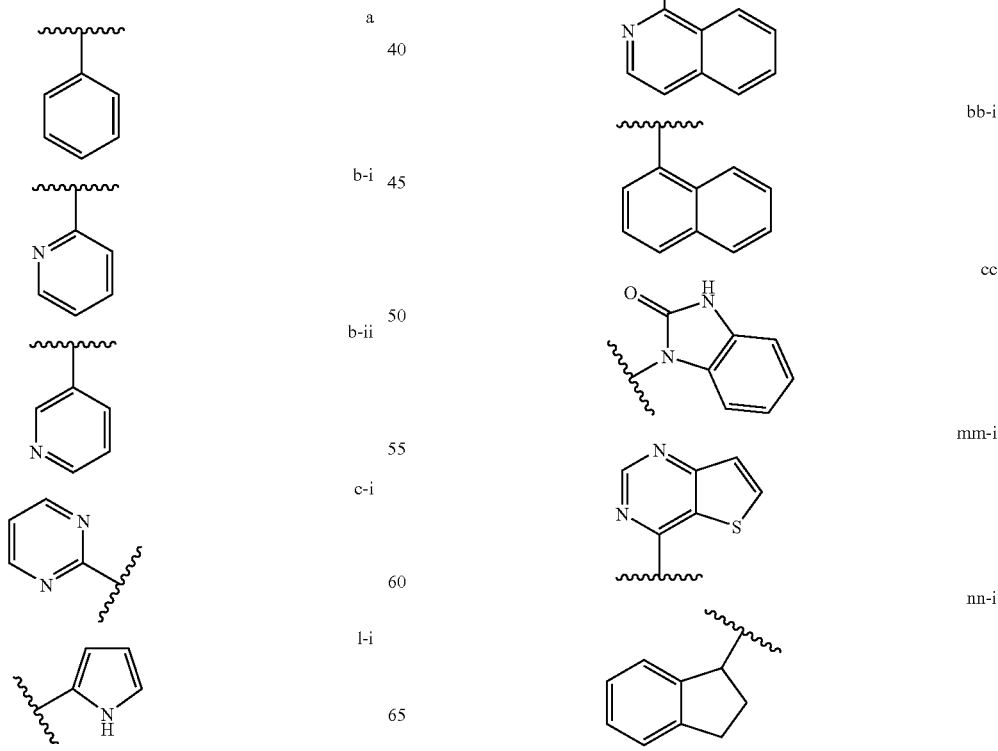

-continued

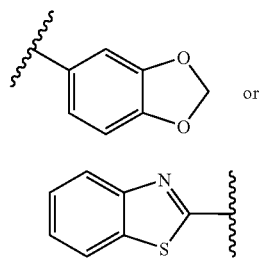
qq-i or

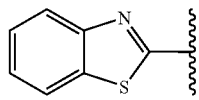
rr wherein Cy² is substituted with:

0, 1, or 2 occurrences of —$R^{6a}$ and each occurrence of —$R^{6a}$, when present, is independently —Cl, —Br, —F, —CN, —NO$_2$, —OR$^{7a}$, —SR$^{7a}$, —N(R$^{7a}$)$_2$, —COOR$^{7a}$, —COR$^{7a}$, —SO$_2$N(R$^{7a}$)$_2$, —NR$^{7a}$SO$_2$R$^{7b}$, —CON(R$^{7a}$)$_2$, —NR$^{7a}$COR$^{7a}$, or optionally substituted C$_1$-C$_6$alkyl, wherein each occurrence of R$^{7a}$ is independently hydrogen, or optionally substituted C$_1$-C$_6$alkyl; and 0 or 1 occurrence of —$R^{6b}$, wherein —$R^{6b}$, when present is —OR$^{7b}$, —SR$^{7b}$, —N(R$^{7b}$)(R$^{7c}$), —COOR$^{7b}$, —COR$^{7b}$, —SO$_2$N(R$^{7b}$)(R$^{7c}$), —NR$^{7c}$SO$_2$R$^{7b}$, —CON(R$^{7b}$)(R$^{7c}$), —NR$^{7c}$COR$^{7b}$, or an optionally substituted 3-6-membered saturated, partially unsaturated, or aromatic ring having 0-3 heteroatoms independently selected from nitrogen, oxygen, or sulfur, wherein each occurrence of R$^{7b}$ is independently an optionally substituted 3-6-membered saturated, partially unsaturated, or aromatic ring having 0-3 heteroatoms independently selected from nitrogen, oxygen, or sulfur, and each occurrence of R$^{7c}$ is independently hydrogen or an optionally substituted group selected from C$_1$-C$_6$alkyl or an optionally substituted 3-6-membered saturated, partially unsaturated, or aromatic ring having 0-3 heteroatoms independently selected from nitrogen, oxygen, or sulfur;

d) Q is —CO—, —CH$_2$—, —COCH$_2$—, —CH$_2$CO—, —CH$_2$OCO—, —SO$_2$—, or —C(R$^{5d}$)(R$^{5e}$)CO—, wherein R$^{5d}$ is hydrogen, optionally substituted C$_1$-C$_3$alkyl, optionally substituted phenyl, —OH, or —NH$_2$, and R$^{5e}$ is hydrogen, optionally substituted C$_1$-C$_3$alkyl, or optionally substituted phenyl; and e) Cy¹ is:

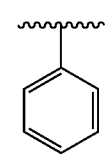
i

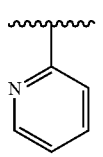
ii-a

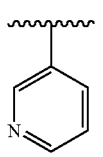
ii-b

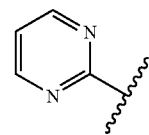
iii-a

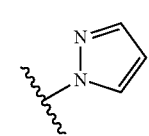
xi-a

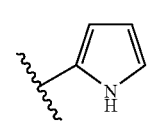
xii-a

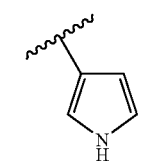
xii-b

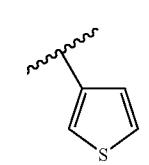
xv-a

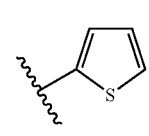
xv-b

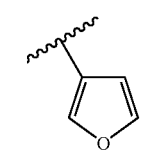
xx-a

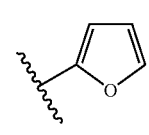
xx-b

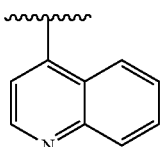
xxiv-a

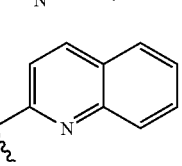
xxiv-b

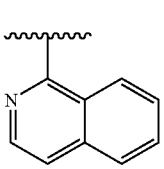
xxv-a

-continued xxvii-a xxix-a xxx xxxi-a xxxii-a xxxiii-a xxxiv-a xLii-a xLiv-a xLiv-b xLvi

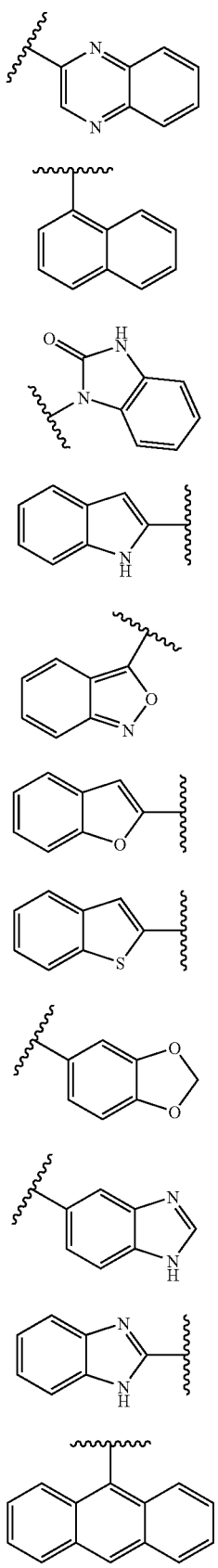

-continued xLvii xLviii

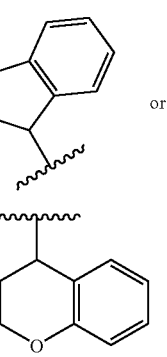

wherein $Cy^1$ is substituted with:

0, 1, or 2 occurrences of $—R^{10a}$ and each occurrence of $—R^{10a}$, when present, is independently —Cl, —Br, —F, —CN, —NO$_2$, —OR$^{11a}$, —SR$^{11a}$, —N(R$^{11a}$)$_2$, —NR$^{11a}$COR$^{11a}$, —CON(R$^{11a}$)$_2$, —SO$_2$N(R$^{11a}$)$_2$, —NR$^{11a}$SO$_2$R$^{11a}$, COOR$^{11a}$, COR$^{11a}$, or optionally substituted C$_1$-C$_6$alkyl, wherein each occurrence of R$^{11a}$ is independently hydrogen, or optionally substituted C$_1$-C$_6$alkyl; and 0 or 1 occurrence of —R$^{10b}$, J-R$^{10b}$, or W-J-R$^{10b}$, wherein W is —N(R$^{11b}$) or —O—, J is a C$_1$-C$_2$alkyl chain, and —R$^{10b}$, when present is —OR$^{11b}$, —SR$^{11b}$, —N(R$^{11b}$)(R$^{11c}$), —NR$^{11c}$COR$^{11b}$, CON(R$^{11b}$)(R$^{11c}$), —SO$_2$N(R$^{11c}$)(R$^{11b}$), —NR$^{11c}$SO$_2$R$^{11b}$, —COOR$^{11b}$, COR$^{11b}$, or an optionally substituted 3-6-membered saturated, partially unsaturated, or aromatic ring having 0-3 heteroatoms independently selected from nitrogen, oxygen, or sulfur, wherein each occurrence of R$^{11b}$ is independently an optionally substituted 3-6-membered saturated, partially unsaturated, or aromatic ring having 0-3 heteroatoms independently selected from nitrogen, oxygen, or sulfur, and each occurrence of R$^{11c}$ is independently hydrogen or an optionally substituted group selected from C$_1$-C$_6$alkyl or an optionally substituted 3-6-membered saturated, partially unsaturated, or aromatic ring having 0-3 heteroatoms independently selected from nitrogen, oxygen, or sulfur.

In still other embodiments, for the subsets of compounds of formulae II-A and II-A-i described directly above, each of the substituents are further selected from:

a) q is 0 or 1 and ring A has the structure:

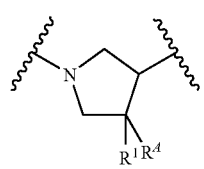

wherein $R^1$ is —OR$^4$, and —R$^A$ is —CH$_3$, CH$_2$CH$_3$, or F;

b) r is 0, 1, or 2, and —R$^B$ is methyl;

c) R$^2$ is -Cy$^2$ or -T-Cy$^2$, and when X is N, then T, when present, is —CO—, or —CH$_2$—, or when X is CR$^8$, then T, when present, is —O— or —NR$^{5c}$—, and R$^8$ is hydrogen, C$_1$-C$_3$alkyl, —OH, or —O(C$_1$-C$_3$alkyl);

d) Cy² is:

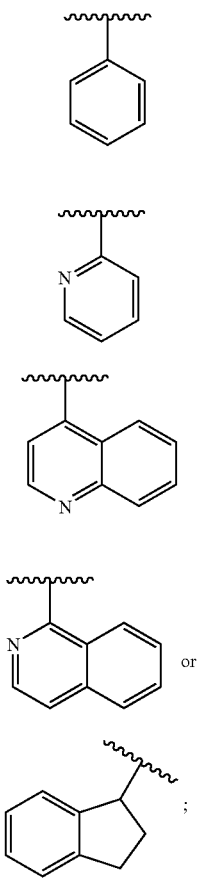

a b-i w-i x-i nn-i wherein Cy² is substituted with 0, 1, or 2 occurrences of —R⁶ᵃ and each occurrence of —R⁶ᵃ, when present, is independently —Cl, —Br, —F, —CN, —OCH₃, —OCH₂CH₃, —OCH₂CH₂CH₃, —CF₃, —CH₃, —CH₂CH₃, —CH₂CH₂CH₃, —CH(CH₃)₂; —C(CH₃)₃, —COOH, —COOCH₃, —COOCH₂CH₃;

e) Q is —CO—, —CH₂—, —COCH₂—, —CH₂CO—, —CH₂OCO—, —SO₂—, or —C(R⁵ᵈ)(R⁵ᵉ)CO—, wherein R⁵ᵈ is hydrogen, optionally substituted C₁-C₃alkyl, optionally substituted phenyl, —OH, or —NH₂, and R⁵ᵉ is hydrogen, optionally substituted C₁-C₃alkyl, or optionally substituted phenyl;

f) Cy¹ is:

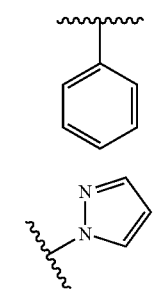

i xi-a

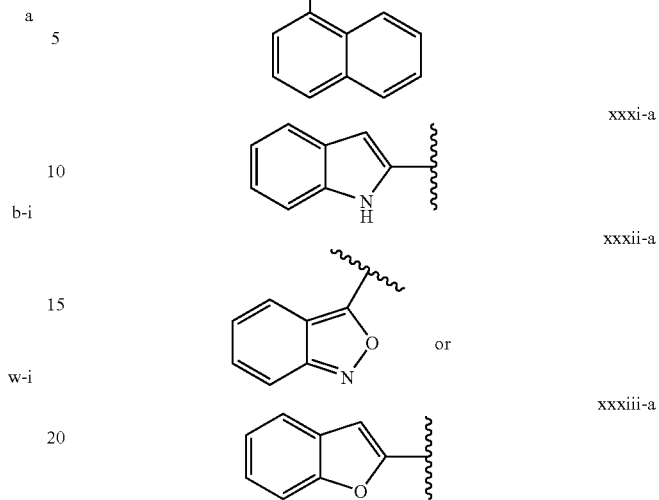

xxix-a xxxi-a xxxii-a xxxiii-a wherein Cy¹ is substituted with:
0, 1, or 2 occurrences of R¹⁰ᵃ, and each occurrence of —R¹⁰ᵃ is independently —Cl, —Br, —F, —NO₂, —CN, —OCH₃, —OCH₂CH₃, —OCH₂CH₂CH₃, —CF₃, —OCF₃, —CH₃, —CH₂CH₃, —CH₂CH₂CH₃, —C(CH₃)₃, —CH(CH₃)₂, —NHCOCH₃, —NHCONHCH₃, —SCH₃, —SCH₂CH₃, —SCH₂CH₂CH₃, —NH₂, —NHCH₃, —SO₂NH₂, —COOH, —COOCH₃, —NHCH₃, —N(CH₃)₂, —NH(CH₂CH₃), —N(CH₂CH₃)₂, —OC(CH₃)₂CO₂H, —OCH₂CO₂H, or —C(CH₃)₂OH and 0 or 1 occurrence of —R¹⁰ᵇ, J-R¹⁰ᵇ, or W-J-R¹⁰ᵇ, and —R¹⁰ᵇ, J-R¹⁰ᵇ, or W-J-R¹⁰ᵇ is phenyl, benzyl, —NHCO(phenyl), —NHCO(benzyl), —NH(phenyl), —NHCH₂(phenyl), —NH(benzyl), —S(phenyl), —S(benzyl), —O(phenyl), or —O(benzyl), wherein the phenyl and benzyl groups are optionally substituted.

In yet other embodiments, for the subsets of compounds of formulae II-A and II-A-i described directly above, R¹ is —OH.

In still other embodiments, for the subsets of compounds of formulae II-A and II-A-i described directly above, q is 0.

In other embodiments, for the subsets of compounds of formulae II-A and II-A-i described directly above, r is 0.

In still other embodiments, for the subsets of compounds of formulae II-A and II-A-i described directly above, Cy² is substituted with 1 or 2 occurrences of —R⁶ᵃ, and each occurrence of —R⁶ᵃ is independently —Cl, —F, —CF₃, —CH₃, or —Br.

In yet other embodiments, for the subsets of compounds of formulae II-A and II-A-i described directly above, Cy² is substituted with 1 occurrence of —R⁶ᵃ, and —R⁶ᵃ is —Cl.

In other embodiments, for the subsets of compounds of formulae II-A and II-A-i described directly above, Cy² is:

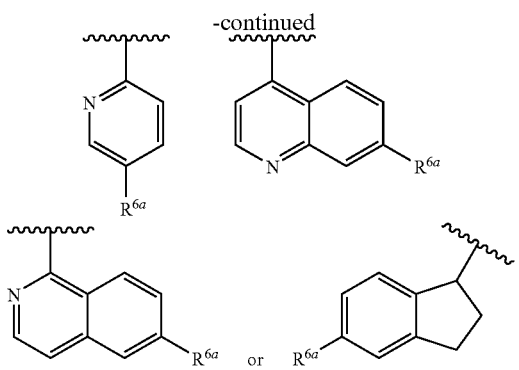

and each occurrence of $R^{6a}$ is independently —Cl, —Br, —CH$_3$, —CF$_3$, or —F.

In other embodiments, for the subsets of compounds of formulae II-A and II II-A-i described directly above, Cy$^2$ is phenyl substituted with 1 or 2 occurrences of —R$^{6a}$, and each occurrence of —R$^{6a}$ is independently —Cl, —F, —CF$_3$, —CH$_3$, or —Br.

In still other embodiments, for the subsets of compounds of formulae II-A and II-A-i described directly above, Cy$^2$ is phenyl substituted with 1 occurrence of —R$^{6a}$, and —R$^{6a}$ is —Cl.

In other embodiments, for the subsets of compounds of formulae II-A and II-A-i described directly above, Q is —CO—.

In other embodiments, for the subsets of compounds of formulae II-A and II-A-i described directly above, Cy$^1$ is phenyl. In still other embodiments, Cy$^1$ is substituted with 1, 2, or 3 occurrences of R$^{10a}$, and each occurrence of R$^{10a}$ is independently —Cl, —Br, —F, —CH$_3$, or —CF$_3$.

Representative examples of compounds are set forth below in Table 1. Compounds can be prepared as an enantiomeric mixture of the (3R,4R and 3S,4S)-trans-4-piperazinylpyrrolidin-3-ol, or can be separated to provide both the (3R, 4R) and (3S, 4S) compounds. For certain compounds in Table 1, the (3R, 4R) and (3S, 4S) enantiomers are specifically designated.

TABLE 1

Examples of Compounds of Formula I-A:

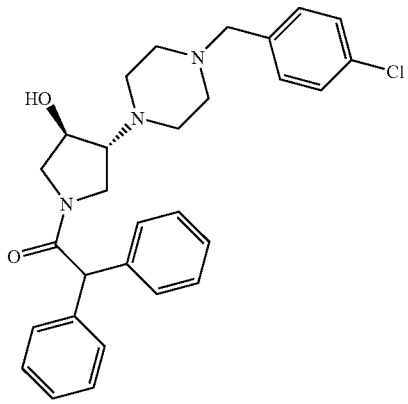 [SMILES: O=C(C(c1ccccc1)c1ccccc1)N1C[C@@H](O)[C@H](N2CCN(Cc3ccc(Cl)cc3)CC2)C1]

1

4-[4-(4-chlorobenzyl)piperazin-1-yl]-1-(diphenylacetyl)pyrrolidin-3-ol

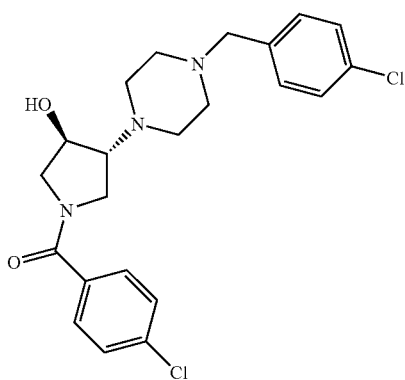 [SMILES: O=C(c1ccc(Cl)cc1)N1C[C@@H](O)[C@H](N2CCN(Cc3ccc(Cl)cc3)CC2)C1]

2

1-(4-chlorobenzoyl)-4-[4-(4-chlorobenzyl)piperazin-1-yl]pyrrolidin-3-ol

TABLE 1-continued
Examples of Compounds of Formula I-A:
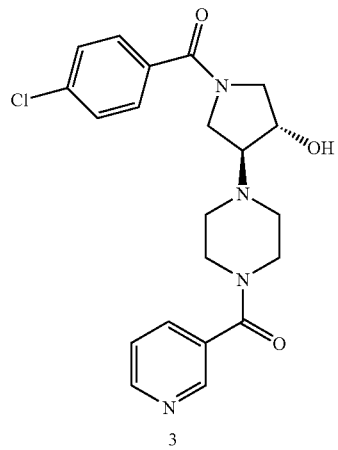
3
1-(4-chlorobenzoyl)-4-[4-(pyridin-3-
ylcarbonyl)piperazin-1-yl]pyrrolidin-3-ol
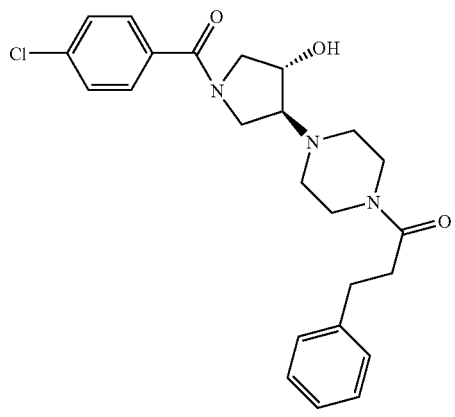 [SMILES: O=C(CCc1ccccc1)N1CCN([C@H]2CN(C(=O)c3ccc(Cl)cc3)C[C@@H]2O)CC1]
4
1-(4-chlorobenzoyl)-4-[4-(3-
phenylpropanoyl)piperazin-1-yl]pyrrolidin-3-ol
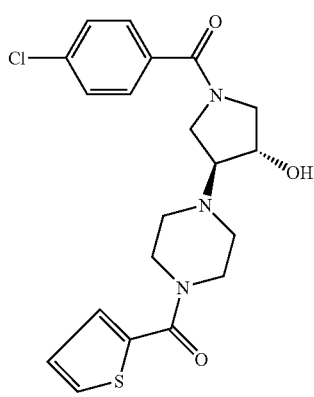 [SMILES: O=C(c1ccc(Cl)cc1)N1C[C@H](O)[C@@H](N2CCN(C(=O)c3cccs3)CC2)C1]
5
1-(4-chlorobenzoyl)-4-[4-(2-
thienylcarbonyl)piperazin-1-yl]pyrrolidin-3-ol TABLE 1-continued
Examples of Compounds of Formula I-A:
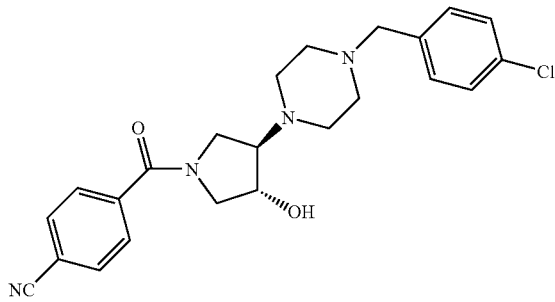
6
3-({3-[4-(4-chlorobenzyl)piperazin-1-yl]-4-
hydroxypyrrolidin-1-
yl}carbonyl)benzonitrile
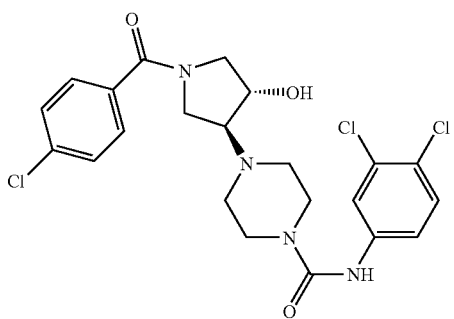 [SMILES: O=C(Nc1ccc(Cl)c(Cl)c1)N1CCN([C@H]2CN(C(=O)c3ccc(Cl)cc3)C[C@@H]2O)CC1]
7
4-[1-(4-chlorobenzoyl)-4-hydroxypyrrolidin-
3-yl]-N-(3,4-dichlorophenyl)piperazine-1-
carboxamide
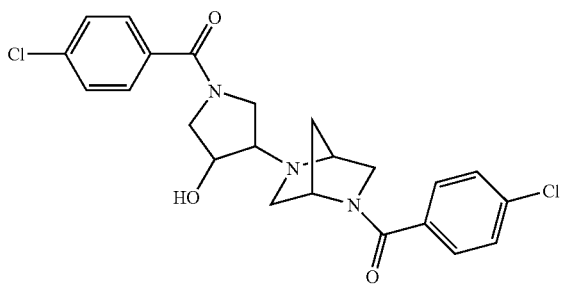 [SMILES: O=C(c1ccc(Cl)cc1)N1CC(O)C(N2CC3CC2CN3C(=O)c2ccc(Cl)cc2)C1]
8
1-(4-chlorobenzoyl)-4-[5-(4-chlorobenzoyl)-
2,5-diazabicyclo[2.2.1]hept-2-yl]pyrrolidin-3-ol
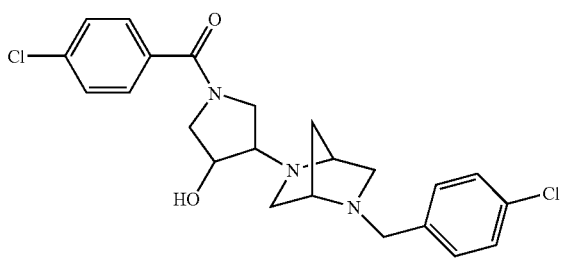 [SMILES: O=C(c1ccc(Cl)cc1)N1CC(O)C(N2CC3CC2CN3Cc2ccc(Cl)cc2)C1]
9
1-(4-chlorobenzoyl)-4-[5-(4-chlorobenzyl)-
2,5-diazabicyclo[2.2.1]hept-2-yl]pyrrolidin-3-ol TABLE 1-continued
Examples of Compounds of Formula I-A:
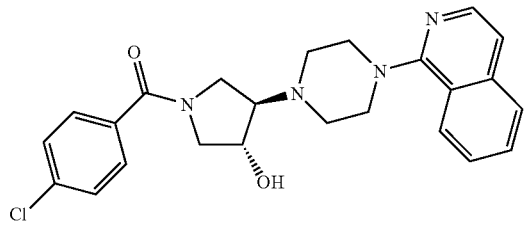 [SMILES: O=C(c1ccc(Cl)cc1)N1C[C@@H](O)[C@H](N2CCN(c3nccc4ccccc34)CC2)C1]
10
1-(4-chlorobenzoyl)-4-(4-isoquinolin-1-
ylpiperazin-1-yl)pyrrolidin-3-ol
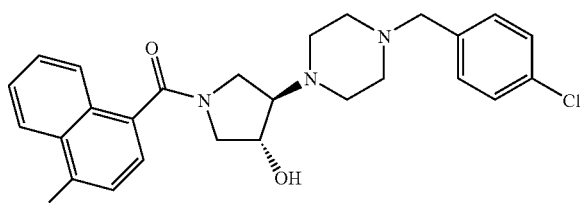
11
4-[4-(4-chlorobenzyl)piperazin-1-yl]-1-(4-
fluoro-1-naphthoyl)pyrrolidin-3-ol
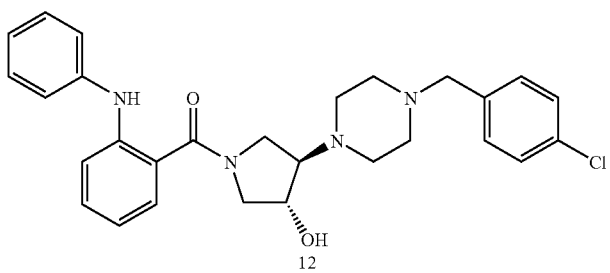
12
1-(2-anilinobenzoyl)-4-[4-(4-chlorobenzyl)-
piperazin-1-yl]pyrrolidin-3-ol
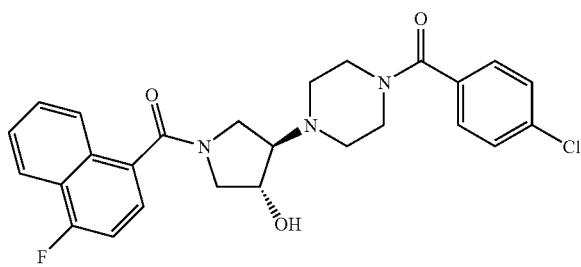 [SMILES: O=C(c1ccc(Cl)cc1)N1CCN([C@@H]2CN(C(=O)c3ccc(F)c4ccccc34)C[C@H]2O)CC1]
13
4-[4-(4-chlorobenzoyl)piperazin-1-yl]-1-(4-
fluoro-1-naphthoyl)pyrrolidin-3-ol
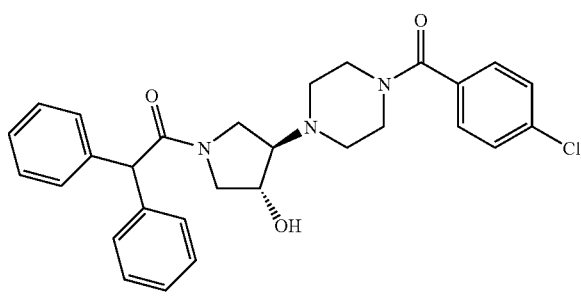 [SMILES: O=C(c1ccc(Cl)cc1)N1CCN([C@@H]2CN(C(=O)C(c3ccccc3)c3ccccc3)C[C@H]2O)CC1]
14
4-[4-(4-chlorobenzoyl)piperazin-1-yl]-1-
(diphenylacetyl)pyrrolidin-3-ol TABLE 1-continued
Examples of Compounds of Formula I-A:
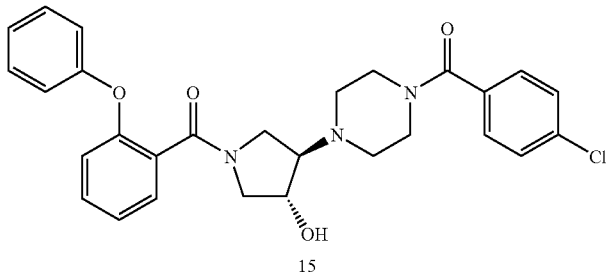
15
4-[4-(4-chlorobenzoyl)piperazin-1-yl]-1-(2-phenoxybenzoyl)pyrrolidin-3-ol
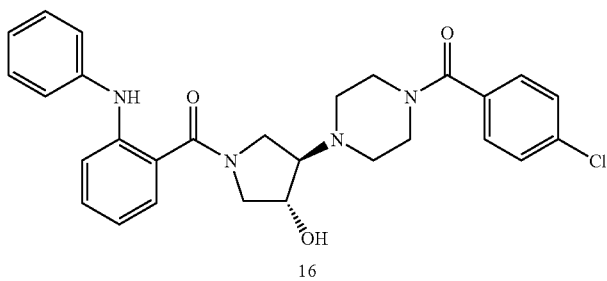
16
1-(2-anilinobenzoyl)-4-[4-(4-chlorobenzoyl)piperazin-1-yl]pyrrolidin-3-ol
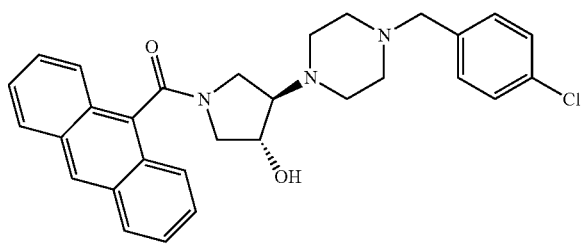 [SMILES: O=C(c1c2ccccc2cc2ccccc12)N1C[C@@H](O)[C@H](N2CCN(Cc3ccc(Cl)cc3)CC2)C1]
17
1-(9-anthrylcarbonyl)-4-[4-(4-chlorobenzyl)-piperazin-1-yl]pyrrolidin-3-ol
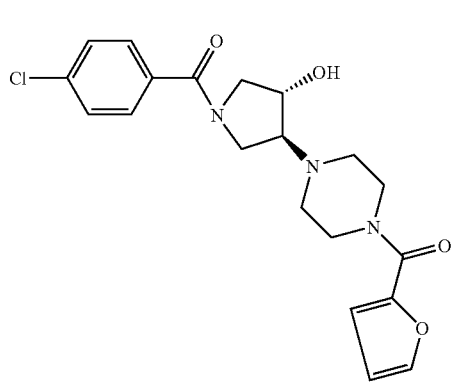 [SMILES: O=C(c1ccc(Cl)cc1)N1C[C@H](O)[C@@H](N2CCN(C(=O)c3ccco3)CC2)C1]
18
1-(4-chlorobenzoyl)-4-[4-(2-furoyl)piperazin-1-yl]pyrrolidin-3-ol TABLE 1-continued
Examples of Compounds of Formula I-A:
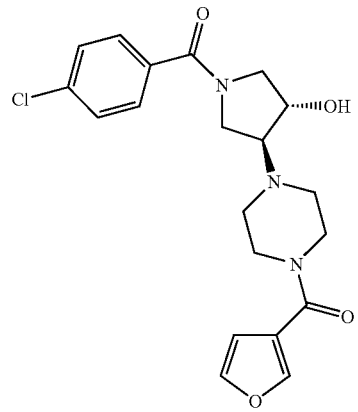 [SMILES: O=C(c1ccoc1)N1CCN([C@H]2CN(C(=O)c3ccc(Cl)cc3)C[C@@H]2O)CC1]
19
1-(4-chlorobenzoyl)-4-[4-(3-furoyl)piperazin-1-yl]pyrrolidin-3-ol
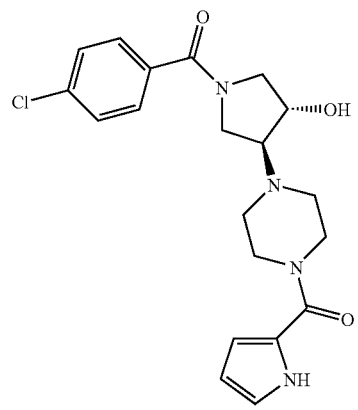 [SMILES: O=C(c1ccc(Cl)cc1)N1C[C@H](O)[C@@H](N2CCN(C(=O)c3ccc[nH]3)CC2)C1]
20
1-(4-chlorobenzoyl)-4-[4-(1H-pyrrol-2-ylcarbonyl)piperazin-1-yl]pyrrolidin-3-ol
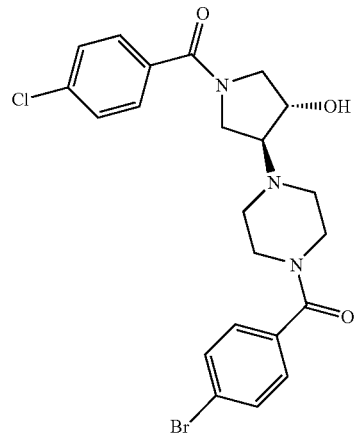 [SMILES: O=C(c1ccc(Br)cc1)N1CCN([C@H]2CN(C(=O)c3ccc(Cl)cc3)C[C@@H]2O)CC1]
21
4-[4-(4-bromobenzoyl)piperazin-1-yl]-1-(4-chlorobenzoyl)pyrrolidin-3-ol TABLE 1-continued
Examples of Compounds of Formula I-A:
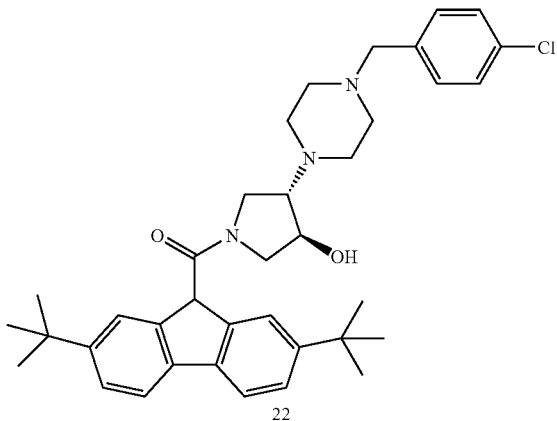
22
4-[4-(4-chlorobenzyl)piperazin-1-yl]-1-[(2,7-
di-tert-butyl-9H-fluoren-9-yl)carbonyl]-
pyrrolidin-3-ol
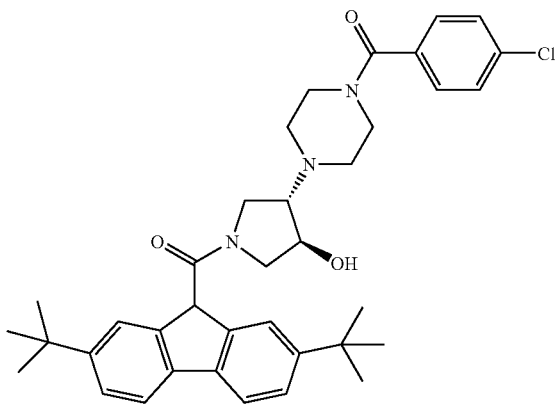 [SMILES: CC(C)(C)c1ccc2c(c1)C(C(=O)N1C[C@H](O)[C@@H](N3CCN(C(=O)c4ccc(Cl)cc4)CC3)C1)c1cc(C(C)(C)C)ccc1-2]
23
4-[4-(4-chlorobenzoyl)piperazin-1-yl]-1-
[(2,7-di-tert-butyl-9H-fluoren-9-yl)carbonyl]-
pyrrolidin-3-ol
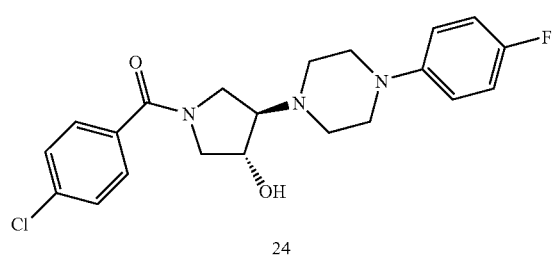
24
1-(4-chlorobenzoyl)-4-[4-(4-fluorophenyl)-
piperazin-1-yl]pyrrolidin-3-ol
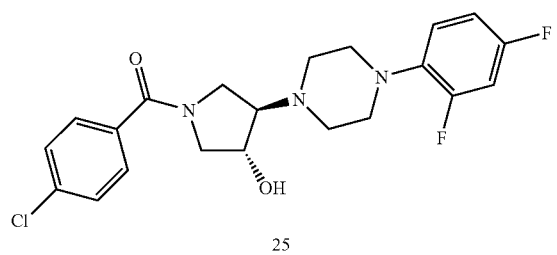
25
1-(4-chlorobenzoyl)-4-[4-(2,4-difluoro-
phenyl)piperazin-1-yl]pyrrolidin-3-ol TABLE 1-continued
Examples of Compounds of Formula I-A:
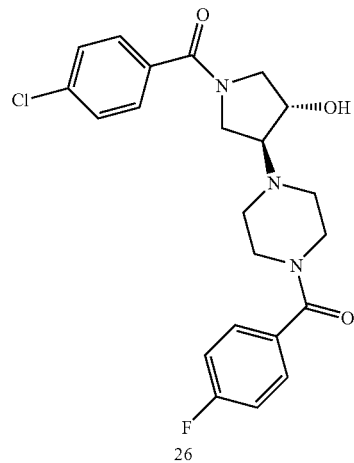
26
1-(4-chlorobenzoyl)-4-[4-(4-fluorobenzoyl)-
piperazin-1-yl]pyrrolidin-3-ol
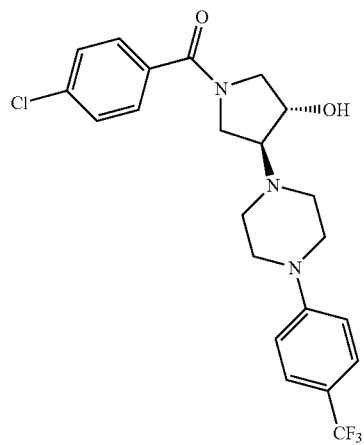 [SMILES: O=C(c1ccc(Cl)cc1)N1C[C@H](O)[C@@H](N2CCN(c3ccc(C(F)(F)F)cc3)CC2)C1]
27
1-(4-chlorobenzoyl)-4-{4-[4-
(trifluoromethyl)-phenyl]piperazin-1-
yl}pyrrolidin-3-ol
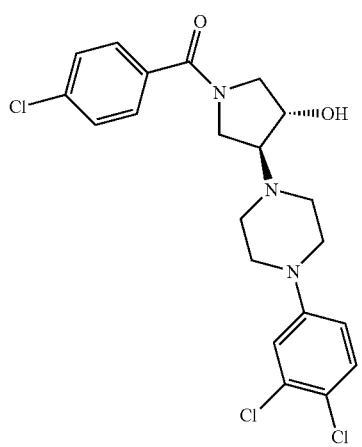 [SMILES: O=C(c1ccc(Cl)cc1)N1C[C@H](O)[C@@H](N2CCN(c3ccc(Cl)c(Cl)c3)CC2)C1]
28
1-(4-chlorobenzoyl)-4-[4-(3,4-dichloro-
phenyl)piperazin-1-yl]pyrrolidin-3-ol TABLE 1-continued Examples of Compounds of Formula I-A:

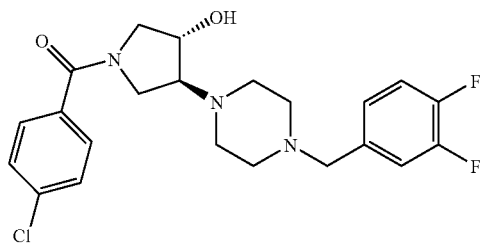 [SMILES: O=C(c1ccc(Cl)cc1)N1C[C@H](O)[C@@H](N2CCN(Cc3ccc(F)c(F)c3)CC2)C1]

29
1-(4-chlorobenzoyl)-4-[4-(3,4-
difluorobenzyl)-piperazin-1-yl]pyrrolidin-3-ol

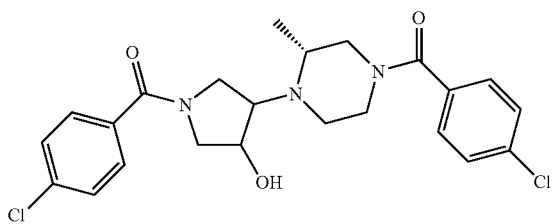 [SMILES: C[C@@H]1CN(C(=O)c2ccc(Cl)cc2)CCN1C1CN(C(=O)c2ccc(Cl)cc2)CC1O]

30
1-(4-chlorobenzoyl)-4-[(2R)-4-(4-chloro-
benzoyl)-2-methylpiperazin-1-yl]pyrrolidin-3-ol

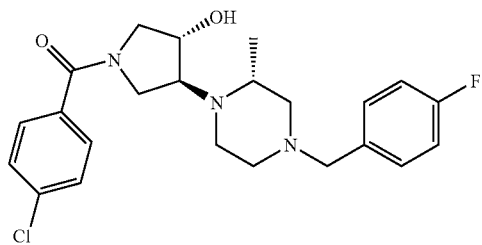 [SMILES: C[C@@H]1CN(Cc2ccc(F)cc2)CCN1[C@H]1CN(C(=O)c2ccc(Cl)cc2)C[C@@H]1O]

31
1-(4-chlorobenzoyl)-4-[(2R)-4-(4-fluoro-
benzyl)-2-methylpiperazin-1-yl]pyrrolidin-3-ol

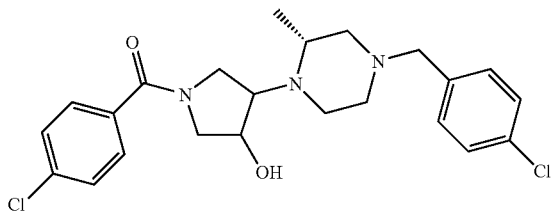 [SMILES: C[C@@H]1CN(Cc2ccc(Cl)cc2)CCN1C1CN(C(=O)c2ccc(Cl)cc2)CC1O]

32
1-(4-chlorobenzoyl)-4-[(2R)-4-(4-chloro-
benzyl)-2-methylpiperazin-1-yl]pyrrolidin-3-ol

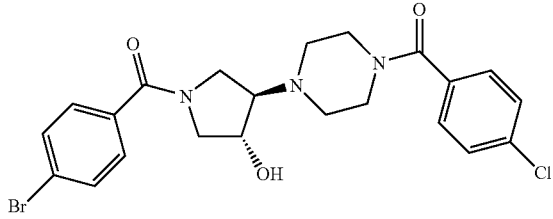 [SMILES: O=C(c1ccc(Cl)cc1)N1CCN([C@@H]2CN(C(=O)c3ccc(Br)cc3)C[C@H]2O)CC1]

33
1-(4-bromobenzoyl)-4-[4-(4-chloro-
benzoyl)piperazin-1-yl]pyrrolidin-3-ol

TABLE 1-continued
Examples of Compounds of Formula I-A:
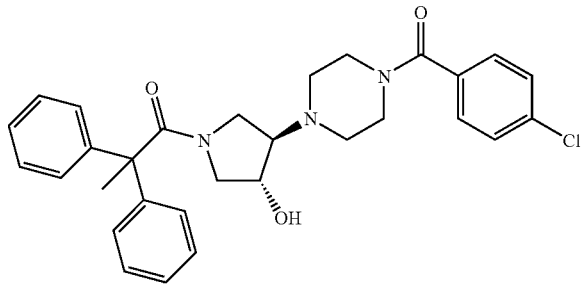 [SMILES: CC(C(=O)N1C[C@@H](O)[C@H](N2CCN(C(=O)c3ccc(Cl)cc3)CC2)C1)(c1ccccc1)c1ccccc1]
34
4-[4-(4-chlorobenzoyl)piperazin-1-yl]-1-(2,2-
diphenylpropanoyl)pyrrolidin-3-ol
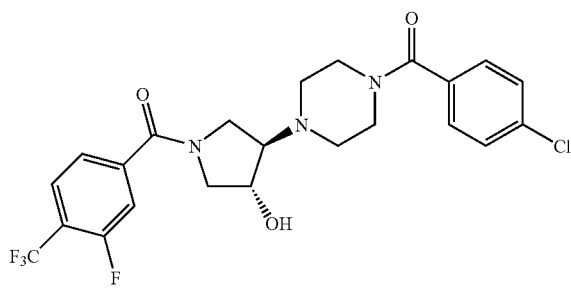 [SMILES: O=C(c1ccc(Cl)cc1)N1CCN([C@@H]2CN(C(=O)c3ccc(C(F)(F)F)c(F)c3)C[C@H]2O)CC1]
35
4-[4-(4-chlorobenzoyl)piperazin-1-yl]-1-[3-
fluoro-4-(trifluoromethyl)benzoyl]pyrrolidin-3-ol
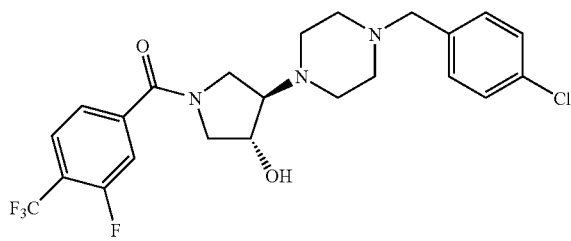 [SMILES: O=C(c1ccc(C(F)(F)F)c(F)c1)N1C[C@@H](O)[C@H](N2CCN(Cc3ccc(Cl)cc3)CC2)C1]
36
4-[4-(4-chlorobenzyl)piperazin-1-yl]-1-[3-
fluoro-4-(trifluoromethyl)benzoyl]pyrrolidin-3-ol
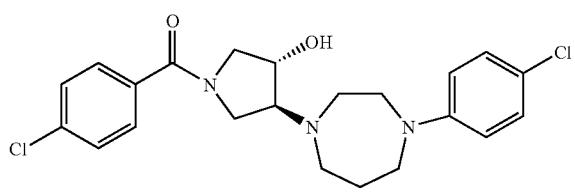 [SMILES: O=C(c1ccc(Cl)cc1)N1C[C@H](O)[C@@H](N2CCCN(c3ccc(Cl)cc3)CC2)C1]
37
1-(4-chlorobenzoyl)-4-[4-(4-chlorophenyl)-
1,4-diazepan-1-yl]pyrrolidin-3-ol TABLE 1-continued
Examples of Compounds of Formula I-A:
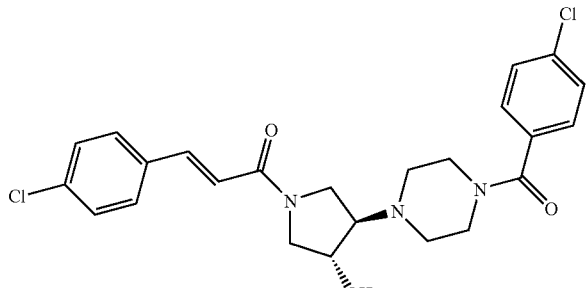
38
4-[4-(4-chlorobenzoyl)piperazin-1-yl]-1-
[(2E)-3-(4-chlorophenyl)prop-2-
enoyl]pyrrolidin-3-ol
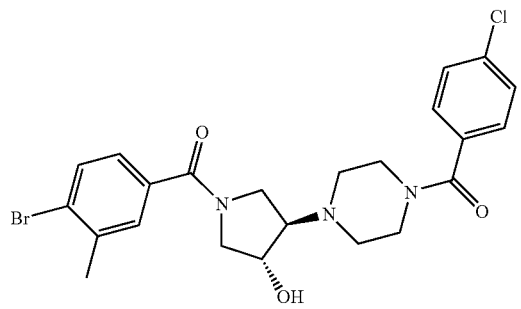 [SMILES: Cc1cc(C(=O)N2C[C@@H](O)[C@H](N3CCN(C(=O)c4ccc(Cl)cc4)CC3)C2)ccc1Br]
39
1-(4-bromo-3-methylbenzoyl)-4-[4-(4-
chlorobenzoyl)piperazin-1-yl]pyrrolidin-3-ol
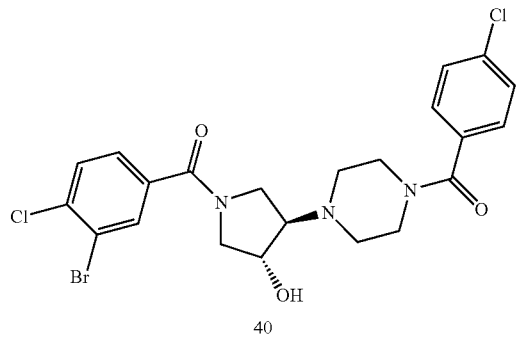
40
1-(3-bromo-4-chlorobenzoyl)-4-[4-(4-
chlorobenzoyl)piperazin-1-yl]pyrrolidin-3-ol
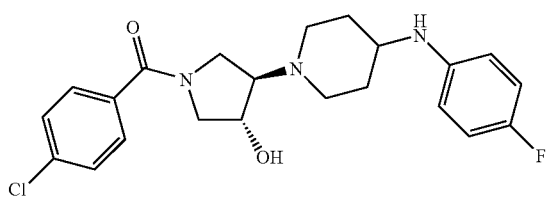 [SMILES: O=C(c1ccc(Cl)cc1)N1C[C@@H](O)[C@H](N2CCC(Nc3ccc(F)cc3)CC2)C1]
41
1-(4-chlorobenzoyl)-4-{4-[(4-fluorophenyl)-
amino]piperidin-1-yl}pyrrolidin-3-ol TABLE 1-continued
Examples of Compounds of Formula I-A:
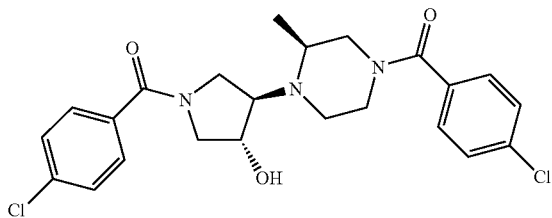 [SMILES: C[C@H]1CN(C(=O)c2ccc(Cl)cc2)CCN1[C@@H]1CN(C(=O)c2ccc(Cl)cc2)C[C@H]1O]
42
1-(4-chlorobenzoyl)-4-[(2S)-4-(4-
chlorobenzoyl)-2-methylpiperazin-1-
yl]pyrrolidin-3-ol
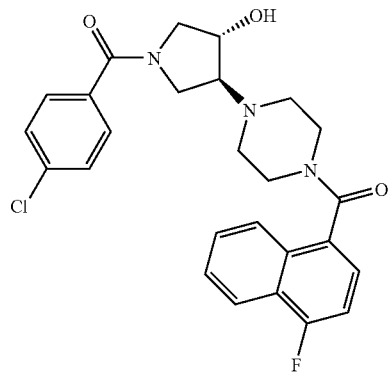 [SMILES: O=C(c1ccc(Cl)cc1)N1C[C@H](O)[C@@H](N2CCN(C(=O)c3ccc(F)c4ccccc34)CC2)C1]
43
1-(4-chlorobenzoyl)-4-[4-(4-fluoro-1-
naphthoyl)piperazin-1-yl]pyrrolidin-3-ol
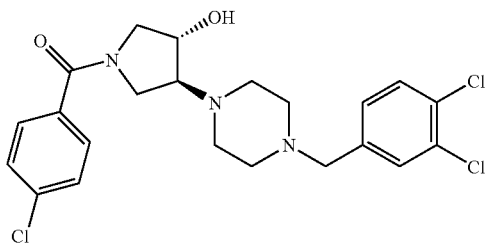 [SMILES: O=C(c1ccc(Cl)cc1)N1C[C@H](O)[C@@H](N2CCN(Cc3ccc(Cl)c(Cl)c3)CC2)C1]
44
1-(4-chlorobenzoyl)-4-[4-(3,4-
dichlorobenzyl)piperazin-1-yl]pyrrolidin-3-ol
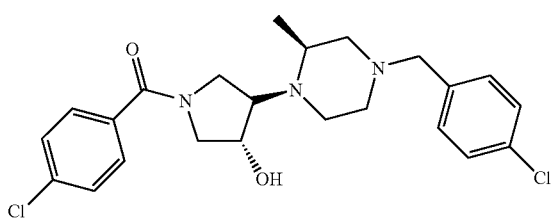
45
(3R, 4R)-1-(4-chlorobenzoyl)-4-[(2S)-4-(4-
chlorobenzyl)-2-methylpiperazin-1-
yl]pyrrolidin-3-ol TABLE 1-continued Examples of Compounds of Formula I-A:

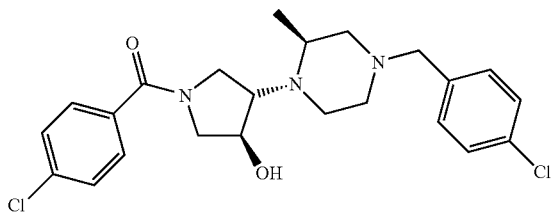

46
(3S, 4S)-1-(4-chlorobenzoyl)-4-[(2S)-4-(4-
chlorobenzyl)-2-methylpiperazin-1-
yl]pyrrolidin-3-ol

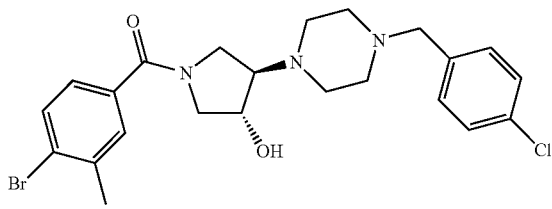 [SMILES: Cc1cc(C(=O)N2C[C@@H](O)[C@H](N3CCN(Cc4ccc(Cl)cc4)CC3)C2)ccc1Br]

47
1-(4-bromo-3-methylbenzoyl)-4-[4-(4-
chlorobenzyl)piperazin-1-yl]pyrrolidin-3-ol

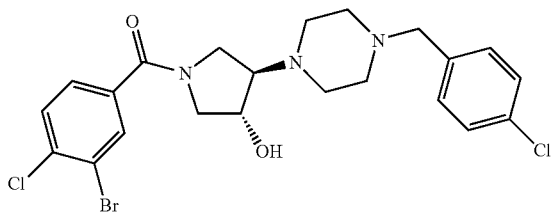

48
1-(3-bromo-4-chlorobenzoyl)-4-[4-(4-
chlorobenzyl)piperazin-1-yl]pyrrolidin-3-ol

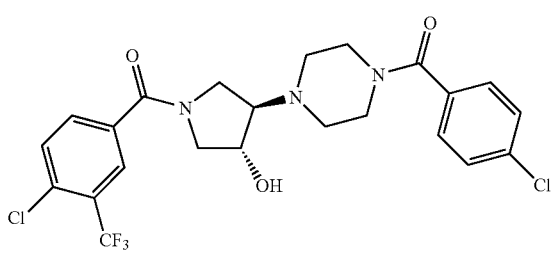 [SMILES: O=C(c1ccc(Cl)cc1)N1CCN([C@@H]2CN(C(=O)c3ccc(Cl)c(C(F)(F)F)c3)C[C@H]2O)CC1]

49
4-[4-(4-chlorobenzoyl)piperazin-1-yl]-1-[4-
chloro-3-
(trifluoromethyl)benzoyl]pyrrolidin-3-ol

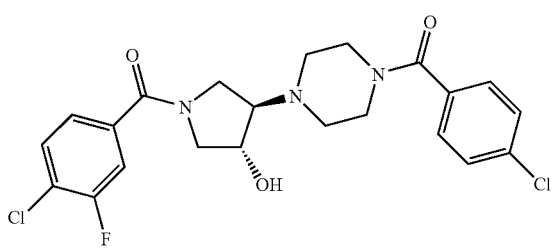 [SMILES: O=C(c1ccc(Cl)cc1)N1CCN([C@@H]2CN(C(=O)c3ccc(Cl)c(F)c3)C[C@H]2O)CC1]

50
4-[4-(4-chlorobenzoyl)piperazin-1-yl]-1-(4-
chloro-3-fluorobenzoyl)pyrrolidin-3-ol TABLE 1-continued Examples of Compounds of Formula I-A:

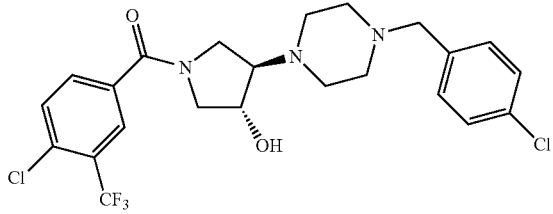 [SMILES: O=C(c1ccc(Cl)c(C(F)(F)F)c1)N1C[C@@H](O)[C@H](N2CCN(Cc3ccc(Cl)cc3)CC2)C1]

51
4-[4-(4-chlorobenzyl)piperazin-1-yl]-1-[4-
chloro-3-
(trifluoromethyl)benzoyl]pyrrolidin-3-ol

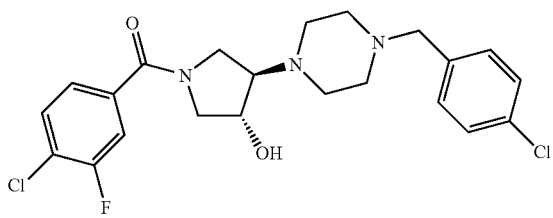 [SMILES: O=C(c1ccc(Cl)c(F)c1)N1C[C@@H](O)[C@H](N2CCN(Cc3ccc(Cl)cc3)CC2)C1]

52
4-[4-(4-chlorobenzyl)piperazin-1-yl]-1-(4-
chloro-3-fluorobenzoyl)pyrrolidin-3-ol

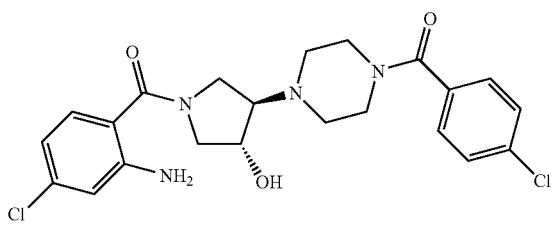 [SMILES: Nc1cc(Cl)ccc1C(=O)N1C[C@@H](O)[C@H](N2CCN(C(=O)c3ccc(Cl)cc3)CC2)C1]

53
1-(2-amino-4-chlorobenzoyl)-4-[4-(4-
chlorobenzoyl)piperazin-1-yl]pyrrolidin-3-ol

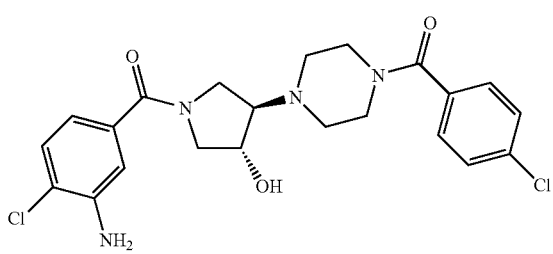

54
1-(3-amino-4-chlorobenzoyl)-4-[4-(4-
chlorobenzoyl)piperazin-1-yl]pyrrolidin-3-ol

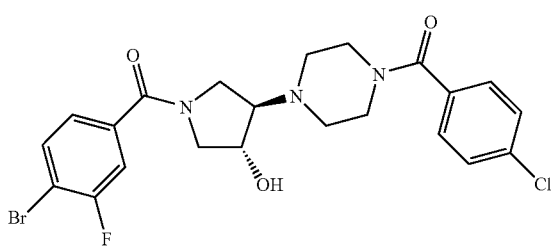

55
1-(4-bromo-3-fluorobenzoyl)-4-[4-(4-
chlorobenzoyl)piperazin-1-yl]pyrrolidin-3-ol TABLE 1-continued Examples of Compounds of Formula I-A:

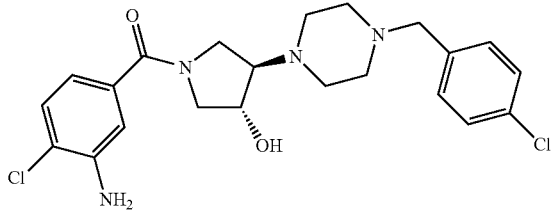 [SMILES: Nc1cc(C(=O)N2C[C@@H](O)[C@H](N3CCN(Cc4ccc(Cl)cc4)CC3)C2)ccc1Cl]

56
1-(3-amino-4-chlorobenzoyl)-4-[4-(4-
chlorobenzyl)piperazin-1-yl]pyrrolidin-3-ol

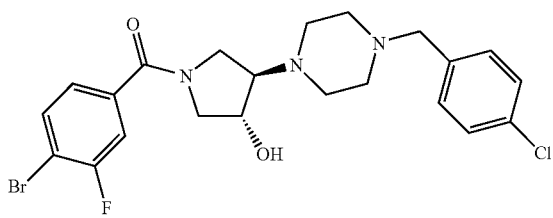

57
1-(4-bromo-3-fluorobenzoyl)-4-[4-(4-
chlorobenzyl)piperazin-1-yl]pyrrolidin-3-ol

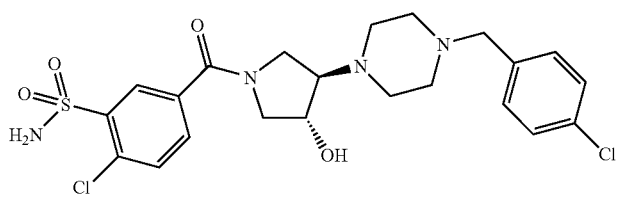 [SMILES: NS(=O)(=O)c1cc(C(=O)N2C[C@@H](O)[C@H](N3CCN(Cc4ccc(Cl)cc4)CC3)C2)ccc1Cl]

58
2-chloro-5-({3-[4-(4-chlorobenzyl)piperazin-
1-yl]-4-hydroxypyrrolidin-1-yl}carbonyl)-
benzenesulfonamide

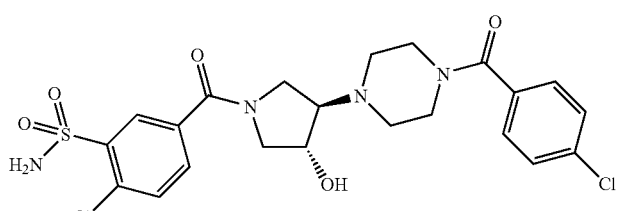

59
2-chloro-5-({3-[4-(4-
chlorobenzoyl)piperazin-1-yl]-4-
hydroxypyrrolidin-1-yl}-
carbonyl)benzenesulfonamide

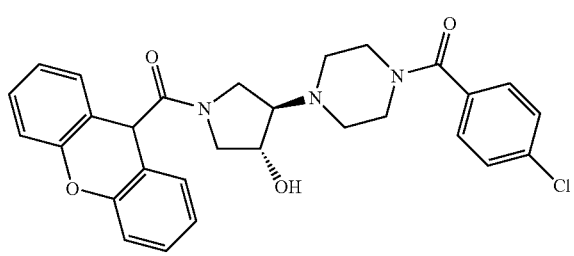 [SMILES: O=C(c1ccc(Cl)cc1)N1CCN([C@@H]2CN(C(=O)C3c4ccccc4Oc4ccccc43)C[C@H]2O)CC1]

60
4-[4-(4-chlorobenzoyl)piperazin-1-yl]-1-(9H-
xanthen-9-ylcarbonyl)pyrrolidin-3-ol TABLE 1-continued
Examples of Compounds of Formula I-A:
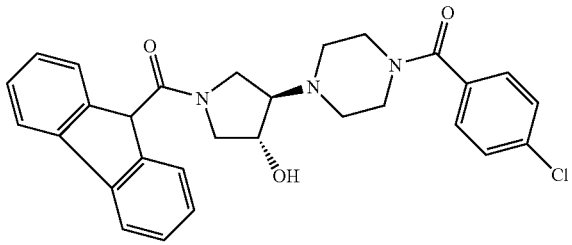 [SMILES: O=C(c1ccc(Cl)cc1)N1CCN([C@@H]2CN(C(=O)C3c4ccccc4-c4ccccc43)C[C@H]2O)CC1]
61
4-[4-(4-chlorobenzoyl)piperazin-1-yl]-1-(9H-
fluoren-9-ylcarbonyl)pyrrolidin-3-ol
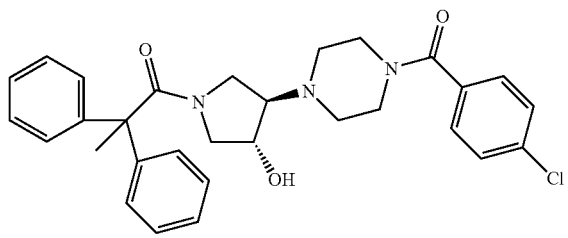 [SMILES: CC(C(=O)N1C[C@@H](O)[C@H](N2CCN(C(=O)c3ccc(Cl)cc3)CC2)C1)(c1ccccc1)c1ccccc1]
62
4-[4-(4-chlorobenzyl)piperazin-1-yl]-1-(2,2-
diphenylpropanoyl)pyrrolidin-3-ol
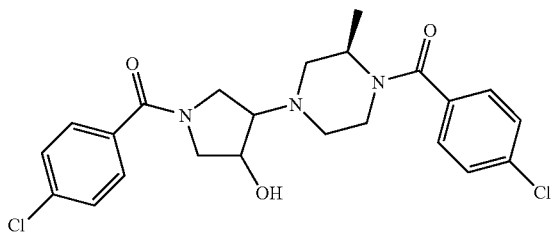 [SMILES: C[C@@H]1CN(C2CN(C(=O)c3ccc(Cl)cc3)CC2O)CCN1C(=O)c1ccc(Cl)cc1]
63
1-(4-chlorobenzoyl)-4-[(3R)-4-(4-chloro-
benzoyl)-3-methylpiperazin-1-yl]pyrrolidin-3-ol
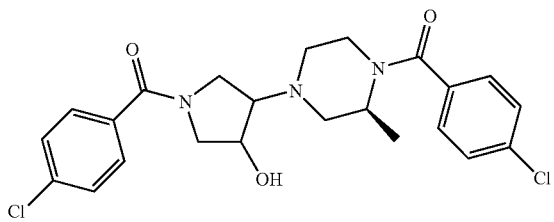 [SMILES: C[C@H]1CN(C2CN(C(=O)c3ccc(Cl)cc3)CC2O)CCN1C(=O)c1ccc(Cl)cc1]
64
1-(4-chlorobenzoyl)-4-[(3S)-4-(4-chloro-
benzoyl)-3-methylpiperazin-1-yl]pyrrolidin-3-ol TABLE 1-continued
Examples of Compounds of Formula I-A:
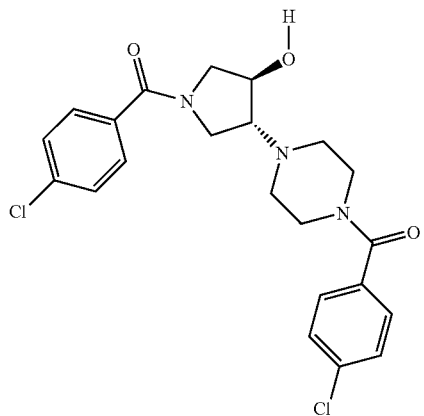 [SMILES: O=C(c1ccc(Cl)cc1)N1CCN([C@@H]2CN(C(=O)c3ccc(Cl)cc3)C[C@H]2O)CC1]
65
1-(4-chlorobenzoyl)-4-[4-(4-chlorobenzoyl)-
piperazin-1-yl]pyrrolidin-3-ol
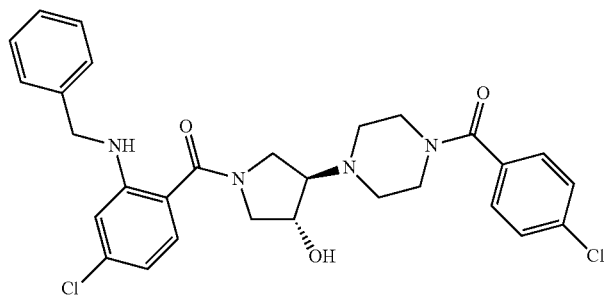 [SMILES: O=C(c1ccc(Cl)cc1)N1CCN([C@@H]2CN(C(=O)c3ccc(Cl)cc3NCc3ccccc3)C[C@H]2O)CC1]
66
1-[2-(benzylamino)-4-chlorobenzoyl]-4-[4-
(4-chlorobenzoyl)piperazin-1-yl]pyrrolidin-3-ol
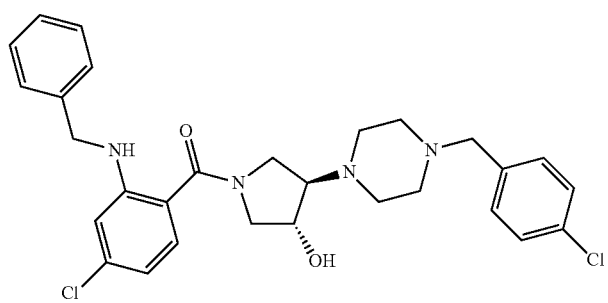 [SMILES: O=C(c1ccc(Cl)cc1NCc1ccccc1)N1C[C@@H](O)[C@H](N2CCN(Cc3ccc(Cl)cc3)CC2)C1]
67
1-[2-(benzylamino)-4-chlorobenzoyl]-4-[4-
(4-chlorobenzyl)piperazin-1-yl]pyrrolidin-3-ol TABLE 1-continued
Examples of Compounds of Formula I-A:
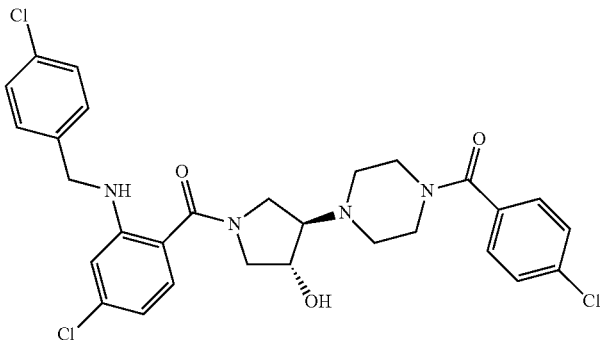 [SMILES: O=C(c1ccc(Cl)cc1)N1CCN([C@@H]2CN(C(=O)c3ccc(Cl)cc3NCc3ccc(Cl)cc3)C[C@H]2O)CC1]
68
4-[4-(4-chlorobenzoyl)piperazin-1-yl]-1-{4-
chloro-2-[(4-chlorobenzyl)amino]benzoyl}-
pyrrolidin-3-ol
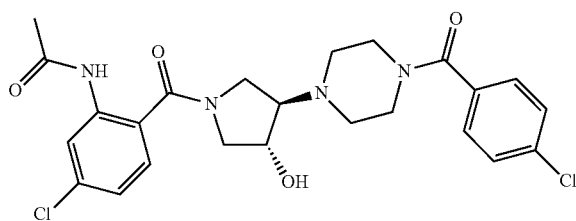 [SMILES: CC(=O)Nc1cc(Cl)ccc1C(=O)N1C[C@@H](O)[C@H](N2CCN(C(=O)c3ccc(Cl)cc3)CC2)C1]
69
N-[5-chloro-2-({3-[4-(4-chlorobenzoyl)-
piperazin-1-yl]-4-hydroxy-pyrrolidin-1-yl}-
carbonyl)phenyl]acetamide
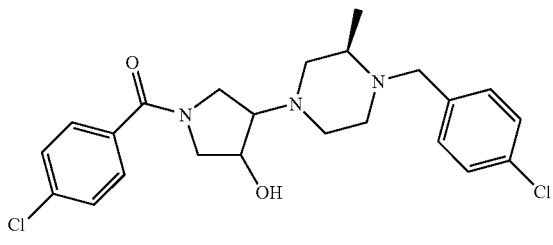 [SMILES: C[C@@H]1CN(C2CN(C(=O)c3ccc(Cl)cc3)CC2O)CCN1Cc1ccc(Cl)cc1]
70
1-(4-chlorobenzoyl)-4-[(3R)-4-(4-chloro-
benzyl)-3-methylpiperazin-1-yl]-pyrrolidin-3-ol
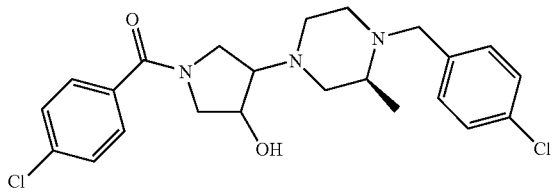 [SMILES: C[C@H]1CN(C2CN(C(=O)c3ccc(Cl)cc3)CC2O)CCN1Cc1ccc(Cl)cc1]
71
1-(4-chlorobenzoyl)-4-[(3S)-4-(4-chloro-
benzyl)-3-methylpiperazin-1-yl]pyrrolidin-3-ol TABLE 1-continued Examples of Compounds of Formula I-A:

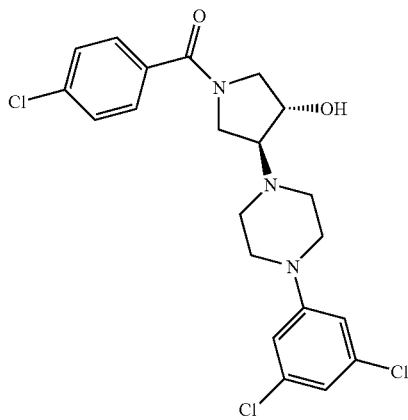 [SMILES: O=C(c1ccc(Cl)cc1)N1C[C@H](O)[C@@H](N2CCN(c3cc(Cl)cc(Cl)c3)CC2)C1]

72
1-(4-chlorobenzoyl)-4-[4-(3,5-dichloro-
phenyl)piperazin-1-yl]pyrrolidin-3-ol

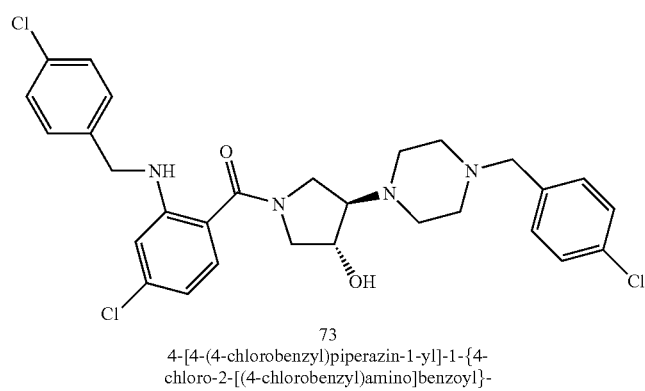

73
4-[4-(4-chlorobenzyl)piperazin-1-yl]-1-{4-
chloro-2-[(4-chlorobenzyl)amino]benzoyl}-
pyrrolidin-3-ol

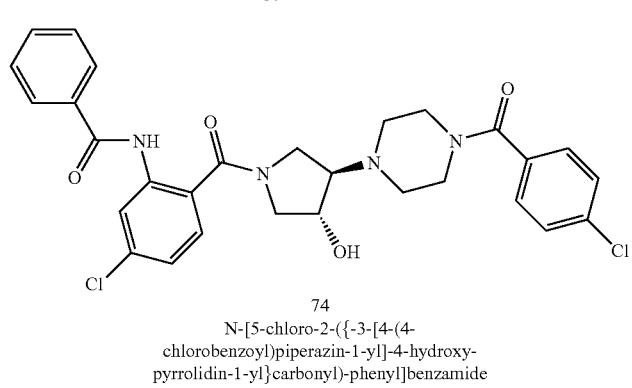

74
N-[5-chloro-2-({-3-[4-(4-
chlorobenzoyl)piperazin-1-yl]-4-hydroxy-
pyrrolidin-1-yl}carbonyl)-phenyl]benzamide

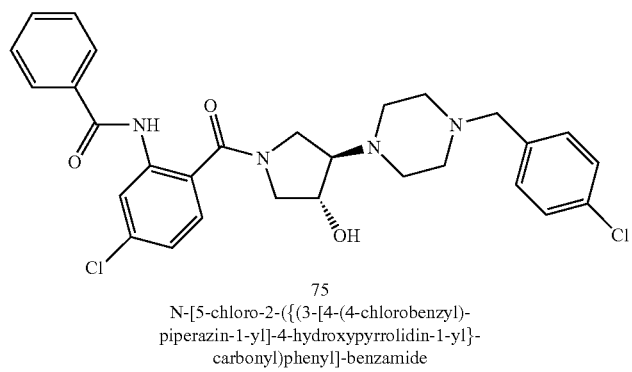

75
N-[5-chloro-2-({(3-[4-(4-chlorobenzyl)-
piperazin-1-yl]-4-hydroxypyrrolidin-1-yl}-
carbonyl)phenyl]-benzamide TABLE 1-continued Examples of Compounds of Formula I-A:

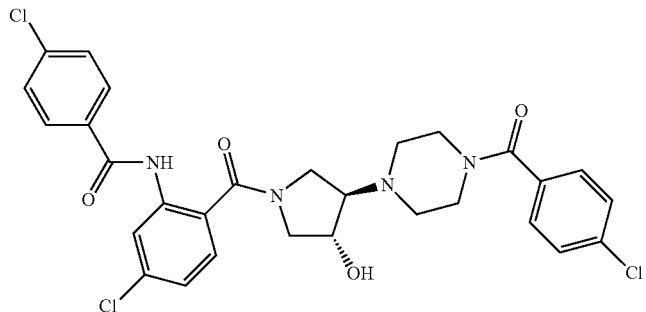 [SMILES: O=C(Nc1cc(Cl)ccc1C(=O)N1C[C@@H](O)[C@H](N2CCN(C(=O)c3ccc(Cl)cc3)CC2)C1)c1ccc(Cl)cc1]

76
4-chloro-N-[5-chloro-2-({(3-[4-(4-chloro-
benzoyl)piperazin-1-yl]-4-
hydroxypyrrolidin-1-yl}carbonyl)-
phenyl]benzamide

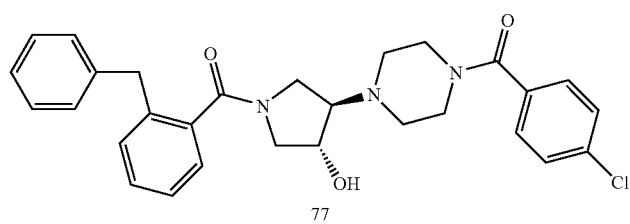

77
1-(2-benzylbenzoyl)-4-[4-(4-chlorobenzoyl)-
piperazin-1-yl]pyrrolidin-3-ol

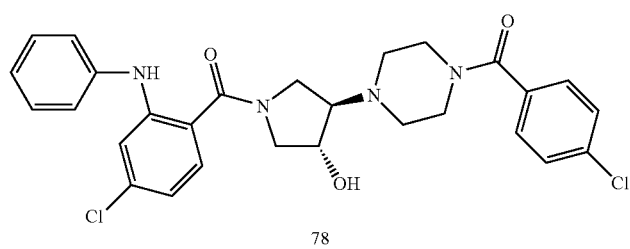

78
1-(2-anilino-4-chlorobenzoyl)-4-[4-(4-
chlorobenzoyl)piperazin-1-yl]pyrrolidin-3-ol

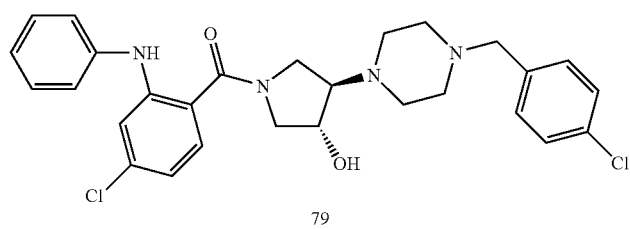

79
1-(2-anilino-4-chlorobenzoyl)-4-[4-(4-
chlorobenzyl)piperazin-1-yl]pyrrolidin-3-ol

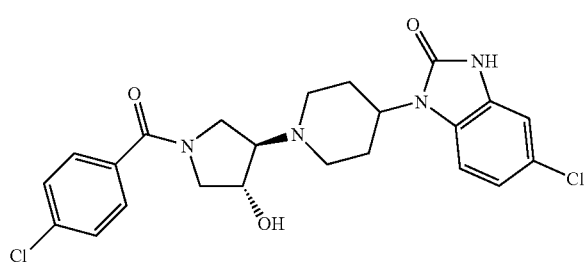 [SMILES: O=C(c1ccc(Cl)cc1)N1C[C@@H](O)[C@H](N2CCC(n3c(=O)[nH]c4cc(Cl)ccc43)CC2)C1]

80
5-chloro-1-{1-[1-(4-chlorobenzoyl)-4-
hydroxypyrrolidin-3-yl]piperidin-4-yl}-1,3-
dihydro-2H-benzimidazol-2-one TABLE 1-continued Examples of Compounds of Formula I-A:

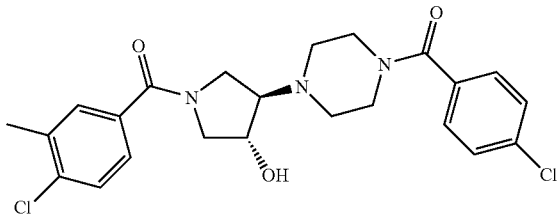 [SMILES: Cc1cc(C(=O)N2C[C@@H](O)[C@H](N3CCN(C(=O)c4ccc(Cl)cc4)CC3)C2)ccc1Cl]

81
4-[4-(4-chlorobenzoyl)piperazin-1-yl]-1-(4-
chloro-3-methylbenzoyl)pyrrolidin-3-ol

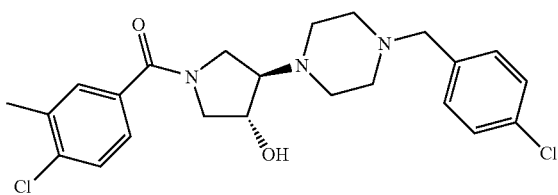 [SMILES: Cc1cc(C(=O)N2C[C@@H](O)[C@H](N3CCN(Cc4ccc(Cl)cc4)CC3)C2)ccc1Cl]

82
4-[4-(4-chlorobenzyl)piperazin-1-yl]-1-(4-
chloro-3-methylbenzoyl)pyrrolidin-3-ol

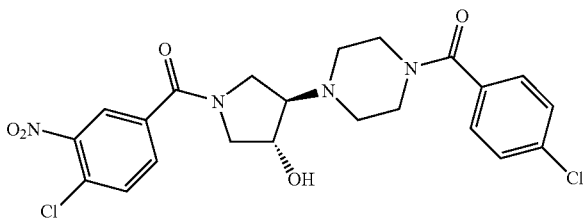 [SMILES: O=C(c1ccc(Cl)cc1)N1CCN([C@@H]2CN(C(=O)c3ccc(Cl)c([N+](=O)[O-])c3)C[C@H]2O)CC1]

83
4-[4-(4-chlorobenzoyl)piperazin-1-yl]-1-(4-
chloro-3-nitrobenzoyl)pyrrolidin-3-ol

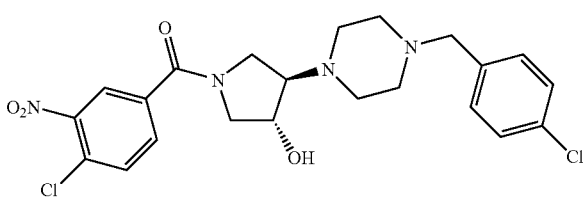 [SMILES: O=C(c1ccc(Cl)c([N+](=O)[O-])c1)N1C[C@@H](O)[C@H](N2CCN(Cc3ccc(Cl)cc3)CC2)C1]

84
4-[4-(4-chlorobenzyl)piperazin-1-yl]-1-(4-
chloro-3-nitrobenzoyl)pyrrolidin-3-ol

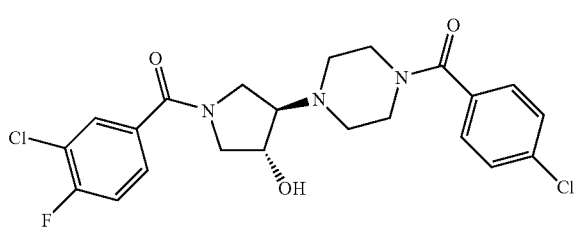 [SMILES: O=C(c1ccc(Cl)cc1)N1CCN([C@@H]2CN(C(=O)c3ccc(F)c(Cl)c3)C[C@H]2O)CC1]

85
4-[4-(4-chlorobenzoyl)piperazin-1-yl]-1-(3-
chloro-4-fluorobenzoyl)pyrrolidin-3-ol TABLE 1-continued Examples of Compounds of Formula I-A:

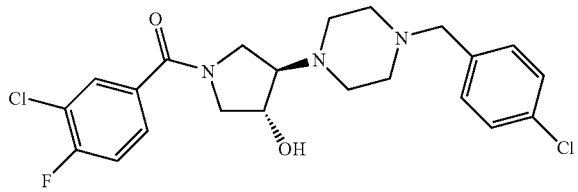 [SMILES: O=C(c1ccc(F)c(Cl)c1)N1C[C@@H](O)[C@H](N2CCN(Cc3ccc(Cl)cc3)CC2)C1]

86
4-[4-(4-chlorobenzyl)piperazin-1-yl]-1-(3-
chloro-4-fluorobenzoyl)pyrrolidin-3-ol

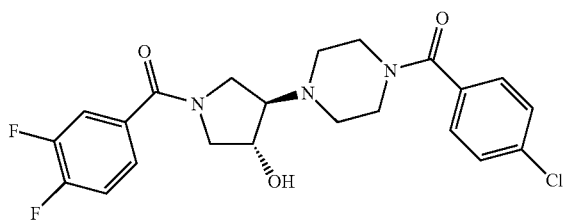 [SMILES: O=C(c1ccc(Cl)cc1)N1CCN([C@@H]2CN(C(=O)c3ccc(F)c(F)c3)C[C@H]2O)CC1]

87
4-[4-(4-chlorobenzoyl)piperazin-1-yl]-1-(3,4-
difluorobenzoyl)pyrrolidin-3-ol

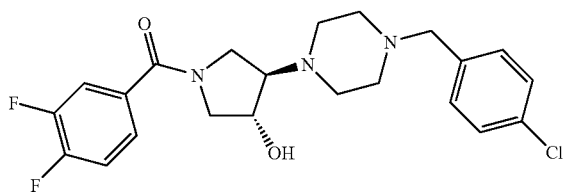 [SMILES: O=C(c1ccc(F)c(F)c1)N1C[C@@H](O)[C@H](N2CCN(Cc3ccc(Cl)cc3)CC2)C1]

88
4-[4-(4-chlorobenzyl)piperazin-1-yl]-1-(3,4-
difluorobenzoyl)pyrrolidin-3-ol

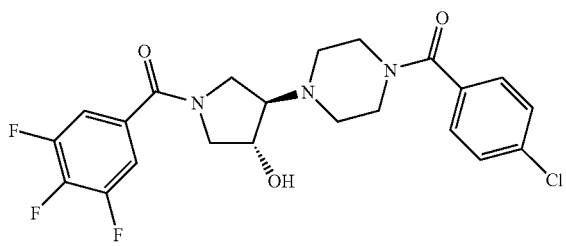 [SMILES: O=C(c1ccc(Cl)cc1)N1CCN([C@@H]2CN(C(=O)c3cc(F)c(F)c(F)c3)C[C@H]2O)CC1]

89
4-[4-(4-chlorobenzoyl)piperazin-1-yl]-1-
(3,4,5-trifluorobenzoyl)pyrrolidin-3-ol

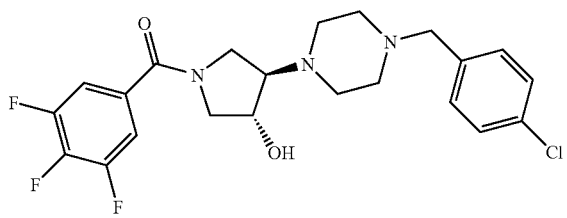 [SMILES: O=C(c1cc(F)c(F)c(F)c1)N1C[C@@H](O)[C@H](N2CCN(Cc3ccc(Cl)cc3)CC2)C1]

90
4-[4-(4-chlorobenzoyl)piperazin-1-yl]-1-
(3,4,5-trifluorobenzoyl)pyrrolidin-3-ol TABLE 1-continued Examples of Compounds of Formula I-A:

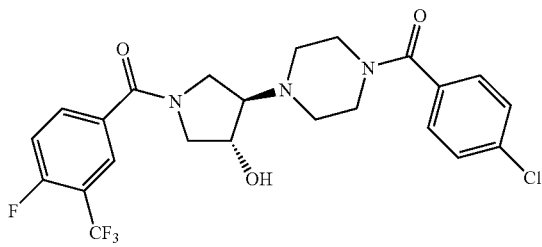 [SMILES: O=C(c1ccc(Cl)cc1)N1CCN([C@@H]2CN(C(=O)c3ccc(F)c(C(F)(F)F)c3)C[C@H]2O)CC1]

91
4-[4-(4-chlorobenzoyl)piperazin-1-yl]-1-[4-
fluoro-3-(trifluoromethyl)benzoyl]pyrrolidin-3-ol

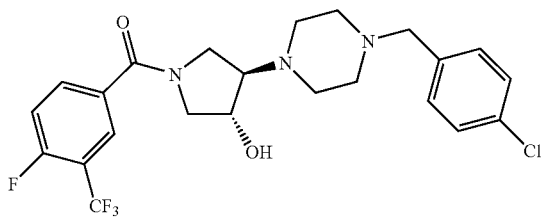 [SMILES: O=C(c1ccc(F)c(C(F)(F)F)c1)N1C[C@@H](O)[C@H](N2CCN(Cc3ccc(Cl)cc3)CC2)C1]

92
4-[4-(4-chlorobenzyl)piperazin-1-yl]-1-[4-
fluoro-3-(trifluoromethyl)benzoyl]pyrrolidin-3-ol

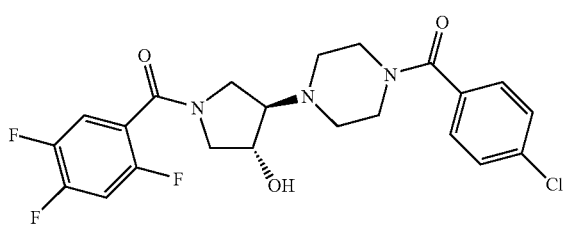 [SMILES: O=C(c1ccc(Cl)cc1)N1CCN([C@@H]2CN(C(=O)c3cc(F)c(F)cc3F)C[C@H]2O)CC1]

93
4-[4-(4-chlorobenzoyl)piperazin-1-yl]-1-
(2,4,5-trifluorobenzoyl)pyrrolidin-3-ol

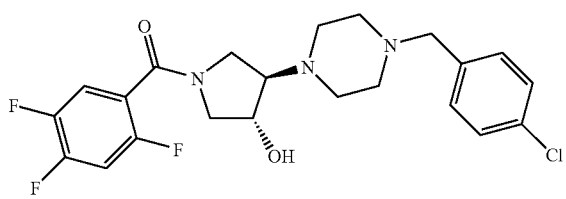 [SMILES: O=C(c1cc(F)c(F)cc1F)N1C[C@@H](O)[C@H](N2CCN(Cc3ccc(Cl)cc3)CC2)C1]

94
4-[4-(4-chlorobenzyl)piperazin-1-yl]-1-
(2,4,5-trifluorobenzoyl)pyrrolidin-3-ol

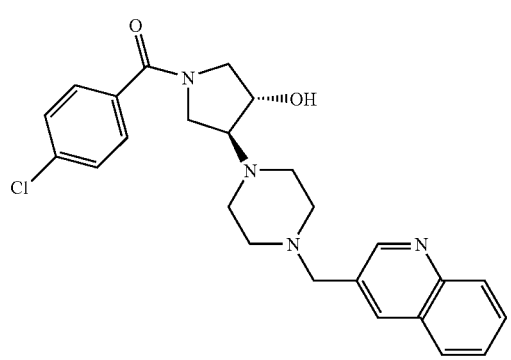 [SMILES: O=C(c1ccc(Cl)cc1)N1C[C@H](O)[C@@H](N2CCN(Cc3cnc4ccccc4c3)CC2)C1]

95
1-(4-chlorobenzoyl)-4-[4-(quinolin-3-
ylmethyl)piperazin-1-yl]pyrrolidin-3-ol TABLE 1-continued
Examples of Compounds of Formula I-A:
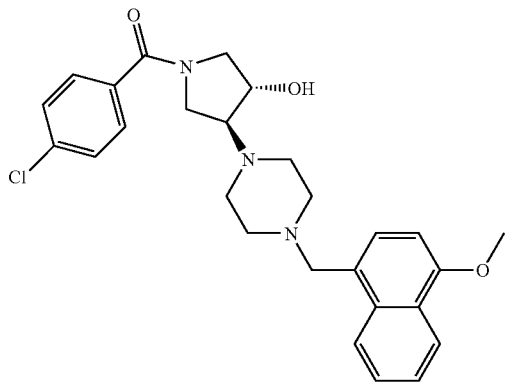 [SMILES: COc1ccc(CN2CCN([C@H]3CN(C(=O)c4ccc(Cl)cc4)C[C@@H]3O)CC2)c2ccccc12]
96
1-(4-chlorobenzoyl)-4-{4-[(4-methoxy-1-
naphthyl)methyl]piperazin-1-yl}pyrrolidin-3-ol
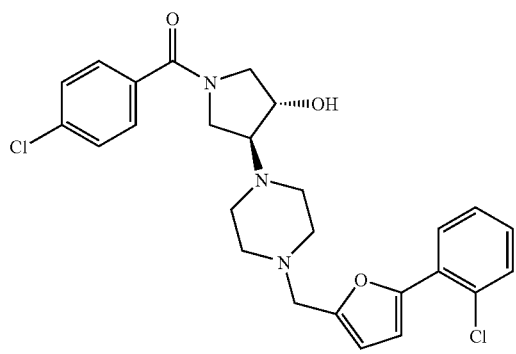 [SMILES: O=C(c1ccc(Cl)cc1)N1C[C@H](O)[C@@H](N2CCN(Cc3ccc(-c4ccccc4Cl)o3)CC2)C1]
97
1-(4-chlorobenzoyl)-4-(4-{[5-(2-
chlorophenyl)-2-furyl]methyl}piperazin-1-
yl)pyrrolidin-3-ol
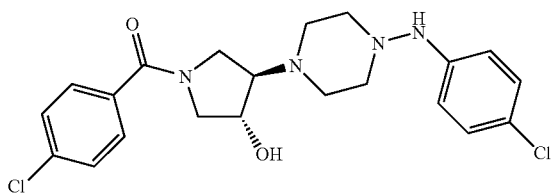 [SMILES: O=C(c1ccc(Cl)cc1)N1C[C@@H](O)[C@H](N2CCN(Nc3ccc(Cl)cc3)CC2)C1]
98
1-(4-chlorobenzoyl)-4-{4-[(4-chloro-
phenyl)amino]piperidin-1-yl}pyrrolidin-3-ol
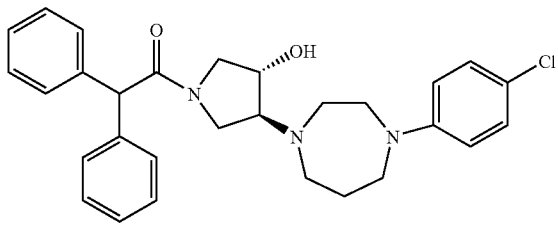 [SMILES: O=C(C(c1ccccc1)c1ccccc1)N1C[C@H](O)[C@@H](N2CCCN(c3ccc(Cl)cc3)CC2)C1]
99
4-[4-(4-chlorophenyl)-1,4-diazepan-1-yl]-1-
(diphenylacetyl)pyrrolidin-3-ol TABLE 1-continued
Examples of Compounds of Formula I-A:
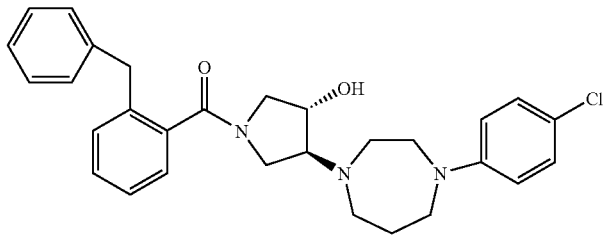 [SMILES: O=C(c1ccccc1Cc1ccccc1)N1C[C@H](O)[C@@H](N2CCCN(c3ccc(Cl)cc3)CC2)C1]
100
1-(2-benzylbenzoyl)-4-[4-(4-chlorophenyl)-
1,4-diazepan-1-yl]pyrrolidin-3-ol
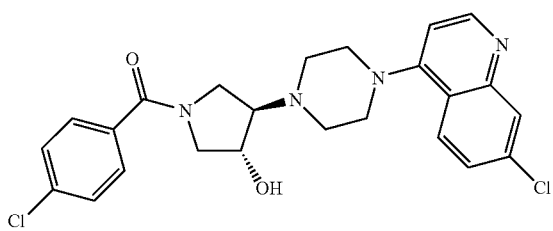 [SMILES: O=C(c1ccc(Cl)cc1)N1C[C@@H](O)[C@H](N2CCN(c3ccnc4cc(Cl)ccc34)CC2)C1]
101
1-(4-chlorobenzoyl)-4-[4-(7-chloroquinolin-
4-yl)piperazin-1-yl]pyrrolidin-3-ol
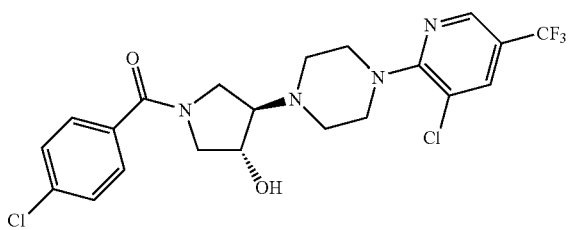 [SMILES: O=C(c1ccc(Cl)cc1)N1C[C@@H](O)[C@H](N2CCN(c3ncc(C(F)(F)F)cc3Cl)CC2)C1]
102
1-(4-chlorobenzoyl)-4-{4-[3-chloro-5-
(trifluoromethyl)pyridin-2-yl]piperazin-1-
yl}pyrrolidin-3-ol
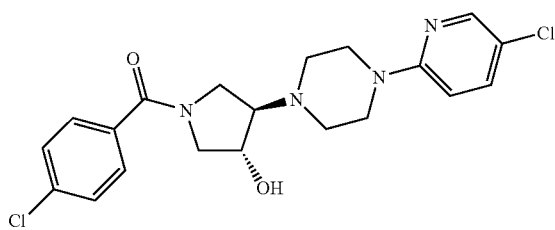 [SMILES: O=C(c1ccc(Cl)cc1)N1C[C@@H](O)[C@H](N2CCN(c3ccc(Cl)cn3)CC2)C1]
103
1-(4-chlorobenzoyl)-4-[4-(5-chloropyridin-2-
yl)piperazin-1-yl]pyrrolidin-3-ol

TABLE 1-continued
Examples of Compounds of Formula I-A:
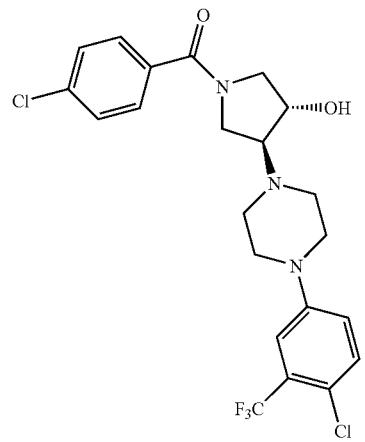 [SMILES: O=C(c1ccc(Cl)cc1)N1C[C@H](O)[C@@H](N2CCN(c3ccc(Cl)c(C(F)(F)F)c3)CC2)C1]
104
1-(4-chlorobenzoyl)-4-{4-[4-chloro-3-
(trifluoromethyl)phenyl]piperazin-1-
yl}pyrrolidin-3-ol
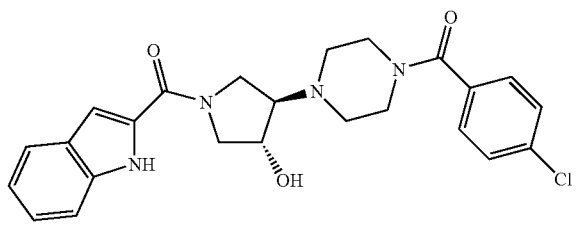 [SMILES: O=C(c1ccc(Cl)cc1)N1CCN([C@@H]2CN(C(=O)c3cc4ccccc4[nH]3)C[C@H]2O)CC1]
105
4-[4-(4-chlorobenzoyl)piperazin-1-yl]-1-(1H-
indol-2-ylcarbonyl)pyrrolidin-3-ol
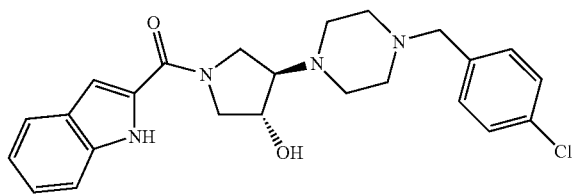 [SMILES: O=C(c1cc2ccccc2[nH]1)N1C[C@@H](O)[C@H](N2CCN(Cc3ccc(Cl)cc3)CC2)C1]
106
4-[4-(4-chlorobenzyl)piperazin-1-yl]-1-(1H-
indol-2-ylcarbonyl)pyrrolidin-3-ol
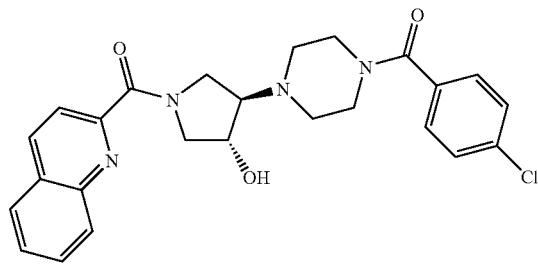 [SMILES: O=C(c1ccc(Cl)cc1)N1CCN([C@@H]2CN(C(=O)c3ccc4ccccc4n3)C[C@H]2O)CC1]
107
4-[4-(4-chlorobenzoyl)piperazin-1-yl]-1-
(quinolin-2-ylcarbonyl)pyrrolidin-3-ol TABLE 1-continued Examples of Compounds of Formula I-A:

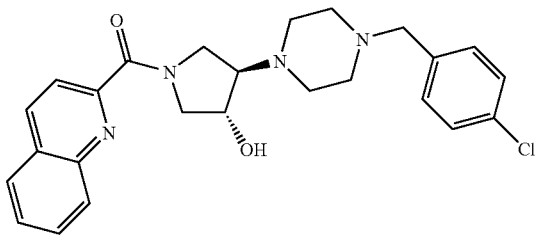 [SMILES: O=C(c1ccc2ccccc2n1)N1C[C@@H](O)[C@H](N2CCN(Cc3ccc(Cl)cc3)CC2)C1]

108
4-[4-(4-chlorobenzyl)piperazin-1-yl]-1-
(quinolin-2-ylcarbonyl)pyrrolidin-3-ol

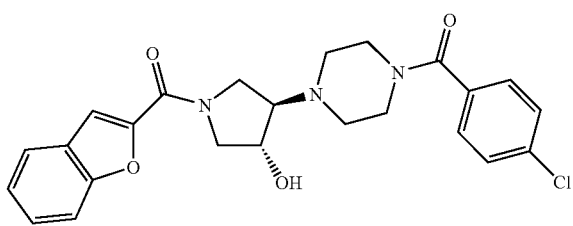 [SMILES: O=C(c1ccc(Cl)cc1)N1CCN([C@@H]2CN(C(=O)c3cc4ccccc4o3)C[C@H]2O)CC1]

109
1-(1-benzofuran-2-ylcarbonyl)-4-[4-(4-
chlorobenzoyl)piperazin-1-yl]pyrrolidin-3-ol

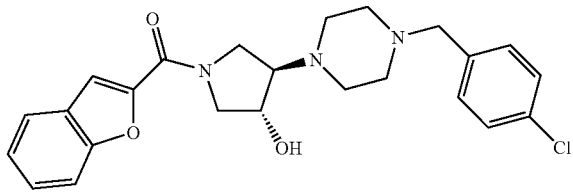 [SMILES: O=C(c1cc2ccccc2o1)N1C[C@@H](O)[C@H](N2CCN(Cc3ccc(Cl)cc3)CC2)C1]

110
1-(1-benzofuran-2-ylcarbonyl)-4-[4-(4-
chlorobenzyl)piperazin-1-yl]pyrrolidin-3-ol

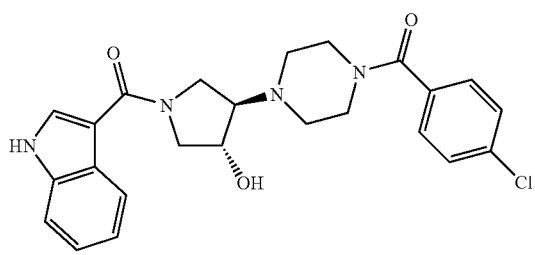 [SMILES: O=C(c1ccc(Cl)cc1)N1CCN([C@@H]2CN(C(=O)c3c[nH]c4ccccc34)C[C@H]2O)CC1]

111
4-[4-(4-chlorobenzoyl)piperazin-1-yl]-1-(1H-
indol-3-ylcarbonyl)pyrrolidin-3-ol

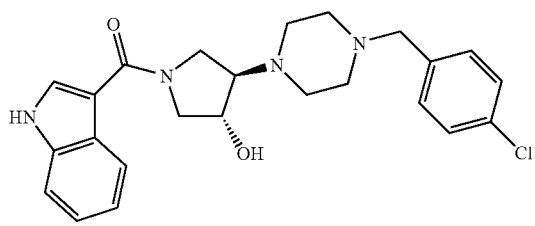 [SMILES: O=C(c1c[nH]c2ccccc12)N1C[C@@H](O)[C@H](N2CCN(Cc3ccc(Cl)cc3)CC2)C1]

113
4-[4-(4-chlorobenzyl)piperazin-1-yl]-1-(1H-
indol-3-ylcarbonyl)pyrrolidin-3-ol TABLE 1-continued Examples of Compounds of Formula I-A:

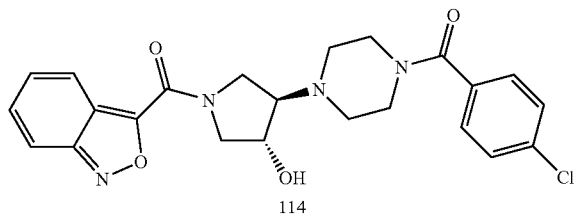

114

1-(2,1-benzisoxazol-3-ylcarbonyl)-4-[4-(4-chlorobenzoyl)piperazin-1-yl]pyrrolidin-3-ol

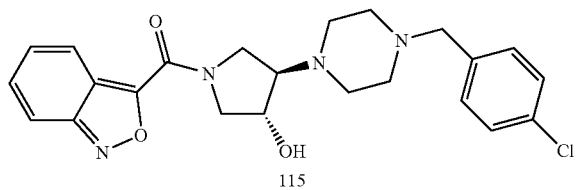

115

1-(2,1-benzisoxazol-3-ylcarbonyl)-4-[4-(4-chlorobenzyl)piperazin-1-yl]pyrrolidin-3-ol

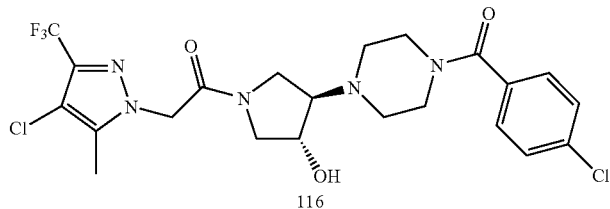

116

4-[4-(4-chlorobenzoyl)piperazin-1-yl]-1-{[4-chloro-5-methyl-3-(trifluoromethyl)-1H-pyrazol-1-yl]acetyl}pyrrolidin-3-ol

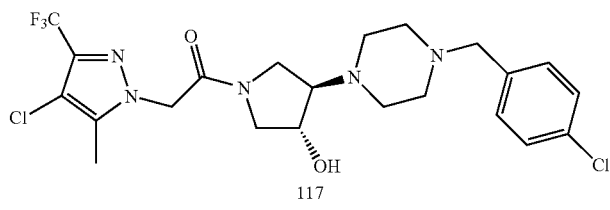

117

4-[4-(4-chlorobenzyl)piperazin-1-yl]-1-{[4-chloro-5-methyl-3-(trifluoromethyl)-1H-pyrazol-1-yl]acetyl}pyrrolidin-3-ol

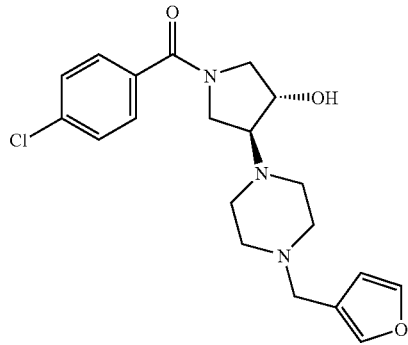 [SMILES: O=C(c1ccc(Cl)cc1)N1C[C@H](O)[C@@H](N2CCN(Cc3ccoc3)CC2)C1]

118

1-(4-chlorobenzoyl)-4-[4-(3-furylmethyl)piperazin-1-yl]pyrrolidin-3-ol

TABLE 1-continued
Examples of Compounds of Formula I-A:
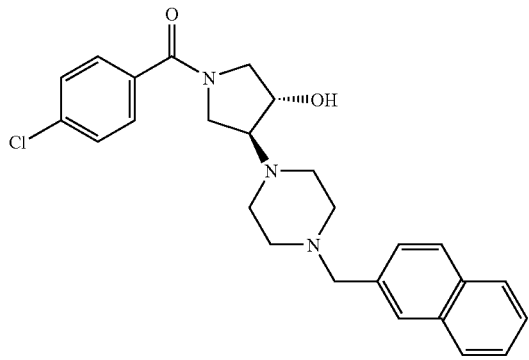 [SMILES: O=C(c1ccc(Cl)cc1)N1C[C@H](O)[C@@H](N2CCN(Cc3ccc4ccccc4c3)CC2)C1]
119
1-(4-chlorobenzoyl)-4-[4-(2-naphthylmethyl)piperazin-1-yl]pyrrolidin-3-ol
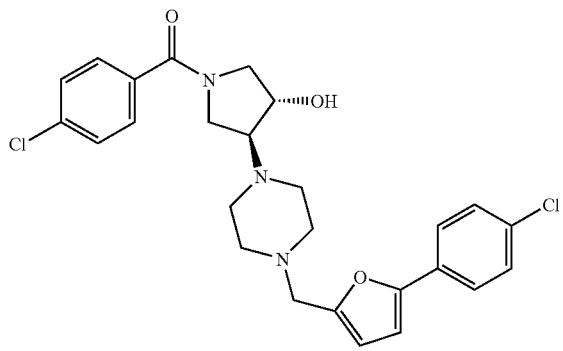 [SMILES: O=C(c1ccc(Cl)cc1)N1C[C@H](O)[C@@H](N2CCN(Cc3ccc(-c4ccc(Cl)cc4)o3)CC2)C1]
120
1-(4-chlorobenzoyl)-4-(4-{[5-(4-chlorophenyl)-2-furyl]methyl}piperazin-1-yl)pyrrolidin-3-ol
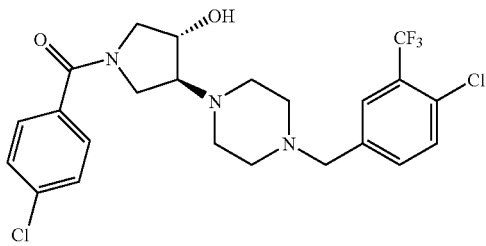 [SMILES: O=C(c1ccc(Cl)cc1)N1C[C@H](O)[C@@H](N2CCN(Cc3ccc(Cl)c(C(F)(F)F)c3)CC2)C1]
121
1-(4-chlorobenzoyl)-4-{4-[4-chloro-3-(trifluoromethyl)benzyl]piperazin-1-yl}pyrrolidin-3-ol
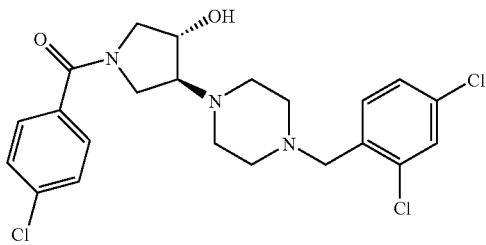 [SMILES: O=C(c1ccc(Cl)cc1)N1C[C@H](O)[C@@H](N2CCN(Cc3ccc(Cl)cc3Cl)CC2)C1]
122
1-(4-chlorobenzoyl)-4-[4-(2,4-dichlorobenzyl)piperazin-1-yl]pyrrolidin-3-ol TABLE 1-continued Examples of Compounds of Formula I-A:

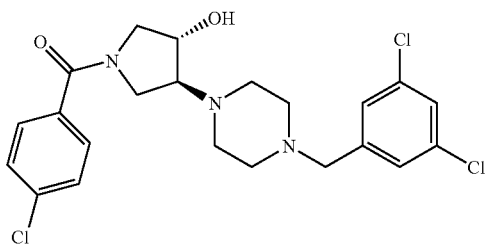 [SMILES: O=C(c1ccc(Cl)cc1)N1C[C@H](O)[C@@H](N2CCN(Cc3cc(Cl)cc(Cl)c3)CC2)C1]

123
1-(4-chlorobenzoyl)-4-[4-(3,5-dichloro-
benzyl)piperazin-1-yl]pyrrolidin-3-ol

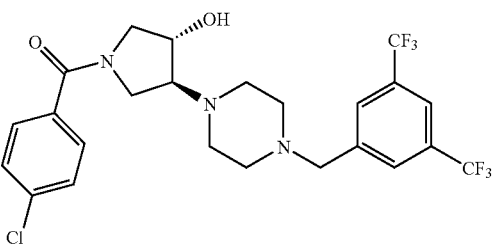 [SMILES: O=C(c1ccc(Cl)cc1)N1C[C@H](O)[C@@H](N2CCN(Cc3cc(C(F)(F)F)cc(C(F)(F)F)c3)CC2)C1]

124
4-{4-[3,5-
bis(trifluoromethyl)benzyl]piperazin-1-yl}-1-
(4-chlorobenzoyl)pyrrolidin-3-ol

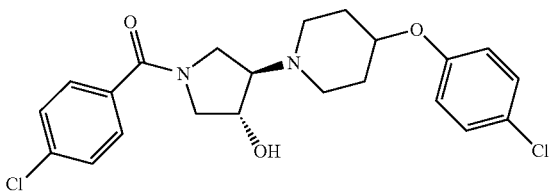 [SMILES: O=C(c1ccc(Cl)cc1)N1C[C@@H](O)[C@H](N2CCC(Oc3ccc(Cl)cc3)CC2)C1]

125
1-(4-chlorobenzoyl)-4-[4-(4-chloro-
phenoxy)piperidin-1-yl]pyrrolidin-3-ol

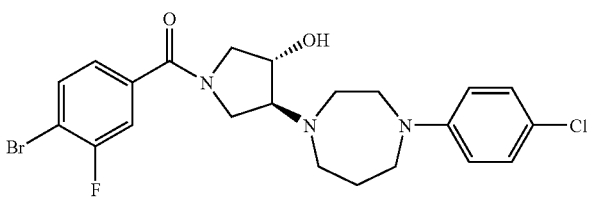 [SMILES: O=C(c1ccc(Br)c(F)c1)N1C[C@H](O)[C@@H](N2CCCN(c3ccc(Cl)cc3)CC2)C1]

126
1-(4-bromo-3-fluorobenzoyl)-4-[4-(4-chloro-
phenyl)-1,4-diazepan-1-yl]pyrrolidin-3-ol

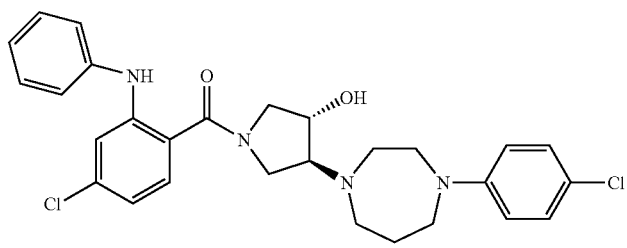 [SMILES: O=C(c1ccc(Cl)cc1Nc1ccccc1)N1C[C@H](O)[C@@H](N2CCCN(c3ccc(Cl)cc3)CC2)C1]

127
1-(2-anilino-4-chlorobenzoyl)-4-[4-(4-
chloro-phenyl)-1,4-diazepan-1-yl]pyrrolidin-3-ol TABLE 1-continued
Examples of Compounds of Formula I-A:
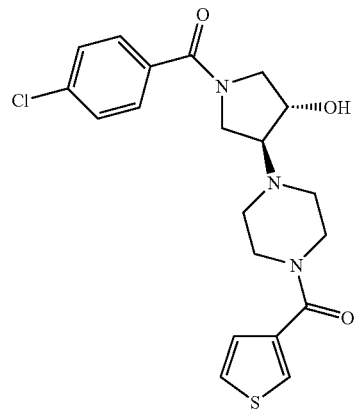 [SMILES: O=C(c1ccsc1)N1CCN([C@H]2CN(C(=O)c3ccc(Cl)cc3)C[C@@H]2O)CC1]
128
1-(4-chlorobenzoyl)-4-[4-(3-thienylcarbonyl)-piperazin-1-yl]pyrrolidin-3-ol
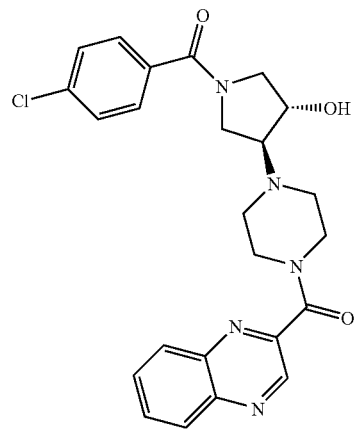 [SMILES: O=C(c1ccc(Cl)cc1)N1C[C@H](O)[C@@H](N2CCN(C(=O)c3cnc4ccccc4n3)CC2)C1]
129
1-(4-chlorobenzoyl)-4-[4-(quinoxalin-2-ylcarbonyl)piperazin-1-yl]pyrrolidin-3-ol
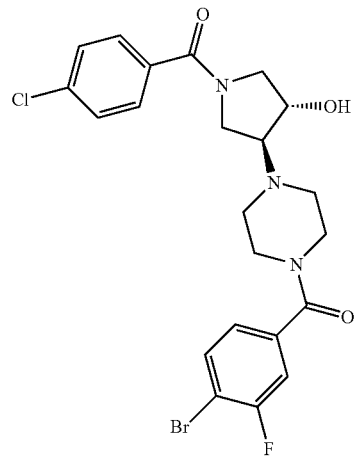 [SMILES: O=C(c1ccc(Br)c(F)c1)N1CCN([C@H]2CN(C(=O)c3ccc(Cl)cc3)C[C@@H]2O)CC1]
130
4-[4-(4-bromo-3-fluorobenzoyl)piperazin-1-yl]-1-(4-chlorobenzoyl)pyrrolidin-3-ol TABLE 1-continued Examples of Compounds of Formula I-A:

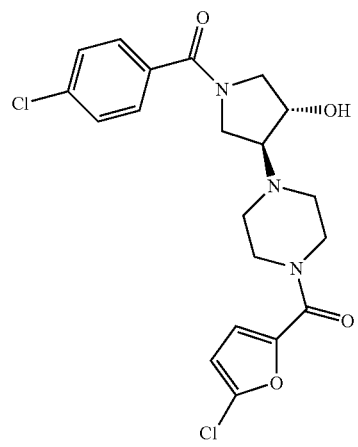 [SMILES: O=C(c1ccc(Cl)cc1)N1C[C@H](O)[C@@H](N2CCN(C(=O)c3ccc(Cl)o3)CC2)C1]

131
1-(4-chlorobenzoyl)-4-[4-(5-chloro-2-
furoyl)piperazin-1-yl]pyrrolidin-3-ol

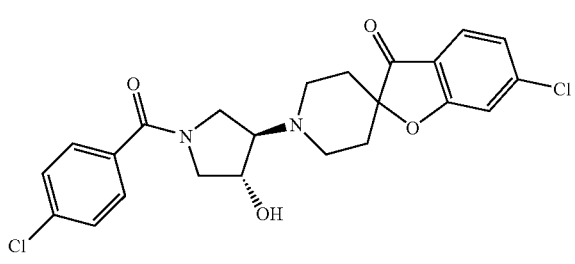 [SMILES: O=C(c1ccc(Cl)cc1)N1C[C@@H](O)[C@H](N2CCC3(CC2)Oc2cc(Cl)ccc2C3=O)C1]

132
6-chloro-1'-[1-(4-chlorobenzoyl)-4-hydroxy-
pyrrolidin-3-yl]-3H-spiro[1-benzofuran-2,4'-
piperidin]-3-one

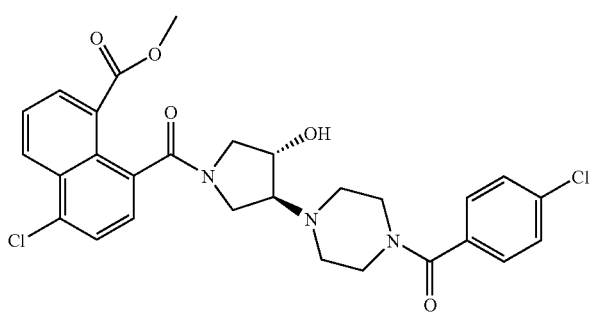 [SMILES: COC(=O)c1cccc2c(Cl)ccc(C(=O)N3C[C@H](O)[C@@H](N4CCN(C(=O)c5ccc(Cl)cc5)CC4)C3)c12]

133
methyl 5-chloro-8-({3-[4-(4-chlorobenzoyl)-
piperazin-1-yl]-4-hydroxypyrrolidin-1-
yl}carbonyl)-1-naphthoate

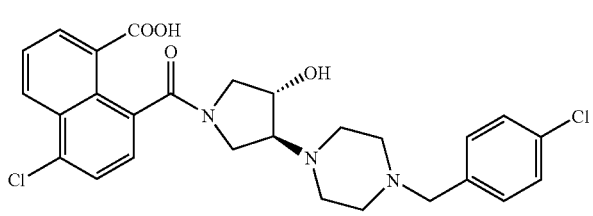 [SMILES: O=C(O)c1cccc2c(Cl)ccc(C(=O)N3C[C@H](O)[C@@H](N4CCN(Cc5ccc(Cl)cc5)CC4)C3)c12]

134
5-chloro-8-({3-[4-(4-chlorobenzyl)piperazin-
1-yl]-4-hydroxypyrrolidin-1-yl}carbonyl)-1-
naphthoic acid TABLE 1-continued
Examples of Compounds of Formula I-A:
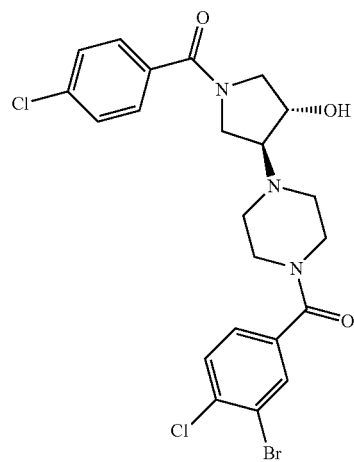
135
4-[4-(3-bromo-4-chlorobenzoyl)piperazin-1-
yl]-1-(4-chlorobenzoyl)pyrrolidin-3-ol
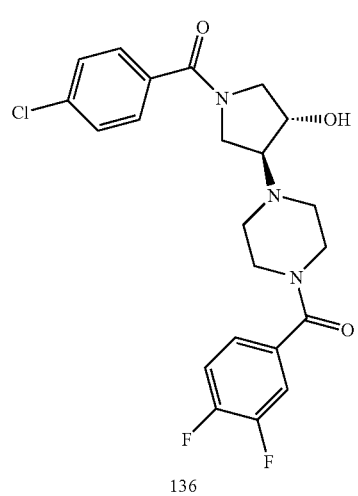
136
1-(4-chlorobenzoyl)-4-[4-(3,4-
difluorobenzoyl)piperazin-1-yl]pyrrolidin-3-ol
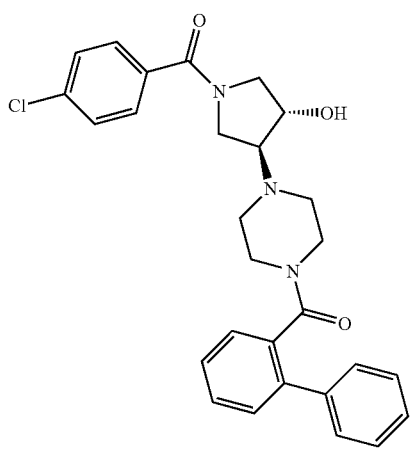 [SMILES: O=C(c1ccc(Cl)cc1)N1C[C@H](O)[C@@H](N2CCN(C(=O)c3ccccc3-c3ccccc3)CC2)C1]
137
4-[4-(biphenyl-2-ylcarbonyl)piperazin-1-yl]-
1-(4-chlorobenzoyl)pyrrolidin-3-ol TABLE 1-continued
Examples of Compounds of Formula I-A:
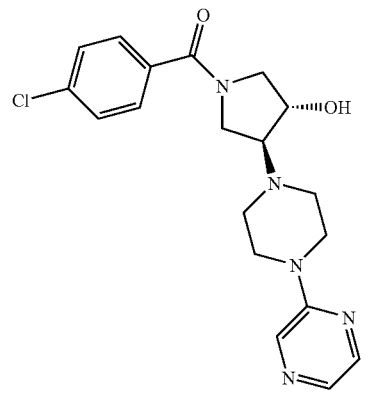 [SMILES: O=C(c1ccc(Cl)cc1)N1C[C@H](O)[C@@H](N2CCN(c3cnccn3)CC2)C1]
138
1-(4-chlorobenzoyl)-4-(4-pyrazin-2-
ylpiperazin-1-yl)pyrrolidin-3-ol
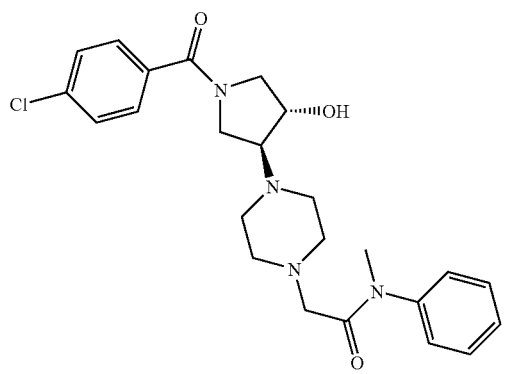 [SMILES: CN(C(=O)CN1CCN([C@H]2CN(C(=O)c3ccc(Cl)cc3)C[C@@H]2O)CC1)c1ccccc1]
139
2-{4-[1-(4-chlorobenzoyl)-4-
hydroxypyrrolidin-3-yl]piperazin-1-yl}-N-
methyl-N-phenylacetamide
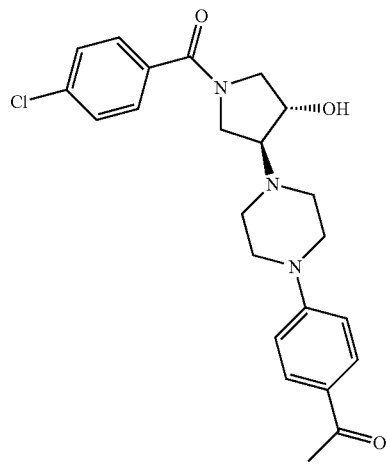 [SMILES: CC(=O)c1ccc(N2CCN([C@H]3CN(C(=O)c4ccc(Cl)cc4)C[C@@H]3O)CC2)cc1]
140
1-(4-{4-[1-(4-chlorobenzoyl)-4-
hydroxypyrrolidin-3-yl]piperazin-1-yl}-
phenyl)ethanone TABLE 1-continued Examples of Compounds of Formula I-A:

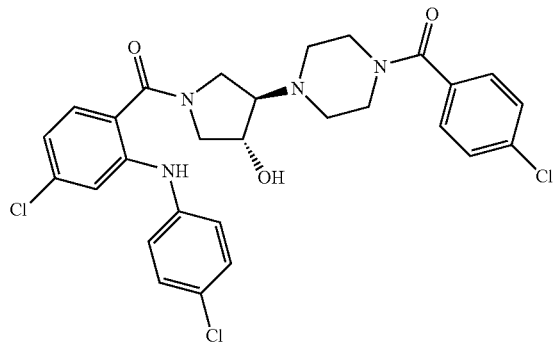 [SMILES: O=C(c1ccc(Cl)cc1)N1CCN([C@@H]2CN(C(=O)c3ccc(Cl)cc3Nc3ccc(Cl)cc3)C[C@H]2O)CC1]

141
4-[4-(4-chlorobenzoyl)piperazin-1-yl]-1-{4-
chloro-2-[(4-chlorophenyl)amino]-benzoyl}-
pyrrolidin-3-ol

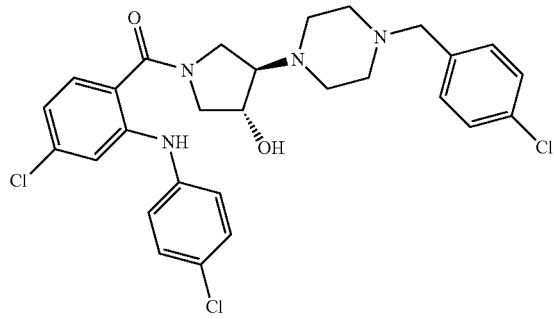 [SMILES: O=C(c1ccc(Cl)cc1Nc1ccc(Cl)cc1)N1C[C@@H](O)[C@H](N2CCN(Cc3ccc(Cl)cc3)CC2)C1]

142
4-[4-(4-chlorobenzyl)piperazin-1-yl]-1-{4-
chloro-2-[(4-chlorophenyl)amino]-benzoyl}-
pyrrolidin-3-ol

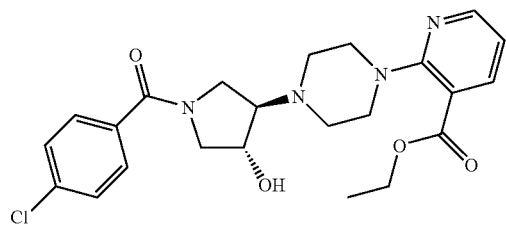 [SMILES: CCOC(=O)c1cccnc1N1CCN([C@@H]2CN(C(=O)c3ccc(Cl)cc3)C[C@H]2O)CC1]

143
Ethyl 2-(4-{1-[(4-chlorophenyl)carbonyl]-4-
hydroxypyrrolidin-3-yl}piperazin-1-
yl)pyridine-3-carboxylate

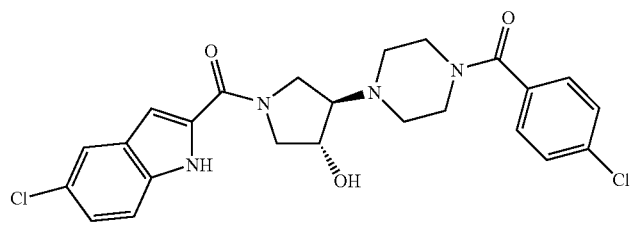 [SMILES: O=C(c1ccc(Cl)cc1)N1CCN([C@@H]2CN(C(=O)c3cc4cc(Cl)ccc4[nH]3)C[C@H]2O)CC1]

144
1-[(5-chloro-1H-indol-2-yl)carbonyl]-4-{4-
[(4-chlorophenyl)carbonyl]piperazin-1-yl}-
pyrrolidin-3-ol TABLE 1-continued Examples of Compounds of Formula I-A:

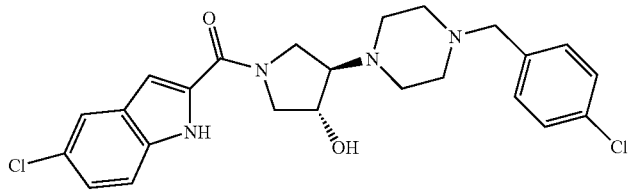 [SMILES: O=C(c1cc2cc(Cl)ccc2[nH]1)N1C[C@@H](O)[C@H](N2CCN(Cc3ccc(Cl)cc3)CC2)C1]

145

1-[(5-chloro-1H-indol-2-yl)carbonyl]-4-{4-
[(4-chlorophenyl)methyl]piperazin-1-
yl}pyrrolidin-3-ol

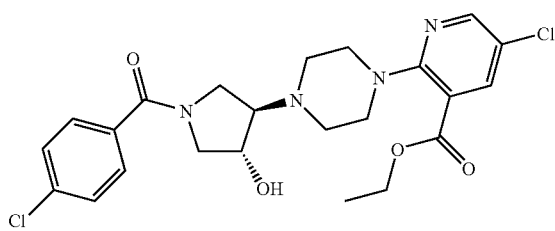 [SMILES: CCOC(=O)c1cc(Cl)cnc1N1CCN([C@@H]2CN(C(=O)c3ccc(Cl)cc3)C[C@H]2O)CC1]

146

Ethyl 5-chloro-2-(4-{-1-[(4-
chlorophenyl)carbonyl]-4-hydroxypyrrolidin-
3-yl}piperazin-1-yl)pyridine-3-carboxylate

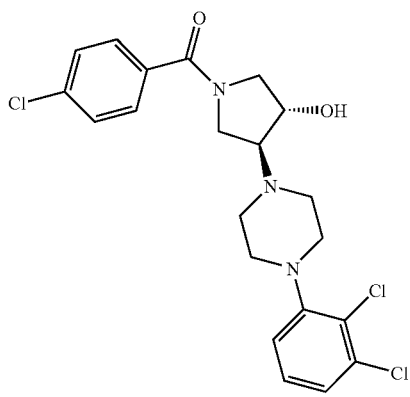 [SMILES: O=C(c1ccc(Cl)cc1)N1C[C@H](O)[C@@H](N2CCN(c3cccc(Cl)c3Cl)CC2)C1]

147

1-[(4-chlorophenyl)carbonyl]-4-[4-(2,3-
dichlorophenyl)piperazin-1-yl]pyrrolidin-3-ol

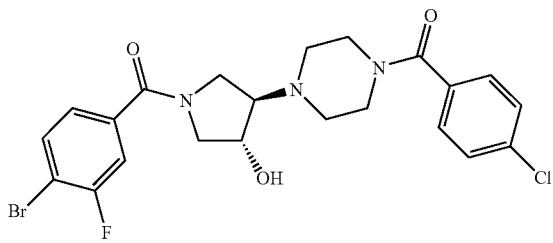

148

1-[(4-bromo-3-fluorophenyl)carbonyl]-4-{4-
[(4-chlorophenyl)carbonyl]piperazin-1-
yl}pyrrolidin-3-ol TABLE 1-continued Examples of Compounds of Formula I-A:

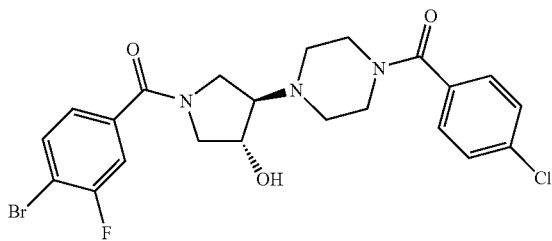 [SMILES: O=C(c1ccc(Cl)cc1)N1CCN([C@@H]2CN(C(=O)c3ccc(Br)c(F)c3)C[C@H]2O)CC1]

149
1-[(4-bromo-3-fluorophenyl)carbonyl]-4-{4-
[(4-chlorophenyl)carbonyl]piperazin-1-
yl}pyrrolidin-3-ol

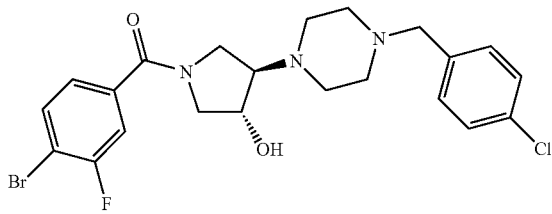

150
1-[(4-bromo-3-fluorophenyl)carbonyl]-4-{4-
[(4-chlorophenyl)methyl]piperazin-1-yl}-
pyrrolidin-3-ol

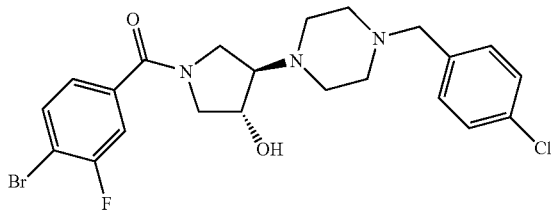

151
1-[(4-bromo-3-fluorophenyl)carbonyl]-4-{4-
[(4-chlorophenyl)methyl]piperazin-1-yl}-
pyrrolidin-3-ol

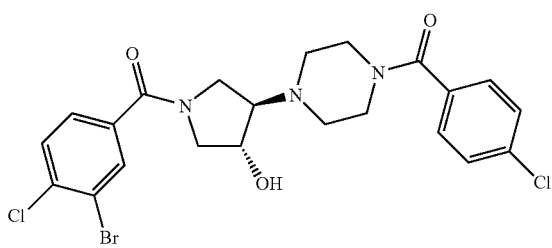 [SMILES: O=C(c1ccc(Cl)cc1)N1CCN([C@@H]2CN(C(=O)c3ccc(Cl)c(Br)c3)C[C@H]2O)CC1]

152
1-[(3-bromo-4-chlorophenyl)carbonyl]-4-{4-
[(4-chlorophenyl)carbonyl]piperazin-1-yl}-
pyrrolidin-3-ol

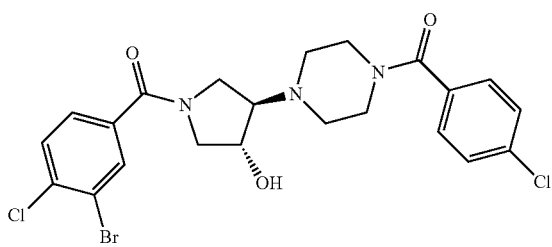 [SMILES: O=C(c1ccc(Cl)cc1)N1CCN([C@@H]2CN(C(=O)c3ccc(Cl)c(Br)c3)C[C@H]2O)CC1]

153
1-[(3-bromo-4-chlorophenyl)carbonyl]-4-{4-
[(4-chlorophenyl)carbonyl]piperazin-1-yl}-
pyrrolidin-3-ol TABLE 1-continued Examples of Compounds of Formula I-A:

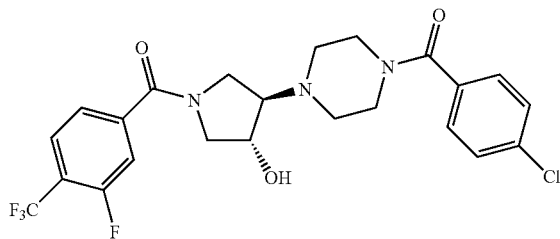 [SMILES: O=C(c1ccc(Cl)cc1)N1CCN([C@@H]2CN(C(=O)c3ccc(C(F)(F)F)c(F)c3)C[C@H]2O)CC1]

154

4-{4-[(4-chlorophenyl)carbonyl]piperazin-1-
yl}-1-{[3-fluoro-4-(trifluoromethyl)phenyl]-
carbonyl}pyrrolidin-3-ol

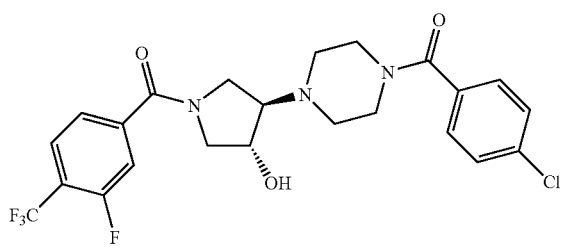 [SMILES: O=C(c1ccc(Cl)cc1)N1CCN([C@@H]2CN(C(=O)c3ccc(C(F)(F)F)c(F)c3)C[C@H]2O)CC1]

155

4-{4-[(4-chlorophenyl)carbonyl]piperazin-1-
yl}-1-{[3-fluoro-4-(trifluoromethyl)phenyl]-
carbonyl}pyrrolidin-3-ol

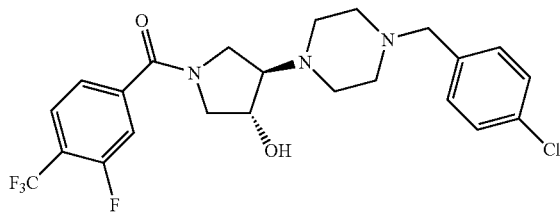 [SMILES: O=C(c1ccc(C(F)(F)F)c(F)c1)N1C[C@@H](O)[C@H](N2CCN(Cc3ccc(Cl)cc3)CC2)C1]

156

4-{4-[(4-chlorophenyl)methyl]piperazin-1-
yl}-1-{[3-fluoro-4-(trifluoromethyl)phenyl]-
carbonyl}pyrrolidin-3-ol

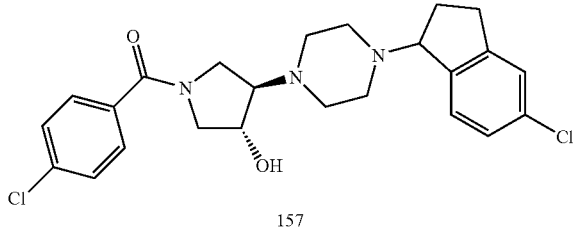

157

4-[4-(5-chloro-2,3-dihydro-1H-inden-1-
yl)piperazin-1-yl]-1-[(4-chlorophenyl)-
carbonyl]pyrrolidin-3-ol

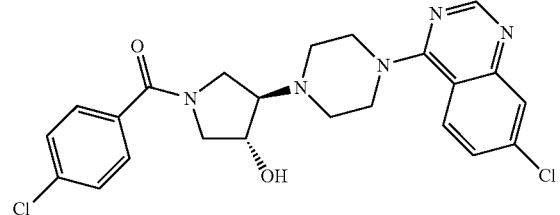

158

1-[(4-chlorophenyl)carbonyl]-4-[4-(7-
chloroquinazolin-4-yl)piperazin-1-
yl]pyrrolidin-3-ol TABLE 1-continued Examples of Compounds of Formula I-A:

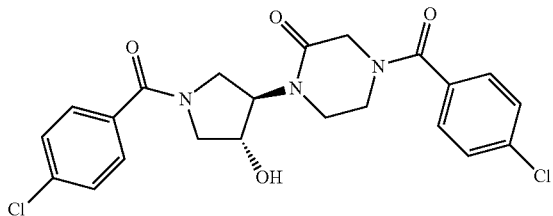 [SMILES: O=C(c1ccc(Cl)cc1)N1CCN([C@@H]2CN(C(=O)c3ccc(Cl)cc3)C[C@H]2O)C(=O)C1]

159
4-[(4-chlorophenyl)carbonyl]-1-{1-[(4-
chlorophenyl)carbonyl]-4-hydroxypyrrolidin-
3-yl}piperazin-2-one

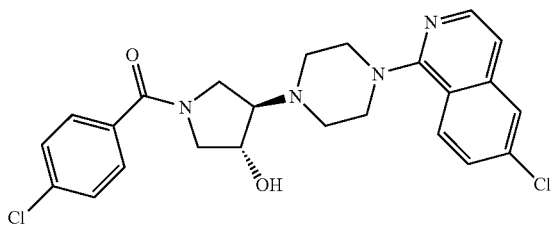 [SMILES: O=C(c1ccc(Cl)cc1)N1C[C@@H](O)[C@H](N2CCN(c3nccc4cc(Cl)ccc34)CC2)C1]

160
4-[4-(6-chloroisoquinolin-1-yl)piperazin-1-
yl]-1-[(4-chlorophenyl)carbonyl]pyrrolidin-3-ol

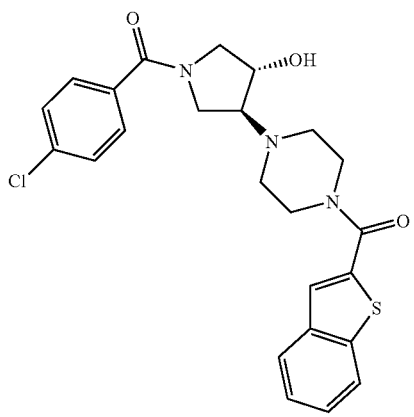 [SMILES: O=C(c1ccc(Cl)cc1)N1C[C@H](O)[C@@H](N2CCN(C(=O)c3cc4ccccc4s3)CC2)C1]

161
4-[4-(1-benzothien-2-ylcarbonyl)piperazin-1-
yl]-1-[(4-chlorophenyl)carbonyl]pyrrolidin-3-ol

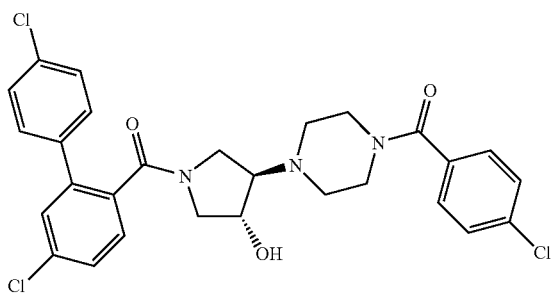 [SMILES: O=C(c1ccc(Cl)cc1)N1CCN([C@@H]2CN(C(=O)c3ccc(Cl)cc3-c3ccc(Cl)cc3)C[C@H]2O)CC1]

162
4-{4-[(4-chlorophenyl)carbonyl]piperazin-1-
yl}-1-[(4',5-dichlorobiphenyl-2-yl)carbonyl]-
pyrrolidin-3-ol Examples of Compounds of Formula I-A:
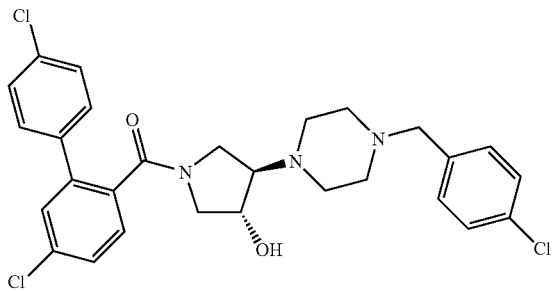 [SMILES: O=C(c1ccc(Cl)cc1-c1ccc(Cl)cc1)N1C[C@@H](O)[C@H](N2CCN(Cc3ccc(Cl)cc3)CC2)C1]
163
4-{4-[(4-chlorophenyl)methyl]piperazin-1-
yl}-1-[(4',5-dichlorobiphenyl-2-yl)carbonyl]-
pyrrolidin-3-ol
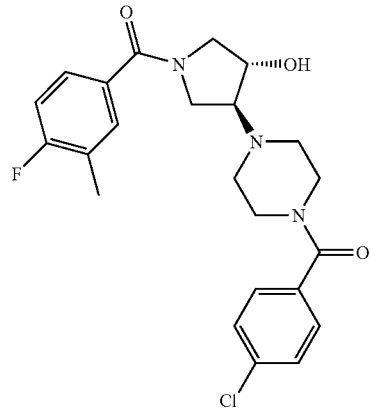 [SMILES: Cc1cc(C(=O)N2C[C@H](O)[C@@H](N3CCN(C(=O)c4ccc(Cl)cc4)CC3)C2)ccc1F]
164
4-{4-[(4-chlorophenyl)carbonyl]piperazin-1-
yl}-1-[(4-fluoro-3-methylphenyl)carbonyl]-
pyrrolidin-3-ol
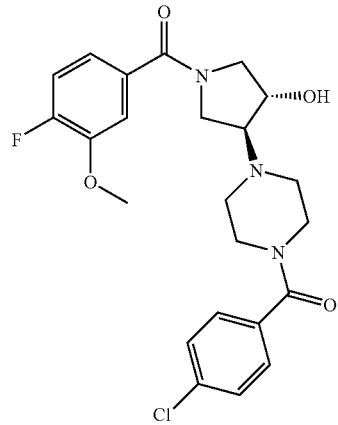 [SMILES: COc1cc(C(=O)N2C[C@H](O)[C@@H](N3CCN(C(=O)c4ccc(Cl)cc4)CC3)C2)ccc1F]
165
4-{4-[(4-chlorophenyl)carbonyl]piperazin-1-
yl}-1-{[4-fluoro-3-(methyloxy)phenyl]-
carbonyl}-pyrrolidin-3-ol TABLE 1-continued
Examples of Compounds of Formula I-A:
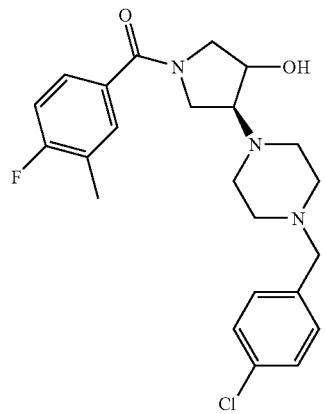 [SMILES: Cc1cc(C(=O)N2CC(O)[C@@H](N3CCN(Cc4ccc(Cl)cc4)CC3)C2)ccc1F]
166
(4S)-4-{4-[(4-
chlorophenyl)methyl]piperazin-1-yl}-1-[(4-
fluoro-3-methylphenyl)-carbonyl]-pyrrolidin-3-ol
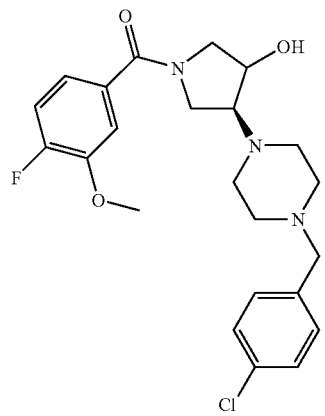 [SMILES: COc1cc(C(=O)N2CC(O)[C@@H](N3CCN(Cc4ccc(Cl)cc4)CC3)C2)ccc1F]
167
(4S)-4-{4-[(4-
chlorophenyl)methyl]piperazin-1-yl}-1-{[4-
fluoro-3-(methyloxy)phenyl]-
carbonyl}pyrrolidin-3-ol
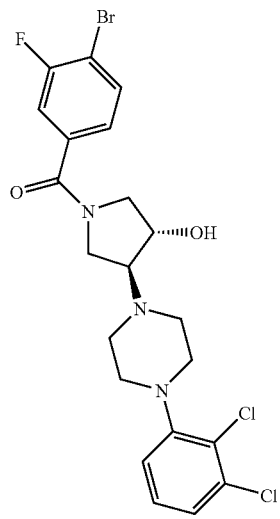 [SMILES: O=C(c1ccc(Br)c(F)c1)N1C[C@H](O)[C@@H](N2CCN(c3cccc(Cl)c3Cl)CC2)C1]
168
1-[(4-bromo-3-fluorophenyl)carbonyl]-4-[4-
(2,3-dichlorophenyl)piperazin-1-
yl]pyrrolidin-3-ol TABLE 1-continued Examples of Compounds of Formula I-A:

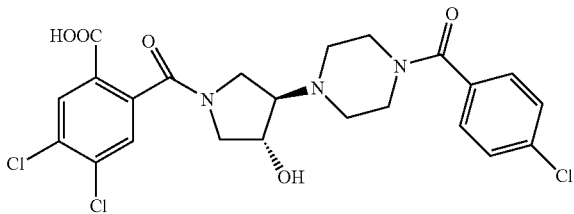 [SMILES: O=C(O)c1cc(Cl)c(Cl)cc1C(=O)N1C[C@@H](O)[C@H](N2CCN(C(=O)c3ccc(Cl)cc3)CC2)C1]

169

4,5-dichloro-2-[3-{4-[(4-chlorophenyl)-
carbonyl]piperazin-1-yl}-4-
hydroxypyrrolidin-1-yl)carbonyl]benzoic acid

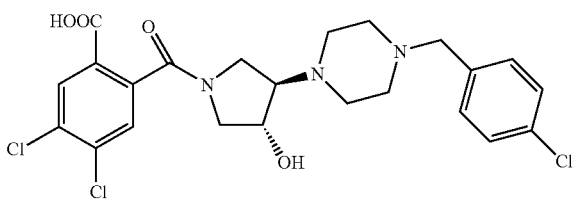 [SMILES: O=C(O)c1cc(Cl)c(Cl)cc1C(=O)N1C[C@@H](O)[C@H](N2CCN(Cc3ccc(Cl)cc3)CC2)C1]

170

4,5-dichloro-2-[(3-{4-[(4-chlorophenyl)-
methyl]piperazin-1-yl}-4-hydroxypyrrolidin-
1-yl)carbonyl]benzoic acid

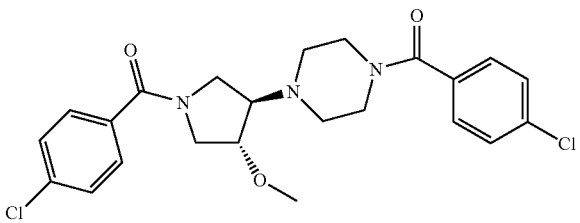 [SMILES: CO[C@@H]1CN(C(=O)c2ccc(Cl)cc2)C[C@H]1N1CCN(C(=O)c2ccc(Cl)cc2)CC1]

171

1-[(4-chlorophenyl)carbonyl]-4-[1-[(4-
chlorophenyl)carbonyl]-4-(methyloxy)-
pyrrolidin-3-yl]piperazine

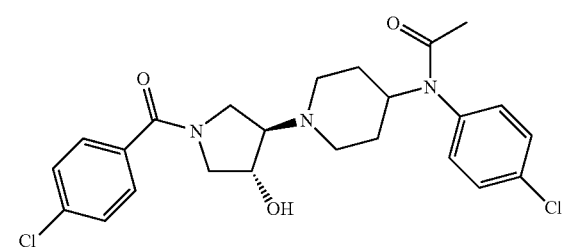 [SMILES: CC(=O)N(c1ccc(Cl)cc1)C1CCN([C@@H]2CN(C(=O)c3ccc(Cl)cc3)C[C@H]2O)CC1]

172

N-(4-chlorophenyl)-N-(1-{1-[(4-
chlorophenyl)-carbonyl]-4-
hydroxypyrrolidin-3-yl}piperidin-4-
yl)acetamide TABLE 1-continued
Examples of Compounds of Formula I-A:
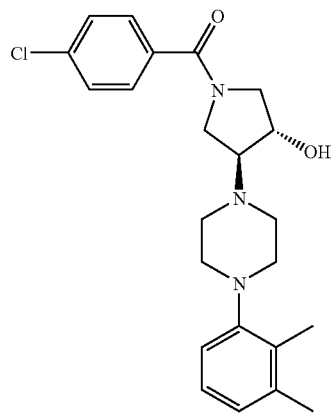 [SMILES: Cc1cccc(N2CCN([C@H]3CN(C(=O)c4ccc(Cl)cc4)C[C@@H]3O)CC2)c1C]
173
1-[(4-chlorophenyl)carbonyl]-4-[4-(2,3-
dimethylphenyl)piperazin-1-yl]pyrrolidin-3-ol
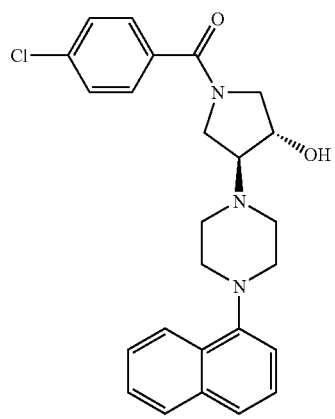 [SMILES: O=C(c1ccc(Cl)cc1)N1C[C@H](O)[C@@H](N2CCN(c3cccc4ccccc34)CC2)C1]
174
1-[(4-chlorophenyl)carbonyl]-4-(4-
naphthalen-1-ylpiperazin-1-yl)pyrrolidin-3-ol
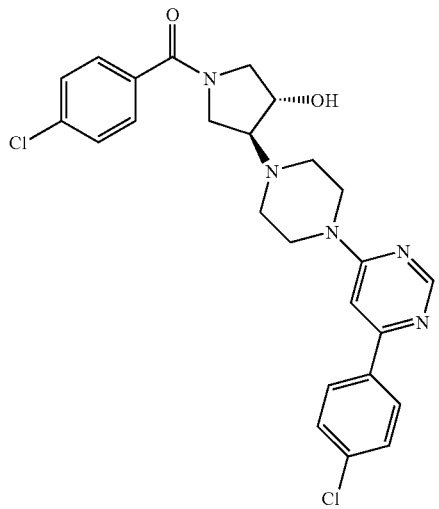 [SMILES: O=C(c1ccc(Cl)cc1)N1C[C@H](O)[C@@H](N2CCN(c3cc(-c4ccc(Cl)cc4)ncn3)CC2)C1]
175
1-[(4-chlorophenyl)carbonyl]-4-{4-[6-(4-
chlorophenyl)pyrimidin-4-yl]piperazin-1-yl}-
pyrrolidin-3-ol TABLE 1-continued
Examples of Compounds of Formula I-A:
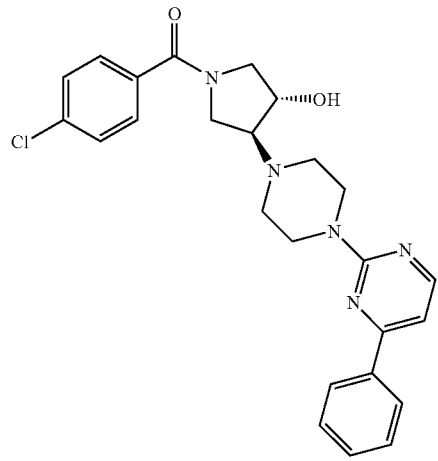 [SMILES: O=C(c1ccc(Cl)cc1)N1C[C@H](O)[C@@H](N2CCN(c3nccc(-c4ccccc4)n3)CC2)C1]
176
1-[(4-chlorophenyl)carbonyl]-4-[4-(4-
phenyl-pyrimidin-2-yl)piperazin-1-
yl]pyrrolidin-3-ol
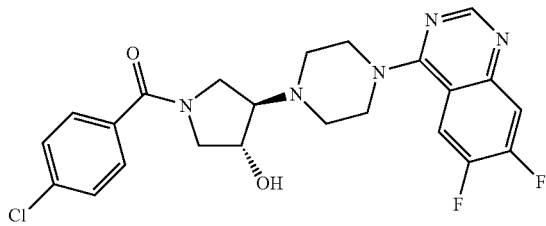 [SMILES: O=C(c1ccc(Cl)cc1)N1C[C@@H](O)[C@H](N2CCN(c3ncnc4cc(F)c(F)cc34)CC2)C1]
177
1-[(4-chlorophenyl)carbonyl]-4-[4-(6,7-
difluoroquinazolin-4-yl)piperazin-1-
yl]pyrrolidin-3-ol
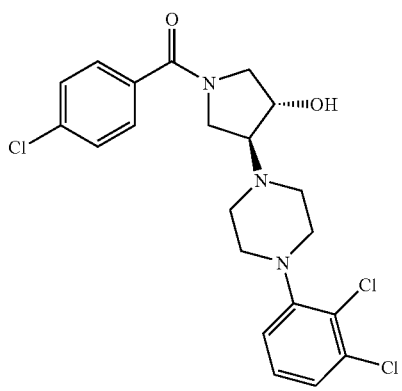 [SMILES: O=C(c1ccc(Cl)cc1)N1C[C@H](O)[C@@H](N2CCN(c3cccc(Cl)c3Cl)CC2)C1]
178
(3S, 4S)-1-[(4-chlorophenyl)carbonyl]-4-[4-
(2,3-dichlorophenyl)piperazin-1-
yl]pyrrolidin-3-ol TABLE 1-continued
Examples of Compounds of Formula I-A:
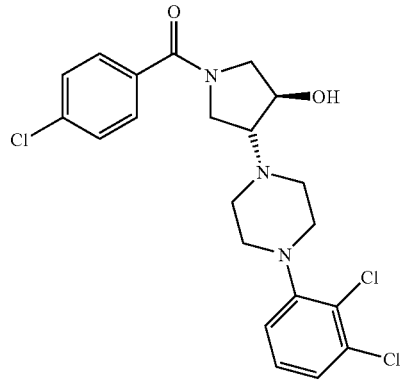
179
(3R,4R)-1-[(4-chlorophenyl)carbonyl]-4-[4-
(2,3-dichlorophenyl)piperazin-1-
yl]pyrrolidin-3-ol
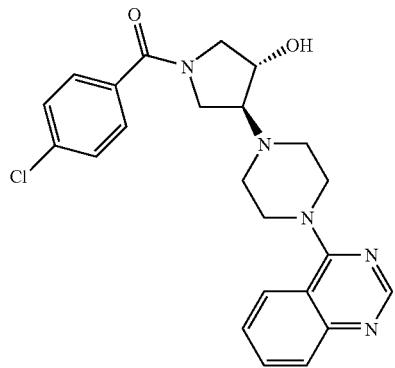 [SMILES: O=C(c1ccc(Cl)cc1)N1C[C@H](O)[C@@H](N2CCN(c3ncnc4ccccc34)CC2)C1]
180
1-[(4-chlorophenyl)carbonyl]-4-(4-
quinazolin-4-ylpiperazin-1-yl)pyrrolidin-3-ol
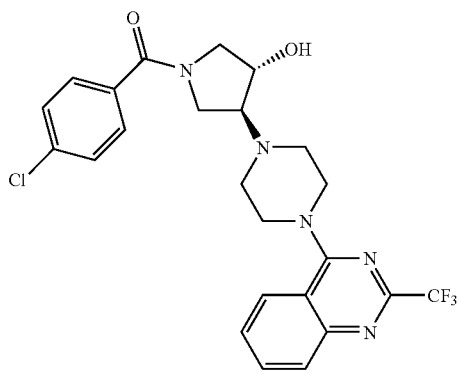 [SMILES: O=C(c1ccc(Cl)cc1)N1C[C@H](O)[C@@H](N2CCN(c3nc(C(F)(F)F)nc4ccccc34)CC2)C1]
181
1-[(4-chlorophenyl)carbonyl]-4-{4-[2-
(trifluoromethyl)quinazolin-4-yl]piperazin-1-
yl}pyrrolidin-3-ol TABLE 1-continued Examples of Compounds of Formula I-A:

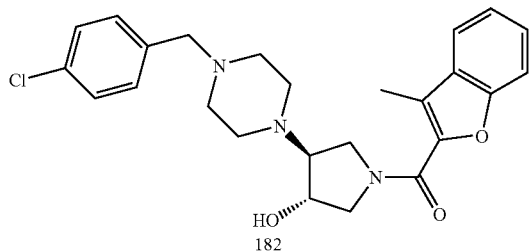

182
4-[4-(4-chlorobenzyl)piperazin-1-yl]-1-[(3-
methyl-1-benzofuran-2-
yl)carbonyl]pyrrolidin-3-ol

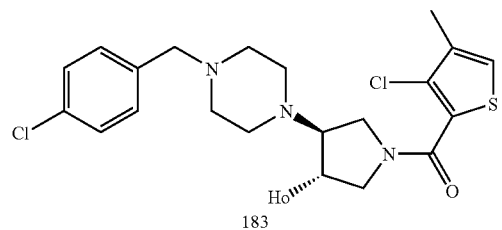

183
4-[4-(4-chlorobenzyl)piperazin-1-yl]-1-[(3-
chloro-4-methyl-2-
thienyl)carbonyl]pyrrolidin-3-ol

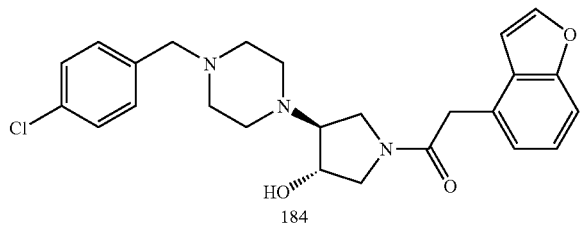

184
1-(1-benzofuran-4-ylacetyl)-4-[4-(4-
chlorobenzyl)piperazin-1-yl]pyrrolidin-3-ol

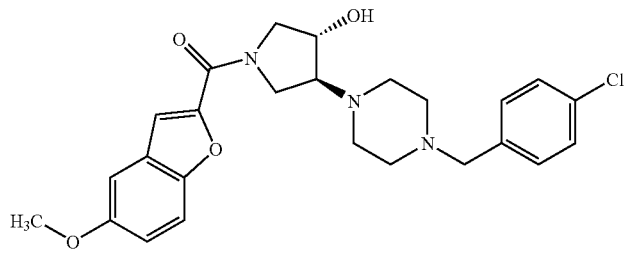 [SMILES: COc1ccc2oc(C(=O)N3C[C@H](O)[C@@H](N4CCN(Cc5ccc(Cl)cc5)CC4)C3)cc2c1]

185
4-[4-(4-chlorobenzyl)piperazin-1-yl]-1-[(5-
methoxy-1-benzofuran-2-
yl)carbonyl]pyrrolidin-3-ol

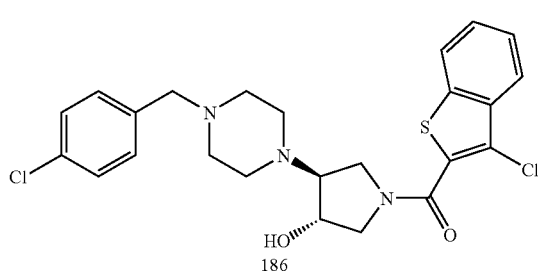

186
1-[(3-chloro-1-benzothien-2-yl)carbonyl]-4-
[4-(4-chlorobenzyl)piperazin-1-yl]pyrrolidin-3-ol TABLE 1-continued Examples of Compounds of Formula I-A:

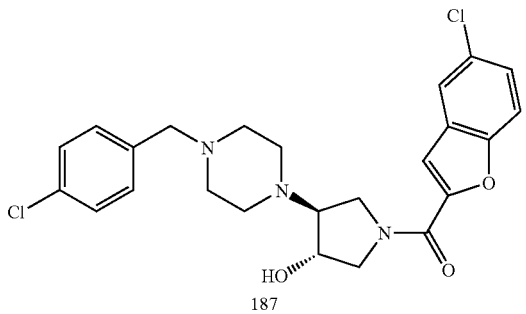

187
1-[(5-chloro-1-benzofuran-2-yl)carbonyl]-4-
[4-(4-chlorobenzyl)piperazin-1-yl]pyrrolidin-3-ol

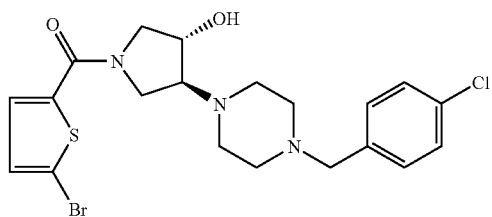 [SMILES: O=C(c1ccc(Br)s1)N1C[C@H](O)[C@@H](N2CCN(Cc3ccc(Cl)cc3)CC2)C1]

188
1-[(5-bromo-2-thienyl)carbonyl]-4-[4-(4-
chlorobenzyl)piperazin-1-yl]pyrrolidin-3-ol

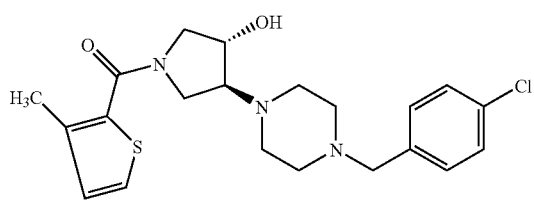 [SMILES: Cc1ccsc1C(=O)N1C[C@H](O)[C@@H](N2CCN(Cc3ccc(Cl)cc3)CC2)C1]

189
4-[4-(4-chlorobenzyl)piperazin-1-yl]-1-[(3-
methyl-2-thienyl)carbonyl]pyrrolidin-3-ol

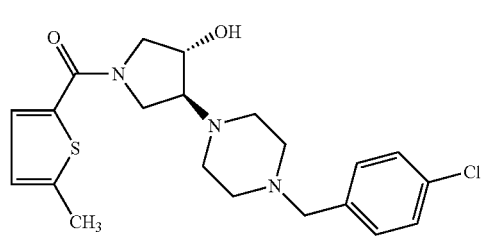 [SMILES: Cc1ccc(C(=O)N2C[C@H](O)[C@@H](N3CCN(Cc4ccc(Cl)cc4)CC3)C2)s1]

190
4-[4-(4-chlorobenzyl)piperazin-1-yl]-1-[(5-
methyl-2-thienyl)carbonyl]pyrrolidin-3-ol

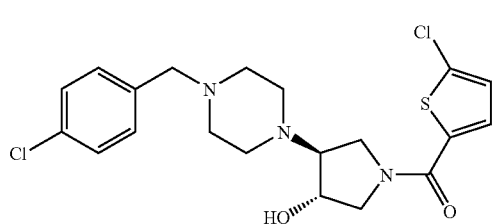 [SMILES: O=C(c1ccc(Cl)s1)N1C[C@H](O)[C@@H](N2CCN(Cc3ccc(Cl)cc3)CC2)C1]

191
4-[4-(4-chlorobenzyl)piperazin-1-yl]-1-[(5-
chloro-2-thienyl)carbonyl]pyrrolidin-3-ol TABLE 1-continued Examples of Compounds of Formula I-A:

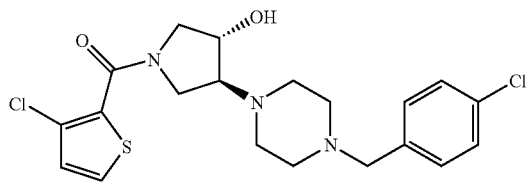 [SMILES: O=C(c1sccc1Cl)N1C[C@H](O)[C@@H](N2CCN(Cc3ccc(Cl)cc3)CC2)C1]

192
4-[4-(4-chlorobenzyl)piperazin-1-yl]-1-[(3-chloro-2-thienyl)carbonyl]pyrrolidin-3-ol

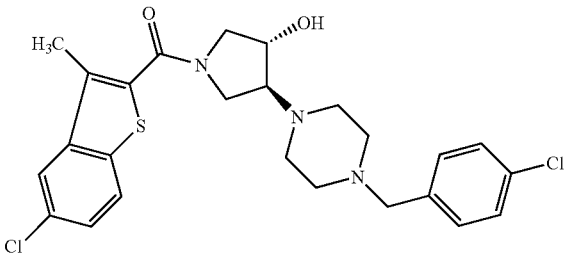 [SMILES: Cc1c(C(=O)N2C[C@H](O)[C@@H](N3CCN(Cc4ccc(Cl)cc4)CC3)C2)sc2ccc(Cl)cc12]

193
4-[4-(4-chlorobenzyl)piperazin-1-yl]-1-[(5-chloro-3-methyl-1-benzothien-2-yl)carbonyl]pyrrolidin-3-ol

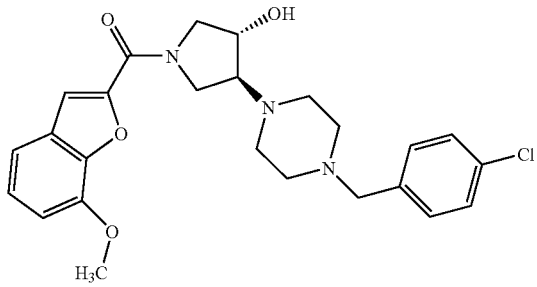 [SMILES: COc1cccc2cc(C(=O)N3C[C@H](O)[C@@H](N4CCN(Cc5ccc(Cl)cc5)CC4)C3)oc12]

194
4-[4-(4-chlorobenzyl)piperazin-1-yl]-1-[(7-methoxy-1-benzofuran-2-yl)carbonyl]pyrrolidin-3-ol

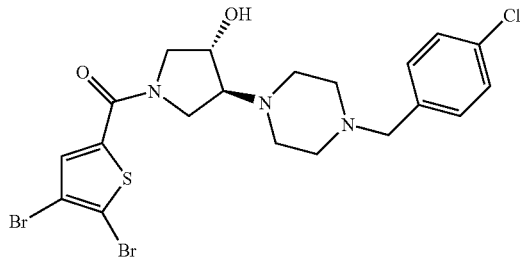 [SMILES: O=C(c1cc(Br)c(Br)s1)N1C[C@H](O)[C@@H](N2CCN(Cc3ccc(Cl)cc3)CC2)C1]

195
4-[4-(4-chlorobenzyl)piperazin-1-yl]-1-[(4,5-dibromo-2-thienyl)carbonyl]pyrrolidin-3-ol

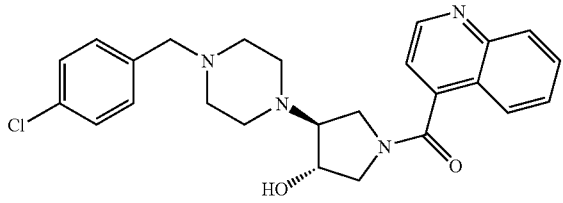 [SMILES: O=C(c1ccnc2ccccc12)N1C[C@H](O)[C@@H](N2CCN(Cc3ccc(Cl)cc3)CC2)C1]

196
4-[4-(4-chlorobenzyl)piperazin-1-yl]-1-(quinolin-4-ylcarbonyl)pyrrolidin-3-ol TABLE 1-continued
Examples of Compounds of Formula I-A:
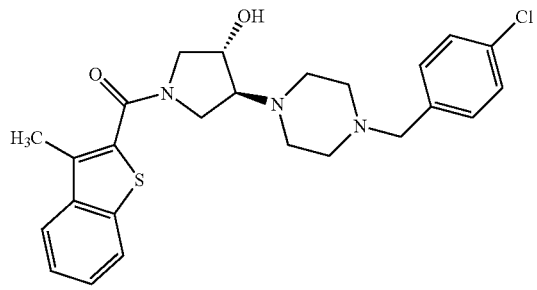 [SMILES: Cc1c(C(=O)N2C[C@H](O)[C@@H](N3CCN(Cc4ccc(Cl)cc4)CC3)C2)sc2ccccc12]
197
4-[4-(4-chlorobenzyl)piperazin-1-yl]-1-[(3-
methyl-1-benzothien-2-
yl)carbonyl]pyrrolidin-3-ol
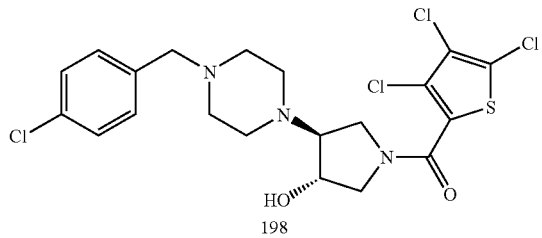
198
4-[4-(4-chlorobenzyl)piperazin-1-yl]-1-
[(3,4,5-trichloro-2-
thienyl)carbonyl]pyrrolidin-3-ol
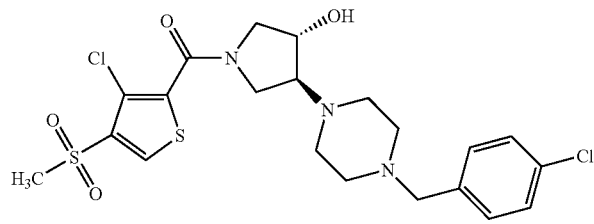 [SMILES: CS(=O)(=O)c1csc(C(=O)N2C[C@H](O)[C@@H](N3CCN(Cc4ccc(Cl)cc4)CC3)C2)c1Cl]
199
4-[4-(4-chlorobenzyl)piperazin-1-yl]-1-{[3-
chloro-4-(methylsulfonyl)-2-
thienyl]carbonyl}pyrrolidin-3-ol
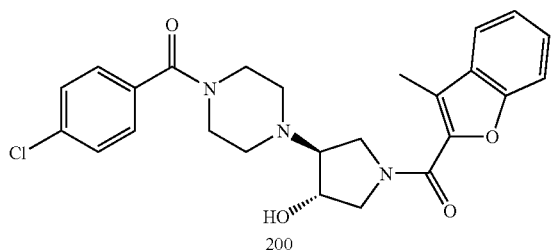
200
4-[4-(4-chlorobenzoyl)piperazin-1-yl]-1-[(3-
methyl-1-benzofuran-2-
yl)carbonyl]pyrrolidin-3-ol TABLE 1-continued
Examples of Compounds of Formula I-A:
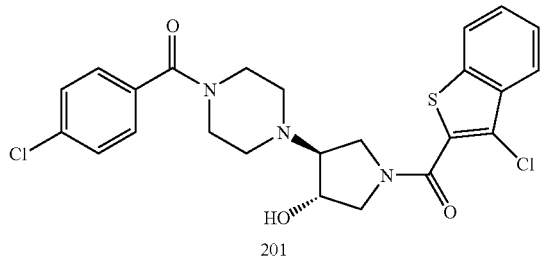
201
1-[(3-chloro-1-benzothien-2-yl)carbonyl]-4-
[4-(4-chlorobenzoyl)piperazin-1-
yl]pyrrolidin-3-ol
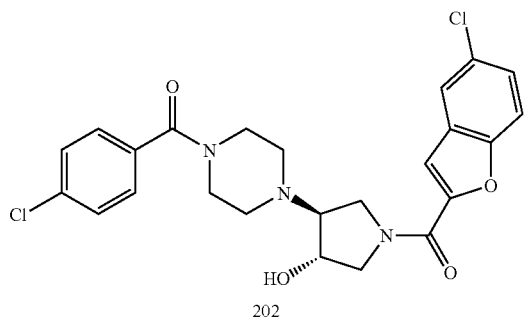
202
1-[(5-chloro-1-benzofuran-2-yl)carbonyl]-4-
[4-(4-chlorobenzoyl)piperazin-1-
yl]pyrrolidin-3-ol
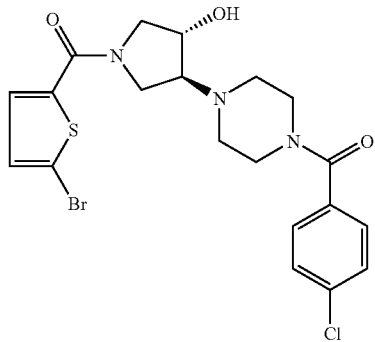 [SMILES: O=C(c1ccc(Cl)cc1)N1CCN([C@H]2CN(C(=O)c3ccc(Br)s3)C[C@@H]2O)CC1]
203
1-[(5-bromo-2-thienyl)carbonyl]-4-[4-(4-
chlorobenzoyl)piperazin-1-yl]pyrrolidin-3-ol
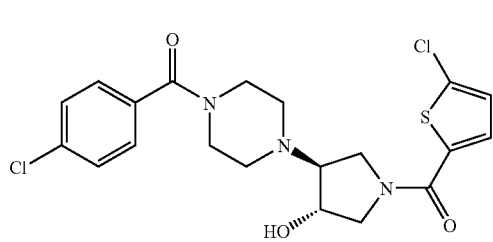 [SMILES: O=C(c1ccc(Cl)cc1)N1CCN([C@H]2CN(C(=O)c3ccc(Cl)s3)C[C@@H]2O)CC1]
204
4-[4-(4-chlorobenzoyl)piperazin-1-yl]-1-[(5-
chloro-2-thienyl)carbonyl]pyrrolidin-3-ol TABLE 1-continued
Examples of Compounds of Formula I-A:
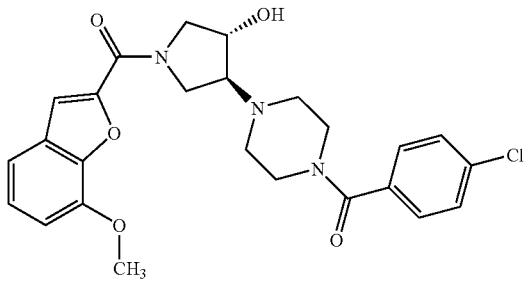 [SMILES: COc1cccc2cc(C(=O)N3C[C@H](O)[C@@H](N4CCN(C(=O)c5ccc(Cl)cc5)CC4)C3)oc12]
205
4-[4-(4-chlorobenzoyl)piperazin-1-yl]-1-[(7-
methoxy-1-benzofuran-2-
yl)carbonyl]pyrrolidin-3-ol
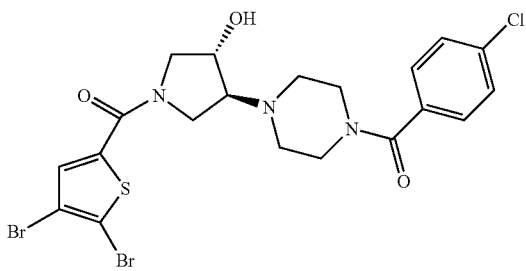 [SMILES: O=C(c1ccc(Cl)cc1)N1CCN([C@H]2CN(C(=O)c3cc(Br)c(Br)s3)C[C@@H]2O)CC1]
206
4-[4-(4-chlorobenzoyl)piperazin-1-yl]-1-
[(4,5-dibromo-2-thienyl)carbonyl]pyrrolidin-3-ol
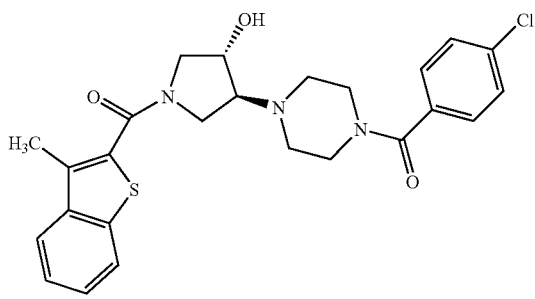 [SMILES: Cc1c(C(=O)N2C[C@H](O)[C@@H](N3CCN(C(=O)c4ccc(Cl)cc4)CC3)C2)sc2ccccc12]
207
4-[4-(4-chlorobenzoyl)piperazin-1-yl]-1-[(3-
methyl-1-benzothien-2-
yl)carbonyl]pyrrolidin-3-ol
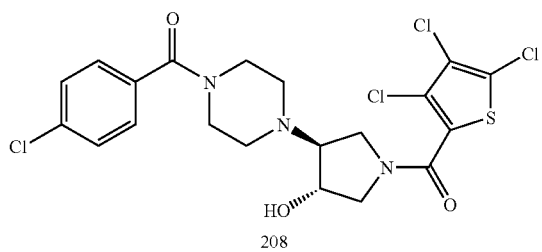
208
4-[4-(4-chlorobenzoyl)piperazin-1-yl]-1-
[3,4,5-trichloro-2-
thienyl)carbonyl]pyrrolidin-3-ol TABLE 1-continued Examples of Compounds of Formula I-A:

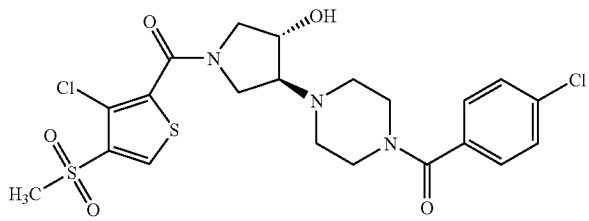 [SMILES: CS(=O)(=O)c1csc(C(=O)N2C[C@H](O)[C@@H](N3CCN(C(=O)c4ccc(Cl)cc4)CC3)C2)c1Cl]

209
4-[4-(4-chlorobenzoyl)piperazin-1-yl]-1-{[3-
chloro-4-(methylsulfonyl)-2-
thienyl]carbonyl}pyrrolidin-3-ol 4. General Synthetic Methods The compounds of this invention may be prepared in general by methods known to those skilled in the art for analogous compounds, as illustrated by the general schemes below, and the preparative examples that follow.

Scheme I below shows a general method for preparing certain exemplary compounds of the invention. The route is exemplified for compounds where Ring A is a pyrrolidine ring, Ring B is a piperazine ring and $R^2$ is 4-chlorobenzoyl. It will be apparent to one skilled in the art that other compounds of formula I, where Ring B and $R^2$ are varied, may be prepared in an analogous manner.

Scheme 1

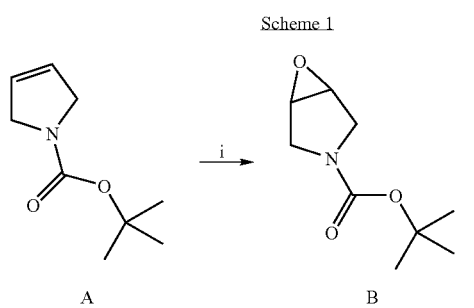

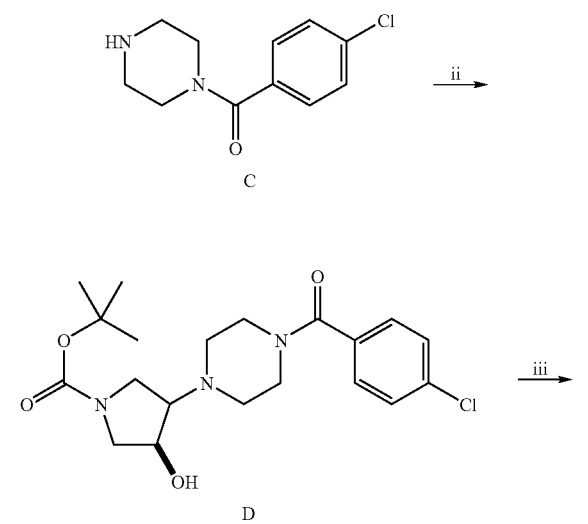

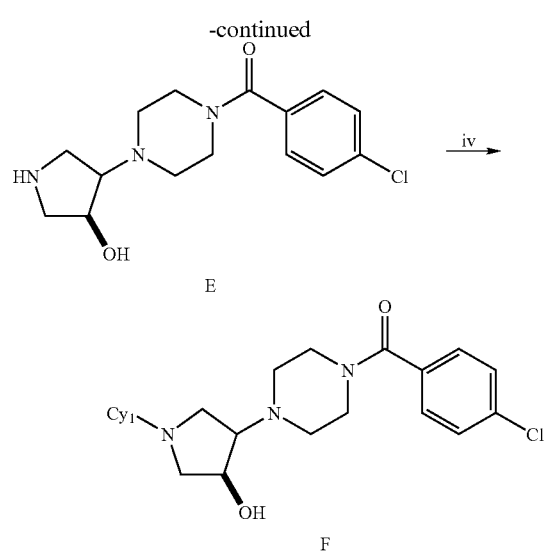

Reagents and conditions: (i) mCPBA, $CH_2Cl_2$; (ii) Procedure A: 130° C. or Procedure B: $Ca(OTf)_2$, $CH_3CN$, reflux; (iii) 4N HCl; (iv) Procedure C: $Cy^1COOH$, HATU, DIPEA, DMF; or Procedure D: $Cy^1COCl$, DIPEA, DMF.

Scheme II below shows a general method for preparing certain exemplary compounds of the invention where $R^2$ is 4-chlorobenzyl.

Scheme II

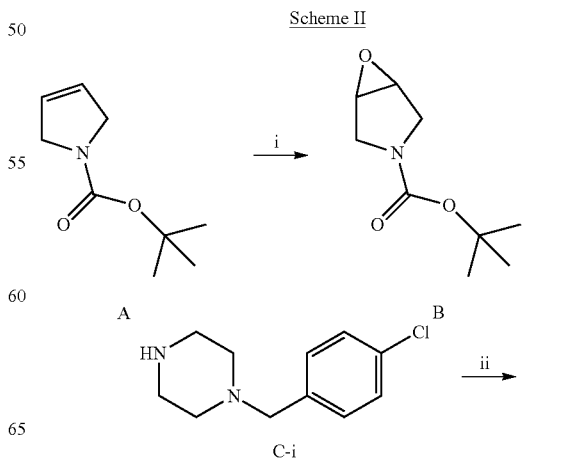

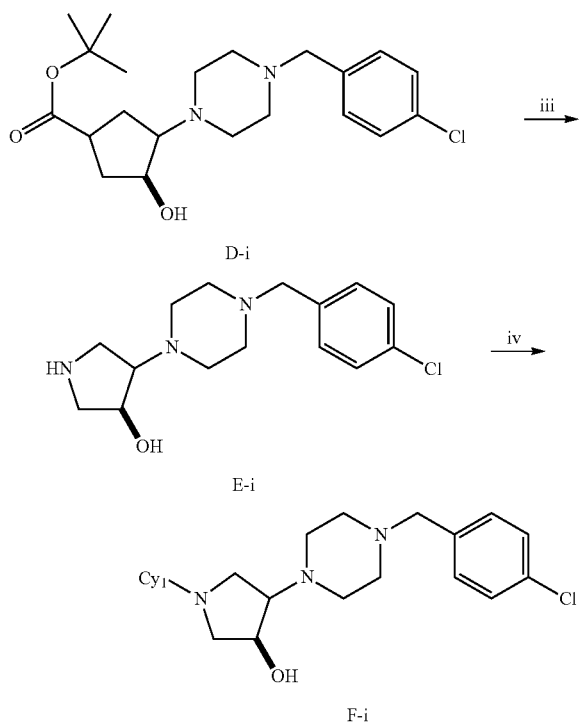

D-i

E-i

F-i

Reagents and conditions: (i) mCPBA, CH$_2$Cl$_2$; (ii) Procedure A: 130° C. or Procedure B: Ca(OTf)$_2$, CH$_3$CN, reflux; (iii) 4N HCl; (iv) Procedure C: Cy$^1$COOH, HATU, DIPEA, DMF; or Procedure D: Cy$^1$COCl, DIPEA, DMF.

Certain intermediates that are useful for making the compounds of this invention are novel, Useful intermediates are compounds of formulae V, VI, VII, VIII, and IX:

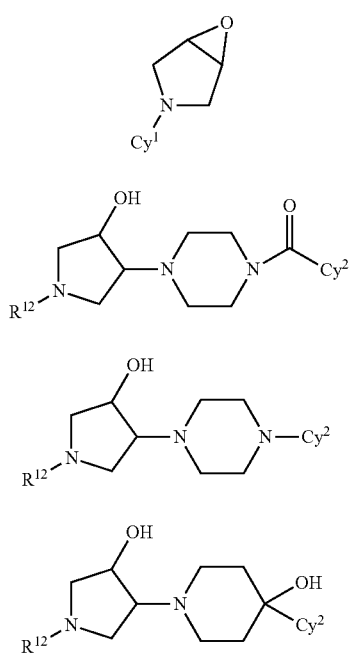

V

VI

VII

VIII

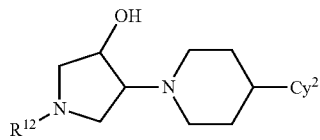

IX where Cy$^1$ and Cy$^2$ are as described above and R$^{12}$ is hydrogen or a protecting group. Suitable protecting groups are well known to those skilled in the art and include ester groups as tert-butoxycarbonyl and benzyloxycarbonyl, as well as other known protecting groups such as benzyl. Rings A and B of intermediates V-IX may be substituted as described above.

Although certain exemplary embodiments are depicted and described herein, it will be appreciated that compounds of the invention can be prepared according to the methods described generally above using appropriate starting materials by methods generally available to one of ordinary skill in the art. Additional embodiments are exemplified in more detail herein.

5. Uses, Formulation and Administration

As discussed above, the present invention provides compounds that are useful as inhibitors of chemokine receptors, preferably CCR1, and thus the present compounds are useful for treating or lessening the severity of a variety of acute or chronic inflammatory diseases, conditions, or disorders including, but not limited to, inflammatory arthritis, inflammatory demyelinating disease, atherosclerosis, arteriosclerosis, restenosis, ischemia/reperfusion injury, diabetes mellitus, psoriasis, inflammatory bowel diseases, rejection of a transplanted graft, graft versus host disease, allergy, asthma, cancer (including multiple myeloma), and osteolytic bone disorders.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a chemokine receptor, preferably CCR1.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, low eralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of an acute or chronic inflammatory disease or disorder is provided comprising administering an effective amount of a compound, or a pharmaceutical composition to a subject in need thereof. In yet another aspect, a method for treating or lessening the severity of cancer or an osteolytic bone disorder is provided comprising administering an effective amount of a compound, or a pharmaceutical composition to a subject in need thereof. In certain embodiments of the present invention an "effective amount" of the compound or pharmaceutical composition is that amount effective for treating or lessening the severity of an acute or chronic inflammatory disease or disorder, or is that amount effective for treating or lessening the severity of cancer or an osteolytic bone disorder, In other embodiments, an "effective amount" of a compound is an amount which inhibits binding of chemokine to receptor (e.g., CCR1) and thereby inhibits one or more processes mediated by the binding in a subject with a disease associated with pathogenic leukocyte recruitment, pathogenic leukocyte activation or pathogenic leukocyte recruitment and activation. Examples of such processes include leukocyte migration, integrin activation, transient increases in the concentration of intracellular free calcium $[Ca^{2+}]_i$ and granule release of proinlammatory mediators. An "effective amount" of a compound can achieve a desired therapeutic and/or prophylactic effect, such as an amount which results in the prevention of or a decrease in the symptoms associated with a disease associated with pathogenic leukocyte recruitment, pathogenic leukocyte activation or pathogenic leukocyte recruitment and activation.

The compounds and compositions, according to the method of the present invention, may be administered using any amount and any route of administration effective for treating or lessening the severity of an acute or chronic inflammatory disease or disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight pol ethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery ora compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of chemokine receptor interactions and thus the invention further relates to a method for treating (e.g., palliative, curative, prophylactic) a disease or disorder associated with pathogenic leukocyte recruitment, activation or recruitment and activation, mediated by chemokines or chemokine receptor function including chronic and acute inflammatory disorders.

In one embodiment, the compounds and compositions of the invention are inhibitors of CCR1, and thus, without wishing to be bound by any particular theory, the compounds and compositions are particularly useful for treating or lessening the severity of a disease, condition, or disorder where activation of CCR1 is implicated in the disease, condition, or disorder. When activation of CCR1 is implicated in a particular disease, condition, or disorder, the disease, condition, or disorder may also be referred to as a "CCR1-mediated disease" or disease symptom. Accordingly, in another aspect, the present invention provides a method for treating or lessening the severity of a disease, condition, or disorder where activation or one or more of CCR1 is implicated in the disease state.

As used herein "pathogenic leukocyte recruitment, activation or recruitment and activation" refers to leukocyte recruitment (e.g., accumulation of leukocytes at a sight of inflammation or injury) and/or activation (e.g., physiologic state in which leukocytes perform effector functions) that contributes to the conditions, processes or results of the disease or disorder to be treated. For example, in a subject afflicted with multiple sclerosis, recruitment and/or activation of T cells in the central nervous system is considered "pathogenic leukocyte recruitment, pathogenic leukocyte activation or pathogenic leukocyte recruitment and activation," because recruited and activated T cells contribute to the demyelination characteristic of that disease. Similarly, in a subject afflicted with rheumatoid arthritis, recruitment and/or activation of T cells in joints (e.g., synovial tissue or fluid) is considered "pathogenic leukocyte recruitment, pathogenic leukocyte activation or pathogenic leukocyte recruitment and activation," because recruited and activated T cells contribute to the tissue destruction characteristic of rheumatoid arthritis.

Diseases and disorders characterized by pathogenic leukocyte recruitment, pathogenic leukocyte activation or pathogenic leukocyte recruitment and activation that can be treated according to the methods described herein include, for example, acute and chronic inflammatory disorders characterized by the presence of CCL2 (MCP-1) CCL3 (MIP-1α), CCL4 (MIP-1β, CCL5 (RANTES), CCL7 (MCP-3), CCL8 (MCP-2), CCL13 (MCP-4), CCL14 (HCC-1), CCL15 (Lkn-1) and/or CCL23 (MPIF-1) responsive cells, such as T cells, monocytes or eosinophils. Such diseases or disorders include, but are not limited to, inflammatory arthritis (e.g., rheumatoid arthritis), inflammatory demyelinating disease (e.g., multiple sclerosis), atherosclerosis, arteriosclerosis, restenosis, ischemia/reperfusion injury, diabetes mellitus (e.g., type 1 diabetes mellitus), psoriasis, chronic obstructive pulmonary disorder (COPD), inflammatory bowel diseases such as ulcerative colitis and Crohn's disease, rejection (acute or chronic) of transplanted organs and tissues (e.g., acute allograft rejection, chronic allograft rejection), graft versus host disease, as well as allergies and asthma. Other diseases associated with aberrant leukocyte recruitment and/or activation which can be treated (including prophylactic treatments) with the methods disclosed herein are inflammatory diseases associated with viral (e.g., Human Immunodeficiency Virus (HIV)), bacterial or fungal infection, such as, AIDS associated encephalitis, AIDS related maculopapular skin eruption, AIDS related interstitial pneumonia, AIDS related enteropathy, AIDS related periportal hepatic inflammation and AIDS related glomerulo nephritis. Still other diseases include, but are not limited to cancer and osteolytic bone disorders. The method comprises administering to the subject in need of treatment an effective amount of a compound (i.e., one or more compounds) described herein.

As used herein "inflammatory demyelinating disease" refers to acute and chronic inflammatory diseases characterized by demyelination of central nervous system tissue. The inflammatory demyelinating disease can be an acute inflammatory demyelinating disease, for example, acute disseminated encephalomyelitis, Guillain-Barre syndrome or acute hemorrhagic leukoencephalitis. In other embodiments, the inflammatory demyelinating disease can be a chronic inflammatory demyelinating disease, for example, multiple sclerosis, chronic inflammatory demyelinating polyradiculoneuropathy.

In a preferred embodiment, the invention provides a method of treating multiple sclerosis, comprising administering an effective amount of compounds of general formula I (and subsets thereof as described herein) to a subject in need thereof. The manifestation of MS is variable and the clinical course of MS can be grouped into four categories: relapsing-remitting, primary progressive, secondary progressive and progressive-relapsing. The method of the invention can be used to treat MS which presents with each of the recognized clinical courses. Accordingly, a compourid of the invention can be administered to a patient with a progressive course of MS to retard or prevent the progression of neurological impairment. A compound of the invention can also be administered to a subject with relapsing-remitting, secondary progressive or progressive-relapsing MS to inhibit relapse (e.g., an acute attack). For example, a compound of the invention can be administered to a subject with relapsing-remitting MS during the remitting phase of the disease to prevent or delay relapse.

As used herein, "inflammatory arthritis" refers to those diseases of joints where the immune system is causing or exacerbating inflammation in the joint, and includes rheumatoid arthritis, juvenile rheumatoid arthritis and spondyloarthropathies, such as ankylosing spondylitis, reactive arthritis, Reiter's syndrome, psoriatic arthritis, psoriatic spondylitis, enteropathic arthritis, enteropathic spondylitis, juvenile-onset spondyloarthropathy and undifferentiated spondyloarthropathy, Inflammatory arthritis is generally characterized by infiltration of the synovial tissue and/or synovial fluid by leukocytes.

In another preferred embodiment, the invention provides a method of treating rheumatoid arthritis, comprising administering an effective amount of a compound of general formula I (and subsets as described herein) to a subject in need thereof.

The activity of compounds of the present invention can be assessed using suitable assays, such as receptor binding assays or chemotaxis assays. For example, as described in the Examples, small molecule antagonists of MIP-1α binding have been identified utilizing THP-1 cells membranes. Specifically, a high through-put receptor binding assay, which monitors $^{125}$I-MIP-1α binding to THP-1 cell membranes, was used to identify small molecule antagonists which block binding of MIP-1α. Compounds of the present invention can also be identified by virtue of their ability to inhibit the activation steps triggered by binding of a chemokine (e.g., CCL2 (MCP-1) CCL3 (MIP-1α), CCL4 (MIP-1β, CCL5 (RANTES), CCL7 (MCP-3), CCL8 (MCP-2), CCL13 (MCP-4), CCL14 (HCC-1), CCL15 (Lkn-1), CCL23 (MPIF-1)) to its receptor (CCR-1), such as chemotaxis, integrin activation and granule mediator release. They can also be identified by virtue of their ability to block chemokine (e.g., CCL2 (MCP-1) CCL3 (MIP-1α), CCL4 (MIP-1β, CCL5 (RANTES), CCL7 (MCP-3), CCL8 (MCP-2), CCL13 (MCP-4), CCL14 (HCC-1), CCL15 (Lkn-1), CCL23 (MPIF-1)) induced chemotaxis of, for example, HL-60 cells, T-cells, peripheral blood mononuclear cells or eosinophils.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

For example, compounds of the invention can also be administered in combination with one or more additional therapeutic agents, such as, theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNδ-1b)), anticancer agents, and the like.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Another aspect of the invention relates to inhibiting chemokinc receptor, preferably CCR1, activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of chemokine receptor, preferably CCR1, activity in a biological sample is useful for a variety of purposes that are known to one of skill in the art. Examples of such purposes include, but are not limited to, blood transfusion, organ-transplantation, biological specimen storage, and biological assays.

EXAMPLES

General Methods

The compounds were analyzed by ESI MS using WATERS Alliance HT-ZQ LC-MS system. Column: YMC Pack Pro $C_{18}$ (S-5, 120 Å, 2×50 mm); Solvents: $H_2O$, MeCN, and 1% TFA in $H_2O$; Gradient: 2% to 85% MeCN in 7 min, an additional pump was used to keep the TFA concentration at 0.1% throughout the complete run; Flow rate: 1 mL/min.

The crude compounds were purified using the following general procedure using a WATERS Fractionlynx preparative LC-MS system. Column: YMC Pack Pro $C_{18}$ (5μ, 120 Å, 50×20 mm); Solvents: $H_2O$, MeCN, and 2% TFA in $H_2O$; Gradient: in 7 min from 5% MeCN to 85% MeCN, in 0.2 min from 85% MeCN to 95% MeCN, 0.8 min at 95% MeCN, in 0.2 min from 95% MeCN to 5% MeCN; an additional pump was used to keep the TFA concentration at 0.1% throughout the complete run; and Flow rate: 35 mL/min. In some cases, formic acid was used as a modifier, instead of TFA.

The optical rotations, for various compounds were measured on a Perkin Elmer 341 polarimeter. A Hubert Minichiller maintained the temperature. A concentration of 0.5% compound was used (2.5 mg were dissolved in 500 μl of solvent).

Scheme 3 below depicts a solid-phase synthesis approach used for certain compounds shown herein (Examples 1-134).

Scheme 3
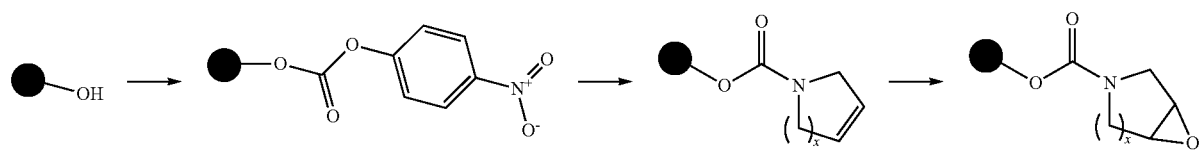
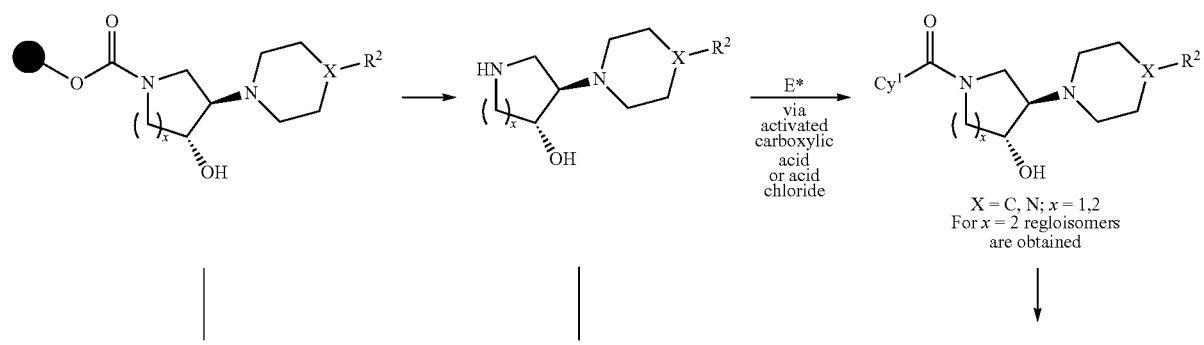
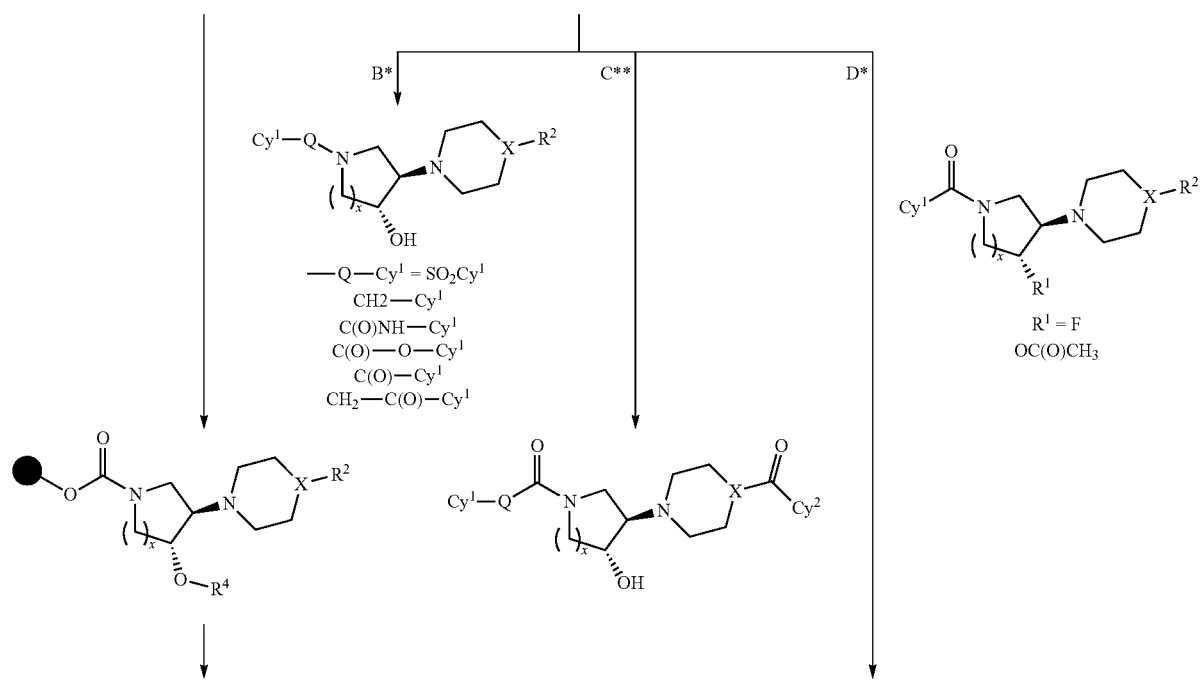

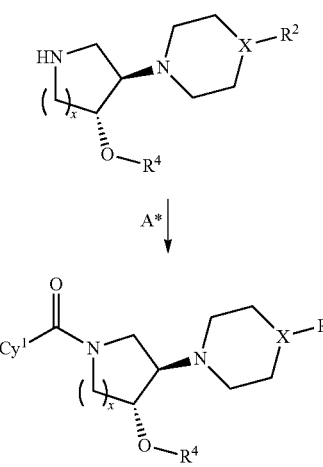

A*↓

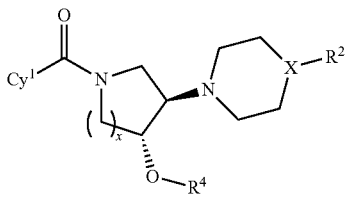

-continued

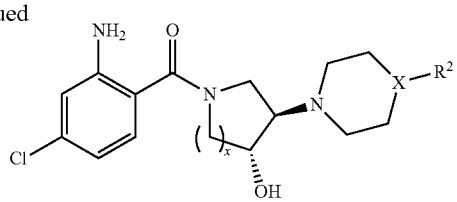

↓

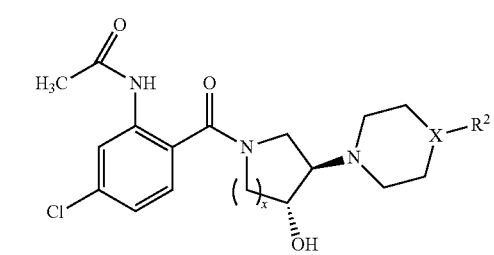

or

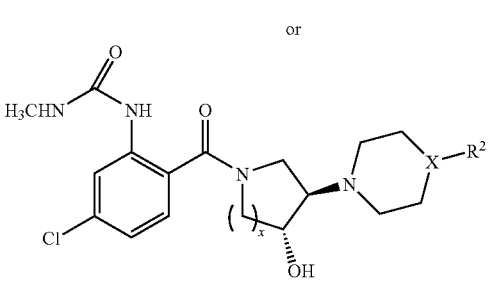

* Steps A, B, D and E: X = N or C; and R² = aryl, benzyl, aralkyl, aralkenyl, heteroaryl, heteroaralkyl or alkyl.
** Step C: X = N; and R² = hydrogen Syntheses of Resin Bound Epoxides p-Nitrophenyl carbonate Wang resin Wang resin (156 g, 250 mmol, 1.6 mmol/g; p-Wang-LCC resin; 193 microns, *LCC Engineering*) was placed in a glass reactor for semi-automated synthesis and swollen in dry $CH_2Cl_2$ under $N_2$. After filtration of the solvent, a solution of p-nitrophenyl chloroformate (251 g, 1.25 mol) in dry $CH_2Cl_2$ (500 mL) was added, followed by slow addition of a solution of dry pyridine (198 mL, 2.5 mol) in dry $CH_2Cl_2$ (200 mL). The suspension was shaken for 48 h at room temperature under $N_2$. The carbonate resin was washed on a semi-automated shaking-vessel machine with dioxane:methanol 1:1 (1×5 min and 5×2 min), dioxane dichloroethane 1:1 (1×5 min and 5×2 min) isopropyl alcohol (2×2 min) and dried under high vacuum, to yield 185 g of p-nitrophenyl carbonate Wang resin. Elemental analysis: N, 2.03; loading of 1.4 mmol/g.

1-(2,5-Dihydro-pyrrol-1-yl) carbamate Wang resin p-Nitrophenyl carbonate resin (150 g, 180 mmol, 1.2 mmol/g; 203 microns, *LCC Engineering*) was placed in a glass reactor for semi-automated synthesis. The resin was swollen in dry DMF and 3-pyrroline (25 mL, 360 mmol) and DIPEA (123 mL, 720 mmol) were successively added. After 72 h shaking at room temperature the solvent was filtered off and washed on a semi-automated shaking-vessel machine with DMF (4×4 min), isopropyl alcohol (3×4 min), dioxane:dichloroethane (1:1; 3×4 min), isopropyl alcohol (5×3 min) and dried under high vacuum, to yield resin 1-(2,5-dihydropyrrol-1-yl) carbamate Wang resin.

3,4-Epoxypyrrolidine carbamate Wang resin 1-(2,5-Dihydro-pyrrol-1-yl) carbamate resin (180 mmol) was placed into a 2 L three-neck flask with mechanical stirrer and $CH_2Cl_2$ (1.5 L) was added. Solid m-CPBA (239 g, 900 mmol, 70-75% from ACROS) and $CH_2Cl_2$ (200 mL) were added and the suspension was shaken for 16 h at room temperature. The suspension was filtered off and washed three times with $CH_2Cl_2$. The resin was transfer glass reactor for semi-automated synthesis washed on a semi-automated shaking-vessel machine with DMF (3×4 min), isopropyl alcohol (3×4 min), DMF (3×4 min), isopropyl alcohol (5×4 min), and dried under high vacuum, to yield 164 g of 3,4-epoxypyrrolidine carbamate Wang resin. Anal. found: N, 1.2 mmol/g. This reaction should not be run in an oven. Accordingly, the reaction should be conducted in glass vials under a fume hood and must reach room temperature before opening.

Example 1

Mixture of (3R,4R; 3S,4S)-4-(4-chloro-phenyl)-1-(4-hydroxy-pyrrolidin-3-yl)-piperidin-4-ol bis-trifluoroacetate 3,4-Epoxypyrrolidine carbamate Wang resin (1.5 g, 1.8 mmol) was placed in a glass reaction vessel (50 mL). A solution of $LiClO_4$ in acetonitrile (0.36 M, 10 mL, 3.6 mmol), 4-(4-chloro-phenyl)-piperidin-4-ol (1.52 g, 7.2 mmol) and acetonitrile (5 mL) were added successively. The glass reactor was closed with a screw cap and the reaction mixture was heated at 80° C. for 24 h. The resin was transferred into syringes and washed with DMF (3×), isopropyl alcohol (3×), DMF (3×), isopropyl alcohol (4×) and $CH_2Cl_2$ (5×). A solution of TFA:$CH_2Cl_2$:$H_2O$ 70:30:2.5 (18 mL) was added and the suspension was shaken for 4 h. The solution and one subsequent wash with TFA:$CH_2Cl_2$:$H_2O$ 70:30:2.5 (15 mL) were collected and combined. Cleavage from the resin was repeated using TFA:$CH_2Cl_2$:$H_2O$ 70:30:0.5 (15 mL) for 3 h. The solvent was removed to afford 399 mg of the title compound as the bistrifluoroacetate salt. ESIMS ($[M+H]^+$): 297.1 (100).

Example 2

Mixture of (3R,4R; 3S,4S)-4-[4-(3-Chloro-phenyl)-piperazin-1-yl]-pyrrolidin-3-ol bis-trifluoroacetate The title compound is prepared essentially as described in Example 1 using 3-chloro-phenyl-piperazine (1.41 g, 7.2 mmol), to yield 324 mg as the bistrifluoroacetate salt. ESIMS ($[M+H]^+$): 282.1 (100).

Example 3

Mixture of (3R,4R; 3S,4S)-4-(4-pyridin-2-yl-piperazin-1-yl)-pyrrolidin-3-ol bistrifluoroacetate The title compound is prepared essentially as described in Example 1 using 4-pyridin-2-yl-piperazine (1.17 g, 7.2 mmol), to yield 317 mg as the bistrifluoroacetate salt. ESIMS ($[M+H]^+$): 249.2 (100).

Example 4

Mixture of (3R,4R; 3S,4S)-4-[4-(3-trifluoromethyl-phenyl)-piperazin-1-yl]-pyrrolidin-3-ol bistri-fluoroacetate The title compound is prepared essentially as described in Example 1 using 4-(3-trifluoromethyl-phenyl)-piperazine (1.65 g, 7.2 mmol), to yield 390 mg as the bistrifluoroacetate salt. ESIMS ($[M+H]^+$): 316.2 (100).

Example 5

Mixture of (3R,4R; 3S,4S)-4-(4-Benzyl-piperazin-1-yl)-pyrrolidin-3-ol bistrifluoroacetate The title compound is prepared essentially as described in Example 1 using 4-benzyl-piperazine (1.26 g, 7.2 mmol), to yield 578.1 mg as the bistrifluoroacetate salt. ESIMS ($[M+H]^+$): 262.2 (100).

Example 6

Mixture of (3R,4R; 3S,4S)-4-[4-(2-Chloro-phenyl)-piperazin-1-yl]-pyrrolidin-3-ol bistrifluoroacetate The title compound is prepared essentially as described in Example 1 using 4-(2-chloro-phenyl)-piperazine (1.40 g, 7.2 mmol), to yield 395.3 mg as the bistrifluoroacetate salt. ESIMS ($[M+H]^+$): 282.1 (100).

Example 7

Mixture of (3R,4R; 3S,4S)-4-(4-Benzothiazol-2-yl-piperidin-1-yl)-pyrrolidin-3-ol bistrifluoroacetate The title compound is prepared essentially as described in Example 1 using 4-benzothiazol-2-yl-piperidine (1.57 g, 7.2 mmol) to yield 341.5 mg as the bistrifluoroacetate salt. ESIMS ($[M+H]^+$): 304.1 (100).

Example 8

Mixture of (3R,4R; 3S,4S)-4-[4-(4-Chloro-benzyl)-piperazin-1-yl]-pyrrolidin-3-ol bistrifluoroacetate The title compound is prepared essentially as described in Example 1 using 4-(4-chloro-benzyl)-piperazine (1.52 g, 7.2 mmol), to yield 376.2 mg as the bistrifluoroacetate salt. ESIMS ($[M+H]^+$): 296.1 (100). The title compound can be converted into the corresponding dihydrochloride salt by dissolving it in dioxane:$H_2O$:1 N aq HCl (2:1:0.2) and then performing appropriate lyophilization.

Example 9

Mixture of (3R,4R; 3S,4S)-4-(4-Pyrimidin-2-yl-piperazin-1-yl)-pyrrolidin-3-ol bistrifluoroacetate The title compound is prepared essentially as described in Example 1 using 4-pyrimidin-2-yl-piperazine (1.1 g, 7.2 mmol), to yield 396 mg as the bistrifluoroacetate salt. ESIMS ($[M+H]^+$): 250.2 (100).

Example 10

Mixture of (3R,4R; 3S,4S)-4-(4-m-Tolyl-piperazin-1-yl)-pyrrolidin-3-ol bistrifluoroacetate The title compound is prepared essentially as described in Example 1 using 4-m-tolyl-piperazine (1.26 g, 7.2 mmol), to yield 498 mg as the bistrifluoroacetate salt. ESIMS ($[M+H]^+$): 262.2 (100).

Example 11

Mixture of (3R,4R; 3S,4S)-4-(4-Phenyl-piperidin-1-yl)-pyrrolidin-3-ol bistrifluoroacetate The title compound is prepared essentially as described in Example 1 using 4-phenyl-piperidine (1.1 g, 72 mmol), to yield 333.4 mg as the bistrifluoroacetate salt. ESIMS ($[M+H]^4$): 247.2 (100).

Example 12

Mixture of (3R,4R; 3S,4S)-4-[4-(3-Chloro-phenyl)-piperazin-1-yl]-pyrrolidin-3-ol bistrifluoroacetate The title compound is prepared essentially as described in Example 1 using 4-(3-chloro-phenyl)-piperazine (1.41 g, 7.2 mmol), to yield 324.5 mg as the bistrifluoroacetate salt. ESIMS ($[M+H]^+$): 282.1 (100).

Example 13

Mixture of (3R,4R; 3S,4S)-1-(4-Hydroxy-pyrrolidin-3-yl)-4-phenyl-piperidin-4-ol bistrifluoroacetate The title compound is prepared essentially as described in Example 1 using 4-phenyl-piperidin-4-ol (1.27 g, 7.2 mmol), to yield 362.5 mg as the bistrifluoroacetate salt. ESIMS ($[M+H]^+$): 263.2 (100).

Example 14

Mixture of (3R,4R; 3S,4S)-4-(4-Pyridin-2-ylmethyl-piperazin-1-yl)-pyrrolidin-3-ol bistrifluoroacetate The title compound is prepared essentially as described in Example 1 using 4-pyridin-2-yl-methyl-piperazine (1.27 g, 7.2 mmol), to yield 446.9 mg as the bistrifluoroacetate salt. ESIMS ([M+H]$^+$): 263.2 (100).

Example 15

Mixture of (3R,4R; 3S,4S)-4-(4-Benzo[1,3]dioxol-5-ylmethyl-piperazin-1-yl)-pyrrolidin-3-ol bistri-fluoroacetate The title compound is prepared essentially as described in Example 1 using 4-benzo[1,3]dioxol-5-ylmethyl-piperazine (1.58 g, 7.2 mmol), to yield 624.1 mg as the bistrifluoroacetate salt. ESIMS ([M+H]$^+$); 306.2 (100).

Example 16

Mixture of (3R,4R; 3S,4S)-4-[4(E)-3-Phenyl-allyl)-piperazin-1-yl]-pyrrolidin-3-ol bistrifluoroacetate The title compound is prepared essentially as described in Example 1 using 4-((E)-3-phenyl-allyl)-piperazine (1.45 g, 7.2 mmol), to yield 446.3 mg as the bistrifluoroacetate salt. ESIMS ([M+H]$^+$): 288.2 (100).

Example 17

Mixture of (3R,4R; 3S,4S)-4-(4-phenethyl-piperazin-1-yl)-pyrrolidin-3-ol]bistrifluoroacetate The title compound is prepared essentially as described in Example 1 using 4-phenethyl-piperazine (1.45 g, 7.2 mmol), to yield 430.3 mg as the bistrifluoroacetate salt. ESIMS ([M+H]$^+$): 276.4 (100).

Example 18

Mixture of (3R,4R; 3S,4S)-4-[4-(4-Chloro-phenyl)-piperazin-1-yl]-pyrrolidin-3-ol bistrifluoroacetate The title compound is prepared essentially as described in Example 1 using 4-(4-chloro-phenyl)-piperazine (1.41 g, 7.2 mmol), to yield 320.5 mg as the bistrifluoroacetate salt. ESIMS ([M+H]$^+$): 282.1 (100).

Example 19

Mixture of (3R,4R; 3S,4S)-4-(4-Phenyl-piperazin-1-yl)-pyrrolidin-3-ol bistrifluoroacetate The title compound is prepared essentially as described in Example 1 using 4-phenyl-piperazine (1.16 g, 7.2 mmol), to yield 313.3 mg as the bistrifluoroacetate salt. ESIMS ([M+H]$^+$): 248.2 (100).

Example 20

Mixture of (3R,4R; 3S,4S)-4-Benzyl-1-(4-hydroxy-pyrrolidin-3-yl)-piperidin-4-ol

The title compound is prepared essentially as described in Example 1 using 4-benzyl-piperidin-4-ol bistrifluoroacetate (1.37 g, 7.2 mmol). The reaction was done in parallel and on the same scale, in a separate reactor. The cleavage solutions were then combined, to yield 791 mg as the bistrifluoroacetate salt. ESIMS ([M+H]$^+$): 277.2 (100).

Example 21

Mixture of (3R,4R; 3S,4S)-4-(4-Methyl-piperazin-1-yl)-pyrrolidin-3-ol bistrifluoroacetate The title compound is prepared essentially as described in Example 1 using 4-methyl-piperazine (0.77 g, 7.2 mmol) to yield 338.1 mg as the bistrifluoroacetate salt. ESIMS ([M+H]$^+$): 186.2 (100).

Example 22

Mixture of (3R,4R; 3S,4S)-4-(4-Benzyl-piperidin-1-yl)-pyrrolidin-3-ol bistrifluoroacetate The title compound is prepared essentially as described in Example 1 using 4-benzyl-piperidine (1.26 g, 7.2 mmol). The reaction was done in parallel and on the same scale, in a separate reactor. The cleavage solutions were then combined, to yield 670 mg as the bistrifluoroacetate salt. ESIMS ([M+H]$^+$): 261.2 (100).

Example 23

Mixture of (3R,4R; 3S,4S)-4-[4-(6-Methyl-pyridin-2-yl)-piperazin-1-yl]-pyrrolidin-3-ol bistri-fluoroacetate The title compound is prepared essentially as described in Example 1 using 4-(6-Methyl-pyridin-2-yl)-piperazine (1.36 g, 7.2 mmol). The reaction was done in parallel and on the same scale, in a separate reactor. The cleavage solutions were then combined, to yield 670 mg as the bistrifluoroacetate salt. ESIMS ([M+H]$^+$): 263.2 (100).

Example 24

Mixture of (3R,4R; 3S,4S)-(4-Fluoro-phenyl)-[1-(4-hydroxy-pyrrolidin-3-yl)-piperidin-4-yl]-methanone bistrifluoroacetate The title compound is prepared essentially as described in Example 1 using (4-fluoro-phenyl)-piperidin-4-yl-methanone (1.49 g, 7,2 mmol). The reaction was done in parallel and on the same scale, in a separate reactor. The cleavage solutions were then combined, to yield 1.2 g as the bistrifluoroacetate salt. ESIMS ([M+H]$^+$): 293.2 (100).

Example 25

Mixture of (3R,4R; 3S ,4S)-4-[4-(2-Trifluoromethyl-phenyl)-piperazin-1-yl]-pyrrolidin-3-ol bistrifluoroacetate The title compound is prepared essentially as described in Example 1 using 4-(2-trifluoromethyl-phenyl)-piperazine (1.6 g, 7.2 mmol), to yield 458 mg as the bistrifluoroacetate salt. ESIMS ([M+H]$^+$): 316.2 (100).

Example 26

Mixture of (3R,4R; 3S,4S)-4-[4-(5-Trifluoromethyl-pyridin-2-yl)-piperazin-1-yl]-pyrrolidin-3-ol bistrifluoroacetate The title compound is prepared essentially as described in Example 1 using 4-(5-Trifluorotnethyl-pyridin-2-yl)-piperazine (1.6 g, 7,2 mmol), to yield 475 mg as the bistrifluoroacetate salt. ESIMS ([M+H]$^+$): 317.2 (100).

Example 27

Mixture of (3R,4R; 3S,4S)-4-(4-Biphenyl-4-yl-piperazin-1-yl)-pyrrolidin-3-ol bistrifluoroacetate The title compound is prepared essentially as described in Example 1 using 4-biphenyl-4-yl-piperazine (1.7 g, 7.2 mmol), to yield 414 mg as the bistrifluoroacetate salt. ESIMS ([M+H]$^+$): 324.2 (100).

Example 28

Mixture of (3R,4R; 3S,4S)-4-[4-(3-Trifluoromethyl-pyridin-2-yl)-piperazin-1-yl]-pyrrolidin-3-ol bistrifluoroacetate The title compound is prepared essentially as described in Example 1 using 4-(3-trifluoromethyl-pyridin-2-yl)-piperazine (1.6 g, 7.2 mmol), to yield 578 mg as the bistrifluoroacetate salt. ESIMS ([M+H]$^+$): 316.2 (100).

Example 29

Mixture of (3R,4R; 3S,4S)-4-[4-(4-Bromo-benzyl)-piperazin-1-yl]-pyrrolidin-3-ol bistrifluoroacetate The title compound is prepared essentially as described in Example 1 using 4-(4-Bromo-benzyl)-piperazine (1.82 g, 7.2 mmol), to yield 717 mg as the bistrifluoroacetate salt. ES1MS ([M+H]$^+$): 340.1 (100).

Example 30

Mixture of (3R,4R; 3S,4S)-4-[4-(2-Chloro-benzyl)-piperazin-1-yl]-pyrrolidin-3-ol bistrifluoroacetate The title compound is prepared essentially as described in Example 1 using 4-(2-chloro-benzyl)-piperazine (1.51 g, 7.2 mmol), to yield 489 mg as the bistrifluoroacetate salt. ESIMS ([M+H]$^+$); 296.2 (100).

Example 31

Mixture of (3R,4R; 3S,4S)-4-(4-Thieno[3,2-d]pyrimidin-4-yl-piperazin-1-yl)-pyrrolidin-3-ol bistrifluoroacetate The title compound is prepared essentially as described in Example 1 using 4-thieno[3,2-d]pyrimidin-4-yl-piperazine (1.58 g, 7.2 mmol), to yield 608 mg as the bistrifluoroacetate salt. ESIMS ([M+H]$^+$): 306.1 (100).

Example 32

Mixture of (3R,4R; 3S,4S)-4-[4-(4-Fluoro-benzyl)-piperazin-1-yl]-pyrrolidin-3-ol bistrifluoroacetate The title compound is prepared essentially as described in Example 1 using 4-(4-fluoro-benzyl)-piperazine (1.4 g, 7.2 mmol), to yield 580 mg as the bistrifluoroacetate salt. ESIMS ([M+H]$^+$): 280.1 (100).

Example 33

Mixture of (3R,4R; 3S,4S)-4-[4-(4-Chloro-phenyl)-piperidin-1-yl]-pyrrolidin-3-ol bistrifluoroacetate 3,4-Epoxypyrrolidine carbamate Wang resin (125 mg, 0.15 mmol) was placed in a glass reaction vessel (10 mL). A solution of LiClO$_4$ in acetonitrile (0.36 M, 0.083 mL, 0.3 mmol), 4-(4-chloro-phenyl)-piperidine hydrochloride (138 mg, 0.6 mmol), 1,8-diazabicyclo[5.4.0]undec-7-ene (90 □L, 0.6 mmol) and acetonitrile (0.8 mL) were added successively. The glass reactor was closed with a screw cap and the reaction mixture was heated at 80° C. for 24 h. The resin was transferred into syringes and washed with DMF (3×), isopropyl alcohol (3×), DMF (3×), isopropyl alcohol (4×) and CH$_2$Cl$_2$ (5×). A solution of TFA:CH$_2$Cl$_2$:H$_2$O 70:30:2.5 (18 mL) was added and the suspension was shaken for 4 h. The solution and one subsequent wash with TFA:CH$_2$Cl$_2$:H$_2$O 70:30:2.5 (15 mL) were collected and combined. Cleavage from the resin was repeated using TFA:CH$_2$Cl$_2$:H$_2$O 70:30:0.5 (15 mL) for 3 h. The solvent was removed to afford 68 mg of the title compound as the bistrifluoroacetate salt. ESIMS ([M+H]$^+$): 281.1 (100).

Example 34

Mixture of (3R,4R; 3S,4S)-[(S)-4-(4-Chloro-phenyl)-1-(4-hydroxy-pyrrolidin-3-yl)-3,3-dimethyl-piperidin-4-ol] bistrifluoroacetate The title compound is prepared essentially as described in Example 33 using 3,4-epoxypyrrolidine carbamate Wang resin (58 mg, 0.07 mmol), LiClO$_4$ in acetonitrile (0.36 M, 0.068 mL, 0.14 mmol), (S)-4-(4-chloro-phenyl)-3,3-dimethyl-piperidin-4-ol monotartrate salt (109 mg, 0.28 mmol), 1,8-diazabicyclo[5.4.0]undec-7-ene (0.041 mL, 0.28 mmol) and acetonitrile (0.8 mL), to yield 31 mg as the bistrifluoroacetate salt. ESIMS ([M+H]$^+$): 325.2 (100).

Example 35

Mixture of (3R,4R; 3S,4S)-[4-(4-Chloro-phenyl)-1-(4-hydroxy-pyrrolidin-3-yl)-3,3-dimethyl-piperidin-4-ol]bistrifluoroacetate The title compound is prepared essentially as described in Example 34 using 4-(4-Chloro-phenyl)-3,3-dimethyl-piperidin-4-ol camphersulfonic acid salt (132 mg, 0.28 mmol), to yield 27 mg as the bistrifluoroacetate salt. ESIMS ([M+H]$^+$): 325.2 (100).

Example 36

Mixture of (3R,4R; 3S,4S)-{1-[4-(4-Chloro-phenoxy)-pyrrolidin-3-yl]-piperidin-4-yl}-(4-fluoro-phenyl)-methanone bistrifluoroacetate 3,4-Epoxypyrrolidine carbamate Wang resin (1.5 g, 1.8 mmol) was placed in a glass reaction vessel (50 mL). A solution of LiClO₄ in acetonitrile (0.36 M, 10 mL, 3.6 mmol), 4-(4-fluorobenzoyl)piperidine (1.48 g, 7.2 mmol) and acetonitrile (5 mL) were added successively. The glass reactor was closed with a screw cap and the reaction mixture was heated at 80° C. for 24 h. The resin was transferred into syringes and washed with DMF (3×), isopropyl alcohol (3×), DMF (3×), isopropyl alcohol (5×) and dried under high vacuum. The aminoalcohol resin (1 g, 1 mmol) was placed into a glass reactor under $N_2$. Dry tetrahydrofuran (5 mL) was added through a septum and the suspension was cooled to 5° C. Triphenylphosphine (1.3 g, 5 mmol) and 4-chloro-phenol (494 mg, 5 mmol) were placed into a glass reactor and tetrahydrofuran (5 mL) was added through a septum under $N_2$. Diazopropyl azodicarboxylate (970 uL, 5 mmol) was slowly added under $N_2$. 3,3-Dimethyl-[1,2,5]thiadiazolidine 1,1-dioxide (751 mg, 5 mmol) was added as a solid under $N_2$ and the reaction mixture was shaken for 5 min. The suspension was added to the resin at 5° C. under N2 and the suspension was shaken for 16 h at room temperature. The resin reactors were transferred into a syringe and washed with DMF (3×), methanol (3×), DMF (3×), toluene (3×), $CH_2Cl_2$ and dried. A solution of TFA:$CH_2Cl_2$:$H_2O$ 50:50:5 (14 mL) was added and the suspension was shaken for 2 h. The solution and one subsequent wash with TFA:$CH_2Cl_2$:$H_2O$ 70:30:2.5 (12 mL) were collected and combined. The solvent was removed to yield 452 mg of the title compound as the bistrifluoroacetate salt. ESIMS ([M+H]⁺): 403.1 (100).

Example 37

Mixture of (3R,4R. 3S,4S)-{(4-Fluoro-phenyl)-[1-(4-phenoxy-pyrrolidin-3-yl)-piperidin-4-yl]-methanone bistrifluoroacetate The title compound is prepared essentially as described in Example 36 using phenol (494 mg, 5 mmol) instead of 4 chloro-phenol, to yield 389 mg as the bistrifluoroacetate salt. ESIMS ([M+H]⁺): 369.2 (100).

Example 38

Mixture of (3'R,4'R or 3'S,4'S)-4-(4-Chloro-phenyl)-[1,3']bipiperidinyl-4,4'-diol bistrifluoroacetate and (3'R,4'R or 3'S,4'S)-4-(4-chloro-phenyl)-[1,4']bipiperidinyl-4,3'-diol bistrifluoroacetate 2,3,6-Trihydropyridine carbamate Wang resin p-Nitrophenyl carbonate Wang (35 g, 42.5 mmol) was suspended in dry DMF and 1,2,3,6-tetrahydropyridine (7.8 mL, 85 mmol) and DIPEA (36.3 mL, 212.5 mmol) were successively added. After 24 h shaking at room temperature the solvent was filtered off and the resin was washed on a semi-automated shaking-vessel machine with DMF (4×4 min), isopropyl alcohol (4×2 min), DMF (4×4 min), isopropyl alcohol (4×2 min) $CH_2Cl_2$ (4×2 min) and dried under high vacuum to obtain 2,3,6-trihydropyridine carbamate Wang resin.

3,4-Epoxypiperidine carbamate Wang resin 2,3,6-Trihydropyridine carbamate Wang resin was placed in twenty-four different syringes (3.87 g, 6.2 mmol in each syringe) and swollen with $CH_2Cl_2$ (40 mL). Solid m-CPBA (6.1 g, 24.8 mmol, 70-75% from ACROS) and $CH_2Cl_2$ (20 mL) were added and the suspension was shaken for 4.5 h at room temperature. The suspension was filtered off and washed three times with $CH_2Cl_2$. The resin was transferred to a large reactor and washed on a semi-automated shaking-vessel machine with DMF (3×5 min), isopropyl alcohol (4×4 min), DMF (3×5 min), isopropyl alcohol (5×4 min), and dried under high vacuum, to yield 93 g of 3,4-epoxypiperidine carbamate Wang resin. Anal. found: N, 1.3. This reaction should not be run in an oven. Accordingly, the reaction should be conducted in glass vials under a fume hood and must reach room temperature before opening.

3,4-Epoxypiperidine carbamate Wang resin (4.14 g, 5.4 mmol) was placed glass reaction vessel. A solution of LiClO₄ in acetonitrile (0.36 M, 30 mL, 10.8 mmol), 4-(4-chlorophenyl)-piperidin-4-ol (4.5 g, 21.6 mmol) and acetonitrile (10 mL) were added successively. The glass reactor was closed with a screw cap and the reaction mixture was heated at 80° C. for 24 h. The resin was transferred in syringes and washed with DMF (4× at 50° C.), dioxane:$H_2O$ 1:1 (3×), DMF (1×), isopropyl alcohol (3×), DMF (3×), isopropyl alcohol (3×) and $CH_2Cl_2$ (5×). A solution of TFA:$CH_2Cl_2$:$H_2O$ 60:40:05 (40 mL) was added and the suspension was shaken for 4 h. The solution and one subsequent wash with TFA:$CH_2Cl_2$:$H_2O$ 60:40:0.5 (20 mL) were collected and combined. Cleavage from the resin was repeated using TFA:$CH_2Cl_2$:$H_2O$ 70:30:0.5 (15 mL) for 3 h. The solvent was removed to yield 1.4 g of the title compound as the trifluoroacetate salts. ESIMS ([M+H]⁺): 311.1 (100).

Example 39

Mixture of (3R,4R; 3S,4S)-1-{3-[4-(4-Chloro-phenyl)-4-hydroxy-piperidin-1-yl]-4-hydroxy-pyrrolidin-1-yl}-2,2-diphenyl-ethanone trifluoroacetate Amine (3R, 4R; 3S, 4S)-4-(4-chloro-phenyl)-1-(4-hydroxy-pyrrolidin-3-yl)-piperidin-4-ol bistrifluoroacetate (the product from Example 1, 15.7 mg, 0.03 mmol) was dissolved in DMF (0.05 mL) and DIPEA (0.012 mL, 2.5 equiv) was added. Diphenyl acetic acid (5.8 mg, 0.033 mmol) was dissolved in DMF (0.05 mL). A solution of N-[(dimethylamino)-1H-1,2,3-triazolo[4,5,b]-pyridin-1-ylmethylmethaminium hexafluorophosphate N-oxide (HATU) in DMF (0.066 mL, 0.033 mmol, 0.5 M), followed by a solution of DIPEA in DMF (0.066 mL, 0.099 mmol, 1.5 M) were added to the carboxylic acid solution. After 5 min, the preactivated carboxylic acid solution was added to the amine solution. The reaction mixture was shaken for 30 min and the product was directly purified using preparative LC-MS, to yield 7.2 mg of the title compound as the trifluoroacetate salt. ESIMS ([M+H]⁺): 491.2 (100).

Example 40

Mixture of 1-{(3R,4R; 3S,4S)-3-[4-(4-Chloro-phenyl)-4-hydroxy-piperidin-1-yl]-4-hydroxy-pyrrolidin-1-yl}-2,2-diphenyl-ethanone (3R,4R; 3 S,4S)-4-(4-chloro-phenyl)-1-(4-hydroxy-pyrrolidin-3-yl)-piperidin-4-ol bistrifluoroacetate (2.8. g, 4 mmol) was dissolved in DMF (15 mL) and DIPEA (1.6 mL, 3 equiv) was added. Diphenyl-acetic acid (679 mg, 3.2 mmol) was dissolved in DMF (2 mL) and a solution of N-[(dimethylamino)-1H-1,2,3-triazolo[4,5,b]-pyridin-1-ylmethyl-methaminium hexafluorophosphate N-oxide (HATU) in DMF (6.4 mL, 3.2 mmol, 0.5 M), followed by a solution of DIPEA in DMF (3.2 mL, 9.6 mmol, 1.5 M) were added. After 5 min the preactivated carboxylic acid solution was added to the amine solution. The reaction mixture was shaken for 30 min. The solvent was evaporated and the residue dissolved in CH$_2$Cl$_2$ (40 mL). The organic phase was extracted with H$_2$O (5×10 mL). The aqueous phases were extracted once with CH$_2$Cl$_2$ (40 mL), the organic extracts were combined and the solvent was evaporated. Flash chromatography was performed on a Biotage silica gel column and eluted with CH$_2$Cl$_2$, CH$_2$Cl$_2$:MeOH 98:2, and CH$_2$Cl$_2$:MeOH 95:5, to yield 128 mg of the title compound. ESIMS ([M+H]$^+$): 491.2 (100).

Example 41

1-{(3R,4R or 3S,4S)-3-[4-(4-Chloro-phenyl)-4-hydroxy-piperidin-1-yl]-4-hydroxy-pyrrolidin-1-yl}-2,2-diphenyl-ethanone The chiral separation of a mixture of 1-{(3R,4R; 3S,4S)-3-[4-(4-Chloro-phenyl)-4-hydroxy-piperidin-1-yl]-4-hydroxy-pyrrolidin-1-yl}-2,2-diphenyl-ethanone was performed using a WHELK O1S,S column (10µ 21.2×300 mm, 980 g) at a flow rate of 10 mL/min and detection at 254 nm. The mixture (100 mg) was dissolved in heptane:ethanol (10:20, % v/v) and then separated by eluting with heptane:ethanol:MeOH:Et$_3$N (80:15:5:0.1,% v/v). The solvent was evaporated to afford 35 mg of the title compound. ESIMS ([M+H]+): 491.2 (100). $[\alpha]_D^{25}$=no measurable value, sign+ observed (MeOH), Absolute stereochemistry unknown.

Example 42

1-{(3R,4R or 3S,4S)-3-[4-(4-Chloro-phenyl)-4-hydroxy-piperidin-1-yl]-4-hydroxy-pyrrolidin-1-yl}-2,2-diphenyl-ethanone The title compound is prepared essentially as described in Example 41, to yield 28.4 mg of the title compound. $[\alpha]_D^{25}$=no measurable value, sign–observed (MeOH). ESIMS ([M+H]+): 491.2 (100). Absolute stereochemistry unknown.

Example 43

Mixture of (3R,4R; 3S,4S)-{3-[4-(4-Chloro-phenyl)-4-hydroxy-piperidin-1-yl]-4-hydroxy-pyrrolidin-1-yl}-(2-trifluoromethyl-phenyl)-methanone trifluoroacetate The title compound is prepared essentially as described in Example 39 using 2-trifluoromethyl-benzoic acid (6.3 mg, 0.033 mmol), to yield 7.4 mg as the trifluoroacetate salt. ESIMS ([M+H]+): 469.1 (100).

Example 44

Mixture of (3R,4R; 3S,4S)-Acetic acid 4-[4-(4-chloro-phenyl)-4-hydroxy-piperidin-1-yl]-1-(2-trifluoromethyl-benzoyl)-pyrrolidin-3-yl ester trifluoroacetate A mixture of (3R,4R; 3S,4S)-{3-[4-(4-Chloro-phenyl)-4-hydroxy-piperidin-1-yl]-4-hydroxy-pyrrolidin-1-yl}-(2-trifluoromethyl-phenyl)-methanone trifluoroacetate (2.2 mg, 0.005 mmol, see Example 43 for preparation) was dissolved in DMF (0.4 mL) and acetic anhydride was added. The reaction mixture was shaken for 2 h and directly used for LC-MS purification, to yield 1.1 mg of the title compound as the trifluoroacetate salt. ESIMS ([M+H]+): 511.2 (100).

Example 45

Mixture of {(3R,4R; 3S,4S)-3-[4-(4-Chloro-phenyl)-4-hydroxy-piperidin-1-yl]-4-hydroxy-pyrrolidin-1-yl}-(2-trifluoromethyl-phenyl)-methasone A mixture of (3R,4R; 3S,4S)-4-(4-chloro-phenyl)-1-(4-hydroxy-pyrrolidin-3-yl)-piperidin-4-ol bistrifluoroacetate (517 mg, 1.4 mmol) was dissolved in DMF (5 mL) and DIPEA (0.75 mL, 4.2 mmol) was added. 2-trifluoromethyl-benzoylchloride (511 mg, 1,05 mmol) was slowly added, the solution was shaken for 1 h and then the DMF was evaporated. The residue was dissolved in CH$_2$Cl$_2$ (10 mL) and extracted with H$_2$O (3×5 mL). The phases were separated and the organic extracts were combined and the solvent was evaporated. Flash chromatography was performed on a Biotage silica gel column and eluted with CH$_2$Cl$_2$, CH$_2$Cl$_2$:MeOH 98:2, and CH$_2$Cl$_2$:MeOH 96:4, to yield 243 mg of the title compound. ESIMS ([M+H]+): 469.1 (100).

Example 46

{(3R,4R) or (3S,4S)-3-[4-(4-Chloro-phenyl)-4-hydroxy-piperidin-1-yl]-4-hydroxy-pynrolidin-1-yl}-(2-trifluoromethyl-phenyl)-methanone The chiral separation of a mixture of {(3R,4R; 3S,4S)-3-[4-(4-Chloro-phenyl)-4-hydroxy-piperidin-1-yl]-4-hydroxy-pyrrolidin-1-yl}-(2-trifluoromethyl-phenyl)-methanone was performed using a Chiracel OJ column (20 µL, 6×35 mm) at a flow rate of 90 mL/min and detecting at 265 nm. The mixture (189 mg) was dissolved in EtOH:heptane (10:100, % v/v) and was then separated by eluting with heptane:ethanol:MeOH (88:10:2, % v/v). The solvent was evaporated to afford the title compound. ESIMS ([M+H]+): 469.1 (100). $[\alpha]_D^{25}$=+4.2+/−0.4 (MeOH). Absolute stereochemistry unknown.

Example 47

{(3R,4R) or (3S,4S)-3-[4-(4-Chloro-phenyl)-4-hydroxy-piperidin-1-yl]-4-hydroxy-pyrrolidin-1-yl}-(2-trifluoromethyl-phenyl)-methanone The title compound is prepared essentially as described in Example 46, to yield 104 mg. ESIMS ([M+H]+): 469.1 (100), $[\alpha]_D^{25}$=−5.6+/−0.5 (MeOH). Absolute stereochemistry unknown.

Example 48

Mixture of (3R,4R: 3S, 4S)-{3-[4-(4-Chloro-phenyl)-4-fluoro-piperidin-1-yl]-4-fluoro-pyrrolidin-1-yl}-(2-trifluoromethyl-phenyl)-methanone To the solution of a mixture of (3R,4R; 3S, 4S)-{3-[4-(4-chloro-phenyl)-4-hydroxy-piperidin-1-yl]-4-hydroxy-pyrrolidin-1-yl}-(2-trifluoromethyl-phenyl)-methanone (see Example 45 for preparation) (4.7 mg, 0.01 mmol) in dry DCM (0.2 mL) was added morpholinosulfur trifluoride (0.2 N solution in DCM, 0.2 mL, 4 eq.) at −78° C. and under N$_2$. The mixture was stirred at this temperature for 20 minutes, and then warmed to RT and stirred for additional 20 hours. After the reaction, a few drops of saturated aqueous NaHCO$_3$ was added. DCM was then removed, and the residue was re-dissolved into DMF (1 mL). The mixture was purified by preparative LC-MS, to yield 1.1. mg of the title compound as the trifluoroacetate salt. ESIMS ([M+H]+): 473.3 (75). 1H NMR (600 MHz, DMSO-d6, mixtures of 2 rotamers, room temp.) δ (PPM): 7.86 (d, J=7.8 Hz, 1H), 7.80 (t, J=7.7 Hz, 1H), 7.72 (t, J=7.5 Hz, 1H), 7.59 (t, J=7.2 Hz, 1H), 7.56-7.42 (m, 4H), [5.88 (m), 5.77 (m), 5.68 (m) (1H)], 4.55-4.37 (m, 1H), [4.32 (dd, J=8.8, 13.2 Hz), 4.10 (ddd, J=6.8, 13.7, 19 Hz) (1H)], 3.91-3.30 (m, 7H), 2.49-2.16 (m, 4H).

Example 49

Mixture of (3R,4R; 3S,4S)-4-{3-[4-(3-Chloro-phenyl)-piperazin-1-yl]-4-hydroxy-pyrrolidine-1-carbonyl}-benzonitrile trifluoroacetate The title compound is prepared essentially as described in Example 39 using a mixture of (3R,4R; 3S,4S)-4-[4-(3-chloro-phenyl)-piperazin-1-yl]-pyrrolidin-3-ol bistrifluoroacetate (15.2 mg, 0.03 mmol) and 4-cyano-benzoic acid (4.9 mg, 0.033 mmol), instead of diphenyl acetic acid, to yield 6.7 mg as the trifluoroacetate salt. ESIMS ([M+H]+); 411.2 (100).

Example 50

Mixture of (3R,4R; 3S,4S)-(4-Chloro-phenyl)-[3-hydroxy-4-(4-pyridin-2-yl-piperazin-1-yl)-pyrrolidin-1-yl]-methanone trifluoroacetate The title compound is prepared essentially as described in Example 39 using a mixture of (3R,4R; 3S,4S)-4-(4-pyridin-2-yl-piperazin-1-yl)-pyffolidin-3-ol bistrifluoroacetate (14.1 mg, 0.03 mmol) and 4-chloro-benzoic acid (5.2 mg, 0.033 mmol), instead of diphenyl acetic acid, to yield 6.9 mg as the trifluoroacetate salt. ESIMS ([M+H]+): 387.2 (100).

Example 51

Mixture of (3R,4R; 3S,4S)-(4-Chloro-phenyl)-{3-hydroxy-4-[4-(3-trifluoromethyl-phenyl)-piperazin-1-yl]-pyrrolidin-1-yl}-methanone trifluoroacetate The title compound is prepared essentially as described in Example 39 using a mixture of (3R,4R; 3S,4S)-4-[4-(3-trifluoromethyl-phenyl)-piperazin-1-yl]-pyrrolidin-3ol bistrifluoroacetate (16.3 mg, 0.03 mmol) and 4-chloro-benzoic acid (5.2 mg, 0.033 mmol), instead of diphenyl acetic acid, to yield 5.1 mg as the trifluoroacetate salt. ESIMS ([M+H]+): 454.1 (100).

Example 52

Mixture of (3R,4R; 3S,4S)-[3-(4-Benzothiazol-2-yl-piperidin-1-yl)-4-hydroxy-pyrrolidin-1-yl]-naphthalen-2-yl-methanone trifluoroacetate The title compound is prepared essentially as described in Example 39 using a mixture of (3R,4R; 3S,4S)-4-(4-Benzothiazol-2-yl-piperidin-1-yl)-pyrrolidin-3-ol bistrifluoroacetate (15.9 mg, 0.033 mmol) and naphthalene-2-carboxylic acid (5.7 mg, 0.033 mmol), instead of diphenyl acetic acid, to yield 8.9 mg as the trifluoroacetate salt. ESIMS ([M+H]+): 458.2 (100).

Example 53

Mixture of (3R,4R; 3S,4S)-1,3-Benzodioxol-5-yl-{3-[4-(4-chloro-benzyl)-piperazin-1-yl]-4-hydroxy-pyrrolidin-1-yl}-methanone trifluoroacetate The title compound is prepared essentially as described in Example 39 using a mixture of (3R,4R; 3S,4S)-4-[4-(4-chloro-benzyl)-piperazin-1-yl]-pyrrolidin-3-ol bistrifluoroacetate (15.7 mg, 0.033 mmol) and benzo[1,3]dioxole-5-carboxylic acid (5.5 mg, 0.033 mmol), instead of diphenyl acetic acid, to yield 6.1 mg as the trifluoroacetate salt. ESIMS ([M+H]+): 444.2 (100).

Example 54

Mixture of (3R,4R; 3S,4S)-Benzo[b]thiophen-2-yl-{3-[4-(4-chloro-benzyl)-piperazin-1-yl]-4-hydroxy-pyrrolidin-1-yl}-methanone trifluoroacetate The title compound is prepared essentially as described in Example 39 using a mixture of (3R,4R; 3S,4S)-4-[4-(4-chloro-benzyl)-piperazin-1-yl]-pyrrolidin-3-ol bistrifluoroacetate (15.7 mg, 0.033 mmol) and Benzo[b]thiopheno-2-carboxylic acid (5.6 mg, 0.033 mmol), instead of diphenyl acetic acid, to yield 7 mg as the trifluoroacetate salt. ESIMS ([M+H]+): 456.1 (100).

Example 55

Mixture of (3R,4R; 3S,4S)-{3-[4-(4-Chloro-benzyl)-piperazin-1-yl]-4-hydroxy-pyrrolidin-1-yl}-(4-chloro-phenyl)-methanone trifluoroacetate The title compound is prepared essentially as described in Example 39 using a mixture of (3R,4R; 3S,4S)-4-[4-(4-chloro-benzyl)-piperazin-1-yl]-pyrrolidin-3-ol bistrifluoroacetate (15.7 mg, 0.033 mmol) and 4-chloro-benzoic acid (5.2 mg, 0.033 mmol), instead of diphenyl acetic acid, to yield 3.3 mg as the trifluoroacetate salt. ESIMS ([M+H]+): 434.1 (100).

Example 56

Mixture of (3R,4R; 3S,4S)-3-[4-(4-chloro-benzyl)-piperazin-1-yl]-4-hydroxy-pyrrolidin-1-yl}-(4-chloro-phenyl)-methanone A mixture of (3R,4R; 3S,4S)-4-[4-(4-Chloro-benzyl)-piperazin-1-yl]-pyrrolidin-3-ol dihydrochloride (922 mg, 2.5 mmol) was dissolved in CH$_2$Cl$_2$ (20 mL) and DIPEA (2.4 mL) was added. 4-chlorobenzoylchloride (0.24 mL, 0.75 equiv) was added, the solution was shaken for 20 min and then transferred into a separation funnel. CH$_2$Cl$_2$ (10 mL), H$_2$O (5 mL) and aq NaOH (2 mL) were added. The phases were separated and the organic phase was extracted with H$_2$O (5×5 mL). The aqueous phase was extracted once with CH$_2$Cl$_2$ (20 mL), the organic extracts were combined and the solvent was evaporated. Flash chromatography of the yellowish solid was performed on a Biotage silica gel column and eluted with CH$_2$Cl$_2$:MeOH 98:2, and CH$_2$Cl$_2$:MeOH 95:5, to yield 478 mg of the title compound. ESIMS ([M+H]+): 434.1 (100).

Example 57

{(3R,4R) or (3S,4S)-3-[4-(4-Chloro-benzyl)-piperazin-1-yl]-4-hydroxy-pyrrolidin-1-yl}-(4-chlorophenyl)-methanone The chiral separation of a mixture of (3R,4R; 3S,4S)-3-[4-(4-chloro-benzyl)-piperazin-1-yl]-4-hydroxy-pyrrolidin-1-yl}-(4-chloro-phenyl)-methanone was performed using a CHIRALPAK AD column (20μ, 60×400 mm, 800 g) at a flow rate of 100 mL/min and detecting at 254 nm. The mixture (400 mg) was dissolved in heptane:ethanol (50:70, % v/v) before injection and then separated by eluting with heptane:ethanol:Et$_3$N (50:70:0.2, % v/v). The solvent was evaporated to afford 194 mg of the title compound. ESIMS ([M+H]+): 434.1 (100). $[\alpha]_D^{25}$=−22.6+/−0.7 (MeOH). Absolute stereochemistry unknown.

Example 58

{(3S,4S) or (3R,4R)-3-[4-(4-Chloro-benzyl)-piperazin-1-yl]-4-hydroxy-pyrrolidin-1-yl}-(4-chlorophenyl)-methanone The title compound is prepared essentially as described in Example 57, to yield 190 mg. ESIMS ([M+H]+): 434.1 (100). $[\alpha]_D^{25}$=+23.3+/−0.8 (MeOH). Absolute stereochemistry unknown.

Example 59

Mixture of (3R,4R; 3S, 4S)-{3-[4-(4-Chloro-benzyl)-piperazin-1-yl]-4-fluoro-pyrrolidin-1-yl}-(4-chloro-phenyl)-methanone To a solution of 0.40 g (0.92 mmol) mixture of (3R,4R; 3S,4S)-3-[4-(4-chloro-benzyl)-piperazin-1-yl]-4-hydroxy-pyrrolidin-1-yl}-(4-chloro-phenyl)-methanone (see Example 56 for preparation) in DCM (3 mL), was added morpholinosulfur trifluoride (322 mg, 2 eq.) dropwise at RT and under N$_2$. The mixture was stirred at RT and under N$_2$ for 1 hour. 10 mL of dilute NaHCO$_3$ aq. solution was added to the reaction mixture (pH 7~8). The mixture was then extracted with ethyl acetate (3×30 mL). The organic layers were combined, washed with brine (1×5mL), dried over Na$_2$SO$_4$, filtered and dried. The title compound was purified by silica gel flash column chromatography (ethyl acetate+0.1% TEA) to yield 0.109 g of the title compound. ESIMS ([M+H]$^+$): 436.3 (100). $^1$H NMR (600 MHz, DMSO-d6, mixtures of 2 rotamers, room temp.) δ (PPM): 7.56-7.49 (m, 4H), 7.38-7.22 (m, 4H), [5.29 (d, J=52 Hz), 5.20 (d, J=52 Hz) (1H)], 3.93-3.33 (m, 7H), 3.14-2.97 (m, 1H), 2.65-2.16 (m, 7H).

Example 60

{(3S,4S or 3R,4R)-3-[4-(4-Chloro-benzyl)-piperazin-1-yl]-4-fluoro-pyrrolidin-1-yl}-(4-chloro-phenyl)-methanone The chiral separation of a mixture of {(3S,4S; (3R,4R)-3-[4-(4-chloro-benzyl)-piperazin-1-yl]-4-fluoro-pyrrolidin-1-yl}-(4-chloro-phenyl)-methanone (see Example 59 for preparation) was performed using a CHIRAL PAK AD column (10μ, 21.2×250 mm) at a flow rate of 9 mL/min and detecting at 265 nm. The mixture (95 mg) was dissolved in ethanol:Et$_3$N (3:1) and then separated by eluting with ethanol:Et$_3$N (3:1). The solvent was evaporated to yield 41.6 mg of the title compound. ESIMS ([M+H]+): 436.1 (100). $[\alpha]_D^{25}$=+11.1+/−0.6 (MeOH). Absolute stereochemistry unknown.

Example 61

{(3R,4R or 3S,4S)-3-[4-(4-Chloro-benzyl)-piperazin-1-yl]-4-fluoro-pyrrolidin-1-yl}-(4-chloro-phenyl)-methanone The title compound is prepared essentially as described in Example 60, to yield 35.4 mg. ESIMS([M+H]+): 436.1 (100). $[\alpha]_D^{25}$=−11.3+/−0.6 (MeOH). Absolute stereochemistry unknown.

Example 62

Mixture of (3R,4R; 3S,4S)-{3-[4-(4-Chloro-benzyl)-piperazin-1-yl]-4-hydroxy-pyrrolidin-1-yl}-(2-propylsulfanyl-pyridin-3-yl)-methanone trifluoroacetate The title compound is prepared essentially as described in Example 39 using a mixture of (3R,4R; 3S,4S)-4-[4-(4-chloro-benzyl)-piperazin-1-yl]-pyrrolidin-3-ol bistrifluoroacetate (15.7 mg, 0.033 mmol) and 2-propylsulfanyl-nicotinic acid (6.5 mg, 0.033 mmol), instead of diphenyl acetic acid, to yield 9.8 mg as the trifluoroacetate salt. ESIMS ([M+H]+): 475.2 (100).

Example 63

Mixture of (3R,4R; 3S,4S)-(4-Chloro-phenyl)-[3-hydroxy-4-(4-m-tolyl-piperazin-1-yl)-pyrrolidin-1-yl]-methanone trifluoroacetate The title compound is prepared essentially as described in Example 39 using a mixture of (3R,4R; 3S,4S)-4-(4-m-tolyl-piperazin-1-yl)-pyrrolidin-3-ol bistrifluoroacetate (14.6 g, 0.033 mmol) and 4-chloro-benzoic acid (5.2 mg, 0.033 mmol), instead of diphenyl acetic acid to yield 4.9 mg as the trifluoroacetate salt. ESIMS ([M+H]+): 400.2 (100).

Example 64

Mixture of (3R,4R; 3S,4S)-{3-[4-(4-Chloro-benzyl)-piperazin-1-yl]-4-hydroxy-pyrrolidin-1-yl}-(9H-xanthen-9-yl)-methanone trifluoroacetate The title compound is prepared essentially as described in Example 39 using a mixture of (3R,4R; 3S,4S)-4-[4-(4-chloro-benzyl)-piperazin-1-yl]-pyrrolidin-3-ol bistrifluoroacetate (26.4 mg, 0,05 mmol), and 9H-xanthen-9-carboxylic acid (9 mg, 0.04 mmol), instead of diphenyl acetic acid, preactivated by addition of a solution of HATU in DMF (0.08 mL, 0.04 mmol, 0.5 M), followed by a solution of DIPEA in DMF (0.08 mL, 0.12 mmol, 1.5 M), to yield 4.4 mg as the trifluoroacetate salt. ESIMS ([M+H]+): 504.2 (100).

Example 65

Mixture of (3R,4R; 3S,4S)-(3-Chloro-phenyl)-{3-[4-(4-chloro-phenyl)-4-hydroxy-piperidin-1-yl]-4-hydroxy-pyrrolidin-1-yl}-methanone trifluoroacetate The title compound is prepared essentially as described in Example 39 using amine (3R,4R; 3S,4S)-4-(4-chloro-phenyl)-1-(4-hydroxy-pyrrolidin-3-yl)-piperidin-4-ol bistrifluoroacetate (52 mg, 0.1 mmol) and 3-chloro-benzoic acid (12.5 mg, 0.08 mmol), instead of diphenyl acetic acid, preactivated by addition of HATU in DMF (0.160 mL, 0.08 mmol, 0.5 M), followed by a solution of DIPEA in DMF (0.160 mL, 0.24 mmol, 1.5 M), to yield 11.1 mg as the trifluoroacetate salt. ESIMS ([M+H]+): 435.1 (100).

Example 66

Mixture of (3R,4R; 3S,4S)-(1H-Benzimidazol-5-yl)-{3-[4-(4-chloro-phenyl)-4-hydroxy-piperidin-1-yl]-4-hydroxy-pyrrolidin-1-yl}-methanone trifluoroacetate The title compound is prepared essentially as described in Example 65 using 1H-benzimidazole-2-carboxylic acid (13 mg, 0.08 mmol) instead of 3-chloro-benzoic acid, to yield 21.4 mg as the trifluoroacetate salt. ESIMS ([M+H]+): 441.2 (100).

Example 67

Mixture of (3R,4R; 3S,4S)-[3-[4-(4-Chloro-benzyl)-piperazin-1-yl]-4-hydroxy-pyrrolidin-1-yl}-(4-isopropyl-phenyl)-methanone trifluoroacetate The title compound is prepared essentially as described in Example 65 using 4-isopropyl-benzoic acid (13.1 mg, 0.08 mmol) instead of 3-chloro-benzoic acid, to yield 25.1 mg as the trifluoroacetate salt. ESIMS ([M+H]+): 442.2 (100).

Example 68

Mixture of (3R,4R; 3S,4S)-Biphenyl-4-yl-{3-[4-(4-chloro-benzyl)-piperazin-1-yl]-4-hydroxy-pyrrolidin-1-yl}-methanone trifluoroacetate The title compound is prepared essentially as described in Example 65 using biphenyl-4-carboxylic acid (15.9 mg, 0.08 mmol) instead of 3-chloro-benzoic acid, to yield 12 mg as the trifluoroacetate salt. ESIMS ([M+H]+): 476.2 (100).

Example 69

Mixture of (3R,4R; 3S,4S)-{3-[4-(4-Chloro-benzyl)-piperazin-1-yl]-4-hydroxy-pyrrolidin-1-yl)-thiophen-3-yl-methanone trifluoroacetate The title compound is prepared essentially as described in Example 65 using thiophen-3-carboxylic acid (10.3 mg, 0.08 mmol) instead of 3-chloro-benzoic acid, to yield 28.1 mg as the trifluoroacetate salt. ESIMS ([M+H]+): 406.1 (100).

Example 70

Mixture of (3R,4R; 3S,4S)-{3-[4-(4-Chloro-benzyl)-piperazin-1-yl]-4-hydroxy-pyrrolidin-1-yl) -(2-benzyl-phenyl)-methanone trifluoroacetate The title compound is prepared essentially as described in Example 65 using 2-benzyl-benzoic acid (17 mg, 0.08 mmol) instead of 3-chloro-benzoic acid, to yield 28.5 mg as the trifluoroacetate salt. ESIMS ([M+H]+): 490.2 (100).

Example 71

Mixture of (3R,4R; 3S,4S)-{3-[4-(4-Chloro-benzyl)-piperazin-1-yl]-4-hydroxy-pyrrolidin-1-yl}-(2-methoxy-phenyl)-methanone trifluoroacetate The title compound is prepared essentially as described in Example 65 using 2-methoxy-benzoic acid (12 mg, 0.08 mmol) instead of 3-chloro-benzoic acid, to yield 29.5 mg as the trifluoroacetate salt. ESIMS ([M+H]+): 430.2 (100).

Example 72

Mixture of (3R,4R; 3S,4S)-{3-[4-(4-Chloro-benzyl)-piperazin-1-yl]-4-hydroxy-pyrrolidin-1-yl}-phenyl-methanone trifluoroacetate The title compound is prepared essentially as described in Example 65 using benzoic acid (9.8 mg, 0.08 mmol) instead of 3-chloro-benzoic acid, to yield 27.1 mg as the trifluoroacetate salt. ESIMS ([M+H]+): 400.2 (100).

Example 73

Mixture of (3R,4R; 3S,4S)-1-{3-[4-(4-Chloro-benzyl)-piperazin-1-yl]-4-hydroxy-pyrrolidin-1-yl}-2-(4-ehloro-phenyl)-ethanone trifluoroacetate The title compound is prepared essentially as described in Example 65 using (4-chloro-phenyl)-acetic acid (13.6 mg, 0.08 mmol) instead of 3-chloro-benzoic acid, to yield 18.2 mg as the trifluoroacetate salt. ESIMS ([M+H]+): 448.1 (100).

Example 74

Mixture of (3R,4R; 3S,4S)-{3-[4-(4-Chloro-benzyl)-piperazin-1-yl]-4-hydroxy-pyrrolidin-1-yl}-pyridin-3-yl-methanone trifluoroacetate The title compound is prepared essentially as described in Example 65 using nicotinic acid (9.8 mg, 0.08 mmol) instead of 3-chloro-benzoic acid, to yield 17.7 mg as the trifluoroacetate salt. ESIMS ([M+H]+): 401.2 (100).

Example 75

Mixture of (3R,4R; 3S,4S)-{3-[4-(4-Chloro-benzyl)-piperazin-1-yl]-4-hydroxy-pyrrolidin-1-yl]-(4-trifluoromethoxy-phenyl)-inethanone trifluoroacetate The title compound is prepared essentially as described in Example 65 using 4-trifluoromethoxy-benzoic acid (9.8 mg, 0.08 mmol) instead of 3-chloro-benzoic acid, to yield 19.4 mg as the trifluoroacetate salt. ESIMS ([M+H]+): 484.2 (100).

Example 76

Mixture of (3R,4R; 3S,4S)-{3-[4-(4-Chloro-benzyl)-piperazin-1-yl]-4-hydroxy-pyrrolidin-1-yl}-quinoxalin-2-yl-methanone trifluoroacetate The title compound is prepared essentially as described in Example 65 using quinoxaline-2-carboxylic acid (13.9 mg, 0.08 mmol) instead of 3-chloro-benzoic acid, to yield 17.3 mg as the trifluoroacetate salt. ESIMS ([M+H]+): 452.2 (100).

Example 77

Mixture of (3R,4R; 3S,4S)-{3-[4-(4-Chloro-benzyl)-piperazin-1-yl]-4-hydroxy-pyrrolidin-1-1-yl}-pyrazin-2-yl-methanone trifluoroacetate The title compound is prepared essentially as described in Example 65 using pyrazine-2-carboxylic acid (9.9 mg, 0.08 mmol) instead of 3-chloro-benzoic acid, to yield 20.8 mg as the trifluoroacetate salt. ESIMS ([M+H]+): 402.2 (100).

Example 78

Mixture of (3R,4R; 3S,4S)-(2-Amino-4-chloro-phenyl)-{3-[4-(4-chloro-benzyl)-piperazin-1-yl]-4-hydroxy-pyrrolidin-1-yl}-methanone trifluoroacetate The title compound is prepared essentially as described in Example 65 using 2-amino-4-chloro-benzoic acid (13.7 mg, 0.08 mmol) instead of 3-chloro-benzoic acid, to yield 19.5 mg as the trifluoroacetate salt. ESIMS ([M+H]+): 449.1 (100).

Example 79

Mixture of (3R,4R; 3S,4S)-N-(5-Chloro-2-{3-[4-(4-chloro-benzyl)-piperazin-1-yl]-4-hydroxy-pyrrolidin-1-carbonyl}-phenyl)-acetamide trifluoroacetate A mixture of (3R,4R; 3S,4S)-(2-Amino-4-chloro-phenyl)-{3-[4-(4-ehloro-benzyl)-piperazin-1-yl]-4-hydroxy-pyrrolidin-1-yl)-methanone trifluoroacetate (22 mg, 0.05 mmol) was dissolved in DMF and acetic anhydride (20 uL, 0.2 mmol) was added. The reaction mixture was shaken for 1 h and directly used for LC-MS purification, to yield 3.2 mg of the title compound as the trifluoroacetate salt. ESIMS ([M+H]+): 491.2 (100).

Example 80

Mixture of (3R,4R; 3S,4S)-1-(5-Chloro-2-{3-[4-(4-chloro-benzyl)-piperazin-1-yl]-4-hydroxy-pyrrolidine-1-carbonyl}-phenyl)-3-methyl-urea trifluoroacetate A mixture of (3R,4R; 3S,4S)-(2-Amino-4-chloro-phenyl)-{3-[4-(4-chloro-benzyl)-piperazin-1-yl]-4-hydroxy-pyrrolidin-1-yl}-methanone trifluoroacetate (22 mg, 0.05 mmol) was dissolved in DMF and methyl isocyanate (5.8 uL, 0.1 mmol) was added. The reaction mixture was shaken for 1 h and directly used for LC-MS purification to yield 3.4 mg of the title compound as the trifluoroacetate salt. ESIMS ([M+H]+): 506.2 (100).

Example 81

Mixture of (3R,4R; 3S,4S)-[3-Hydroxy-4-(4-pyrimidin-2-yl-piperazin-1-yl)-pyrrolidin-1-yl]-(2-phenoxy-phenyl)-methanone trifluoroacetate The title compound is prepared essentially as described in Example 65 using 2-phenoxy-benzoic acid (17 mg, 0.08 mmol) instead of 3-chloro-benzoic acid, to yield 15.4 mg as the trifluoroacetate salt. ESIMS ([M+H]+): 446.2 (100).

Example 82

Mixture of (3R,4R; 3S,4S)-(4-Chloro-phenyl)-{3-hydroxy-4-[4-(2-trifluoromethyl-phenyl)-piperazin-1-yl]-pyrrolidin-1-yl}-methanone The title compound is prepared essentially as described in Example 39 using a mixture of (3R,4R; 3S,4S)-4-[4-(2-trifluoromethyl-phenyl)-piperazin-1-yl]-pyrrolidin-3-ol bistrifluoroacetate (27 mg, 0.05 mmol) and 4-chloro-benzoic acid (7.8 mg, 0.05 mmol), instead of diphenyl acetic acid, preactivated by addition of a solution of HATU in DMF (0,1 mL, 0.05 mmol, 0.5 M), followed by the addition of a solution of DIPEA in DMF (0.1 mL, 0.05 mmol, 1.5 M), to yield 0.9 mg of the title compound as the trifluoroacetate salt. ESIMS ([M+H]+): 454.1 (100).

Example 83

Mixture of (3R,4R; 3S,4S)-(4-Chloro-phenyl)-{3-hydroxy-4-[4-(5-trifluoromethyl-pyridin-2-yl)-piperazin-1-yl]-pyrrolidin-1-yl}-methanone trifluoroacetate The title compound is prepared essentially as described in Example 82 using a mixture of (3R,4R; 3S,4S)-4-[4-(5-trifluoromethyl-pyridin-2-yl)-piperazin-1-yl]-pyrrolidin-3-ol bistrifluoroacetate (27 mg, 0.05 mmol) instead of a mixture of (3R,4R; 3S,4S)-4-[4-(2-trifluoromethyl-phenyl)-piperazin-1-yl]-pyrrolidin-3-ol bistrifluoroacetate, to yield 1.8 mg as the trifluoroacetate salt. ESIMS ([M+H]+): 455.1 (100).

Example 84

Mixture of (3R,4R; 3S,4S)-[3-(4-Biphenyl-4-yl-piperazin-1-yl)-4-hydroxy-pyrrolidin-1-yl]-(4-chloro-phenyl)-methanone trifluoroacetate The title compound is prepared essentially as described in Example 82 using a mixture of (3R,4R; 3S,4S)-4-(4-biphenyl-4-yl-piperazin-1-yl)-pyrrolidin-3-ol bistrifluoroacetate. (28 mg, 0.05 mmol) instead of a mixture of (3R,4R; 3S,4S)-4-[4-(2-trifluoromethyl-phenyl)-piperazin-1-yl]-pyrrolidin-3-ol bistrifluoroacetate, to yield 1 mg as the trifluoroacetate salt. ESIMS ([M+H]+): 462.2 (100).

Example 85

Mixture of (3R,4R; 3S,4S)-{3-[4-(4-Bromo-benzyl)-piperazin-1-yl)-4-hydroxy-pyrrolidin-1-yl}-(4-chloro-phenyl)-methanone trifluoroacetate The title compound is prepared essentially as described in Example 82 using a mixture of (3R,4R; 3S,4S)-4-[4-(4-bromo-benzyl)-piperazin-1-yl]-pyrrolidin-3-ol bistrifluoroacetate (28 mg, 0.05 mmol) instead of a mixture of (3R,4R; 3S,4S)-4-[4-(2-trifluoromethyl-phenyl)-piperazin-1-yl]-pyrrolidin-3-ol bistrifluoroacetate, to yield 3.8 mg as the trifluoroacetate salt. ESIMS ([M+H]+): 478.1 (100).

Example 86

Mixture of (3R,4R; 3S,4S)(4-Chloro-phenyl)-{3-hydroxy-4-(4-thieno[3,2-d]pyrimidin-4-yl-piperazin-1-yl]-pyrrolidin-1-yl]-methanone trifluoroacetate The title compound is prepared essentially as described in Example 82 using a mixture of (3R,4R; 3S,4S)-4-(4-thieno

[3,2-d]pyrimidin-4-yl-piperazin-1-yl)-pyrrolidin-3-ol bistrifluoroacetate (27 mg, 0.05 mmol) instead of a mixture of (3R,4R; 3S,4S)-4-[4-(2-trifluoromethyl-phenyl)-piperazin-1-yl]-pyrrolidin-3-ol bistrifluoroacetate, to yield 7.3 mg as the trifluoroacetate salt. ESIMS ([M+H]+): 444.1 (100).

Example 87

Mixture of (3R,4R; 3S,4S)-(3,4-Dichloro-phenyl)-{3-hydroxy-4-[4-(5-trifluoromethyl-pyridin-2-yl)-piperazin-1-l]-pyrrolidin-1-yl}-methanone trifluoroacetate The title compound is prepared essentially as described in Example 82 using a mixture of (3R,4R; 3S,4S)-4-[4-(5-trifluoromethyl-pyridin-2-yl)-piperazin-1-yl]-pyrrolidin-3-ol bistrifluoroacetate (27 mg, 0.05 mmol) and 3,4-chloro-benzoic acid (9.5 mg, 0.05 mmol) instead of 4-chloro-benzoic acid, to yield 1.4 mg as the trifluoroacetate salt. ESIMS ([M+H]+): 489.1 (100).

Example 88

Mixture of (3R,4R; 3S,4S)-(3,4-Dichloro-phenyl)-(3-[4-(4-fluoro-benzyl)-piperazin-1-yl]-4-hydroxy-pyrrolidin-1-yl)-methanone trifluoroacetate The title compound is prepared essentially as described in Example 87 using a mixture of (3R,4R; 3S,4S)-4-[4-(4-fluoro-benzyl)-piperazin-1-yl]-pyrrolidin-3-ol bistrifluoroacetate (27 mg, 0.05 mmol) instead of a mixture of (3R,4R; 3S,4S)-4-[4-(5-trifluoromethyl-pyridin-2-yl)-piperazin-1-yl]-pyrrolidin-3-ol bistrifluoroacetate, to yield 8.2 mg as the trifluoroacetate salt. ESIMS ([M+H]+): 452.1 (100).

Example 89

Mixture of (3R,4R; 3S,4S)-(3,4-Dichloro-phenyl)-{3-[4-(4-fluoro-benzoyl)-piperidin-1-yl]-4-hydroxy-pyrrolidin-1-yl}-methanone trifluoroacetate The title compound is prepared essentially as described in Example 87 using a mixture of (3R,4R; 3S,4S)-(4-fluoro-phenyl)-{1-(4-hydroxy-pyrrolidin-3-yl)-piperidin-4-yl]-methanone bistrifluoroacetate (35 mg, 0.05 mmol) instead of a mixture of (3R,4R; 3S,4S)-4-[4-(5-trifluoromethyl-pyridin-2-yl)-piperazin-1-yl]-pyrrolidin-3-ol bistrifluoroacetate, to yield 31.5 mg as the trifluoroacetate salt. ESIMS ([M+H]+): 465.1 (100).

Example 90

Mixture of (3R,4R; 3S,4S)-[3-[4-(4-Chloro-benzyl)-piperazin-1-yl]-4-hydroxy-pyrrolidin-1-yl]-(9H-fluoren-9-yl)-methanone trifluoroacetate The title compound is prepared essentially as described in Example 82 using a mixture of (3R,4R; 3S,4S)-4-[4-(4-chloro-benzyl)-piperazin-1-yl]-pyrrolidin-3-ol (23 mg, 0.05 mmol) and 9H-fluorene-9-carboxylic acid (10.5 mg, 0.05 mmol), instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 1.5 mg as the trifluoroacetate salt. ESIMS ([M+H]+): 488.2 (100).

Example 91

Mixture of (3R,4R; 3S,4S)-1-{3-[4-(4-Chloro-benzyl)-piperazin-1-yl]-4-hydroxy-pyrrolidin-1-yl}-2,2,2-triphenyl-ethanone trifluoroacetate The title compound is prepared essentially as described in Example 82 using a mixture of (3R,4R; 3S,4S)-4-[4-(4-chloro-benzyl)-piperazin-1-yl]-pyrrolidin-3-ol (23 mg, 0.05 mmol) and triphenyl-acetic acid (14 mg, 0.05 mmol), instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 14.4 mg as the trifluoroacetate salt. ESIMS ([M+H]+): 566.3 (100).

Example 92

Mixture of (3R,4R; 3S,4S)-1-{3-[4-(4-Chloro-benzyl)-piperazin-1-yl]-4-hydroxy-pyrrolidin-1-yl}-2,2-bis-(4-chloro-phenyl)-ethanone trifluoroacetate The title compound is prepared essentially as described in Example 91 using bis-(4-chloro-phenyl)-acetic acid (14 mg, 0.05 mmol) instead of triphenyl acetic acid, to yield 5.1 mg as the trifluoroacetate salt. ESIMS ([M+H]+): 558.1 (100).

Example 93

Mixture of (3R,4R; 3S,4S)-1-{3-[4-[4-Chloro-phenyl)-piperidin-1-yl]-4-hydroxy-pyrrolidin-1-yl}-2,2-diphenyl-ethanone trifluoroacetate The title compound is prepared essentially as described in Example 82 using a mixture of (3R,4R; 3S,4S)-4-[4-(4-chloro-phenyl)-piperidin-1-yl]-pyrrolidin-3-ol bistrifluoroacetate (34 mg, 0.05 mmol) and diphenyl acetic acid (8.7 mg, 0.05 mmol) instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 3.6 mg as the trifluoroacetate salt. ESIMS ([M+H]+): 475.2 (100).

Example 94

Mixture of (3R,4R; 3S,4S)-1-{3-[4-(4-Chloro-phenyl)-4-hydroxy-3,3-dimethyl-piperidin-1-yl]-4-hydroxy-pyrrolidin-1-yl}-2,2-diphenyl-ethanone trifluoroacetate The title compound is prepared essentially as described in Example 82 using a mixture of (3R,4R; 3S,4S)-[4-(4-chloro-phenyl)-1-(4-hydroxy-pyrrolidin-3-yl)-3,3-dimethyl-piperidin-4-ol]bistrifluoroacetate (37 mg, 0.05 mmol) and diphenyl-acetic acid (8.7 mg, 0.05 mmol), instead of a mixture of (3R,4R; 3S, 4S)-4-[4-(2-trifluoromethyl-phenyl)-piperazin-1-yl]-pyrrol idin-3-ol bistrifluoroacetate and 4-chloro-benzoic acid, to yield 3.6 mg as the trifluoroacetate salt. ESIMS ([M+H]+): 519.2 (100).

Example 95

Mixture of (3R,4R; 3S,4S)-1-{3-[(S)-4-(4-Chloro-phenyl)-4-hydroxy-3,3-dimethyl-piperidin-1-yl]-4-hydroxy-pyrrolidin-1-yl}-2,2-diphenyl-ethanone trifluoroacetate The title compound is prepared essentially as described in Example 82 using a mixture of (3R,4R; 3 S,4S)-[(S)-4-(4-

Chloro-phenyl)-1-(4-hydroxy-pyrrolidin-3-yl)-3,3-dimethyl-piperidin-4-ol]bistrifluoroacetate (37 mg, 0.05 mmol) and diphenyl-acetic acid (8.7 mg, 0.05 mmol), instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 1.2 mg as the trifluoroacetate salt. ESIMS ([M+H]+): 519.2 (100).

Example 96

Mixture of (3R,4R; 3S,4S)-(4-Chloro-phenyl)-[3-hydroxy-4-(4-phenyl-piperazin-1-yl)-pyrrolidin-1-yl]-methanone formate The title compound is prepared essentially as described in Example 82 using a mixture of (3R,4R; 3S,4S)-4-(4-phenyl-piperazin-1-yl)-pyrrolidin-3-ol bistrifluoroacetate (25 mg, 0.05 mmol) and 4-chlorobenzoic acid (8.6 mg, 0.05 mmol), instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 1.13 mg as the formate salt. ESIMS ([M+H]+): 386.2 (100).

Example 97

Mixture of (3R,4R; 3S,4S)-(4-Chloro-phenyl)-[3-hydroxy-4-(4-phenyl-piperidin-1-yl)-pyrrolidin-1-yl]-methanone formate The title compound is prepared essentially as described in Example 82 using a mixture of (3R,4R; 3S,4S)-4-(4-phenyl-piperidin-1-yl)-pyrrolidin-3-ol bistrifluoroacetate (24 mg, 0.05 mmol) and 4-chlorobenzoic acid (8.6 mg, 0.05 mmol), instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 3.83 mg as the formate salt. ESIMS ([M+H]+): 385.2 (100).

Example 98

Mixture of (3R,4R; 3S,4S)-[3-(4-Benzyl-4-hydroxy-piperidin-1-yl)-4-hydroxy-pyrrolidin-1-yl]-(4-chloro-phenyl)-methanone formate The title compound is prepared essentially as described in Example 82 using a mixture of (3R,4R; 3S,4S)-4-benzyl-1-(4-hydroxy-pyrrolidin-3-yl)-piperidin-4-ol. bistrifluoroacetate (25 mg, 0.05 mmol) and 4-chlorobenzoic acid (8.6 mg, 0.05 mmol), instead of a mixture of (3R, 4R; 3S, 4S)-4-[4-(2-trifluoromethyl-phenyl)-piperazin-1-yl]-pyrrolidin-3-ol bistrifluoroacetate and 4-chloro-benzoic acid, to yield 3.28 mg as the formate salt. ESIMS ([M+H]+): 415.2 (100).

Example 99

Mixture of (3R,4R; 3S,4S)-(4-Chloro-phenyl)-[3-hydroxy-4-(4-methyl-piperazin-1-yl)-pyrrolidin-1-yl]-methanone formate The title compound is prepared essentially as described in Example 82 using a mixture of (3R,4R; 3S,4S)-4-(4-methyl-piperazin-1-yl)-pyrrolidin-3-ol bistrifluoroacetate (20 mg, 0.05 mmol) and 4-chlorobenzoic acid (8.6 mg, 0.05 mmol), instead of a mixture of (3R, 4R; 3S, 4S)-4-[4-(2-trifluoromethyl-phenyl)-piperazin-1-yl]-pyrrolidin-3-ol bistrifluoroacetate and 4-chloro-benzoic acid to yield 5.65 mg as the formate salt. ESIMS ([M+H]+): 324.1 (100).

Example 100

Mixture of (3R,4R; 3S,4S)-[3-(4-Benzyl-piperidin-1-yl)-4-hydroxy-pyrrolidin-1-yl]-(4-chloro-phenyl)-methanone formate The title compound is prepared essentially as described in Example 82 using a mixture of (3R,4R; 3S,4S)-4-(4-benzyl-piperidin-1-yl)-pyrrolidin-3-ol bistrifluoroacetate (24 mg, 0.05 mmol) and 4-chlorobenzoic acid (8.6 mg, 0.05 mmol), instead of a mixture of (3R, 4R; 3S, 4S)-4-[4-(2-trifluoromethyl-phenyl)-piperazin-1-yl]-pyrrolidin-3-ol bistrifluoroacetate and 4-chloro-benzoic acid, to yield 2.83 mg as the formate salt. ESIMS ([M+H]+): 399.2 (100).

Example 101

Mixture of (3R,4R; 3S,4S)-1-[3-(4-Benzyl-piperazin-1-yl)-4-hydroxy-pyrrolidin-1-yl]-2,2-diphenyl-ethanone formate The title compound is prepared essentially as described in Example 82 using a mixture of (3R,4R; 3S,4S)-4-(4-benzyl-piperazin-1-yl)-pyrrolidin-3-ol bistrifluoroacetate (24 mg, 0.05 mmol) and diphenyl-acetic acid (11 mg, 0.05 mmol), instead of a mixture of (3R,4R; 3S, 4S)-4-[4-(2-trifluoromethyl-phenyl)-piperazin-1-yl]-pyrrolidin-3-ol bistrifluoroacetate and 4-chloro-benzoic acid, to yield 10.74 mg as the formate salt. ESIMS ([M+H]+): 456.3 (100).

Example 102

Mixture of {(3R,4R; 3S,4S)-3-(4-Chloro-phenoxy)-4-[4-(4-fluoro-benzoyl)-piperidin-1-yl]-pyrrolidin-1-yl}-furan-3-yl-methanone trifluoroacetate The title compound is prepared essentially as described in Example 39 using a mixture of {1-[(3R,4R; 3S,4S)-4-(4-chloro-phenoxy)-pyrrolidin-3-yl]-piperidin-4-yl}-(4-fluoro-phenyl)-methanone bistrifluoroacetate (27 mg, 0.05 mmol) and furan-3-carboxylic acid (4.5 mg, 0.04 mmol), instead of (3R, 4R; 3S, 4S)-4-(4-chloro-phenyl)-1-(4-hydroxy-pyrrolidin-3-yl)-piperidin-4-ol bistrifluoroacetate and diphenyl acetic acid, preactivated by addition of a solution of HATU in DMF (0.08 mL, 0.04 mmol, 0.5 M), followed by the addition of a solution of DIPEA in DMF (0.08 mL, 0.12 mmol, 1.5 M), to yield 8 mg as the trifluoroacetate salt. ESIMS ([M+H]+): 496.1 (100).

Example 103

Mixture of (3R,4R; 3S,4S)-{3-[4-(4-Fluoro-benzoyl)-piperidin-1-yl]-4-phenoxy-pyrrolidin-1-yl]-furan-3-yl-methanone trifluoroacetate The title compound is prepared essentially as described in Example 102 using a mixture of (3R,4R; 3S,4S)-(4-fluoro-phenyl)-[1-(4-phenoxy-pyrrolidin-3-yl)-piperidin-4-yl]-methanone bistrifluoroacetate instead of (3R,4R; 3S,4S)-{1-[(4-(4-chloro-phenoxy)-pyrrolidin-3-yl]-piperidin-4-yl}-(4-fluoro-phenyl)-methanone bistrifluoroacetate, to yield 11.6 mg as the trifluoroacetate salt. ESIMS (M+H]+): 463.2 (100).

Example 104

Mixture of 1-[(3'R,4'R or 3'S,4'S)-4-(4-Chloro-phenyl)-4,3'-dihydroxy-[1,4']bipiperidinyl-1'-yl]-2,2-diphenyl-ethanone hydrochloride and 1-[(3'R,4'R; 3'S,4'S)-4-(4-Chloro-phenyl)-4,4'-dihydroxy-[1,3'] bipiperidinyl-1'-yl]-2,2-diphenyl-ethanone hydrochloride A mixture of (3'R,4'R or 3'S,4'S)-4-(4-Chloro-phenyl)-[1,3']bipiperidinyl-4,4'-diol bistrifluoroacetate and (3'R,4'R or 3'S,4'S)-4-(4-chloro-phenyl)-[1,4']bipiperidinyl-4,3'-diol bistrifluoroacetate (1.07 g, 2 mmol) was dissolved in DMF (10 mL) and DIPEA (1 mL, 3 equiv) was added. Diphenyl-acetic acid (424 mg, 2 mmol) was dissolved in DMF (8 mL). A solution of N-[(ditnethylamino)-1H-1,2,3-triazolo [4,5,b]-pyridin-1-ylmethylmethaminium hexafluorophosphate N-oxide (HATU) in DMF (4 mL, 2 mmol, 0.5 M), followed by a solution of DIPEA in DMF (4 mL, 6 mmol, 1.5 M) were added to the carboxylic acid solution. After 5 min the preactivated carboxylic acid solution was added to the amine solution. The reaction mixture was shaken for 30 min and the product was directly purified using preparative LC-MS. The fractions were combined and the solvent evaporated. The residue was dissolved in dioxane:H$_2$O:IN aq HCl (2:1:0.2) and lyophilized, to yield 288.7 mg of the title compound. as the hydrochloride salt (regioisomeric mixture of compound A and B). ESIMS ([M+H]+): 505.2 (100).

Example 105

A mixture of the regioisomers from Example 104 were purified using a Hypersil Elite C18 column (5µ) detecting at 254 nm and eluting with MeOH:ammonium acetate pH=5 (52:48, % v/v). The fractions were concentrated and extracted with ethyl acetate and CH$_2$Cl$_2$. The organic phases were washed with H$_2$O, sodium sulfate was added and the suspension was filtered. The solvent was evaporated and the residue dried under high vacuum to afford 165.1 mg of regioisomer A and 107.2 mg of regioisomer B.

Example 106

1-[(3'R,4'R or 3'S,4'S)-4-(4-Chloro-phenyl)-4,3'-dihydroxy-[1,4']bipiperidinyl-1'-yl]-2,2-diphenyl-ethanone The chiral separation of a mixture of regioisomer A from Example 105 was performed using a Chiraeel OD column (20µ, 60×250 mm, 500 G) at a flow rate of 70 mL/min and detecting at 265 nm. The mixture (105 mg) was dissolved in ethanol:heptane (4:7) and then separated by eluting with heptane:ethanol:MeOH:Et$_3$N (85:10:5:0.1). The solvent was evaporated to yield 47.2 mg. ESIMS ([M+H]+): 505.2 (100). [α]$_D^{25}$=no measurable value, sign–observed (CH$_2$Cl$_2$).

Example 107

1-[(3'R,4'R or 3'S,4'S)-4-(4-Chloro-phenyl)-4,3'-dihydroxy-[1,4']bipiperidinyl-1'-yl]-2,2-diphenyl-ethanone The title compound is prepared essentially as described in Example 106, to yield 56.4 mg. ESIMS ([M+H]+): 505.2 (100). [α]$_D^{25}$=no measurable value, sign–observed (CH$_2$Cl$_2$).

Example 108

1-[(3'R,4'R or 3'S,4'S)-4-(4-Chloro-phenyl)-4,4'-dihydroxy-[1,3']bipiperidinyl-1'-yl]-2,2-diphenyl-ethanone The chiral separation of a mixture of regioisomer B from Example 105 was performed using a Whelk OD phase (10µ, 60×350 mm, 700 G) at a flow rate of 70 mL/min and detecting at 254 nm. The mixture (107 mg) was dissolved in ethanol:heptane (4:6) and then separated by eluting with heptane ethanol:Et$_3$N (60:40:0.1). The solvent was evaporated to yield 24.6 mg of the title compound. ESIMS ([M+H]+): 505.2 (100). [α]$_D^{25}$=−26.4+/−0.9 (CH$_2$Cl$_2$).

Example 109. 1-[(3'R,4'R or 3'S,4'S)-4-(4-Chloro-phenyl)-4,4'-dihydroxy-[1,3']bipiperidinyl-1'-yl]-2,2-diphenyl-ethanone The title compound is prepared essentially as described in Example 108, to yield 23 mg. ESIMS ([M+H]+): 505.2 (100). [α]$_D^{25}$=+21.2+/−0.5 (CH$_2$Cl$_2$).

Example 110

Mixture of (3R,4R; 3S,4S)-(4-Chloro-phenyl)-(3-hydroxy-4-[4-(6-methyl-pyridin-2-yl)-piperazin-1-yl]-pyrrolidin-1-yl -methanone trifluoroacetate The title compound is prepared essentially as described in Example 39 using (3R,4R)-4-[4-(6-methyl-pyridin-2-yl)-piperazin-1-yl]-pyrrolidin-3-ol bistrifluoroacetate (14.6 g, 0.033 mmol) and 4-chloro-benzoic acid (5.2 mg, 0.033 mmol), instead of (3R, 4R; 3S, 4S)-4-(4-chloro-phenyl)-1-(4-hydroxy-pyrrolidin-3-yl)-piperidin-4-ol bistrifluoroacetate and diphenyl acetic acid, to yield 6.6 mg as the trifluoroacetate salt. ESIMS ([M+H]+): 401.2 (100).

Example 111

Mixture of (3R,4R; 3S,4S)-(4-Chloro-phenyl)-[3-hydroxy-4-(4-pyridin-2-ylmethyl-perazin-1-yl)-pyrrolidin-1-yl]-methanone trifluoroacetate A mixture of (3R,4R; 3S,4S)-4-(4-pyridin-2-ylmethyl-piperazin-1-yl)-pyrrolidin-3-ol bistrifluoroacetate (24 mg, 0.05 mmol) was dissolved in DMF (0.4 mL) and DIPEA (0,042 mL, 5 equiv) was added. To this solution 4-chloro-benzoic acid chloride (6.4 mg, 0.05 mmol) was added. The reaction mixture was shaken for 30 min and used directly for purification by preparative LC-MS, to yield 6.6 mg of the title compound as the trifluoroacetate salt. ESIMS ([M+H]+): 401.2 (100).

Example 112

Mixture of (3R,4R; 3S,4S)-[3-(4-1,3-Benzodioxol-5-ylmethyl-piperazin-1-yl)-4-hydroxy-pyrrolidin-1-yl]-(4-chloro-phenyn-methanone trifluoroacetate The title compound is prepared essentially as described in Example 111 using a mixture of (3R,4R; 3S,4S)-4-(4-benzo[1,3]dioxol -5-ylmethyl-piperazin-1-yl)-pyrrolidin-3-ol bistrifluoroacetate (24 mg, 0.05 mmol) instead of a mixture of (3R,4R;   3S,4S)-4-(4-pyridin-2-ylmethyl-piperazin-1-yl)- pyrrolidin-3-ol bistrifluoroacetate, to yield 7.6 mg as the trifluoroacetate salt. ESIMS ([M+H]+): 444.2 (100).

Example 113

Mixture of (3R,4R; 3S,4S)-(3-hydroxy-4-(4-hydroxy-4-phenyl-piperidin-1-yl)-pyrrolidin-1-yl)-(2-trifluoromethyl-phenyl)-methanone trifluoroacetate The title compound is prepared essentially as described in Example 111 using a mixture of (3R,4R; 3S,4S)-1-(4-hydroxy-pyrrolidin-3-yl)-4-phenyl-piperidin-4-ol bistrifluoroacetate (24 mg, 0.05 mmol) and 2-trifluorophenyl-benzoic acid chloride (7.1 mg, 0.05 mmol), instead of (3R,4R; 3S,4S)-4-(4-pyridin-2-ylmethyl-piperazin-1-yl)-pyrrolidin-3-ol bistrifluoroacetate and 4-chloro-benzoic acid chloride, to yield 1.3 mg as the trifluoroacetate salt. ESIMS ([M+H]+): 435.1 (100).

Example 114

Mixture of (3R,4R; 3S,4S)-[3-Hydroxy-4-(4-phenethyl-piperazin-1-yl)-pyrrolidin-1-yl]-(2-trifluoromethyl-phenyl)-methanone trifluoroacetate The title compound is prepared essentially as described in Example 111 using a mixture of (3R,4R; 3S,4S)-4-(4-phenethyl-piperazin-1-yl)-pyrrolidin-3-ol]bistrifluoroacetate (23 mg, 0.05 mmol) and 2-trifluorophenyl-benzoic acid chloride (7.1 mg, 0.05 mmol), instead of (3R,4R; 3S,4S)-4-(4-pyridin-2-ylmethyl-piperazin-1-yl)-pyrrolidin-3-ol bistrifluoroacetate and 4-chloro-benzoic acid chloride, to yield 6 mg as the trifluoroacetate salt. ESIMS ([M+H]+): 448.2 (100).

Example 115

Mixture of (3R,4R; 3S,4S)-1-[3-Hydroxy-4-[4-(6-methyl-pyridin-2-yl)-piperazin-1-yl]-pyrrolidin-1-yl]-2,2-diphenyl-ethanone trifluoroacetate The title compound is prepared essentially as described in Example 111 using a mixture of (3R,4R; 3S,4S)-4-(4-pyridin-2-ylmethyl-piperazin-1-yl)-pyrrolidin-3-ol bistrifluoroacetate (22 mg, 0.05 mmol) and diphenyl-acetic acid chloride (10.6 mg, 0.05 mmol), instead of (3R,4R; 3S,4S)-4-(4-pyridin-2-ylmethyl-piperazin-1-yl)-pyrrolidin-3-ol bistrifluoroacetate and 4-chloro-benzoic acid chloride, to yield 8.5 mg as the trifluoroacetate salt. ESIMS ([M+H]+): 457.3 (100).

Example 116

Mixture of (3R,4R; 3S,4S)-1-{3-Hydroxy-4-[4(E)-3-phenyl-allyl)-piperazin-1-yl]-pyrrolidin-1-yl}-2,2-diphenyl-ethanone trifluoroacetate The title compound is prepared essentially as described in Example 111 using a mixture of (3R,4R; 3S,4S)-4-[4(E)-3-phenyl-allyl)-piperazin-1-yl]-pyrrolidin-3-ol bistrifluoroacetate (25 mg, 0.05 mmol) and diphenyl-acetic acid chloride (10.6 mg, 0.05 mmol), instead of (3R,4R; 3S,4S)-4-(4-pyridin-2-ylmethyl-piperazin-1-yl)-pyrrolidin-3-ol bistrifluoroacetate and 4-chloro-benzoic acid chloride, to yield 5.9 mg as the trifluoroacetate salt. ESIMS ([M+H]+): 482.3 (100).

Example 117

Mixture of (3R,4R; 3S, 4S)-{3-[4-(4-Chloro-benzoyl)-piperazin-1-yl]-4-hydroxy-pyrrolidin-1-yl)-(4-chloro-phenyl)-methanone 3,4-Epoxypyrrolidine carbamate Wang resin (0.15 g, 0.18 mmol) was placed in a glass reaction vessel (4 mL). LiClO$_4$ (57 mg, 3 eq.), N-Boc piperazine (186 mg, 5.5 eq.) and acetonitrile (2 mL) were added. The glass reactor was closed with a screw cap and the reaction mixture was heated at 80° C. for 43 h. The resin was transferred into syringes and washed with acetonitrile:H$_2$O (1:1, 2×), DMF (3×), MeOH (3×), DMF (3×), and CH$_2$Cl$_2$ (5×). The BOC group was removed by treating the resin with 10% methyl sulfide in TFA (2 mL) for 1 hour. This solution was saved and later combined with a cleavage solution. The product was further cleaved from resin by shaking with a solution of TFA:CH$_2$Cl$_2$:H$_2$O (2 mL of 70:30:1.5) for 2.5 h (2×). All the solutions were combined and condensed to afford 170 mg of crude 4-piperazin-1-yl-pyrrolidin-3-ol (bistrifluoroacetate salt, used without purification). The crude 4-piperazin-1-yl-pyrrolidin-3-ol was dissolved in DMF (dry, 2 mL). To this solution was added 4-chloro-benzoyl chloride (46L, 0.36 mmol), diisopropyl ethyl amine (620 µL, 3.6 mmol), and DMAP (2 mg). The solution was stirred at RT for 30 minutes, and then separated by preparative LC-MS to yield 16 mg of the title compound as the trifluoroacetate salt. ESIMS ([M+H]$^+$): 448.3 (100).

Example 118

Mixture of {(3S,4S or 3R,4R)-3-[4-(4-chloro-benzyl)-piperazin-1-yl]-4-hydroxy-pyrrolidin-1-yl}-(3,4-dichloro-phenyl)-methanone Mixture of (3R,4R; 3S,4S)-4-[4-(4-Chloro-benzyl)-piperazin-1-yl]-pyrrolidin-3-ol dihydrochloride (655 mg, 1.25 mmol) was dissolved in DMF (15 mL) and DIPEA (0.5 mL, 3 equiv) was added. 3,4-dichlorobenzoic acid (191 mg, 1 mmol) was dissolved in DMF (1.5 mL) and a solution of N-[(dimethylamino)-1H-1,2,3-triazolo[4,5,b]-pyridin-1-ylmethylmethaminium hexafluorophosphate N-oxide (HATU) in DMF (2 mL, 1 mmol, 0.5 M), followed by a solution of DIPEA in DMF (2 mL, 3 mmol, 1.5 M) were added. After 5 min the preactivated carboxylic acid solution was added to the amine solution. The reaction mixture was shaken for 30 min. The solvent was evaporated and the residue dissolved in CH$_2$Cl$_2$ (40 mL). The organic phase was extracted with H$_2$O (5×10 mL). The aqueous phases were extracted once with CH$_2$Cl$_2$ (40 mL), the organic extracts were combined and the solvent was evaporated. Flash chromatography was performed on a Biotage silica gel column and eluted with CH$_2$Cl$_2$, CH$_2$Cl$_2$:MeOH 98:2, and CH$_2$Cl$_2$:MeOH 95 5, to yield 129 mg of the title compound. ESIMS ([M+H]+): 468.1 (100).

Example 119

{(3S,4S or 3R,4R)-3-[4-(4-Chloro-benzyl)-piperazin-1-yl]-4-hydroxy-pyrrolidin-1-yl]-(3,4-dichloro-phenyl)-methanone The chiral separation of a mixture of 1-{(3R,4R; 3S,4S)-3-[4-(4-Chloro-phenyl)-4-hydroxy-piperidin-1-yl]-4-hydroxy-pyrrolidin-1-yl) -2,2-diphenyl-ethanone was performed using a CHIRAL PAK AD column (10µ, 21.2×250 mm) at a flow rate of 10 mL/min and detecting at 254 nm. The mixture (118 mg) was dissolved in heptane:ethanol (1:1.9, % v/v) and the mixture was then separated by eluting with ethanol:Et$_3$N (100:0.1, % v/v). The solvent was evaporated to afford 46.4 mg of the title compound. ESIMS ([114+H]+): 468.1 (100). [α]$_D^{25}$=no measurable value, sign–observed (MeOH). Absolute stereochemistry unknown.

Example 120

{(3R,4R or 3S,4S)-3-{4-(4-Chloro-benzyl)-piperazin-1-yl]-4-hydroxy-pyrrolidin-1-yl}-(3,4-diehlorophenyl)-methanone The title compound is prepared essentially as described in Example 119, to yield 47.3 mg. ESIMS ([M+H]+): 468.1 (100). [α]$_D^{25}$=no measurable value, sign–observed (MeOH). Absolute stereochemistry unknown.

Example 121

Mixture of (3R,4R; 3S,4S)-(4-Chloro-phenyl)-[3-hydroxy-4-(4-pyrimidin-2-yl-piperazin-1-yl)-pyrrolidin-1-yl)-methanone hydrochloride A mixture of (3R,4R; 3 S,4S)-4-(4-pyrimidin-2-yl-piperazin-1-yl)-pyrrolidin-3-ol bistrifluoroacetate (1022 mg, 2.1 mmol) was dissolved in DMF (20 mL) and DIPEA (1.4 mL, 8.4 mmol) was added. 4-chloro-benzoic acid (328 mg, 2.1 mmol) and benzotriazole-1-yl-oxy-tris-pyrrolidino-phosphonium hexafluorophosphate (1090 mg, 2.1 mmol) were dissolved in DMF (15 mL) and DIPEA (1.4 mL, 8.4 mmol) was added. After 5 min the preactivated carboxylic acid solution was added to the amine solution and the reaction mixture was shaken for 30 min. The solvent was evaporated and the residue was purified using preparative LC-MS. The white powder was dissolved in dioxane:aqueous HCl (2:1, 10 mL) and lyophilized to yield 138 mg as the hydrochloride salt. ESIMS ([M+H]+): 388.1 (100).

Example 122

(4-Chloro-phenyl)-[(3S,4S or 3R,4R)-3-hydroxy-4-(4-pyrimidin-2-yl-piperazin-1-yl)-pyrrolidin-1-yl]-methanone The chiral separation of a mixture of (3R,4R; 3S,4S)-(4-chloro-phenyl)-[3-hydroxy-4-(4-pyrimidin-2-yl-piperazin-1-yl)-pyrrolidin-1-yl)-methanone hydrochloride was performed using a CHIRAL PAK AD column (10μ, 21.2×250 mm) at a flow rate of 10 mL/min and detecting at 265 nm. The mixture (113 mg) was dissolved in MeOH and then separated by eluting with MeOH. The solvent was evaporated to afford 18.7 mg of the title compound. ESIMS ([M+H]+): 388.1 (100). Absolute stereochemistry unknown.

Example 123

(4-Chloro-phenyl)-[(3S,4S or 3R,4R)-3-hydroxy-4-(4-pyrimidin-2-yl-piperazin-1-yl)-pyrrolidin-1-yl]-methanone The title compound is prepared essentially as described in Example 122, to yield 18.1 mg of the title compound. ESIMS ([M+H]+): 388.1 (100). Absolute stereochemistry unknown.

Example 124

Mixture of (3R,4R; 3S,4S)-1-(4-Chloro-benzyl)-4-[4-(4-chloro-benzyl)-piperazin-1-yl]-pyrrolidin-3-ol trifluoroacetate A mixture of (3R,4R; 3S,4S)-4-[4-(4-chloro-benzyl)-piperazin-1-yl]-pyiTolidin-3-ol bistrifluoroacetate (26.4 g, 0.05 mmol) was dissolved in DMF (0.2 mL) and DIPEA (0.026 mL, 3 equiv) was added. 1-chloro-4-chloromethyl-benzene (6.4 mg, 0.04 mmol) was added. The reaction mixture was shaken for 30 min and the product was directly purified using preparative LC-MS, to yield 6.4 mg of the title compound as the bistrifluoroacetate salt. ESIMS ([M+H]$^+$): 420.2 (100).

Example 125

Mixture of (3R,4R; 3S,4S)-4-(4-Chloro-phenyl)-1-[4-hydroxy-1-(2-trifluoromethyl-benzyl)-pyrrolidin-3-yl]-piperidin-4-ol trifluoroacetate The title compound is prepared essentially as described in Example 124 using (3R,4R; 3S,4S)-4-(4-chloro-phenyl)-1-(4-hydroxy-pyrrolidin-3-yl)-piperidin-4-ol bistrifluoroacetate (from Example 1, 0.05 mmol, 263 mg) and 1-trifluoromethyl-2-chloromethyl-benzene (9.7 mg, 0.04 mmol) was added, instead of (3R,4R; 3S,4S)-4-[4-(4-chloro-benzyl)-piperazin-1-yl]-pyrrolidin-3-ol bistrifluoroacetate and 1-chloro-4-chloromethyl-benzene, to yield 5 mg as the trifluoroacetate salt. ESIMS ([M+H+): 455.2 (100).

Example 126

Mixture of (3R,4R; 3S,4S)-{2-{(3-[4-(4-Chlorophenyl)-4-hydroxy-piperidin-1-yl]-4-hydroxy-pyrrolidin-1-yl}-1-(2-trifluoromethyl-phenyl)-etharione bistrifluoroacetate A mixture of (3R,4R; 3S,4S)-4-(4-chloro-phenyl)-1-(4-hydroxy-pyrrolidin-3-yl)-piperidin-4-ol bistrifluoroacetate (see Example 1 for preparation) (12.7 mg, 0.024 mmol), 2-Brom-1-(2-trifluoromethyl-phenyl)-ethanone (8 mg, 1.2 eq.), diisopropyl ethyl amine (26 μL, 6 eq.) were dissolved into DMF (0.8 mL) at 0° C. The solution was warmed to RT and stirred for 1 h. The mixture was purified by preparative LC-MS to yield 15 mg of the title compound as the bistrifluoroacetate salt. ESIMS ([M+H]$^+$): 483.3 (100).

Example 127

Mixture of (3R,4R; 3S,4S)-(2-{3-[4-(4-Chloro-benzyl)-piperazin-1-yl]-4-hydroxy-pyrrolidin-1-yl) -1-(4-chloro-phenyl)-ethanone bistrifluoroacetate A mixture of (3R,4R; 3S,4S)-4-[4-(4-Chloro-benzyl)-piperazin-1-yl]-pyrrolidin-3-ol bistrifluoroacetate (see Example 8 for preparation) (11 mg, 0.02 mmol), 2-Bromo-1-(4-chlorophenyl)-ethanone (4.7 mg, 1 eq.), diisopropyl ethyl amine (17 μL, 5 eq.) were dissolved into DMF (0.8 mL) at 0° C. The solution was warmed to RT and stirred for 1 h. The mixture was purified by preparative LC-MS to yield 11 mg of the title compound as the bistrifluoroacetate salt. ESIMS ([M+H]$^+$): 448.3 (100).

Example 128

Mixture of (3R,4R; 3S,4S)-3-[4-(4-Chloro-benzyl)-piperazin-1-yl]-4-hydroxy-pyrrolidine-1-carboxylic acid (4-chloro-phenyl)-amide trifluoroacetate A mixture of (3R,4R; 3S,4S)-4-[4-(4-chloro-benzyl)-piperazin-1-yl]-pyrrolidin-3-ol bistrifluoroacetate (26.4 g, 0.05 mmol) was dissolved in DMF (0.2 mL) and DIPEA (0.026 mL, 3 equiv) was added. 4-chloro-phenylisocyanate (6.1 mg, 0.04 mmol) was added. The reaction mixture was shaken for 30 min and the product was directly purified using preparative LC-MS, to yield 8.6 mg of the title compound as the trifluoroacetate salt. ESIMS ([M+H]+): 449.1 (100).

Example 129

Mixture of (3R,4R; 3S,4S)-3-[4-(4-Chloro-phenyl)-4-hydroxy-piperidin-1-yl]-4-hydroxy-pyrrolidine-1-carboxylic acid (2-trifluoromethyl-phenyl)-amide trifluoroacetate The title compound is prepared essentially as described in Example 128 using (3R,4R; 3S,4S)-4-(4-chloro-phenyl)-1-(4-hydroxy-pyrrolidin-3-yl)-piperidin-4-ol bistrifluoroacetate (from Example 1, 0.05 mmol, 26.1 mg) and 2-trifluoromethyl-phenyl isocyanate (9.4 mg, 0.04 mmol), instead of (3R,4R; 3S,4S)-4-[4-(4-chloro-benzyl)-piperazin-1-yl]-pynolidin-3-ol bistrifluoroacetate and 4-chloro-phenylisocyanate, to yield 1.1 mg of the title compound as the trifluoroacetate salt. ESIMS ([M+H]+): 484.2 (100).

Example 130

Mixture of (3R,4R; 3S,4S)-1-(4-Chloro-benzenesulfonyl)-4-(4-pyrimidin-2-yl-piperazin-1-yl)-pyrrolidin-3-ol trifluoroacetate A mixture of (3R,4R; 3S,4S)-1-(4-Chloro-benzenesulfonyl)-4-(4-pyrrolidin-3-ol bistrifluoroacetate (see Example 9 for preparation, 24 mg, 0.05 mmol) was dissolved in DMF (0.2 mL) and DIPEA (0.026 mL, 3 equiv) was added. 4-chloro-benzenesulfonyl chloride (8.4 mg, 0,04 mmol) was added. The reaction mixture was shaken for 30 min and the product was directly purified using preparative LC-MS, to yield 4.1 mg of the title compound as the trifluoroacetate salt. ESIMS ([M+H]+): 424.1 (100).

Example 131

Mixture of (3R,4R; 3S,4S)-4-(4-Chloro-phenyl)-1-[4-hydroxy-1-(2-trifluoromethyl-benzenesulfonyl)-pyrrolidin-3-yl]-piperidin-4-ol trifluoroacetate The title compound is prepared essentially as described in Example 130 using (3R,4R; 3S,4S)-4-(4-chloro-phenyl)-1-(4-hydroxy-pyrrolidin-3-yl)-piperidin-4-ol bistrifluoroacetate (from Example 1, 0.05 mmol, 26.1 mg) and trifluoromethyl benzenesulfonyl chloride (12 mg, 0.05 mmol), instead of (3R,4R; 3S,4S)-4-(4-pyrimidin-2-yl-piperazin-1-yl)-pyrrolidin-3-ol bistrifluoroacetate and 4-chloro-benzenesulfonyl chloride, to yield 6.3 mg as the trifluoroacetate salt. ESIMS ([M+H]+): 505.1 (100).

Example 132

Mixture of (3R,4R; 3S,4S)-3-[4-(4-Chloro-benzyl)-piperazin-1-yl]-4-hydroxy-pyrrolidine-1-carboxylic acid 4-chloro-phenyl ester trifluoroacetate A mixture of (3R,4R; 3S,4S)-4-[4-(4-chloro-benzyl)-piperazin-1-yl]-pyrrolidin-3-ol bistrifluoroacetate (26,4 g, 0.05 mmol) was dissolved in DMF (0.2 mL) and DIPEA (0.026 mL, 3 equiv) was added. 4-chloro-phenycholoroformate (7.6 mg, 0,04 mmol) was added. The reaction mixture was shaken for 30 min and the product was directly purified using preparative LC-MS, to yield 0.3 mg of the title compound as the trifluoroacetate salt. ESIMS ([M+H]+): 450.1 (100).

Example 133

Mixture of (3R,4R; 3S,4S)-3-[4-(4-Chloro-phenyl)-4-hydroxy-piperidin-1-yl]-4-hydroxy-pyrrolidine-1-carboxylic acid 2-trifluoromethyl-phenyl ester trifluoroacetate A mixture of (3R,4R; 3S,4S)-4-(4-chloro-phenyl)-1-(4-hydroxy-pyrrolidin-3-yl)-piperidin-4-ol bistrifluoroacetate (Example 1, 0.05 mmol, 26.1 mg) was dissolved in DMF (0.2 mL) and DIPEA (0.042 mL, 5 equiv) was added. 2-trifluoromethyl-phenol (0.5 mmol, 81 mg) was dissolved in dry DMF and DIPEA (0.086 mL, 1 equiv) was added. To this solution p-nitrophenyl chloroformate (0.5 mmol, 100 mg) was added, the mixture was shaken for 30 min and then added to the amine solution. The reaction mixture was shaken for 30 min and used directly for purification by preparative LC-MS, to yield 1.8 mg of the title compound as the trifluoroacetate salt. ESIMS ([M+H]+): 485.1 (100).

Example 134

Mixture of (3R,4R; 3S,4S)-1-{3-[4-(4-Chloro-phenyl)-4-hydroxy-piperidin-1-yl]-4-hydroxy-pyrrolidin-1-yl]-ethanone formate Amine (3R,4R; 3S,4S)-4-(4-chloro-phenyl)-1-(4-hydroxy-pyrmlidin-3-yl)-piperidin-4-ol bistrifluoroacetate (24 mg, 0.05 mmol) was dissolved in DMF (0.3 mL) and DIPEA (0.042 mL, 5 equiv) was added. Pentafluorophenyl acetate was added and the reaction was shaken for 30 min and then purified using LC-MS, to yield 15.15 mg of the title compound as the formate salt. ESIMS WHIM 339.1 (100).

Example 135

3-[4-(4-Chloro-benzoyl)-piperazin-1-yl]-4-hydroxy-pyrrolidine-1-carboxylic acid tert-butyl ester 6-Oxa-3-aza-bicyclo[3.1.0]hexane-3-carboxylic acid tert-butyl ester (1.85 g 1 eq) and (4-Chloro-phenyl)-piperazin-1-yl-methanone (2.2 g 1 eq) were added into a sealed tube. The mixture was heated to 130° C. for 5 h. The resulting oil was purified by column chromatography (EtOAc:MeOH:Et$_3$N 10:1:0.01) to give 3.38 g of desired product as a sticky oil (84% yield). $^1$H-NMR (300 MHz, DMSO): δ 1.43 (s, 9H), 2.40-2.80 (m, 4H), 3.15-3.85 (m, 9H), 4.26-4.30 (m, 1H), 7.35 (d, 2H), 7.38 (d, 2H). Retention Time (LC, method: Formic acid polar): 1.19 min. MS (M+H$^+$): 410

Example 136

3-[4-(4-Chloro-benzoyl)-piperazin-1-yl]-4-hydroxy-pyrrolidine-1-carboxylic acid tert-butyl ester 6-Oxa-3-aza-bicyclo[3.1.0]hexane-3-carboxylic acid tert-butyl ester (0.5 g 1 eq) and (4-Chloro-phenyl)-piperazin-1-yl-methanone (0.6 g 1 eq) were dissolved in CH$_3$CN (5 mL). Ca(OTf)$_2$ (0.456 g, 0.5 eq) was added into the mixture. Reaction mixture was stirred at RT for overnight, then 80-85° C. for 8 h. After concentrating and adding EtOAc 20 mL to the residue, the organic phase was washed with H$_2$O, dried over Na$_2$SO$_4$. The resulting oil was purified by column chromatography (EtOAc:MeOH:Et$_3$N 10:1:0.01) to give 1.01 g of desired product as a sticky oil (92% yield). * Note: During workup, the organic phase should be washed with H$_2$O and Sat. NaCl solution. DO NOT was with saturated NaHCO$_3$ solution!

Example 137

(4-Chloro-phenyl)-[4-(4-hydroxy-pyrrolidin-3-yl)-piperazin-1-yl]-methanone (intermediate III)

3-[4-(4-Chloro-benzoyl)-piperazin-1-yl]-4-hydroxy-pyrrolidine-1-carboxylic acid tert-butyl ester (26 g) was dissolved in CH$_2$Cl$_2$ (150 mL). 4M HCL/Dioxane (150 mL) was added. The mixture was stirred at RT for 4 h. White precipitate was formed. The mixture was diluted with ether, filtered. The white solid was washed with ether and dried to give the desired product (99% yield). $^1$H-NMR (300 MHz, DMSO, HCl salt): δ 3.0-4.0 (m, 12H), 4.85 (m, 2H), 7.25 (d, 2H), 7.54 (d, 2H). Retention Time (LC, method: Formic acid polar): 1.01 min. MS (M+H$^+$): 310

Example 138

3-[4-(4-Chloro-benzyl)-piperazin-1-yl]-4-hydroxy-pyrrolidine-1-carboxylic acid tert-butyl ester The desired compound was prepared in a manner similar to that described in Example 136 in 80% yield. $^1$H-NMR (300 MHz, CDCl$_3$): δ 1.42 (s, 9H), 2.05-3.0 (s, 9H), 3.15-3.25 (m, 2H), 3.45 (s, 2H), 3.46-3.80 (m, 2H), 4.28 (dd, 1H), 7.20-7.29 (m, 4H). Retention Time (LC, method: Formic acid stardard): 1.09 min. MS (M+H$^+$): 396

6-Oxa-3-aza-bicyclo[3.1.0]hexane-3-carboxylic acid tert-butyl ester (5.0 1.05 eq) and 1-(4-Chloro-benzyl)-piperazine (5.04 g 1 eq) were dissolved in CH$_3$CN (250 mL). Ca(OTf)$_2$ (4.35 g, 0.5 eq) was added into the mixture. Reaction mixture was refluxed overnight. After concentrating, added EtOAc (100 mL) and filtered. The organic phase was washed with satd. NaHCO$_3$ and water. Dried the organic phase over MgSO$_4$ and purified by column chromatography (EtOAc:McOH:Et$_3$N 10:1:0.01) to give 4.5 g of white solid.

Example 139

4-[4-(4-Chloro-benzyl)-piperazin-1-yl]-pyrrolidin-3-ol (intermediate IV)

The desired compound was prepared in a manner similar to that described in Example 137 from 3-[4-(4-Chloro-benzyl)-piperazin-1-yl]-4-hydroxy-pyrrolidine-1-carboxylic acid tert-butyl ester in 99% yield. $^1$H-NMR (300 MHz, DMSO, HCl salt): δ 2.80-3.60 (m, 12H), 4.20-4.35 (m, 4H), 7.51 (d, 2H), 7.66 (d, 2H). Retention Time (LC, method: Formic acid polar): 0.68 min. MS (MAT): 296

Example 140

(4-Chloro-phenyl)-(3-hydroxy-4-piperazin-1-yl-pyrrolidin-1-yl)-methanone (intermediate VI)

The desired compound was prepared in a manner similar to that described in Example 137 from 4-[1-(4-Chloro-benzoyl)-4-hydroxy-pyrrolidin-3-yl]-piperazine-1-carboxylic acid tert-butyl ester in 99% yield. $^1$H-NMR (300 MHz, D$_2$O): δ 2.75 (1H, m), 3.0 (1H, m), 3.15 (4H, m), 3.25 (3H, m), 3.3-3.5 (2H, m), 3.7 (1H, m), 3.9 (1H, m), 4.4 (1H, m), 7.35 (4H, dd). Retention Time (LC, method: ammonium acetate standard): 0.89 min. MS (M+H$^+$): 310.

Example 141

{3-[4-(4-Chloro-benzyl)-piperazin-1-yl]-4-hydroxy-pyrrolidin-1-yl}-(4-chloro-phenyl)-methanone (4-Chloro-phenyl)-(3-hydroxy-4-piperazin-1-yl-pyrrolidin-1-yl)-methanone hydrochloride (100 mg, 0.290 mmol), NaCNBH$_3$ (20 mg, 0.319 mmol), NaOAc (23.8 mg, 0.29 mmol), 4-chloro-benzaldehyde (42.8 mg, 0.30 mmol) were added to methanol (3 mL). The reaction mixture was stirred in room temperature for over night. The mixture was concentrated. K$_2$CO$_3$ and Ethyl acetate were added to the residue. The organic phase was washed with brine, dried over Na$_2$SO$_4$, and concentrated. The crude was purified by column chromatography to give 70 mg of desired product as an oil (56% yield).

Example 142

(4-Chlorophenyl)-{34-4-(2,3-dimethyl phenyl) piperazin-1-yl]-4-hyroxyl-pyrrolidin-1-yl}-methanone To 0.89 mmoles of epoxide in 1mL ethanol, add 0.98 mmoles of dimethylpiperazine. The reaction mixture was heated in a microwave at 130° C. for 40 mins, Fresh ethanol was added and the solid obtained was filtered and vaccum dried to give the title compound in 50% yield. LC-MS (FS) m/z: 413 (M$^+$+1)

Example 143

1-(4-Chloro-phenyl)-[1,4]diazepane (Intermediate VII)

To a solution of [1,4]Diazepane-1-carboxylic acid tert-butyl ester (1.94 mL, 10.0 mmol) in toluene (20 mL) was added 1-Bromo-4-chloro-benzene (2.52 g, 13.0 mmol), Palladium dibenzylideneacetone (Pd$_2$(dba)$_3$, 0.229 g, 0.250 mmol), sodium tert-butoxide (2.50 g, 26 mmol) and BINAP (0.311 g, 0.500 mmol). The solution was stirred at reflux for 23 hours under nitrogen atmosphere. The reaction was filtered trough a pad of celite, and the cake was rinsed with ethyl acetate. The combined organic layers were washed with water, brine, and evaporated in vacuo. The residue was purified by silica gel plug filtration (80:20 hexane:ethyl acetate) to yield 3.1 g (~100%) of the Boc-protected intermediate, which was used without further purification.

The crude 4-(4-Chloro-phenyl)-[1,4]diazepane-1-carboxylic acid tert-butyl ester (3.10 g, 10.0 mmol) was dissolved in methylene chloride (1 mL) and treated with 4 N HCl/dioxane (10 mL, 40 mmol). The solution was stirred at rt for 1 hour, The reaction was concentrated in vacuo. The residue was diluted with saturated aqueous sodium bicarbonate (100 mL) and extracted with ethyl acetate (3×30 mL). The combined organics were washed with brine, dried over MgSO$_4$, and evaporated to yield 1.00 g (48%) of the title compound. $^1$H-NMR (CDCl$_3$) δ: 1.90 (2H, m), 2.23 (1H, brs), 2.83 (2H, m), 3.02 (2H, m), 3.54 (4H, m), 6.58 (2H, d, j=9.3 Hz), 7.13 (2H, d, j=9.3 Hz). ESI-MS m/z: 211 (M+1), FAS method rt: 1.04 min.

Example 144

Trans-3-[4-(4-Chloro-phenyl)-[1,4]diazepan-1-yl]-4-hydroxy-pyrrolidine-1-carboxylic acid tert-butyl ester To a solution of 1-(4-Chloro-phenyl)-[1,4]diazepane (1.00 g, 4.80 mmol) in acetonitrile (10 mL) was added 6-Oxa-3-aza-bicyclo[3.1.0]hexane-3-carboxylic acid tert-butyl ester (0.925 g, 5.00 mmol) and Calcium(II) trifluoromethanesulfonate (0.676 g, 2.00 mmol). The solution was stirred at 80° C. for 17 hours under nitrogen atmosphere. The reaction was concentrated in vacuo. The residue was diluted with saturated aqueous sodium bicarbonate (50 mL) and extracted with ethyl acetate (3×30 mL). The combined organics were washed with brine, dried over MgSO$_4$, and evaporated. The residue was purified by silica gel chromatography (ethyl acetate→87:10:3 ethyl acetate:methanol:triethylamine) to yield 0.819 g (41%) of the title compound. EST-MS m/z: 396 (M+1), FAS method rt: 1.25 min.

Example 145

Trans-4-[4-(4-Chloro-phenyl)-[1,4]diazepan-1-yl]-pyrrolidin-3-ol (intermediate VII)

To a solution of trans-3-[4-(4-Chloro-phenyl)-[1,4]diazepan-1-yl]-4-hydroxy-pyrrolidine-1-carboxylic acid tert-butyl ester (0.820 g, 2.08 mmol) in methylene chloride (1 mL) was added 4 N HCl/dioxane (10 mL, 40 mmol). The solution was stirred at rt for 1 hour, upon which a brown precipitate formed. The reaction was concentrated in vacua to yield 0.930 g (~100%) of the title compound. ESI-MS m/z: 296 (M+1), FAS method rt: 0.83 min.

Example 146

4-[4-(2,3-Dichloro-phenyl)-piperazin-1-yl]-pyrrolidin-3-ol (Intermediate VIII)

In a manner similar to that described in Example 135, the title compound was obtained as a white solid in 54% yield, MS: (EST), M/Z, 4-[4(M+1). Retention time: 1.28 min (FA-standard).

Example 147

3-[4-(4-Chloro-benzyl)-piperazin-1-yl]-4-hydroxy-pyrrol idine-1-carboxylic acid benzyl ester In a manner similar to that described in Example 135, the title compound was obtained as a white solid in 65% yield, MS: (ESI), M/Z, 430 (M+1). Retention time: 1.15 min (FA-standard).

Example 148

4-[1-(4-Chloro-benzoyl)-4-hydroxy-pyrrolidin-3-yl]-piperazine-1-carboxylic acid (3,4-dichloro-phenyl)-amide (4-Chloro-phenyl)-(3-hydroxy-4-piperazin-1-yl-pyrrolidin-1-yl)-methanone (100 mg, 0.32 mmol) and 1,2-dichloro-4-isocyanoto-benzene (63.9 mg, 0.34 mmol) was added to CHCl$_3$ (3 mL) and stirred overnight. A white solid crashed out and was filtered and washed with ether. The desired product 130 mg was obtained in 81% yield.

Example 149

Preparation of 4-chloro-5-methyl-3-trifluoromethyl pyrazole-1-carboxylic acid

To 2.70 mmol of 4-chloro-5-methyl-3-trifluoromethylpyrazole and 3.9 mmol of potassium carbonate in 0.5M solution of acetonitrile add 3.25 mmol of t-butylbromoacetate. The reaction was allowed to stir at room temperature for an hour and then heated at 70° C. for 12 hours. The reaction was filtered, the filtrate concentrated to a crude oil. Fresh ether was added and the mixture was allowed to cool. The white crystals obtained were filtered and vaccum dried to give the desired intermediate 4-chloro-5-methyl -3-trifluoromethyl pyrazole-1-carboxylic acid tertbutyl ester in 95% yield. LC-MS in FP m/z=300 (M$^+$+1)

To a stirred solution of 43.62 mmol of 4-chloro-5-methyl -3-trifluoromethyl pyrazole-1-carboxylic acid tertbutyl ester in 20 mL of dichloromethane, carefully add 40 mL of 4M HCl/dioxane. The reaction mixture was allowed to stir for 2 hours. Add fresh ether and filter the white solid obtained. Vaccum dry to give the title compound 4-chloro-5-methyl -3-trifluoromethyl pyrazole-1-carboxylic acid in 96% yield. LC-MS ink=242 (M$^+$)

Example 150

4-Chloro-phenyl)-piperidin-4-ylamine

Piperidin-4-yl-cabamie acid tert-butyl ester (250 mg, 1.25 mmol), 4-chlorophenylboronic acid (390 mg, 2.5 mmol), copper (II) acetate (453 mg, 2.5 mmol), and triethylamine (1.38 mL, 10 mmol) were mixed together in methylene chloride (12.5 mL). The reaction mixture was stirred at room temperature overnight and concentrated in vacuo. The crude residue was diluted with ethyl acetate and filtered trough a pad of celite, and the cake was rinsed with ethyl acetate. The combined organic layers were evaporated in vacuo. The residue was purified by flash chromatography (hexane to 30% hexane:ethyl acetate) to give 230 mg [1-(4-Chloro-phenyl)-piperidin-4-yl]-carbamic acid tert-butyl ester (yield: 60%). $^1$H-NMR (CDCl$_3$) δ: 1.42 (9H, s), 2.01 (2H, m), 2.80 (2H, m), 3.54 (3H, m), 4.45 (1H, b), 6.80 (2H, d, j=9.3 Hz), 7.18 (2H, d, j=9.3 Hz).

1-(4-Chloro-phenyl)-piperidin-4-yl]-carbamic acid tert-butyl ester (230 mg, 0.71 mmol) was dissolved in methylene chloride (3 mL) and treated with 3 mL TFA. The solution was stirred at room temperature for 2 hours. Ether was added to the reaction mixture. The TFA salt of the title compound crashed out. Treated the TFA salt with base to give 130 mg 1-(4-Chloro-phenyl)-piperidin-4-ylamine (yield: 83%). $^1$H-NMR (CDCl$_3$) δ: 1.42 (4H, m), 1.91 (2H, m), 2.78 (3H, m), 3.57 (2H, m), 6.82 (2H, d, j=9.3 Hz), 7.19 (2H, d, j=9.3 Hz).

Example 151

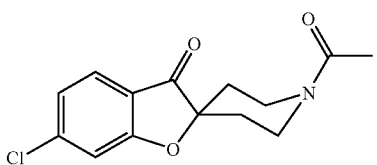 [SMILES: CC(=O)N1CCC2(CC1)Oc1cc(Cl)ccc1C2=O]

Step 1. (4-Chloro-2-fluoro-phenyl)-trimethylsilanyloxyacetonitrile

To a solution of 4-chloro-2-fluoro-benzaldehyde (5.0 g, 31.55 mmol) in $CH_2Cl_2$ (20 mL) at 0° C., was added TMSCN (3.12 g, 31.55 mmol) and Cat. $ZnI_2$ (50 mg). The mixture was stirred at RT for overnight. After concentrating, the desired product was obtained (8.12 g, 100% yield) as a brown oil. $^1H$ NMR $(CDCl_3)\delta$ 0.1 (s, 9H), 5.6 (s, 1H), 7.0 (d, 1H), 7.15 (d, 1H), 7.55 (t, 1H).

Step 2. 1-[4-(4-Chloro-2-fluoro-benzoyl)-4-hydroxy-piperidin-1-yl]-ethanone

To a solution of diisopropylamine (4.42 mL, 31.59 mmol) in THF (20 mL) at 0° C. under Ar, was added n-BuLi (12.63 mL, 31.59 mmol, 2.5 M solution in hexane). The mixture was stirred at 0° C. for 30 min. After cooling to −78° C., (4-chloro-2-fluoro-phenyl)-trimethylsilanyloxyacetonitrile (8.12 g, 31.59 mmol) was added. After stirring at −78° C. for 1.5 h, 1-acetyl-piperidin-4-one (4.45 g, 31.59 mmol) was added. The final mixture was stirred at −20° C. for overnight. After concentration, EtOAc (100 mL) was added. The organic phase was washed with Sat. $NH_4OAc$ solution, Sat. $NaHCO_3$ solution and concentrated. The residue was dissolved in MeOH (30 mL). 1N HCl solution (20 mL) was added. The mixture was stirred at RT for 2 h. After concentrating the mixture, EtOAc (50 mL) was added. The organic layer was basified with Sat. $NaHCO_3$, dried over $Na_2SO_4$ and concentrated. The residue was purified by column chromatography (Ethyl acetate) to give the desired product (4 g, 42% yield) as a white solid. MS: (ESI), M/Z, 300 (M+1). Retention time: 0.87 min (FA-standard).

Step 3. Title Compound

To a solution of 1-[4-(4-chloro-2-fluoro-benzoyl)-4-hydroxy-piperidin-1-yl]-ethanone (3.0 g, 10.03 mmol) in THF (30 mL), was added KOtBu (1.23 g, 11.03 mmol). The mixture was stirred at reflux for overnight. After cooling to RT, EtOAc (50 mL) was added. The organic phase was washed with Sat. $NaHCO_3$, dried over $Na_2SO_4$ and concentrated. The residue was purified by column chromatography (Ethyl acetate) to give desired product (1.1 g, 40% yield) as a sticky oil. MS: (ESI), M/Z, 280 (M+1). Retention time: 1.03 min (FA-standard).

Example 152

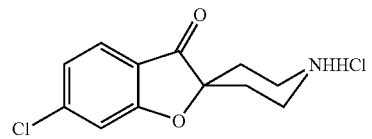

To a solution of acetyl protected spiro-amine (1.1 g, 3.94 mmol), was added 6N HCl solution (7 mL). The mixture was stirred at reflux for overnight. After concentration, the desired product was obtained as a white solid (1.0 g, 100% yield). MS: (ESI), M/Z, 238 (M+1). Retention time: 0.97 min (FA-standard).

Example 153

1-(5-chloroindan-1-yl)-piperazine

The title compound was prepared in two steps by a standard reductive amination starting with 5-chloro-1-indanone and piperazine carboxylic acid tert-butyl ester followed by removal of the t-Boc group with HCl in 30% overall yield.

Example 154

4-(4-Chloro-benzoyl)-1-[1-(4-chloro-benzoyl)-4-hydroxy-pyrrolidin-3-yl]-piperazin-2-one

Step 1. {2-[1-(4-Chloro-benzoyl)-4-hydroxy-pyrrolidin-3-ylamino]-ethyl}-carbamic acid tert-butyl ester In a manner similar to that described in Example 135, the title compound was obtained as a colorless oil (25% yield). MS: (ESI), M/Z, 384 (M+1). Retention time: 1.58 min (FA-polar).

Step 2

{2-[4-(tert-Butyl-dimethyl-silanyloxy)-1-(4-chloro-benzoyl)-pyrrolidin-3-ylamino]-ethyl}-carbamic acid tert-butyl ester To a solution of {2-[1-(4-chloro-benzoyl)-4-hydroxy-pyrrolidin-3-ylamino]ethyl}-carbamic acid tert-butyl ester (750 mg, 1.95 mmol) in DMF (0.25 mL) at 0° C., was added imidazole (663 mg, 9.15 mmol) and TBDMSCl (309 mg, 2.05 mmol). The reaction mixture was stirred for 2 days. EtOAc (5 mL) was added. The organic phase was washed with Sat. $NH_4Cl$, dried over $N_kSO_4$, and concentrated. The residue was purified by column chromatography (Ethyl acetate: MeOH: 10:1) to give the desired product (389 mg, 40% yield) as a colorless oil. MS: (ESI), M/Z, 498 (M+1). Retention time: 2.21 min (FA-polar).

Step 3. {2-[[4-(tert-Butyl-dimethyl-silanyloxy)-1-(4-chloro-benzoyl)-pyrrolidin-3-yl]-(2-chloro-acetyl)-amino]-ethyl}-carbamic acid tert-butyl ester To a solution of {2-[4-(tert-butyl-dimethyl-silanyloxy)-1-(4-chloro-benzoyl)-pyrrolidin-3-ylamino]-ethyl}-carbamic acid tert-butyl ester (389 mg, 0.78 mmol) at 0° C., was added DIPEA (0.150 mL, 0.85 mmol) and chloroacetyl chloride (62 uL, 0.78 mmol). The reaction mixture was stifled at RT for overnight. The organic phase was washed with Sat. $NaHCO_3$, dried over $Na_2SO_4$, and concentrated. The residue was purified by column chromatography (Ethyl acetate:Hexane: 1:2) to give the desired product (260 mg, 58% yield) as a colorless oil. MS: (ESI), M/Z, 574 (M+1). Retention time: 2.78 min (FA-polar).

Step 4. N-(2-Amino-ethyl)-2-chloro-N-[1-(4-chloro-benzoyl)-4-hydroxy-pyrrolidin-3-yl]-acetamide {2-[[4-(tert-Butyl-dimethyl-silanyloxy)-1-(4-chloro-benzoyl)-pyrrolidin-3-yl]-(2-chloro-acetyl)-amino]-ethyl}-carbamic acid tert-butyl ester (260 mg, 0.45 mmol) was dissolved in 1 mL of 4M HCl in dioxane solution. The mixture was stirred at RT for 1.5 h. After concentrating, a white solid was formed (200 mg). The LC-Mass showed two products as showed above. MS: (ESI), M/Z, 360 (M+1). Retention time: 1.31 min (FA-polar). MS: (ESI), M/Z, 474 (M+1). Retention time: 2.20 min (FA-polar).

Step 5. 1-[1-(4-Chloro-benzoyl)-4-hydroxy-pyrrolidin-3-yl]-piperazin-2-one

A mixture of N-(2-amino-ethyl)-N-[4-(tert-butyl-dimethyl-silanyloxy)-1-(4-chloro-benzoyl)-pyrrolidin-3-yl]-2-chloro-acetamide and N-(2-amino-ethyl)-2-chloro-N-[4-(4-chloro-benzoyl)-4-hydroxy-pyrrolidin-3-yl]-acetamide (200 mg) was dissolved in 2 mL of DMF, Then $K_2CO_3$ (117 mg, 0.84 mmol) and Cat. KI were added. The mixture was stirred at 90° C. for overnight. EtOAc (5 mL) was added. The organic phase was washed with Sat. $NaHCO_3$, dried over $Na_2SO_4$, and concentrated. The residue was purified by column chromatography (Ethyl acetate:Methanol:$Et_3$N:3:1:0.04) to give the desired product (50 mg, 37% yield) as a colorless oil. MS (ESI), M/Z, 324 (M+1). Retention time: 1.13 min (FA-polar).

Step 6. 4-(4-Chloro-benzoyl)-1-[1-(4-chloro-benzoyl)-4-hydroxy-pyrrolidin-3-yl]-piperazin-2-one To a solution of 1-[1-(4-Chloro-benzoyl)-4-hydroxy-pyrrolidin-3-yl]-piperazin-2-one (50 mg, 0,15 mmol) in $CH_2Cl_2$ (1 mL) at 0° C., was added DIPEA (27 uL, 0.154 mmol) and 4-Chloro-benzoyl chloride (20 uL, 0.154 mmol). The mixture was stirred at RT for 4 h. The organic phase was washed with Sat. $NaHCO_3$, dried over $Na_2SO_4$, and concentrated. The residue was purified by column chromatography (Ethyl acetate:Methanol:$Et_3$N:10.1:0.1) to give the desired product (36 mg, 50% yield) as a white solid. MS: (ESI), M/Z, 462 (M+1). Retention time: 2.25 min (FA-polar).

Example 155

{3-[4-[4-Chloro-benzoyl)-piperazin-1-yl]-4-methoxy-pyrrolidin-1-yl) -(4-chloro-phenyl)-methanone To a cold (3-5° C.) solution of starting material {3-[4-(4-Chloro-benzoyl)-piperazin-1-yl]-4-hydroxy-pyrrolidin-1-yl}-(4-chloro-phenyl)-methanone in 1 mL of NMP was added NaH (4 mg, 0.17 mmol). The mixture was then stirred at 3-5° C. for 15 mins. MeI (7.5 uL) was then added. After 2 hours, the reaction was quenched by adding 50 µL AcOH. The mixture was then partitioned in EtOAc and 1M $K_2CO_3$. The separated organic phase was washed with brine, dried over $Na_2SO_4$ and concentrated down to dryness. The resulting crude residue was purified by column chromatography on silica (Methanol 1 $CH_2Cl_2$: 0%-10%). The pure product was converted to it HCl salt by precipitation in a mixture of ethanol\ether and conc. HCl, to give 43 mg of salt of {3-[4-(4-Chloro-benzoyl)-piperazin-1-yl]-4-methoxy-pyrrolidin-1-yl}-(4-chloro-phenyl)-methanone as a white solid.

Example 156

N-{1-[1-(4-Chloro-benzoyl)-4-hydroxy-pyrrolidin-3-yl]-piperidin-4-yl}-N-(4-chloro-phenyl)-acetamide The starting materials (4-Chloro-phenyl)-{3-[4-(4-chloro-phenylamino)-piperidin-1-yl]-4-hydroxy-pyrrolidin-1-yl}-methanone (48 mg, 0.11 mmol) and $Ac_2O$ (16 uL, 0.17 mmol) were added in pyridine (0.5 mL) and stirred at room temperature overnight. The reaction mixture was concentrated down to dryness. The resulting crude residue was purified by column chromatography on silica (Methanol\$CH_2Cl_2$: 0%-6%).

The pure compound was converted to 56 mg of HCl salt of N-{1-{1-(4-Chloro-benzoyl)-4-hydroxy-pyrrolidin-3-yl]-piperidin-4-yl}-N-(4-chloro-phenyl)-acetamide by precipitation in a mixture of ethanol and ether using conc. HCl.

In addition to the solid-phase approach exemplified above, compounds of the invention can also be prepared using the following methods (referring to Schemes I and II in the specification above):

Examples 157-161 below depict the synthesis of intermediates A, B, C, D, and E, as referred to in Scheme I, which intermediates are useful for the preparation of compounds of the invention.

Example 157

Synthesis of 2,5-Dihydro-pyrrole-1-carboxylic acid tert-butyl ester (A) and 6-Oxa-3-aza-bicyclo[3.1.0] hexane-3-carboxylic acid tert-butyl ester (B)

2,5-Dihydro-pyrrole-1-carboxylic acid tert-butyl ester (A)

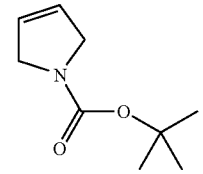

A

Pyrroline (65% purity, 20 g) was dissolved in $CH_2Cl_2$ (500 mL), $Et_3$N (44 mL, 1.1 eq) was added. The mixture was cooled to 0° C. Boc anhydide (68 g, 1.01 eq) was added very slowly at 0° C. Finally the reaction mixture was stirred at 0° C. to RT for overnight. The reaction mixture was washed with 1N NaOH solution (2×100 mL). The organic phase was dried over $Na_2SO_4$. The resulting oil was purified by column chromatography (Hexane:Ethyl Acetate 3:1) to give 46.46 g of desired product as a colorless oil (95%yield, 65% purity). $^1$H-NMR (300 MHz, $CDCl_3$): δ 1.45 (s, 9H), 4.08 (d, 4H), 5.73 (d, 2H)

6-Oxa-3-aza-bicyclo[3.1.0]hexane-3-carboxylic acid tert-butyl ester (B)

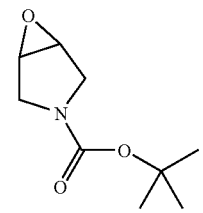

B 2,5-Dihydro-pyrrole-1-carboxylic acid tert-butyl ester (46 g, 65% purity) was dissolved in $CH_2Cl_2$ (500 mL). The solution was cooled to 0° C. mCPBA (122 g, 2 eq, 77% purity) was slowly added to the solution at 0° C. The reaction mixture was stirred at 0° C. to RT for overnight. The mixture was concentrated to 200 ml, and filtered. The organic phase was washed with 1 N NaOH solution (4×100 mL), dried over $Na_2SO_4$. The resulting oil was purified by column chromatography (hexane:ethyl acetate 3:1) to give 28 g of desired product as a colorless oil (87% yield). $^1$H-NMR (300 MHz, $CDCl_3$): δ 1.41 (s, 9H), 3.26 (dd, 2H), 3.25-3.80 (m, 4H)

Example 158

Synthesis of (4-Chloro-phenyl)-piperazin-1-yl-methanone (C)

Step 1:
4-(4-Chloro-benzoyl)-piperazine-1-carboxylic acid tert-butyl ester

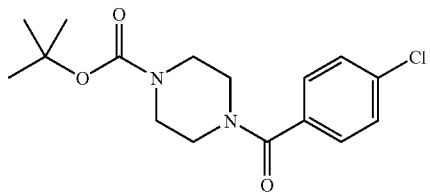 [SMILES: CC(C)(C)OC(=O)N1CCN(C(=O)c2ccc(Cl)cc2)CC1]

Piperazine-1-carboxylic acid tert-butyl ester (16 g) was dissolved in $CH_2Cl_2$ (150 mL). $Et_3N$ (13.16 mL, 1.1 eq) and Cat. DMAP were added. The mixture was cooled to 0° C. Acid chloride (11.47 mL, 1.05 eq) was added very slowly at 0° C. Finally the reaction mixture was stirred at 0° C. to RT for overnight. The reaction mixture was washed with 1N NaOH solution (2×100 mL). The organic phase was dried over $Na_2SO_4$. The desired product was purified by recrystallization in EtOAc (26 g, 93% yield). $^1$H-NMR (300 MHz, $CDCl_3$): δ 1.44 (s, 9H), 3.20-3.80 (m, 8H), 7.34 (d, 2H), 7.36 (d, 2H) Retention Time (LC, method: Formic acid standard): 1.81 min. MS (M+H$^+$): 325

Step 2: (4-Chloro-phenyl)-piperazin-1-yl-methanone (C)

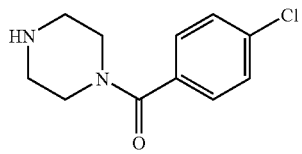

4-(4-Chloro-benzoyl)-piperazine-1-carboxylic acid tert-butyl ester (26 g) was dissolved in $CH_2Cl_2$ (350 mL). 4M HCL/Dioxane (150 mL) was added. The mixture was stirred at RT for 4 h. White precipitate was formed. The mixture was concentrated. The white solid was washed with $Et_2O$. After the white solid was treated with 1N NaOH (200 mL) and extracted with Ethyl acetate (3×100 mL), the combined organic phase was dried over $Na_2SO_4$ and concentrated to give 17.79 g of desired product (99% yield). $^1$H-NMR (for HCl salt) (300 MHz, MeOD): δ 2.80-2.90 (m, 4H), 3.20-3.80 (m, 4H), 7.29-7.36 (m, 4H).

Example 159

3-[4-(4-Chloro-benzoyl)-piperazin-1-yl]-4-hydroxy-pyrrolidine-1-carboxylic acid tert-butyl ester (D)

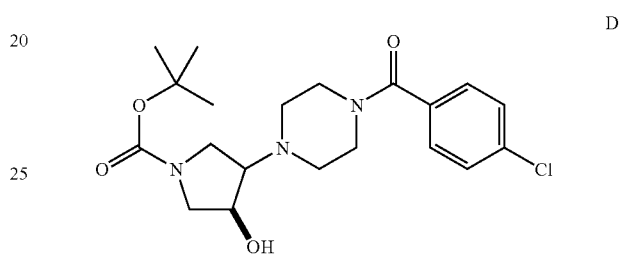

This is an example of Procedure A in Scheme 1 above. 6-Oxa-3-aza-bicyclo[3.1.0]hexane-3-carboxylic acid tert-butyl ester (1.85 g 1 eq) and (4-Chloro-phenyl)-piperazin-1-yl-methanone (2.2 g 1 eq) were added into a sealed tube. The mixture was heated to 130° C. for 5 h. The resulting oil was purified by column chromatography (EtOAc:MeOH:$Et_3N$ 10:1:0,01) to give 3.38 g of desired product as a sticky oil (84% yield). $^1$H-NMR (300 MHz, DMSO): δ 1.43 (s, 9H), 2.40-2.80 (m, 4H), 3.15-3.85 (m, 9H), 4.26-4.30 (m, 1H), 7.35 (d, 2H), 7.38 (d, 2H) Retention Time (LC, method: Formic acid polar): 1.19 min. MS (M+H$^+$): 410

Example 160

3-[4-(4-Chloro-benzoyl)-piperazin-1-yl]-4-hydroxy-pyrrolidine-1-carboxylic acid tent-butyl ester (D) (same as Example 159 Using a Different Procedure)

This is an example of Procedure B in Scheme 1 above. 6-Oxa-3-aza-bicyclo[3.1.0]hexane-3-carboxylic acid tert-butyl ester (0.5 g 1 eq) and (4-Chloro-phenyl)-piperazin-1-yl-methanone (0.6 g 1 eq) were dissolved in $CH_3CN$ (5 mL). $Ca(OTf)_2$ (0.456 g, 0.5 eq) was added into the mixture. Reaction mixture was stirred at RT for overnight, then 80-85° C. for 8 h. After concentrating and adding EtOAc 20 mL to the residue, the organic phase was washed with $H_2O$, dried over $Na_2SO_4$. The resulting oil was purified by column chromatography (EtOAc:MeOH:$Et_3N$ 10:1:0.01) to give 1.01 g of desired product as a sticky oil (92% yield). *It is important to note that during workup, the organic phase should be washed with $H_2O$ and saturated NaCl solution, not saturated $NaHCO_3$ solution.

Example 161

(4-Chloro-phenyl)-[4-(4-hydroxy-pyrrolidin-3-yl)-piperazin-1-yl]-methanone (E)

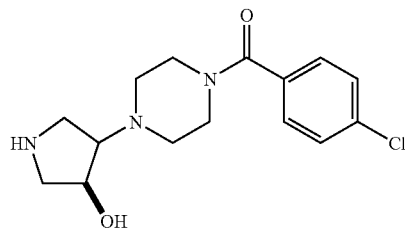

E

3-[4-(4-Chloro-benzoyl)-piperazin-1-yl]-4-hydroxy-pyrrolidine-1-carboxylic acid tert-butyl ester was dissolved in CH$_2$Cl$_2$. 4M HCl/dioxane (150 mL) was added. The mixture was stirred at RT for 4 h. White precipitate was formed. The mixture was diluted with ether, filtered. The white solid was washed with ether and dried to give desired product (99% yield). $^1$H-NMR (300 MHz, DMSO, HCl salt): δ 3.0-4.0 (m, 12H), 4.85 (m, 2H), 7.25 (d, 2H), 7.54 (d, 2H) Retention Time (LC method: formic acid polar): 1.01 min. MS (M+H$^+$): 310

Examples 162 and 163 below describe the synthesis of intermediates D-i, and E-i, as referred to in Scheme II, which intermediates are useful for the preparation of compounds of the invention.

Example 162

3-[4-(4-Chloro-benzyl)-piperazin-1-yl]-4-hydroxy-pyrrolidine-1-carboxylic acid tert-butyl ester (D-i)

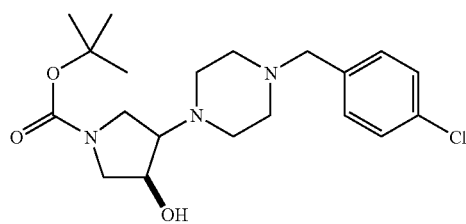

D-i

6-Oxa-3-aza-bicyclo[3.1.0]hexane-3-carboxylic acid tert-butyl ester (5.0 1.05 eq) and 1-(4-Chloro-benzyl)-piperazine (5.04 g 1 eq) were dissolved in CH$_3$CN (250 mL).a(OTf)$_2$ (4.35 g, 0.5 eq) was added into the mixture. Reaction mixture was refluxed overnight. After concentrating, added EtOAc (100 mL) and filtered. The organic phase was washed with said. NaHCO$_3$ and water. Dried the organic phase over MgSO$_4$ and purified by column chromatography (EtOAc:MeOH:Et$_3$N 10:1:0.01) to give 4.5 g of white solid. $^1$H-NMR (300 MHz, CDCl$_3$): δ 1.42 (s, 9H), 2.05-3.0 (s, 9H), 3.15-3.25 (m, 2H), 3.45 (s, 2H), 3.46-3.80 (m, 2H), 4.28 (dd, 1H), 7.20-7.29 (m, 4H) Retention Time (LC, method: Formic acid standard): 1.09 min. MS (M+H$^+$): 396

Example 163

4-[4-(4-Chloro-benzyl)-piperazin-1-yl]-pyrrolidin-3-ol

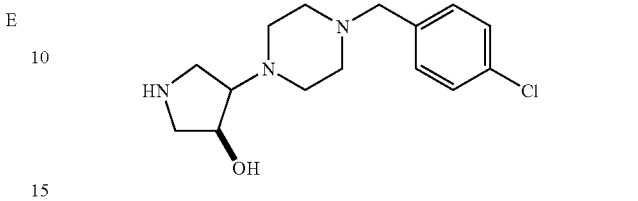

E-i

The desired compound was prepared from 3-[4-(4-Chloro-benzyl)-piperazin-1-yl]-4-hydroxy-pyrrolidine-1-carboxylic acid tert-butyl ester in a manner similar to that described in Example 161. $^1$H-NMR (300 MHz, DMSO, HCl salt): δ 2.80-3,60 (m, 12H), 4.20-4.35 (m, 4H), 7.51 (d, 2H), 7.66 (d, 2H). Retention Time (LC, method: Formic acid polar): 0.68 min. MS (M+H$^+$): 296

Examples 164-166 exemplify the synthesis of intermediates useful for preparation of compounds of the invention where Ring B is a [1,4]diazepane ring. The unprotected pyrrolidinyl-diazepane ring can then be coupled to a desired Cy$^1$ group using the conditions described for Procedure C, D, or E (as shown in Schemes I and II and as described generally above).

Example 164

1-(4-Chloro-phenyl)-[1,4]diazepane

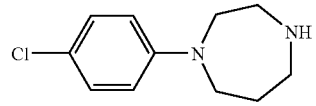

To a solution of [1,4]-diazepane-1-carboxylic acid tert-butyl ester (1.94 mL, 10.0 mmol) in toluene (20 mL) was added 1-Bromo-4-chloro-benzene (2.52 g, 13.0 mmol), Palladium dibenzylideneacetone (Pd$_2$(dba)$_3$, 0.229 g, 0.250 mmol), sodium tert-butoxide (2.50 g, 26 mmol) and BINAP (0.311 g, 0.500 mmol). The solution was stirred at reflux for 23 hours under nitrogen atmosphere. The reaction was filtered trough a pad of celite, and the cake was rinsed with ethyl acetate. The combined organic layers were washed with water, brine, and evaporated in vacuo. The residue was purified by silica gel plug filtration (80:20 hexane:ethyl acetate) to yield 3.1 g (~100%) of the Boc-protected intermediate, which was used without further purification.

The crude 4-(4-Chloro-phenyl)-[1,4]diazepane-1-carboxylic acid tert-butyl ester (3.10 g, 10.0 mmol) was dissolved in methylene chloride (1 mL) and treated with 4 N HCl/dioxane (10 mL, 40 mmol). The solution was stirred at rt for 1 hour. The reaction was concentrated in vacuo. The residue was diluted with saturated aqueous sodium bicarbonate (100 mL) and extracted with ethyl acetate (3×30 mL). The combined organics were washed with brine, dried over MgSO$_4$, and evaporated to yield 1.00 g (48%) of the title compound. $^1$H-NMR (CDCl$_3$) δ: 1.90 (2H, m), 2.23 (1H, brs), 2.83 (2H, m), 3.02 (2H, m), 3.54 (4H, m), 6.58 (2H, d, j=9.3 Hz), 7.13 (2H, d, j=9.3 Hz). ESI-MS m/z: 211 (M+1), FAS method rt: 1.04 min.

Example 165

Trans-3-[4-(4-Chloro-phenyl)-[1,4]diazepan-1-yl]-4-hydroxy-pyrrolidine-1-carboxylic acid tert-butyl ester

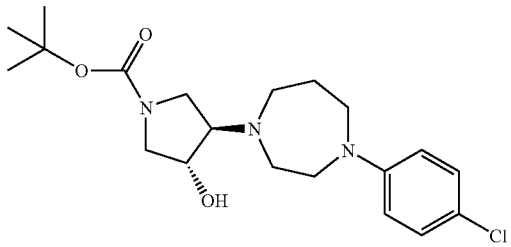 [SMILES: CC(C)(C)OC(=O)N1C[C@@H](O)[C@H](N2CCCN(c3ccc(Cl)cc3)CC2)C1]

To a solution of 1-(4-Chloro-phenyl)-[1,4]diazepane (1.00 g, 4.80 mmol) in acetonitrile (10 mL) was added 6-oxa-3-azabicyclo[3.1.0]hexane-3-carboxylic acid tert-butyl ester (0.925 g, 5.00 mmol) and calcium(II) trifluoromethanesulfonate (0.676 g, 2.00 mmol). The solution was stirred at 80° C. for 17 hours under nitrogen atmosphere. The reaction was concentrated in vacuo. The residue was diluted with saturated aqueous sodium bicarbonate (50 mL) and extracted with ethyl acetate (3×30 mL). The combined organics were washed with brine, dried over $MgSO_4$, and evaporated. The residue was purified by silica gel chromatography (gradient ethyl acetate to 87:10:3 ethyl acetate:methanol:triethylamine) to yield 0.819 g (41%) of the title compound. ESI-MS m/z: 396 (M+1), FAS method rt: 1.25 min

Example 166

Trans -4-[4-(4-Chloro-phenyl)-[1,4]diazepan-1-yl]-pyrrolidin-3-ol

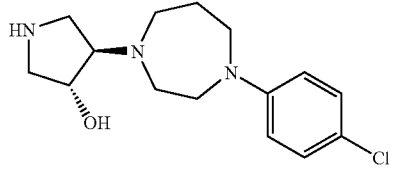 [SMILES: O[C@@H]1CNC[C@H]1N1CCCN(c2ccc(Cl)cc2)CC1]

To a solution of trans-3-[4-(4-Chloro-phenyl)-[1,4]diazepan-1-yl]-4-hydroxy-pyrrolidine-1-carboxylic acid tert-butyl ester (0.820 g, 2.08 mmol) in methylene chloride (1 mL) was added 4 N HCl/dioxane (10 mL, 40 mmol). The solution was stirred at rt for 1 hour, upon which a brown precipitate formed. The reaction was concentrated in vacuo to yield 0.930 g (-100%) of the title compound. ESI-MS m/z: 296 (M+1), FAS method it 0.83 min.

Example 167 below exemplifies the synthesis of an intermediate useful for the preparation of compounds of the invention where Ring B is a piperidinyl ring and $R^2$ is 4-chlorophenyloxy. This intermediate can then be used to prepare other intermediates and ultimately compounds of the invention as described generally above and herein. For example, this compound can be reacted with intermediate B (Schemes I and II above) to generate an intermediate suitable for reacting with a desired $Cy^1$ group.

Example 167

4-(4-Chloro-phenoxy)-piperidinecarboxylic acid t-butylester

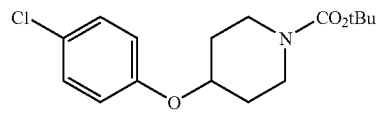 [SMILES: CC(C)(C)OC(=O)N1CCC(Oc2ccc(Cl)cc2)CC1]

4-Hydroxy-piperidine-1-carboxylic acid tert-butyl ester (1.61 g, 8 mmol), 4-chloro-phenol (1.23 g, 9.6 mmol), $Ph_3P$ (2.30 g, 8.8 mmol) and DEAD (1.4 mL, 8.8 mmol) were added to 20 mL THF and let it stir at room temperature for overnight. The reaction mixture was partitioned in ether and 1M NaOH. The organic phase was washed with 1M NaOH, water and brine, dried over $Na_2SO_4$ and concentrated down to dryness. The resulting crude residue was purified by column chromatography on silica (hexane:ethyl acetate 5% to 15%) to give 1.82 g tert-butylester of 4-(4-chloro-phenoxy)-piperidine. From the foregoing ester, 4-(4-chloro-phenoxy)-piperidine was obtained in about 99% by deprotection of the Boc group as described above.

Examples 168-170 below describe general procedures for the coupling of $Cy^1$ to the pyrrolidinyl nitrogen atom (as depicted for some embodiments in Schemes I and II)

Example 168

General Procedure to Synthesize Carboxamide Using Carboxylic Acids

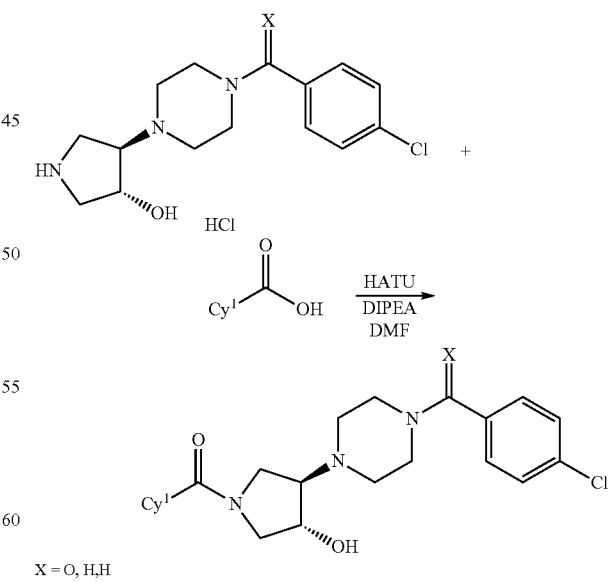

X = O, H,H

The bi-HCl or tri-HCl salt of the desired amines (1 eq) was dissolved in DMF (0.5 mL). The corresponding carboxylic acid (0.9 eq), HATU (1.5 eq) and DIPEA (3-4 eq) were added.

The reaction mixture was stirred at room temperature for overnight. Then, ethyl acetate (2 mL) was added. The organic phase was washed with H₂O (2×1 mL), dried over Na₂SO₄, and concentrated. The residue was purified by column chromatography (Ethyl acetate:Methanol:Et₃N: 10:1:0.1) to give the desired product.

Example 169

General Procedure to Synthesize Carboxamide Using Carboxylic Acid Chlorides

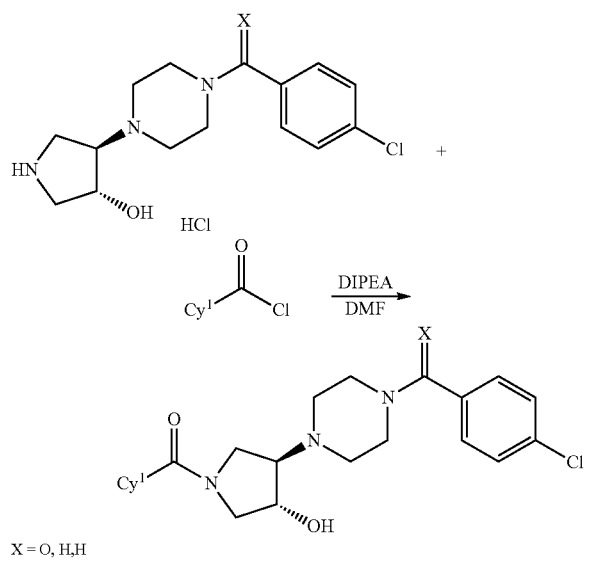

X = O, H,H

The bi-HCl or tri-HCl salt of the desired amines (1 mmol) was dissolved in DMF (0.5 mL) and DIPEA (3-4 equiv) was added. After addition of the corresponding carboxylic acid chloride (0.9 eq), the reaction mixture was stirred at room temperature for overnight. Ethyl acetate (2 mL) was then added and the organic phase was washed with H₂O (2×1 mL), dried over Na₂SO₄, and concentrated. The residue was purified by column chromatography (Ethyl acetate:Methanol: Et₃N: 10:1:0.1) to give the desired product.

Example 170

General Procedure to Synthesize Carboxamide Using Carboxylic Acids

To 0.28 mmoles of intermediate VI in 0.1M soln of pyridine, was added 0.34 mmoles of hydrocinnamic acid. The reaction mixture was allowed to stir for 10 minutes and then 0.57 mmoles of EDCI was added. The reaction mixture was stirred at room temp for a couple of hours. Excess pyridine was removed under pressure and the concentrate was partitioned into 30 mL Ethyl acetate and 30 mL of 1M aq. K₂CO₃ soln. The organic layer was separated, washed with water and brine, dried over MgSO₄, filtered and excess solvent was removed on rotavap. The concentrate obtained was purified on an ISCO column using gradient elution with 10% MeOH—CH₂Cl₂. The tile compound was isolated in 70% yield. LC-MS: (AS) m/z=442 (M⁺+1) ¹H-NMR (D₂O) δ 7.55 (m, 4H's), 7.23(m, 5H's), 5.9 (1H), 3.9-3.70 (m, 8H's), 3.0 (m, 2H's), 2.79 (m, 2H's), 2.63 (m, 2H's), 2.23-2.39 (m, 2H's) HCl salt: The above solid obtained was dissolved in a mixture of ethyl ether/ethyl acetate and 2equiv. of 2M HCl/ether was added. The mixture was concentrated to give the HCl salt of the title compound.

Examples 171-173 below depict the synthesis of an alternate intermediate for use in the preparation of compounds of the invention. Although the synthesis of compounds where Cy¹ is 4-chlorobenzoyl is depicted, it will be appreciated that the general method can be utilized to prepare compounds of the invention where Cy¹ is other than 4-chlorobenzoyl.

Example 171

Synthesis of (4-Chloro-phenyl)-(2,5-dihydro-pyrrol-1-yl)-methanone and (4-Chloro-phenyl)-(6-oxa-3-aza-bicyclo[3.1.0]hex-3-yl)-methanone

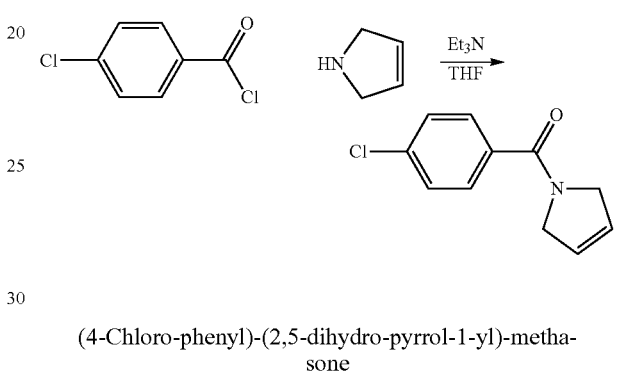

(4-Chloro-phenyl)-(2,5-dihydro-pyrrol-1-yl)-methasone

Pyrroline (4 mL, 54 mmol) was dissolved in THF (100 mL), Et3N (14 mL, 100 mmol) was added. The mixture was cooled to 0° C. 4-chloro-benzoyl chloride (7.6 mL, 60 mmol) was added very slowly at 0° C. Catalytic amount of DMAP was added too. Finally the reaction mixture was stirred at 0° C. to RT for overnight. The reaction mixture was diluted with ether and filtered to remove white solid of Et₃N.HCl. Then evaporated to remove solvent and triturated with hexane/ether to give white solid 10.3 g with ratio of unsaturated/saturated about 3/1 by NMR. Then triturated with hexane/ether again to give 6.68 g white solid with ratio of unsaturated/saturated about 3.7/1 by NMR. ¹H-NMR (300 MHz, CDCl₃): δ 4.3 (4H, d), 5.80 (2H, d), 7.40 (4H, dd)

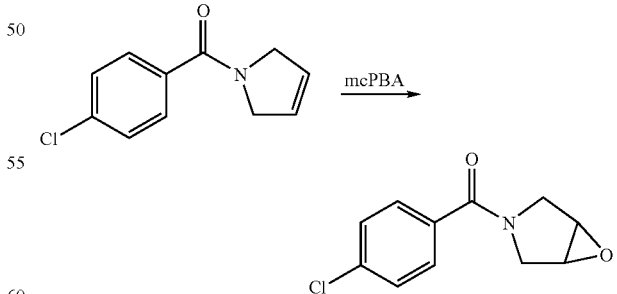

(4-Chloro-phenyl)-(6-oxa-3-aza-bicyclo [3.1.0]hex-3-yl)methan one

The desired compound was prepared according to epoxidation procedures described above from (4-Chloro-phenyl)-

(2,5-dihydro-pyrrol-1-yl)-methanone in 30% yield as a colorless oil (30% yield). $^1$H-NMR (300 MHz, CDCl$_3$): δ 3.5 (2H, dd), 3.7 (3H, m), 4.3 (1H, d), 7.40 (4H, s)

Example 172

Synthesis of 4-[1-(4-Chloro-benzoyl)-4-hydroxy-pyrrolidin-3-yl[-piperazine-1-carboxylic acid tert-butyl ester

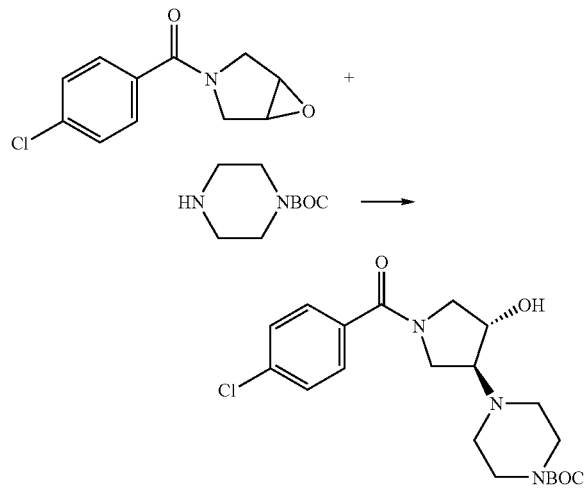

4-[1-(4-Chloro-benzoyl)-4-hydroxy-pyrrolidin-3-yl]-piperazine-1-carboxylic acid tert-butyl ester The desired compound was prepared according to general procedures described above for epoxide opening from (4-Chloro-phenyl)-(6-oxa-3-aza-bicyclo[3.1.0]hex-3-yl)-methanone in 80% yield. $^1$H-NMR (300 MHz, CDCl$_3$): δ 1.4 (9H, s), 2.3-2.7 (5H, m), 2.9 (1H, m), 3.4 (m, 5H), 3.7 (m, 2H), 3.9 (m, 1H), 4.2 (m, 1H), 7.40 (4H, m)

Example 173

Synthesis of (4-Chloro-phenyl)-(3-hydroxy-4-piperazin-1-yl-pyrrolidin-1-yl)-methanone

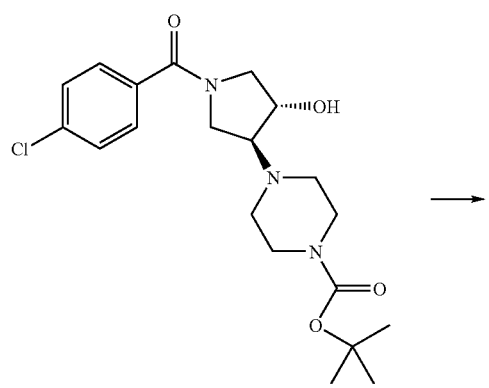

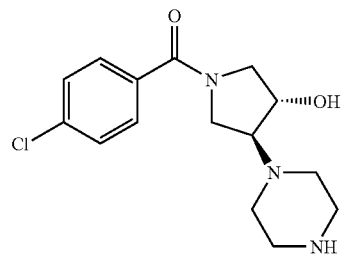

The desired compound was prepared according to Boc deprotection procedures described generally above from 4-[1-(4-Chloro-benzoyl)-4-hydroxy-pyrrolidin-3-yl]-piperazine-1-carboxylic acid tert-butyl ester in 99% yield. $^1$H-NMR (300 MHz, D$_2$O): δ 2.75 (1H, m), 3.0 (1H, m), 3.15 (4H, m), 3.25 (3H, m), 3.3-3.5 (2H, m), 3.7 (1H, m), 3.9 (1H, m), 4.4 (1H, m), 7.35 (4H, dd). Retention Time (LC, method: ammonium acetate standard): 0.89 min. MS (M+H$^+$): 310

Example 174 below depicts a general procedure for coupling the deprotected compound obtained in Example 174, with a desired R$^2$ group (T-Cy$^2$ or Cy$^2$ as described herein)

Example 174

General Procedure for Reductive Amination

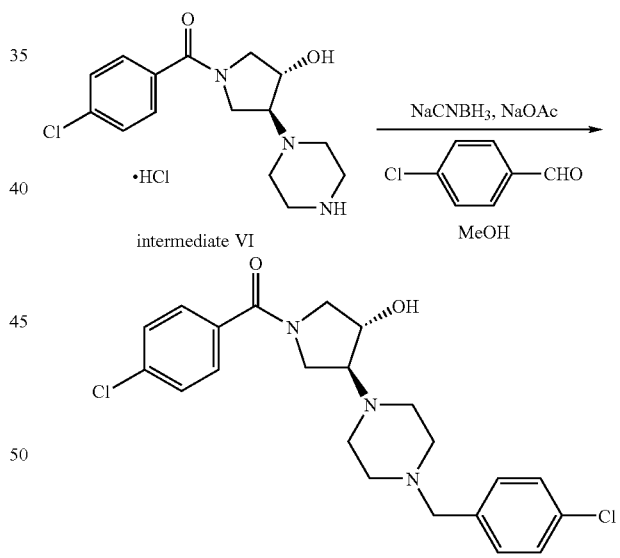

Intermediate VI (100 mg, 0.290 mmol), NaCNBH$_3$ (20 mg, 0.319 mmol), NaOAc (23.8 mg, 0.29 mmol), 4-Chloro-benzaldehyde (42.8 mg, 0.30 mmol) were added to methanol (3 mL). The reaction mixture was stirred in room temperature for over night. The mixture was concentrated. K$_2$CO$_3$ and Ethyl acetate were added to the residue. The organic phase was washed with brine, dried over Na$_2$SO$_4$, and concentrated. The crude was purified by column chromatography to give 70 mg of desired product as an oil (56% yield).

Examples 175-181 below describe the synthesis of certain exemplary compounds of the invention:

Example 175

Synthesis of 2,5-dihydro-pyrrole-1-carboxylic acid benzyl esters

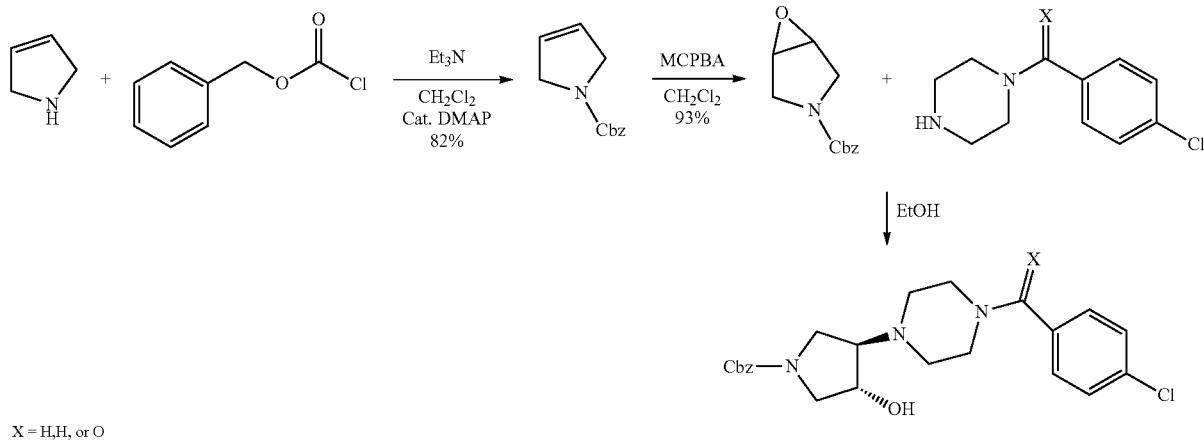

X = H,H, or O

To a solution of 3-pyrroline (20 g, 0.289 mol, 65% purity) in CH$_2$Cl$_2$ (200 mL) at 0° C., was added Et$_3$N (40.2 mL, 0.289 mol), benzyl chloroformate (40.6 mL, 0.289 mol) and Cat. DMAP (50 mg). The reaction mixture was allowed to warm to RT and stirred for overnight. Then the mixture was concentrated. Ethyl acetate (200 mL) was added and filtered. The organic phase was washed with 1N HCl solution (2×100 mL) and Sat. NaCl solution (2×100 mL), dried over Na$_2$SO$_4$, and concentrated. The residue was purified by column chromatography (Ethyl acetate:Hexane: 1:3) to give the desired product as a colorless oil (48.2 g, 82% yield). MS: (ESI), M/Z, 204 (M+1). Retention time: 1.66 min (FA-standard).

6-oxa-3-aza-bicyclo[3.1.0]hexane-3-carboxylic acid benzyl ester

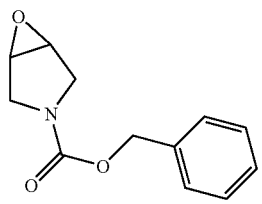 [SMILES: O=C(OCc1ccccc1)N1CC2OC2C1]

Following the general procedures for epoxidation as described generally above, the title compound was obtained as a colorless oil in 93% yield. MS: (EST), M/Z, 220 (M+1). Retention time: 1.36 min (FA-standard).

3-[4-(4-Chloro-benzoyl)-piperazin-1-yl]-4-hydroxy-pyrrolidine-1-carboxylic acid benzyl ester

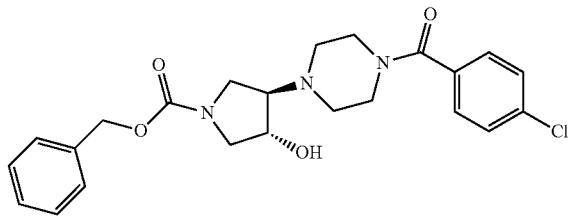 [SMILES: O=C(OCc1ccccc1)N1C[C@@H](O)[C@H](N2CCN(C(=O)c3ccc(Cl)cc3)CC2)C1]

Following the general procedures for epoxide ring opening as described generally above, the title compound was obtained as a white solid in 54% yield, MS: (ESI), MIZ, 444 (M+1). Retention time: 1.28 min (FA-standard).

3-[4-(4-Chloro-benzyl)-piperazin-1-yl]-4-hydroxy-pyrrolidine-1-carboxylic acid benzyl ester

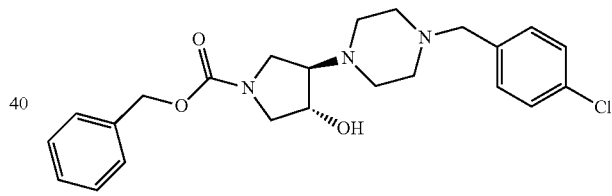

Following the general procedure of epoxide ring-opening as described generally above, the title compound was obtained as a white solid in 65% yield, MS: (ESI), M/Z, 430 (M+1). Retention time: 1.15 min (FA-standard).

Example 176

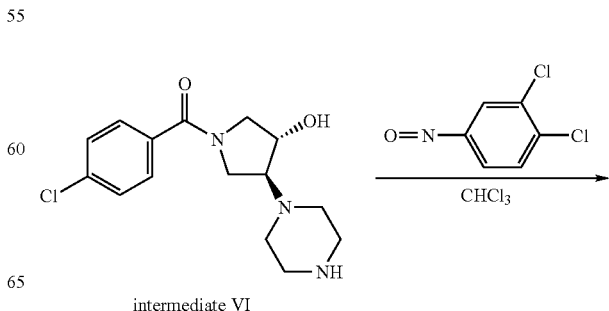

intermediate VI

-continued

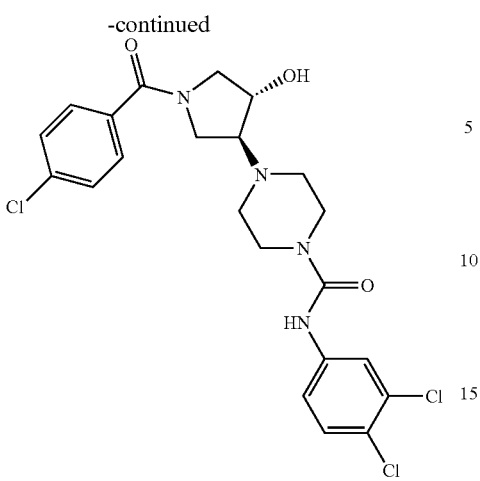

Intermediate VI (100 mg, 0.32 mmol) and 1,2-dichloro-4-isocyanoto-benzene (63.9 mg, 0.34 mmol) was added to CHCl₃ (3 mL) and stirred overnight. A white solid crashed out and was filtered and washed with ether. The desired product 130 mg was obtained in 81% yield.

Example 177

Preparation of Spiro Intermediate for Use in the Preparation of Compounds of the Invention

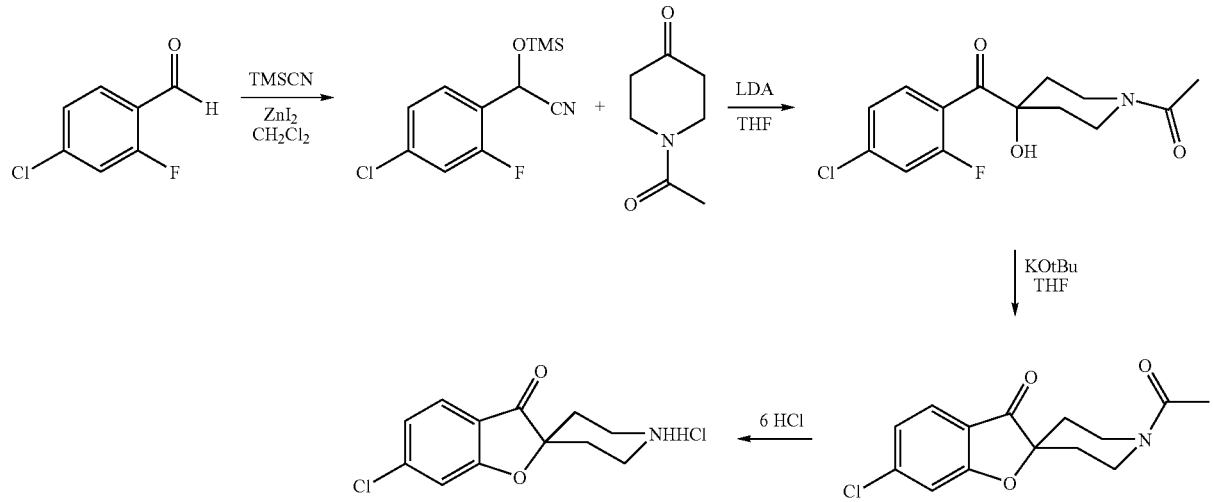

(4-Chloro-2-fluoro-phenyl)-trimethylsilanyloxyacetonitrile

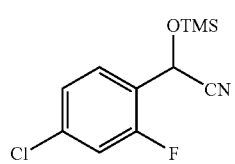

To a solution of 4-chloro-2-fluoro-benzaldehyde (5.0 g, 31.55 mmol) in CH₂Cl₂ (20 mL) at 0° C., was added TMSCN (3.12 g, 31.55 mmol) and Cat. ZnI₂ (50 mg). The mixture was stirred at RT for overnight. After concentrating, the desired product was obtained (8.12 g, 100% yield) as a brown oil. ¹H NMR (CDCl₃) δ 0.1 (s, 9H), 5.6 (s, 1H), 7.0 (d, 1H), 7.15 (d, 1H), 7.55 (t, 1H).

1-[4-(4-Chloro-2-fluoro-benzoyl)-4-hydroxy-piperidin-1-yl]-ethanone

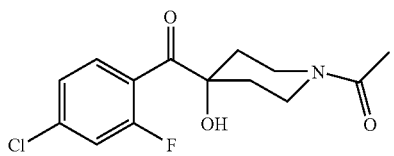 [SMILES: CC(=O)N1CCC(O)(C(=O)c2ccc(Cl)cc2F)CC1]

To a solution of diisopropylamine (4.42 mL, 31.59 mmol) in THF (20 mL) at 0° C. under Ar, was added n-BuLi (12.63 mL, 31.59 mmol, 2.5 M solution in hexane). The mixture was stirred at 0° C. for 30 min. After cooling to −78° C., (4-chloro-2-fluoro-phenyl)-trimethylsilanyloxyacetonitrile (8.12 g, 31.59 mmol) was added. After stirring at −78° C. for 1.5 h, 1-acetyl-piperidin-4-one (4.45 g, 31.59 mmol) was added. The final mixture was stirred at −20° C. for overnight. After concentration, EtOAc (100 mL) was added. The organic phase was washed with Sat. NH₄OAc solution, Sat. NaHCO₃ solution and concentrated. The residue was dissolved in MeOH (30 mL). 1N HCl solution (20 mL) was added. The mixture was stirred at RT for 2 h. After concentrating the mixture, EtOAc (50 mL) was added. The organic layer was basified with Sat. NaHCO₃, dried over Na₂SO₄ and concentrated. The residue was purified by column chromatography (Ethyl acetate) to give the desired product (4 g, 42% yield) as a white solid. MS: (ESI), M/Z, 300 (M+1). Retention time: 0.87 min (FA-standard).

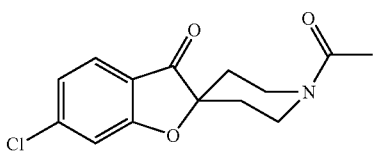 [SMILES: CC(=O)N1CCC2(CC1)Oc1cc(Cl)ccc1C2=O]

To a solution of 1-[4-(4-chloro-2-fluoro-benzoyl)-4-hydroxy-piperidin-1-yl]-ethanone (3.0 g, 10.03 mmol) in THF (30 mL), was added KOtBu (1.23 g, 11.03 mmol). The mixture was stirred at reflux for overnight. After cooling to RT, EtOAc (50 mL) was added. The organic phase was washed with Sat. NaHCO$_3$, dried over Na$_2$SO$_4$ and concentrated. The residue was purified by column chromatography (Ethyl acetate) to give desired product (1.1 g, 40% yield) as a sticky oil, MS: (ESI), M/Z, 280 (M+1). Retention time: 1.03 min (FA-standard).

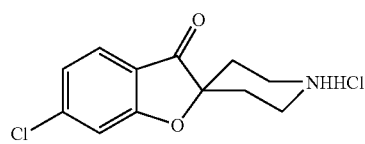

To a solution of actyl protected spiro-amine (1.1 g, 3.94 mmol), was added 6N HCl solution (7 mL). The mixture was stirred at reflux for overnight. After concentration, the desired product was obtained as a white solid (1.0 g, 100% yield). MS: (ESI), M/Z, 238 (M+1). Retention time: 0.97 min (FA-standard).

Example 178

Preparation of 1-(5-chloro-indan-1-yl)-piperazine for Use in the Preparation of Compounds of the Invention

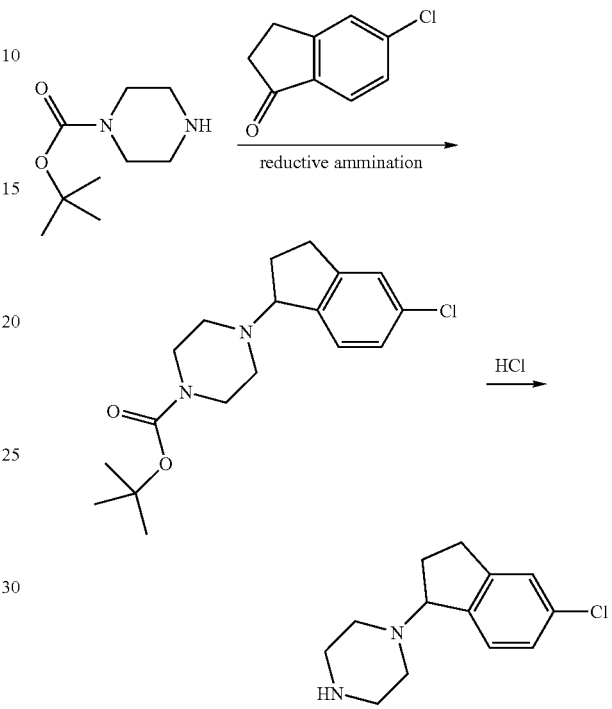

The desired compound 1-(5-chloro-indan-1-yl)-piperazine was prepared according to methods described generally above in two steps with yield of 30% and 99% respectively.

Example 179

4-(4-Chloro-benzoyl)-1-[1-(4-chloro-benzoyl)-4-hydroxy-pyrrolidin-3-yl]-piperazin-2-one

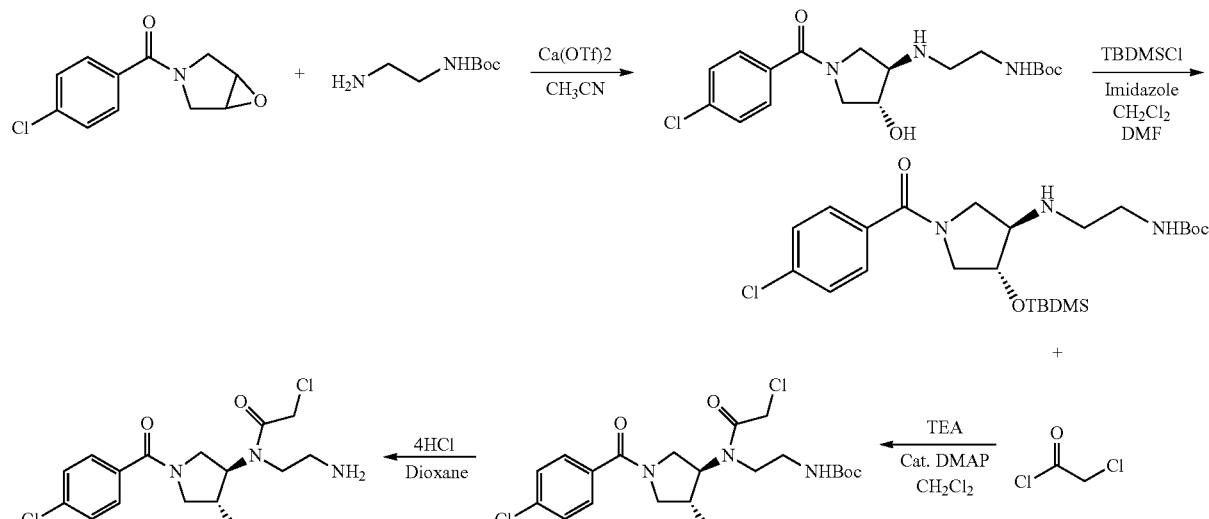

+

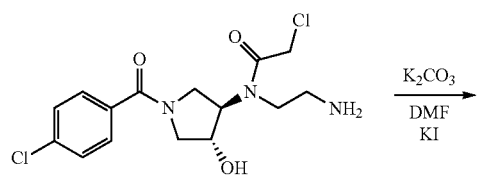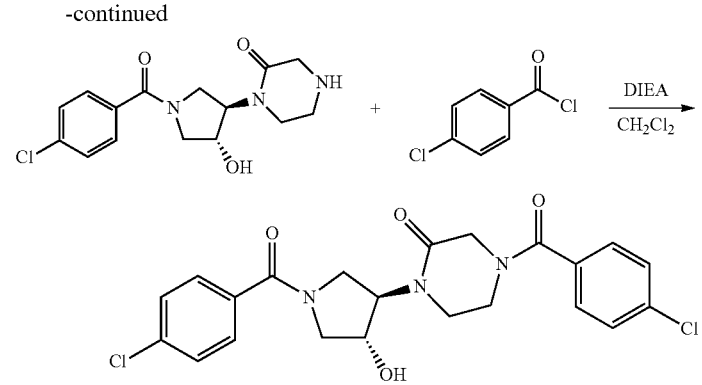

{2-[1-(4-Chloro-benzoyl)-4-hydroxy-pyrrolidin-3-ylamino]-ethyl}-carbamic acid tert-butyl ester

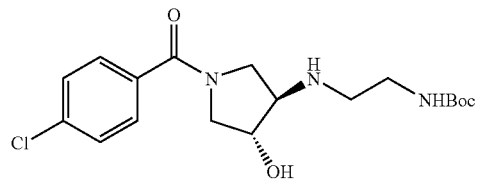 [SMILES: CC(C)(C)OC(=O)NCCN[C@@H]1CN(C(=O)c2ccc(Cl)cc2)C[C@H]1O]

Following the general procedure of epoxide ring-opening described generally above, the title compound was obtained as a colorless oil (25% yield). MS: (ESI), M/Z, 384 (M+1). Retention time: 1.58 min (FA-polar).

{2-[4-(tert-Butyl-dimethyl-silanyloxy)-1-(4-chloro-benzoyl)-pyrrolidin-3-ylamino]-ethyl}-carbamic acid tert-butyl ester

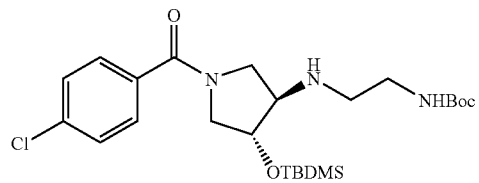 [SMILES: CC(C)(C)OC(=O)NCCN[C@@H]1CN(C(=O)c2ccc(Cl)cc2)C[C@H]1O[Si](C)(C)C(C)(C)C]

To a solution of {2-[1-(4-chloro-benzoyl)-4-hydroxy-pyrrolidin-3-ylamino]-ethyl}-carbamic acid tert-butyl ester (750 mg, 1.95 mmol) in DMF (0.25 mL) at 0° C., was added imidazole (663 mg, 9.15 mmol) and TBDMSCl (309 mg, 2.05 mmol). The reaction mixture was stirred for 2 days. EtOAc (5 mL) was added. The organic phase was washed with Sat. NH₄Cl, dried over Na₂SO₄, and concentrated. The residue was purified by column chromatography (Ethyl acetate: MeOH: 10:1) to give the desired product (389 mg, 40% yield) as a colorless oil. MS: (ESI), M/Z, 498 (M+1). Retention time: 2.21 min (FA-polar).

{2-[[4-(tert-Butyl-dimethyl-silanyloxy)-1-(4-chloro-benzoyl)-pyrrolidin-3-yl]-(2-chloro-acetyl)-amino]-ethyl}-carbamic acid tert-butyl ester

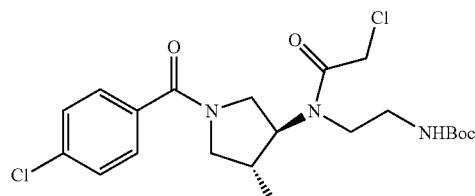

To a solution of {2-[4-(tert-butyl-dimethyl-silanyloxy)-1-(4-chloro-benzoyl)-pyrrolidin-3-ylamino]-ethyl}-carbamic acid tert-butyl ester (389 mg, 0.78 mmol) at 0° C., was added DIPEA (0.150 mL, 0.85 mmol) and chloroacetyl chloride (62 uL, 0.78 mmol). The reaction mixture was stirred at RT for overnight. The organic phase was washed with Sat. NaHCO₃, dried over Na₂SO₄, and concentrated. The residue was purified by column chromatography (Ethyl acetate:Hexane: 1:2) to give the desired product (260 mg, 58% yield) as a colorless oil. MS: (ESI), M/Z, 574 (M+1). Retention time: 2.78 min (FA-polar).

N-(2-Amino-ethyl)-N-[4-(tert-butyl-dimethyl-silanyloxy)-1-(4-chloro-benzoyl)-pyrrolidin-3-yl]-2-chloro-acetamide N-(2-Amino-ethyl)-2-chloro-N-[1-(4-chloro-benzoyl)-4-hydroxy-pyrrolidin-3-yl]-acetamide

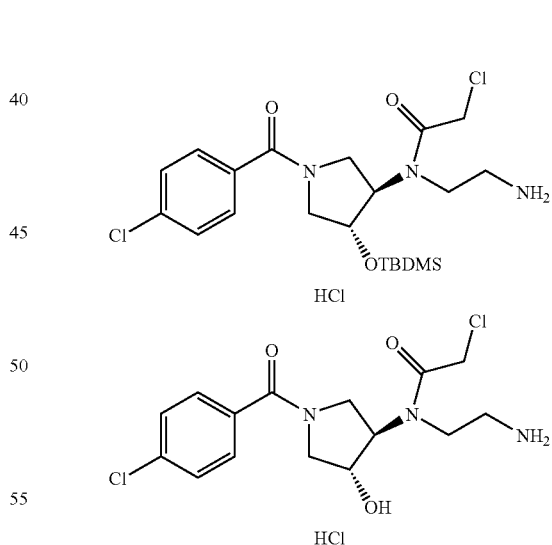

{2-[[4-(tert-Butyl-dimethyl-silanyloxy)-1-(4-chloro-benzoyl)-pyrrolidin-3-yl]-(2-chloro-acetyl)-amino]-ethyl}-carbamic acid tert-butyl ester (260 mg, 0.45 mmol) was dissolved in 1 mL of 4M HCl in dioxane solution. The mixture was stirred at RT for 1.5 h. After concentrating, a white solid was formed (200 mg). The LC-Mass showed two products as showed above. MS: (ESI), M/Z, 360 (M+1). Retention time: 1,31 min (FA-polar). MS: (ESI), M/Z, 474 (M+1). Retention time: 2.20 min (FA-polar).

1-[1-(4-Chloro-benzoyl)-4-hydroxy-pyrrolidin-3-yl]-piperazin-2-one

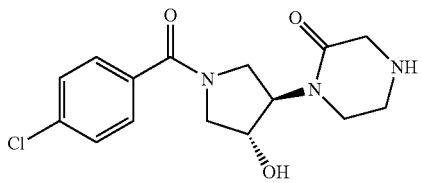 [SMILES: O=C(c1ccc(Cl)cc1)N1C[C@@H](O)[C@H](N2CCNCC2=O)C1]

A mixture of N-(2-amino-ethyl)-N-[4-(tert-butyl-dimethyl-silanyloxy)-1-(4-chloro-benzoyl)-pyrrolidin-3-yl]-2-chloro-acetamide and N-(2-amino-ethyl)-2-chloro-N-[1-(4-chloro-benzoyl)-4-hydroxy-pyrrolidin-3-yl]-acetamide (200 mg) was dissolved in 2 mL of DMF. Then $K_2CO_3$ (117 mg, 0.84 mmol) and Cat. KI were added. The mixture was stirred at 90° C. for overnight. EtOAc (5 mL) was added. The organic phase was washed with Sat. $NaHCO_3$, dried over $Na_2SO_4$, and concentrated. The residue was purified by column chromatography (Ethyl acetate:Methanol:$Et_3$N:3:1:0.04) to give the desired product (50 mg, 37% yield) as a colorless oil. MS (ESI), M/Z, 324 (M+1). Retention time: 1.13 min (FA-polar).

4-(4-Chloro-benzoyl)-1-[1-(4-chloro-benzoyl)-4-hydroxy-pyrrolidin-3-yl]-piperazin-2-one

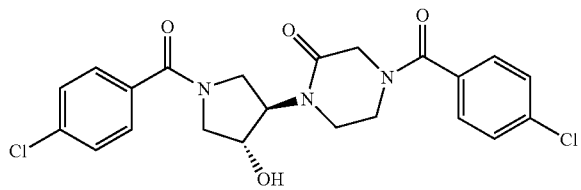 [SMILES: O=C(c1ccc(Cl)cc1)N1CCN([C@@H]2CN(C(=O)c3ccc(Cl)cc3)C[C@H]2O)C(=O)C1]

To a solution of 1-[1-(4-Chloro-benzoyl)-4-hydroxy-pyrrolidin-3-yl]-piperazin-2-one (50 mg, 0.15 mmol) in $CH_2Cl_2$ (1 mL) at 0° C., was added DIPEA (27 uL, 0.154 mmol) and 4-Chloro-benzoyl chloride (20 uL, 0.154 mmol). The mixture was stirred at RT for 4 h. The organic phase was washed with Sat. $NaHCO_3$, dried over $Na_2SO_4$, and concentrated. The residue was purified by column chromatography (Ethyl acetate:Methanol:$Et_3$N:10.1:0.1) to give the desired product (36 mg, 50% yield) as a white solid. MS: (ESI), M/Z, 462 (M+1). Retention time: 2.25 min (FA-polar).

Example 180

{3-[4-(4-Chloro-benzoyl)-piperazin-1-yl]-4-methoxy-pyrrolidin-1-yl}-(4-chloro-phenyl)-methanone

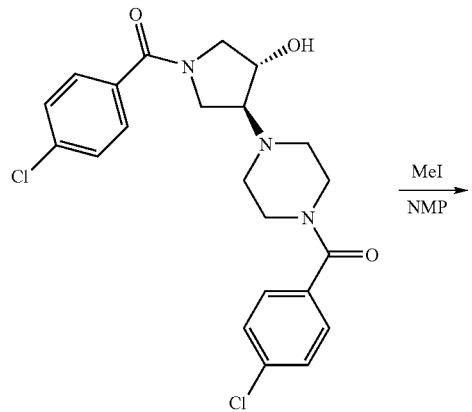

To a cold (3-5° C.) solution of starting material {3-[4-(4-Chloro-benzoyl)-piperazin-1-yl]-4-hydroxy-pyrrolidin-1-yl}-(4-chloro-phenyl)-methanone in 1 mL of NMP was added NaH (4 mg, 0.17 mmol). The mixture was then stirred at 3-5° C. for 15 mins. MeI (7.5 uL) was then added. After 2 hours, the reaction was quenched by adding 50 μL AcOH. The mixture was then partitioned in EtOAc and 1M $K_2CO_3$. The separated organic phase was washed with brine, dried over $Na_2SO_4$ and concentrated down to dryness. The resulting crude residue was purified by column chromatography on silica (Methanol 1 $CH_2Cl_2$: 0%-10%). The pure product was converted to it HCl salt by precipitation in a mixture of ethanol 1 ether and conc. HCl, to give 43 mg of salt of {3-[4-(4-Chloro-benzoyl)-piperazin-1-yl]-4-methoxy-pyrrolidin-1-yl}-(4-chloro-phenyl)-methanone as a white solid.

Example 181

Preparation of N-{1-[1-(4-Chloro-benzoyl)-4-hydroxy-pyrrolidin-3-yl]-piperidin-4-yl}-N-(4-chloro-phenyl)-acetamide

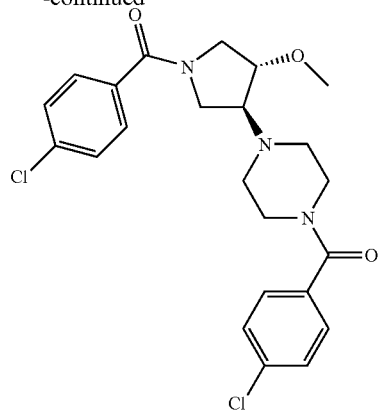

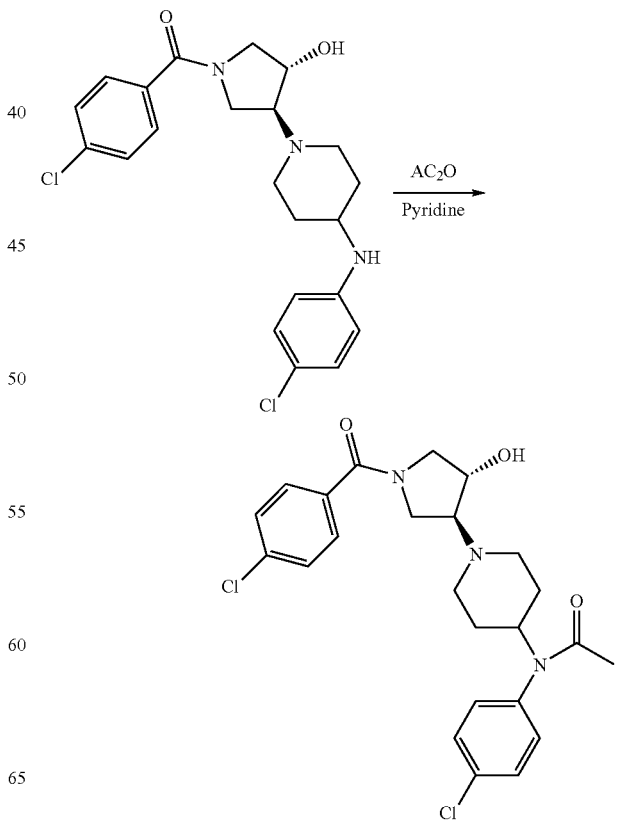

The starting materials (4-Chloro-phenyl)-{3-[4-(4-chloro-phenylamino)-piperidin-1-yl]-4-hydroxy-pyrrolidin-1-yl}-methanone (48 mg, 0.11 mmol) and Ac₂O (16 uL, 0.17 mmol) were added in pyridine (0.5 mL) and stirred at room temperature overnight. The reaction mixture was concentrated down to dryness. The resulting crude residue was purified by column chromatography on silica (Methanol\CH₂Cl₂: 0%-6%).

The pure compound was converted to 56 mg of HCl salt of N-{1-[1-(4-Chloro-benzoyl)-4-hydroxy-pyrrolidin-3-yl]-piperidin-4-yl}-N-(4-chloro-phenyl)-acetamide by precipitation in a mixture of ethanol and ether using conc. HCl.

Compounds 101, 143, 144, 158, 160, 175, 176, 177, 180, and 181 (as referred to in Table 1) can be prepared using Schemes 1 and 2. The piperazine intermediates required for the synthesis of these compounds can be prepared by the synthetic sequence shown in Scheme 4.

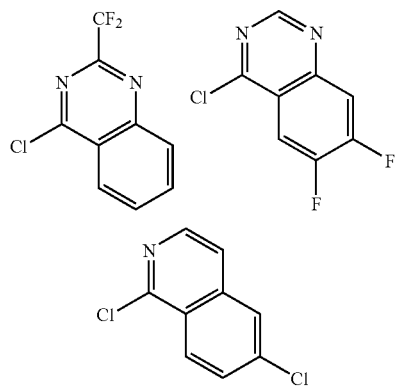

Scheme 4

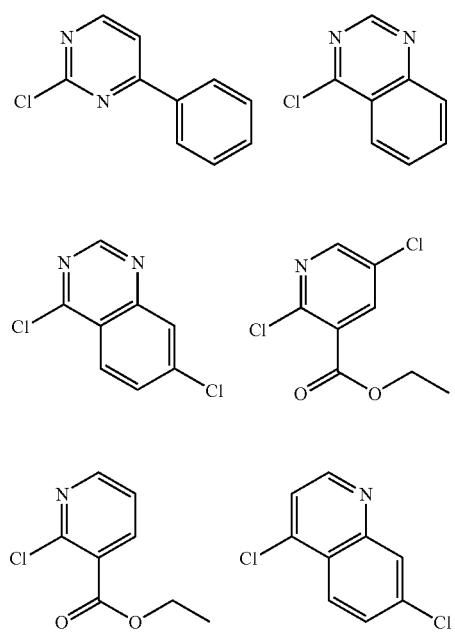

Reagents and conditions: (i) DBU (5 eq.), NMP or CH₃CN, 80° C., 16-18 h.; (ii) 4N HCl, r.t., 3 h.

The following aryl chlorides (R²—Cl) are commercially available:

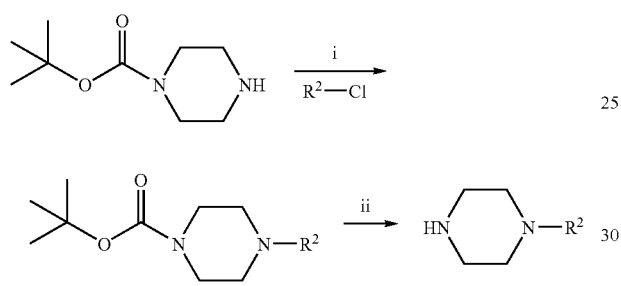

The following aryl chlorides were prepared as shown in Scheme 5, 6 and 7

Scheme 5

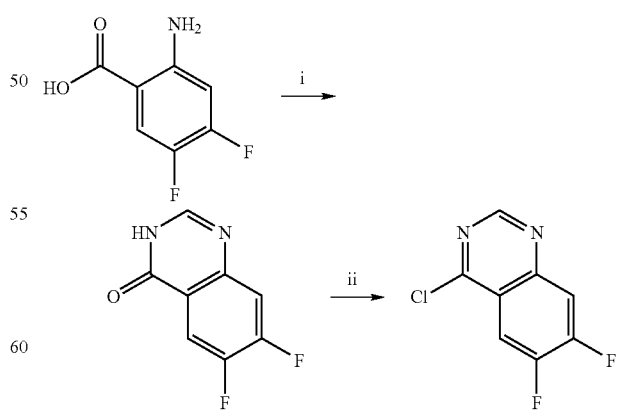

Reagents and conditions: (i) (CF₃CO)₂O, Pyridine/CH₃CN, 0° C.-r.t., 2 h. (no work-up) (ii) (NH₄)₂CO₃, 0° C.-r.t., 16-18 h; (no work-up, evaporate solvent) (iii) CH₃CO₂H, 120° C. 3 h. (iv) PCl₅, dichloroethane, 150° C., 0.5 h. microwave.

Scheme 6

Reagents and conditions: (i) HCONH₂, 150° C., 20 min. microwave. (ii) PCl₅, dichloroethane, 150° C., 20 min. microwave.

Scheme 7

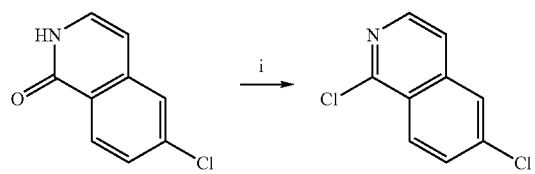

Reagents and conditions: (i) PCl₅, dichloroethane, 150° C., 20 min. microwave.

Note: 6-chloroisoquinolin-1(2H)-one was prepared as described in Briet, N. et al Tetrahedron 58, pp 5761-5766, 2002.

It will be appreciated that additional compounds of the invention, as exemplified generally herein and in Table 1, can be prepared according to methods described above.

Biological Testing

THP-1 FLIPR Assay

The primary screening assay is a FLIPR® (Fluorometric Imaging Plate Reader, available from Molecular Devices Corporation, Sunnyvale, Calif.) assay using THP-1 cells (ATCC, Catalog No. TIB 202), a monocytic derived cell line that endogenously expresses CCR1.

The cells were resuspended at 1×10⁶ cells/ml in dye loading media (growth media (RPMI+10% FBS (Fetal Bovine serum)+5.5×10⁻⁵M 2-mercaptoethanol)+10 mM HEPES (N-2-hydroxyethylpiperazine-N'-2-ethane-sulfonic acid)+ 2.5 mM probenecid+fluo-3 (1:250)). The cells were incubated for 1 hour at 37° C. and then washed in FLIPR wash buffer (100 mL 10× HBSS (Hanks Buffered Saline Solution) (w/Ca++/Mg++)+20 mL 1M HEPES+1 g BSA+10 mL 250 mM probenecid+water (to make 1 L)) and plated at 50,000 cells/well in black/clear 384 well plates. The plates were transferred to FLIPR where the ability of different concentrations of compounds to inhibit RANTES induced calcium flux was assessed. Inhibition of the CCR1 response was reflected by a decrease of the fluorescence signal relative to the positive controls (RANTES alone).

THP-1 Whole Cell Radioligand Binding Assay

The cells were washed with PBS (phosphate buffered saline) and resuspended in binding buffer (10 mM HEPES pH 7.2, 1× HUSS (w/ Ca²⁺, Mg²⁺) 0.5% BSA, 0.02% Na-azide) at 4×10⁶ cells/ml (for 200, 000 cells/well). Cells were incubated with 0.1 to 0.2 nM [¹²⁵I]-labeled MIP-1α with or without unlabeled competitor (MIP-1α) or various concentrations of compounds for 60 minutes at room temperature. The assay was terminated by vacuum filtration through glass fiber filters (GF/B, Packard) which were presoaked in 0.3% polyethyleneimine. The filters were washed with wash buffer (10 mM HEPES, pH 7.2, 1 mM CaCl₂, 5 mM MgCl₂ 0.5M NaCl), dried and the amount of bound radioactivity was determined by scintillation counting.

Compounds of the invention were found to inhibit CCR1.

In some embodiments, the following compounds of the invention were found to have activity less than 1 µM: 2, 3, 5, 9, 10, 11, 12, 13 15, 16, 21, 27, 29, 30, 31, 32, 34, 35, 38, 39, 41, 43, 46, 47, 48, 49, 50, 51, 52, 53, 54, 55, 56, 57, 58, 62, 64, 65, 67, 69, 72, 73, 74, 77, 78, 79, 80, 81, 82, 83, 84, 85, 86, 88, 89, 90, 91, 92, 98, 101, 103, 104, 105, 106, 109, 110, 113, 114, 116, 120, 121, 122, 125, 126, 130, 131, 133, 134, 135, 136, 137, 138, 139, 141, 142, 145, 146, 147, 149, 150, 152, 154, 156, 157, 158, 160, 162, 164, 165, 166, 167, 168, 170, 173, 174, 176, 179, 181, 200,.202, 203, 204, 205, 206, and 208.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound of formula II-B:

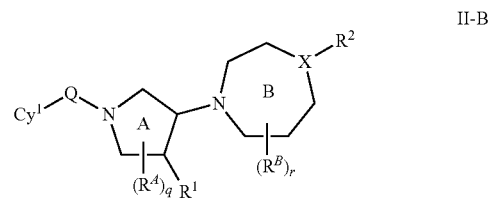

or a pharmaceutically acceptable salt thereof, wherein:

$R^1$ is $-OR^4$, fluoro, $-OCOR^4$, $-NR^4SO_2R^3$, or $-NR^4COR^4$;

$R^3$ is an optionally substituted group selected from $C_1$-$C_6$ aliphatic or a 3-7-membered saturated, partially unsaturated, or aromatic monocyclic ring having 0-3 heteroatoms independently selected from nitrogen, oxygen, or sulfur;

each occurrence of $R^4$ is independently hydrogen or an optionally substituted group selected from $C_1$-$C_6$ aliphatic or a 3-7-membered saturated, partially unsaturated, or aromatic monocyclic ring having 0-3 heteroatoms independently selected from nitrogen, oxygen, or sulfur, or two $R^4$ on the same nitrogen atom, taken together with the nitrogen atom, form an optionally substituted 3-6-membered saturated, partially saturated, or aromatic ring having 0-2 additional heteroatoms independently selected from nitrogen, oxygen, or sulfur;

ring A is substituted with q occurrences of $R^A$, wherein q is 0-2 and each occurrence of $R^A$ is independently fluoro, $-SO_2N(R^C)_2$, $-OR^C$, $-SR^C$, $-SO_2R^C$, $-COR^C$, $-CO_2R^C$, $-N(R^C)_2$, $-CON(R^C)_2$, $-N(R^C)COR^C$, $-N(R^C)CO_2R^C$, $-N(R^C)CON(R^C)_2$, or an optionally substituted group selected from $C_1$-$C_6$ aliphatic or a 3-7-membered saturated, partially unsaturated, or aromatic monocyclic ring having 0-3 heteroatoms independently selected from nitrogen, oxygen, or sulfur, or two occurrences of $R^A$, or $R^A$ and $R^1$, taken together with their intervening atom(s), form an optionally substituted spiro or fused 3-6-membered saturated or partially unsaturated ring having 0-3 heteroatoms independently selected from nitrogen, oxygen, or sulfur, wherein each occurrence of $R^C$ is independently hydrogen or an optionally substituted group selected from $C_1$-$C_6$ aliphatic or a 3-7-membered saturated, partially unsaturated, or aromatic monocyclic ring having 0-3 heteroatoms independently selected from nitrogen, oxygen, or sulfur, or two occurrences of $R^C$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

ring B is substituted with r occurrences of $-R^B$ or -L-$R^B$, wherein r is 0-2, L is a $C_{1-4}$ alkylene and each occurrence of $R^B$ is independently fluoro, —$OR^D$, —$SR^D$, $COR^D$, —$CO_2R^D$, —$N(R^D)_2$, —$CON(R^D)_2$, —$N(R^D)COR^D$, or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^B$, taken together with their intervening atom(s), form an optionally substituted spiro, fused or bridged 3-6-membered saturated, partially unsaturated, or aromatic ring having 0-3 heteroatoms independently selected from nitrogen, oxygen, or sulfur; wherein each occurrence of $R^D$ is independently hydrogen or an optionally substituted group selected from $C_1$-$C_6$aliphatic or a 3-7-membered saturated, partially unsaturated, or aromatic monocyclic ring having 0-3 heteroatoms independently selected from nitrogen, oxygen, or sulfur, or two occurrences of $R^D$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

$R^2$ is -T-$Cy^2$ or -$Cy^2$, wherein T, when present, is a $C_1$-$C_3$alkylene chain, wherein the alkylene chain is substituted with 0 or 1 occurrence of $R^{5a}$, and 0, 1, or 2 independent occurrences of $R^{5b}$, and wherein one or more methylene units in the $C_1$-$C_3$alkylene chain, as valency and stability permit, is optionally replaced by one or more independent occurrences of —$CR^{5c}$=$CR^{5c}$—, —CO—, —$SO_2$—, —O—, —S—, or —$NR^{5c}$—;

$R^{5a}$ is fluoro, —CN, —$OR^{5c}$, —$N(R^5e)_2$, —$SR^5c$, or an optionally substituted group selected from $C_1$-$C_6$aliphatic, or a 3-7-membered saturated, partially unsaturated, or aromatic monocyclic ring having 0-3 heteroatoms independently selected from nitrogen, oxygen, or sulfur;

$R^{5b}$ is an optionally substituted group selected from $C_1$-$C_6$aliphatic, or a 3-7-membered saturated, partially unsaturated, or aromatic monocyclic ring having 0-3 heteroatoms independently selected from nitrogen, oxygen, or sulfur;

$R^{5c}$ is hydrogen, or an optionally substituted group selected from $C_1$-$C_4$aliphatic, or a 3-7-membered saturated, partially unsaturated, or aromatic monocyclic ring having 0-3 heteroatoms independently selected from nitrogen, oxygen, or sulfur, or two occurrences of $R^{5c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

$Cy^2$ is an optionally substituted group selected from a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur; wherein $Cy^2$ is substituted with m independent occurrences of —$R^{6a}$, -G-$R^{6a}$, or —V-G-$R^{6a}$, and k occurrences of =O, =S, =$NR^{7a}$, =$NR^{7b}$, —$R^{6b}$, -G-$R^{6b}$, or -V-G-$R^{6b}$, wherein:

m is 0-3;
k is 0-2;
V is —O—, —S—, —SO—, —$SO_2$—, —$SO_2N(R^{7a})$—, —$N(R^{7a})SO_2$—, —CO—, —$CON(R^{7a})$—, —$N(R^{7a})$CO—, or —$CO_2$—;

G is an optionally substituted straight or branched $C_1$-$C_4$alkylene chain that is optionally replaced by —$CR^{7a}$=$CR^{7a}$—, —O—, —$N(R^{7a})$—, —S—, —SO—, —$SO_2$—, —$SO_2N(R^{7a})$—, —$N(R^{7a})SO_2$—, —CO—, —$CON(R^{7a})$—, —$N(R^{7a})$CO—, or —$CO_2$—, provided that the replacing group is not directly bonded to V, —$R^{6a}$, or —$R^{6b}$;

each occurrence of —$R^{6a}$ is independently optionally substituted $C_1$-$C_6$ aliphatic, halogen, —$OR^{7a}$, —CN, —$NO_2$, —$SR^{7a}$, —$SO_2N(R^{7a})_2$, —$NR^{7a}SO_2R^{7b}$, —$SO_2R^{7a}$, —$COR^{7a}$, —$CO_2R^{7a}$, —$N(R^{7a})_2$, —CON$(R^{7a})_2$, —$N(R^{7a})COR^{7a}$, —$N(R^{7a})CO_2R^{7a}$, or —$N(R^{7a})CON(R^{7a})_2$;

each occurrence of —$R^{6b}$ is independently —$OR^{7b}$, —$SR^{7b}$, —$SO_2N(R^{7b})(R^{7c})$, $NR^{7c}SO_2R^{7b}$, —$SO_2R^{7b}$, —$COR^{7b}$, —$CO_2R^{7b}$, —$N(R^{7b})(R^{7c})$, —$CON(R^{7b})(R^{7c})$, —$N(R^{7c})COR^{7b}$, —$N(R^{7c})CO_2R^{7b}$, —$N(R^{7c})CON(R^{7b})(R^{7c})$, or an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring system having 0-5 heteroatoms independently selected from nitrogen, oxygen, or sulfur; or two occurrences of $R^{6b}$, taken together with their intervening atom(s), form a spiro, fused, or bridged optionally substituted 5-7-membered saturated, partially unsaturated, or aromatic ring having 0-3 heteroatoms independently selected from nitrogen, oxygen, or sulfur;

each occurrence of $R^{7a}$ is hydrogen or an optionally substituted $C_1$-$C_6$aliphatic group;

each occurrence of $R^{7b}$ is an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and each occurrence of $R^{7c}$ is hydrogen or an optionally substituted group selected from a $C_1$-$C_6$aliphatic group, a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; or $R^{7b}$ and $R^{7c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur;

X is N;
Q is a $C_1$-$C_3$alkylene chain, wherein the alkylene chain is substituted with 0 or 1 occurrence of $R^{5d}$, and 0, 1, or 2 independent occurrences of $R^{5e}$, wherein one or more methylene units in the $C_1$-$C_3$alkylene chain, as valency and stability permit, is optionally replaced by one or more independent occurrences of —$CR^{5f}$=$CR^{5f}$—, —CO—, —$SO_2$—, —O—, —S—, or —$NR^{5f}$—, wherein $R^{5d}$ is $R^{5a}$, $R^{5e}$ is $R^{5b}$, and $R^{5f}$ is $R^{5c}$;

$Cy^1$ is an optionally substituted group selected from a 5-8-membered partially unsaturated or aromatic unsaturated monocyclic ring having 0-3 heteroatoms independently selected from nitrogen, oxygen, or sulfur, or an 8-14-membered partially unsaturated or aromatic bicyclic or tricyclic ring system having 0-5 heteroatoms independently selected from nitrogen, oxygen, or sulfur;

wherein $Cy^1$ is substituted with p independent occurrences of —$R^{10a}$, -J-$R^{10a}$, W-J-$R^{10a}$, and j occurrences of =O, =S, =$NR^{11a}$, =$NR^{11b}$, —$R^{10b}$, -J-$R^{10b}$, or —W-J-$R^{10b}$, wherein:

p is 0-3;

j is 0-2;

W is —O—, —N($R^{11a}$)—, —S—, —SO—, —$SO_2$—, —$SO_2$N($R^{11a}$)—, —N($R^{11a}$)$SO_2$—, —CO—, —CON($R^{11a}$)—, —N($R^{11a}$)CO—, or —$CO_2$—;

J is an optionally substituted straight or branched $C_1$-$C_4$alkylene chain that is optionally replaced by —$CR^{11a}$=$CR^{11a}$—, —O—, —S—, —SO—, —$SO_2$—, —$SO_2$N($R^{11a}$)—, —N($R^{11a}$)$SO_2$—, —CO—, —CON($R^{11a}$)—, —N($R^{11a}$)CO—, or —$CO_2$—, provided that the replacing group is not directly bonded to W, —$R^{10a}$, or —$R^{10b}$;

each occurrence of —$R^{10a}$ is independently optionally substituted $C_1$-$C_6$ aliphatic, halogen, —$OR^{11a}$, —CN, —$NO_2$, —$SR^{11a}$, —$SO_2$N($R^{11a}$)$_2$, —$NR^{11a}SO_2R^{11a}$, —$SO_2R^{11a}$, —$COR^{11a}$, —$CO_2R^{11a}$, —N($R^{11a}$)$_2$, —CON($R^{11a}$)$_2$, —N($R^{11a}$)$COR^{11a}$, —N($R^{11a}$)$CO_2R^{11a}$, or —N($R^{11a}$)CON($R^{11a}$)$_2$;

each occurrence of —$R^{10b}$ is independently —$OR^{11b}$, —$SR^{11b}$, —$SO_2$N($R^{11b}$)($R^{11c}$), —$NR^{11c}SO_2R^{11b}$, —$SO_2R^{11b}$, —$COR^{11b}$, —$CO_2R^{11b}$, —N($R^{11b}$)($R^{11c}$), —CON($R^{11b}$)($R^{11c}$), —N($R^{11c}$)$COR^{11b}$, —N($R^{11a}$)$CO_2R^{11b}$, —N($R^{11c}$)CON($R^{11b}$)($R^{11c}$), or an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring system having 0-5 heteroatoms independently selected from nitrogen, oxygen, or sulfur; or two occurrences of $R^{10b}$, taken together with their intervening atom(s), form a Spiro, fused, or bridged optionally substituted 5-7-membered saturated, partially unsaturated, or aromatic ring having 0-3 heteroatoms independently selected from nitrogen, oxygen, or sulfur;

each occurrence of $R^{11a}$ is hydrogen or an optionally substituted $C_1$-$C_6$aliphatic group;

each occurrence of $R^{11b}$ is an optionally substituted group selected from a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; and each occurrence of $R^{11c}$ is hydrogen or an optionally substituted group selected from a $C_1$-$C_6$aliphatic group, a 3-7-membered saturated, partially unsaturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur; or $R^{11b}$ and $R^{11c}$, taken together with the nitrogen atom to which they are bound, form an optionally substituted 3-6-membered saturated, partially unsaturated, or aromatic ring having 0-2 additional heteroatoms independently selected from nitrogen, oxygen, or sulfur.

2. The compound of claim 1 wherein:

q is 0, 1, or 2, and —$R^A$ is fluoro, an optionally substituted linear or branched $C_1$-$C_6$alkyl, an optionally substituted $C_3$-$C_6$cycloalkyl ring, or two occurrences of $R^A$, taken together with the carbon atom(s) to which they are bound form an optionally substituted fused or Spiro $C_3$-$C_6$cycloalkyl ring; or $R^1$ and $R^A$ taken together with the carbon atom(s) to which they are bound form an optionally substituted fused or spiro $C_3$-$C_6$cycloalkyl ring;

r is 0, 1, or 2, and —$R^B$ is fluoro, or an optionally substituted group selected from $C_1$-$C_6$alkyl, $C_3$-$C_6$cycloalkyl, or a fused or bridged 5- or 6-membered saturated ring having 0 heteroatoms;

$R^2$ is -$Cy^2$ or -T-$Cy^2$, and

T, when present, is a $C_1$-$C_3$alkylene chain substituted with 0 or 1 occurrence of $R^{5a}$, and 0, 1, or 2 independent occurrences of $R^{5b}$, and wherein the $C_1$-$C_3$alkylene chain is optionally replaced by —CO— or —$SO_2$;

$Cy^2$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur, wherein $Cy^2$ is substituted with 0, 1, or 2 independent occurrences —$R^{6a}$, -G-$R^{6a}$, or —V-G-$R^{6a}$, and 0 or 1 occurrence of =O, =S, =$NR^{7a}$, =$NR^{7b}$, —$R^{6b}$, -G-$R^{6b}$, or —V-G-$R^{6b}$, wherein:

each occurrence of —$R^{6a}$, -G-$R^{6a}$, or —V-G-$R^{6a}$, when present, is independently —CN, —$NO_2$, —$OR^{7a}$, —$(CH_2)_{1-4}OR^{7a}$, —$SR^{7a}$, —$(CH_2)_{1-4}SR^{7a}$, halogen, —$COOR^{7a}$, —$(CH_2)_{1-4}COOR^{7a}$, —$COR^{7a}$, —$(CH_2)_{1-4}COR^{7a}$, —CON($R^{7a}$)$_2$, —$(CH_2)_{1-4}$CON($R^7$a)$_2$, —N($R^{7a}$)$_2$, —$(CH_2)_{1-4}$N($R^{7a}$)$_2$, —$SO_2$N($R^{7a}$)$_2$, —$(CH_2)_{1-4}SO_2$N($R^{7a}$)$_2$, —$NR^{7a}SO_2R^{7b}$, or —$(CH_2)_{1-4}NR^{7a}SO_2R^{7b}$, or an optionally substituted $C_1$-$C_6$aliphatic group; and each occurrence of —$R^{6b}$, -G-$R^{6b}$, —V-G-$R^{6b}$ is —$OR^{7b}$, —$(CH_2)_{1-4}OR^{7b}$, —$SR^{7b}$, —$(CH_2)_{1-4}SR^{7b}$, —$COOR^{7b}$, —$(CH_2)_{1-4}COOR^{7b}$, —$COR^{7b}$, —$(CH_2)_{1-4}COR^{7b}$, —CON($R^{7b}$)($R^{7c}$), —$(CH_2)_{1-4}$CON($R^{7b}$)($R^{7c}$), —N($R^{7b}$)($R^{7c}$), —$(CH_2)_{1-4}$N($R^{7b}$)($R^{7c}$), —$SO_2$N($R^{7b}$)($R^{7c}$), —$(CH_2)_{1-4}SO_2$N($R^{7b}$)($R^{7c}$), —$NR^{7c}SO_2R^{7b}$, —$(CH_2)_{1-4}NR^{7c}SO_2R^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur;

Q is —CO—, —C($R^{5d}$)($R^{5e}$)—, —COC($R^{5d}$)($R^{5e}$)—, —$NR^{5f}$CO—, —$SO_2$—, —OCO—, —C($R^{5d}$)($R^{5e}$)CO—, —C($R^{5d}$)($R^{5e}$)OCO—, or —$CR^{5e}$=$CR^{5e}$CO—; and $Cy^1$ is an optionally substituted ring selected from phenyl, naphthyl, a 5-6-membered monocyclic heteroaryl ring having 1-3 heteroatoms selected from nitrogen, oxygen, or sulfur, or an 8-10-membered bicyclic heteroaryl ring having 1-3 heteroatoms selected from nitrogen, oxygen, or sulfur, wherein $Cy^1$ is substituted with 0, 1, 2, or 3 independent occurrences of —$R^{10a}$, -J-$R^{10a}$, or —W-J-$R^{R10a}$, and 0 or 1 occurrence of =O, =S, =$NR^{11a}$, =$NR^{11b}$, —$R^{10b}$, -J-$R^{10b}$, or —W-J-$R^{10b}$, wherein:

each occurrence of —$R^{10a}$, -J-$R^{10a}$, or —W-J-$R^{10a}$, when present, is independently —CN, —$NO_2$, —$OR^{11a}$, —$(CH_2)_{1-4}OR^{11a}$, $SR^{11a}$, halogen, —$COOR^{11a}$, —$(CH_2)_{1-4}COOR^{11a}$, —$COR^{11a}$, —$(CH_2)_{1-4}COR^{11a}$, —CON($R^{11a}$)$_2$, —(CH$_2$)$_{1-4}$CON($R^{11a}$)$_2$, —N($R^{11}$a)$_2$, (CH$_2$)$_{1-4}$N($R^{11a}$)$_2$, —SO$_2$N($R^{11a}$)$_2$, —(CH$_2$)$_{1-4}$SO$_2$N ($R^{11a}$)$_2$, —NR$^{11a}$SO$_2$R$^{11a}$, or —(CH$_2$)$_{1-4}$ NR$^{11a}$SO$_2$R$^{11a}$, or an optionally substituted C$_1$-C$_6$aliphatic group; and each occurrence of —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_{2$\,$1-4}$SR$^{11b}$, —COOR$^{11b}$, —(CH$_2$)$_{1-4}$COOR$^{11b}$, —COR$^{11b}$, (CH$_2$)$_{1-4}$COR$^{11b}$, —CON(R$^{11b}$)(R$^{11c}$), —(CH$_2$)$_{1-4}$ CON(R$^{11b}$)(R$^{11c}$), —N(R$^{11b}$)(R$^{11c}$), —(CH$_2$)$_{1-4}$N (R$^{11b}$)(R$^{11c}$), SO$_2$N(R$^{11b}$)(R$^{11c}$), —(CH$_2$)$_{1-4}$SO$_2$N (R$^{11b}$)(R$^{11c}$), —NR$^{11c}$SO$_2$R$^{11b}$, —(CH$_2$)$_{1-4}$ NR$^{11c}$SO$_2$R$^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

3. The compound of claim 1 wherein:

q is 0, 1, or 2, and —R$^A$ is fluoro, an optionally substituted linear or branched C$_1$-C$_6$alkyl, an optionally substituted C$_3$-C$_6$cycloalkyl ring, or two occurrences of R$^A$, taken together with the carbon atom(s) to which they are bound form an optionally substituted fused or Spiro C$_3$-C$_6$cycloalkyl ring; or R$^1$ and R$^{A'}$ taken together with the carbon atom(s) to which they are bound form an optionally substituted fused or Spiro C$_3$-C$_6$cycloalkyl ring;

r is 0, 1, or 2, and —R$^B$ is fluoro, or an optionally substituted group selected from C$_1$-C$_6$alkyl, C$_3$-C$_6$cycloalkyl, or a fused or bridged 5- or 6-membered saturated ring having 0 heteroatoms;

R$^2$ is -Cy$^2$ or -T-Cy$^2$, and

T, when present, is a C$_1$-C$_3$alkylene chain substituted with 0 or 1 occurrence of R$^{5a}$, and 0, 1, or 2 independent occurrences of R$^{5b}$, and wherein the C$_1$-C$_3$alkylene chain is optionally replaced by —CO— or —SO$_2$, Cy$^2$ is selected from the group consisting of phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-one, quinolinyl, isoquinolinyl, quinazolinyl, quinoxalinyl, [1,8] naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, indazolyl, anthracenyl, fluorenyl, indanyl and xanthenyl;

wherein Cy$^2$ is substituted with 0, 1, or 2 independent occurrences of —R$^{6a}$, -G-R$^{6a}$, or —V-G-R$^{6a}$, and 0 or 1 occurrence of =O, =S, =NR$^{7a}$, —R$^{6b}$, -G-R$^{6b}$, or —V-G-R$^{6b}$, wherein:

each occurrence of —R$^{6a}$, -G-R$^{6a}$, or —V-G-R$^{6a}$, when present, is independently —CN, —NO$_2$, —OR$^{7a}$, —(CH$_2$)$_{1-4}$OR$^{7a}$, —SR$^{7a}$, —(CH$_2$)$_{1-4}$SR$^{7a}$, halogen, —COOR$^{7a}$, —(CH$_2$)$_{1-4}$COOR$^{7a}$, COR$^{7a}$, —(CH$_2$)$_{1-4}$COR$^{7a}$, —CON(R$^{7a}$)$_2$, —(CH$_2$)$_{1-4}$CON (R$^{7a}$)$_2$, —N(R$^{7a}$)$_2$, —(CH$_2$)$_{1-4}$N(R$^{7a}$)$_2$, —SO$_2$N(R$^{7a}$)$_2$, —(CH$_2$)$_{1-4}$SO$_2$N(R$^{7a}$)$_2$, —NR$^{7a}$SO$_2$R$^{7b}$, or —(CH$_2$)$_{1-4}$NR$^{7a}$SO$_2$R$^{7b}$, or an optionally substituted C$_1$-C$_6$aliphatic group; and each occurrence of —R$^{6b}$, -G-R$^{6b}$, or —V-G-R$^{6b}$ is —OR$^{7b}$, —(CH$_2$)$_{1-4}$OR$^{7b}$, —SR$^{7b}$, —(CH$_2$)$_{1-4}$SR$^{7b}$, —COOR$^{7b}$, —(CH$_2$)$_{1-4}$COOR$^{7b}$, —COR$^{7b}$, —(CH$_2$)$_{1-4}$COR$^{7b}$, —CON(R$^{7b}$)(R$^{7c}$), —(CH$_2$)$_{1-4}$CON (R$^{7b}$)(R$^{7c}$), —N(R$^{7b}$)(R$^{7c}$), —(CH$_2$)$_{1-4}$N(R$^{7b}$)(R$^{7c}$), —SO$_2$N(R$^{7b}$)(R$^{7c}$), —(CH$_2$)$_{1-4}$SO$_2$N(R$^{7b}$)(R$^{7c}$), —NR$^{7c}$SO$_2$R$^{7b}$, —(CH$_2$)$_{1-4}$NR$^{7c}$SO$_2$R$^{7b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur;

Q is —CO—, —C(R$^{5d}$)(R$^{5e}$)—, —COC(R$^{5d}$)(R$^{5e}$)—, —NR$^{5f}$CO—, —SO$_2$—, —OCO—, —C(R$^{5d}$)(R$^{5e}$) CO—, —C(R$^{5d}$)(R$^{5e}$)OCO—, or —CR$^{5e}$=CR$^{5e}$CO—; and Cy$^1$ is selected from the group consisting of phenyl, pyridyl, pyrimidinyl, pyrazinyl, pyridazinyl, 1,2,4-triazinyl, 1,3,5-triazinyl, 1,2,3-triazolyl, 1,2,4-triazolyl, imidazolyl, pyrazolyl, pyrrolyl, thiazolyl, isothiazolyl, thienyl, 1,3,4-thiadiazolyl, 1,2,4-thiadiazolyl, isoxazolyl, oxazolyl, furanyl, 1,3,4-oxadiazolyl, 1,2,4-oxadiazolyl, 1,3-dihydroimidazol-2-one, quinolinyl, isoquinolinyl, quinazolinyl, quinoxalinyl, [1,8] naphthyridinyl, naphthyl, 1,3-dihydro-benzoimidazol-2-on-1-yl, indolyl, benzo[c]isoxazolyl, benzofuranyl, benzothienyl, benzo[c]isothiazolyl, benzooxazol-2-yl, 5H-pyrrolo[3,2-d]pyrimidinyl, furo[3,2-d]pyrimidinyl, thieno[3,2-d]pyrimidinyl, benzo[d]isothiazolyl, benzo[d]isoxazolyl, benzo[1,3]dioxolyl, benzothiazolyl, benzimidazolyl, indazolyl, anthracenyl, fluorenyl, indanyl and xanthenyl;

wherein Cy$^1$ is substituted with 0, 1, 2, or 3 independent occurrences of —R$^{10a}$, -J-R$^{10a}$, or —W-J-R$^{10a}$, and 0 or 1 occurrence of =O, =S, =NR$^{11a}$, —NR$^{11b}$, —R$^{10b}$, -J-R$^{10b}$, or —W-J-R$^{10b}$, wherein:

each occurrence of —R$^{10a}$, -J-R$^{10a}$, or —W-J-R$^{10a}$, when present, is independently —CN, —NO$_2$, OR$^{11a}$, —(CH$_2$)$_{1-4}$OR$^{11a}$, —SR$^{11a}$, —(CH$_2$)$_{1-4}$SR$^{11a}$, halogen, —COOR$^{11a}$, —(CH$_2$)$_{1-4}$COOR$^{11a}$, —COR$^{11a}$, —(CH$_2$)$_{1-4}$COR$^{11a}$, —CON(R$^{11a}$)$_2$, —(CH$_2$)$_{1-4}$CON (R$^{11a}$)$_2$, —N(R$^{11a}$)$_2$, —(CH$_2$)$_{1-4}$N(R$^{11a}$)$_2$, —SO$_2$N (R$^{11a}$)$_2$, —(CH$_2$)$_{1-4}$SO$_2$N(R$^{11a}$)$_2$, NR$^{11a}$SO$_2$R$^{11a}$, or —(CH$_2$)$_{1-4}$NR$^{11a}$SO$_2$R$^{11a}$, or an optionally substituted C$_1$-C$_6$aliphatic group; and each occurrence of —R$^{10b}$, -J-R$^{10b}$, or —W-J-R$^{10b}$ is —OR$^{11b}$, —(CH$_2$)$_{1-4}$OR$^{11b}$, —SR$^{11b}$, —(CH$_2$)$_{1-4}$SR$^{11b}$, —COOR$^{11b}$, —(CH$_2$)$_{1-4}$COOR$^{11b}$, —COR$^{11b}$, —(CH$_2$)$_{1-4}$COR$^{11b}$, —CON(R$^{11b}$)(R$^{11c}$), —(CH$_2$)$_{1-4}$ CON(R$^{11b}$)(R$^{11c}$), —N(R$^{11b}$)(R$^{11c}$), —(CH$_2$)$_{1-4}$N (R$^{11b}$)(R$^{11c}$), —SO$_2$N(R$^{11b}$)(R$^{11c}$), —(CH$_2$)$_{1-4}$SO$_2$N (R$^{11b}$)(R$^{1c}$), —NR$^{11c}$SO$_2$R$^{11b}$, —(CH$_2$)$_{1-4}$ NR$^{11c}$SO$_2$R$^{11b}$, or an optionally substituted group selected from a 3-7-membered saturated, partially saturated, or aromatic monocyclic ring having 0-3 heteroatoms independently selected from nitrogen, oxygen, or sulfur, or an 8-10-membered saturated, partially unsaturated, or aromatic bicyclic ring having 0-5 heteroatoms independently selected from nitrogen, oxygen, or sulfur.

4. The compound of claim 3, wherein:

R$^1$ is —OH, —O(C$_1$-C$_6$alkyl), —OCO(C$_1$-C$_6$alkyl), —NHSO$_2$(C$_2$-C$_6$alkyl), —NHCO(C$_1$-C$_6$alkyl), or —F;

q is 0 or 1 and —R$^A$ is optionally substituted linear or branched C$_1$-C$_6$alkyl, or halogen;

r is 0, 1, or 2, and —$R^B$ is $C_1$-$C_3$alkyl, or two occurrences of $R^B$, taken together with their intervening atom(s), form an optionally substituted fused or bridged 5 or 6-membered saturated, partially unsaturated, or aromatic ring having 0 heteroatoms;

$R^2$ is -$Cy^2$ or -T-$Cy^2$, and

T, when present, is —$CH_2$—, —CO—, —$CH_2CH$=CH—, or —$CH_2CH_2$—, and $Cy^2$ is:

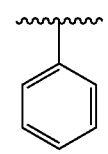
a

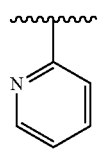
b-i

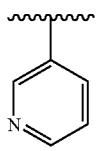
b-ii

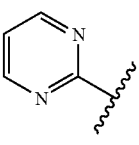
c-i

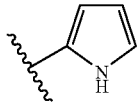
l-i

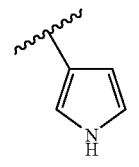
l-ii

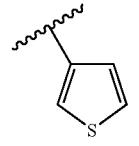
n-i

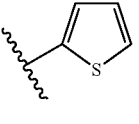
n-ii

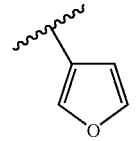
s-i

-continued

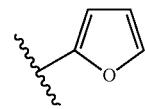
s-ii

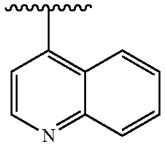
w-i

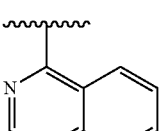
x-i

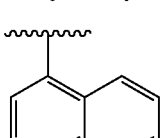
bb-i

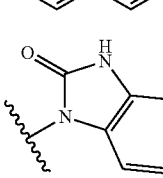
cc

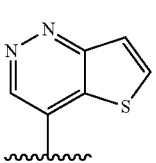
mm-i

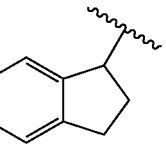
nn-i

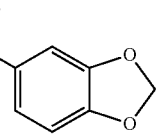
qq-i or

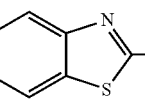
rr wherein $Cy^2$ is substituted with:

0, 1, or 2 occurrences of —$R^{6a}$ and each occurrence of —$R^{6a}$, when present, is independently —Cl, —Br, —F, —CN, —$NO_2$, —$SR^{7a}$, —$N(R^{7a})_2$, —$COOR^{7a}$, —$COR^{7a}$, —$SO_2N(R^{7a})_2$, —$NR^{7a}SO_2R^{7b}$, —CON($R^{7a})_2$, —$NR^{7a}COR^{7a}$, or optionally substituted $C_1$-$C_6$alkyl, wherein each occurrence of $R^{7a}$ is independently hydrogen, or optionally substituted $C_1$-$C_6$alkyl; and 0 or 1 occurrence of —$R^{6b}$, wherein —$R^{6b}$, when present is —$OR^{7b}$, —$SR^{7b}$, —$N(R^{7b})(R^{7e})$, —$COOR^{7b}$, —$COR^{7b}$, —$SO_2N(R^{7b})(R^7c)$, —$NR^{7c}SO_2R^{7b}$, -CON ($R^{7b}$)($R^{7c}$), —$NR^{7c}COR^{7b}$, or an optionally substituted 3-6-membered saturated, partially unsaturated, or aromatic ring having 0-3 heteroatoms independently selected from nitrogen, oxygen, or sulfur, wherein each occurrence of $R^{7b}$ is independently an optionally substituted 3-6-membered saturated, partially unsaturated, or aromatic ring having 0-3 heteroatoms independently selected from nitrogen, oxygen, or sulfur, and each occurrence of $R^{7c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur;

Q is —CO—, —$CH_2$—, —$COCH_2$—, —$CH_2CO$—, —$CH_2OCO$—, —$SO_2$—, or —$C(R^{5d})(R^{5e})CO$—, wherein $R^{5d}$ is hydrogen, optionally substituted $C_1$-$C_3$alkyl, optionally substituted phenyl, —OH, or —$NH_2$, and $R^{5e}$ is hydrogen, optionally substituted $C_1$-$C_3$alkyl, or optionally substituted phenyl;

$Cy^1$ is:

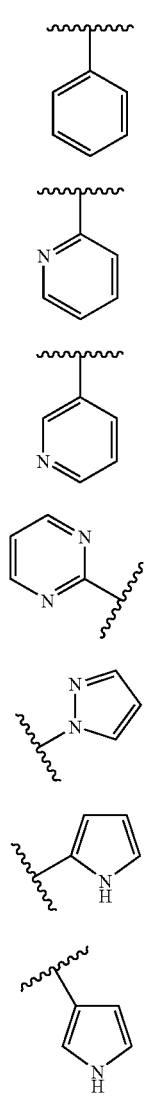

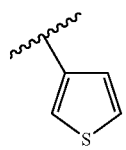  xv-a

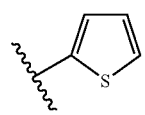  xv-b

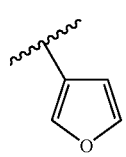  xx-a

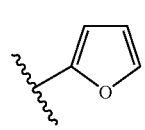  xx-b

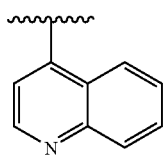  xxiv-a

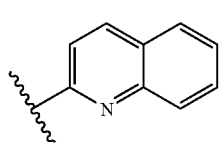  xxiv-b

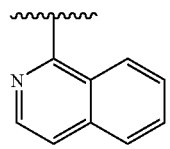  xxv-a

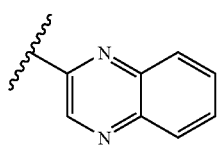  xxvii-a

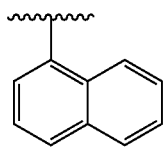  xxix-a

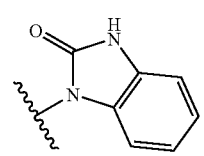  xxx

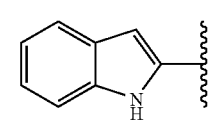  xxxi-a

-continued

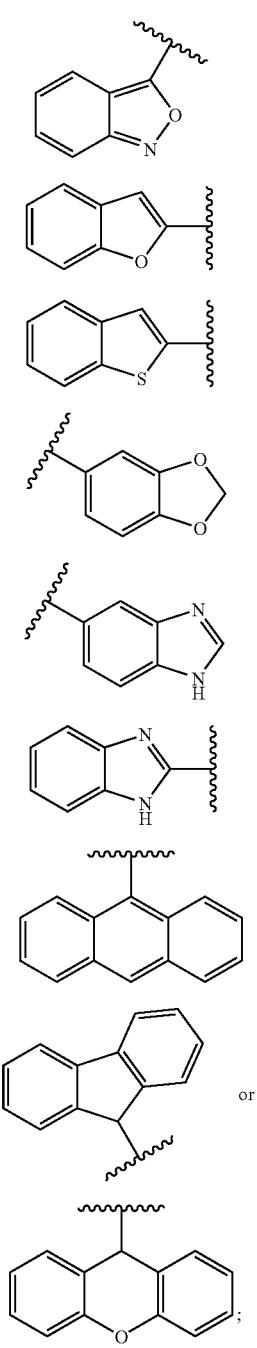

xxxii-a xxxiii-a xxxiv-a xLii-a xLiv-a xLiv-b xLvi xLvii or xLviii wherein Cy¹ is substituted with:
0, 1, or 2 occurrences of —$R^{10a}$ and each occurrence of —$R^{10a}$, when present, is independently —Cl, —Br, —F, —CN, —$NO_2$, —$OR^{11a}$, —$SR^{11a}$, —$NR^{11a}COR^{11a}$, —$CON(R^{11a})_2$, —$SO_2N(R^{11a})_2$, —$NR^{11a}SO_2R^{11a}$, $COOR^{11a}$, $COR^{11a}$, or optionally substituted $C_1$-$C_6$alkyl, wherein each occurrence of $R^{11a}$ is independently hydrogen, or optionally substituted $C_1$-$C_6$alkyl; and
0 or 1 occurrence of —$R^{10b}$, J-$R^{10b}$, or —W-J-$R^{10b}$, wherein W is —$N(R^{11b})$ or —O—, J is a $C_1$-$C_2$alkyl chain, and —$R^{10b}$, when present is —$OR^{11b}$, —$SR^{11b}$, —$N(R^{11b})(R^{11c})$, —$NR^{11c}COR^{11b}$, $CON(R^{11b})(R^{11c})$, —$SO_2N(R^{11c})(R^{11b})$, —$NR^{11c}SO_2R^{11b}$, —$COOR^{11b}$, $COR^{11b}$, or an optionally substituted 3-6-membered saturated, partially unsaturated, or aromatic ring having 0-3 heteroatoms independently selected from nitrogen, oxygen, or sulfur, wherein each occurrence of $R^{11b}$ is independently an optionally substituted 3-6-membered saturated, partially unsaturated, or aromatic ring having 0-3 heteroatoms independently selected from nitrogen, oxygen, or sulfur, and each occurrence of $R^{11c}$ is independently hydrogen or an optionally substituted group selected from $C_1$-$C_6$alkyl or an optionally substituted 3-6-membered saturated, partially unsaturated, or aromatic ring having 0-3 heteroatoms independently selected from nitrogen, oxygen, or sulfur.

5. The compound of claim 4, wherein:
$R^1$ is —OH, or —O($C_1$-$C_6$alkyl);
q is 0 or 1 and —$R^A$ is —$CH_3$, —$CH_2CH_3$; or F;
—$R^B$ is $C_1$-$C_3$alkyl;
$R^2$ is -$Cy^2$ or T-$Cy^2$, and T when present, is —$CH_2$— or —CO—; and $Cy^2$ is:

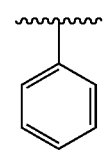

a

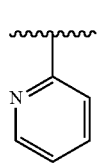

b-i

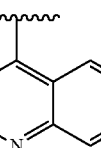

w-i

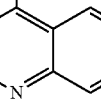

x-i or

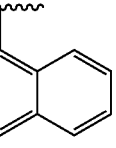

nn-i

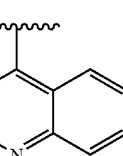

w-i

-continued

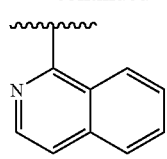
x-i wherein Cy² is substituted with 0, 1, or 2 occurrences of —R⁶ᵃ and each occurrence of —R⁶ᵃ, when present, is independently —Cl, —Br, —F, —CN, —OCH₃, —OCH₂CH₃, —OCH₂CH₂CH₃, —F₃, —CH₃, —CH₂CH₃, —CH₂CH₂CH₃, —CH(CH₃)₂, —C(CH₃)₃, —COOH, —COOCH₃, —COOCH₂CH₃;
Q is —CO—;
Cy¹ is:

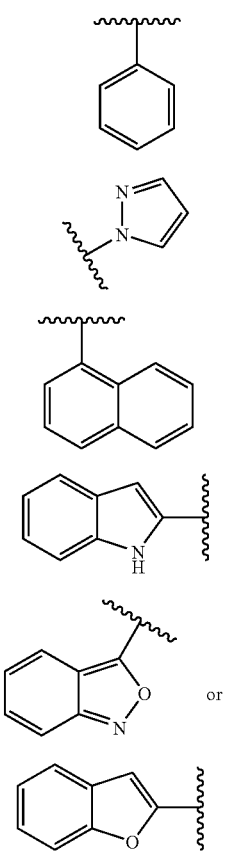

wherein Cy¹ is substituted with:
0, 1, or 2 occurrences of R¹⁰ᵃ, and each occurrence of —R¹⁰ᵃ is independently —Cl, —Br, —F, —NO₂, —CN, —OCH₃, —OCH₂CH₃, —OCH₂CH₂CH₃, —CF₃, —OCF₃, —CH₃, —CH₂CH₃, —CH₂CH₂CH₃, —C(CH₃)₃, —CH(CH₃)₂, —NHCOCH₃, —NHCONHCH₃, —SCH₃, —SCH₂CH₃, —SCH₂CH₂CH₃, —NH₂, —NHCH₃, —SO₂NH₂, —COOH, —COOCH₃, —NHCH₃, —N(CH₃)₂, —NH(CH₂CH₃), —N(CH₂CH₃)₂, —OC(CH₃)₂CO₂H, —OCH₂CO₂H, or —C(CH₃)₂OH and 0 or 1 occurrence of —R¹⁰ᵇ, J-R¹⁰ᵇ, or W-J-R¹⁰ᵇ, and —R¹⁰ᵇ, J-R¹⁰ᵇ, or W-J-R¹⁰ᵇ is phenyl, benzyl, —NHCO(phenyl), —NHCO(benzyl), —NH(phenyl), —NHCH₂(phenyl), —NH(benzyl), —S(phenyl), —S(benzyl), —O(phenyl), or —O(benzyl), wherein the phenyl and benzyl groups are optionally substituted.

6. The compound of claim 5, wherein R¹ is —OH.
7. The compound of claim 5, wherein q is 0.
8. The compound of claim 5, wherein r is 0.
9. The compound of claim 5, wherein Cy² is substituted with 1 or 2 occurrences of —R⁶ᵃ, and each occurrence of —R⁶ᵃ is independently —Cl, —F, —CF₃, —CH₃, or —Br.
10. The compound of claim 5, wherein Cy² is substituted with 1 occurrence of —R⁶ᵃ, and —R⁶ᵃ is —Cl.
11. The compound of claim 5, wherein Cy² is:

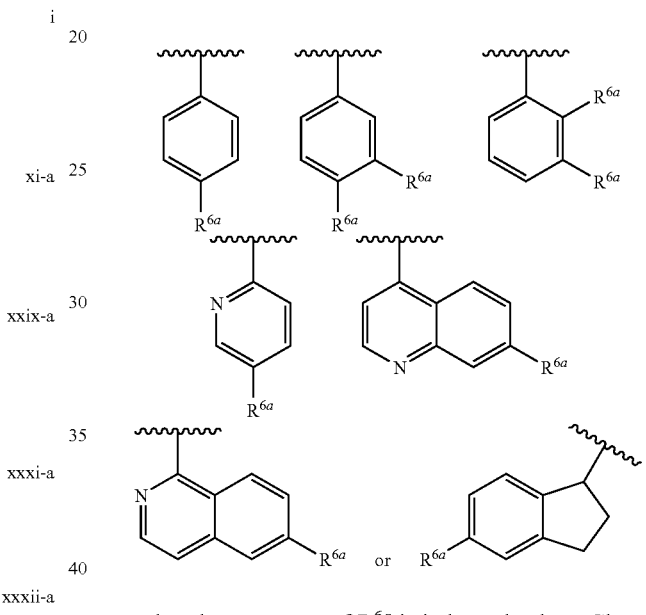

and each occurrence of R⁶ᵃ is independently —Cl, —Br, —CH₃, —CF₃, or —F.

12. The compound of claim 5, wherein Cy² is phenyl substituted with 1 or 2 occurrences of —R⁶ᵃ, and each occurrence of —R⁶ᵃ is independently —Cl, —F, —CF₃, —CH₃, or —Br.
13. The compound of claim 5, wherein Cy² is phenyl substituted with 1 occurrence of —R⁶ᵃ, and —R⁶ᵃ is —Cl.
14. The compound of claim 5, wherein Cy¹ is phenyl.
15. The compound of claim 5, wherein Cy¹ is substituted with 1, 2, or 3 occurrences of R¹⁰ᵃ, and each occurrence of R¹⁰ᵃ is independently —Cl, —Br, —F, —CH₃, or —CF₃.
16. A pharmaceutical composition comprising a therapeutically effective amount of compound of claim 1, and a pharmaceutically acceptable carrier, adjuvant, or vehicle.
17. The composition of claim 16, comprising an additional therapeutic agent.

* * * * *